US008067016B2

(12) United States Patent
Skeiky et al.

(10) Patent No.: US 8,067,016 B2
(45) Date of Patent: Nov. 29, 2011

(54) **FUSION PROTEINS OF *MYCOBACTERIUM TUBERCULOSIS***

(75) Inventors: Yasir Skeiky, Seattle, WA (US); Steven Reed, Bellevue, WA (US); Raymond L. Houghton, Bothell, WA (US); Patricia D. McNeill, Des Moines, WA (US); Davin C. Dillon, Redmond, WA (US); Michael J. Lodes, Seattle, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 12/490,984

(22) Filed: Jun. 24, 2009

(65) Prior Publication Data

US 2009/0306195 A1 Dec. 10, 2009

Related U.S. Application Data

(60) Continuation of application No. 11/809,102, filed on May 30, 2007, which is a division of application No. 09/688,672, filed on Oct. 10, 2000, now Pat. No. 7,311,922.

(60) Provisional application No. 60/158,425, filed on Oct. 7, 1999, provisional application No. 60/158,338, filed on Oct. 7, 1999.

(51) Int. Cl.
*A61K 49/00* (2006.01)
*A61K 39/04* (2006.01)
*A61K 39/02* (2006.01)

(52) U.S. Cl. .... 424/248.1; 424/9.1; 424/9.2; 424/185.1; 424/234.1; 536/23.1; 536/23.7

(58) Field of Classification Search .................. 424/9.1, 424/9.2, 185.1, 234.1, 248.1; 536/23.1, 23.7
See application file for complete search history.

(56) References Cited

U.S. PATENT DOCUMENTS

| | | |
|---|---|---|
| 3,943,119 A | 3/1976 | Tsumita et al. |
| 4,235,877 A | 11/1980 | Fullerton |
| 4,436,727 A | 3/1984 | Ribi |
| 4,603,112 A | 7/1986 | Paoletti et al. |
| 4,689,397 A | 8/1987 | Shinnick et al. |
| 4,751,180 A | 6/1988 | Cousens et al. |
| 4,769,330 A | 9/1988 | Paoletti et al. |
| 4,777,127 A | 10/1988 | Suni et al. |
| 4,866,034 A | 9/1989 | Ribi |
| 4,876,089 A | 10/1989 | Luciw et al. |
| 4,877,611 A | 10/1989 | Cantrell |
| 4,879,213 A | 11/1989 | Fox et al. |
| 4,897,268 A | 1/1990 | Tice et al. |
| 4,912,094 A | 3/1990 | Myers et al. |
| 4,935,233 A | 6/1990 | Bell et al. |
| 4,946,778 A | 8/1990 | Ladner et al. |
| 4,952,395 A | 8/1990 | Shinnick et al. |
| 5,108,745 A | 4/1992 | Horwitz |
| 5,145,684 A | 9/1992 | Liversidge et al. |
| 5,240,856 A | 8/1993 | Goffe et al. |
| 5,330,754 A | 7/1994 | Kapoor et al. |
| 5,466,468 A | 11/1995 | Schneider et al. |
| 5,478,726 A | 12/1995 | Shinnick et al. |
| 5,504,005 A | 4/1996 | Bloom et al. |
| 5,543,158 A | 8/1996 | Gref et al. |
| 5,565,213 A | 10/1996 | Nakamori et al. |
| 5,567,434 A | 10/1996 | Szoka |
| 5,580,579 A | 12/1996 | Ruddy et al. |
| 5,583,112 A | 12/1996 | Kensil et al. |
| 5,599,545 A | 2/1997 | Stanford et al. |
| 5,616,500 A | 4/1997 | Steinert et al. |
| 5,639,653 A | 6/1997 | Bloom et al. |
| 5,714,593 A | 2/1998 | Laqueyrerie et al. |
| 5,780,045 A | 7/1998 | McQuinn et al. |
| 5,783,386 A | 7/1998 | Jacobs, Jr. et al. |
| 5,795,587 A | 8/1998 | Gao et al. |
| 5,804,212 A | 9/1998 | Illum |
| 5,811,128 A | 9/1998 | Tice et al. |
| 5,814,344 A | 9/1998 | Tice et al. |
| 5,817,473 A | 10/1998 | Das et al. |
| 5,820,883 A | 10/1998 | Tice et al. |
| 5,853,763 A | 12/1998 | Tice et al. |
| 5,856,462 A | 1/1999 | Agrawal |
| 5,928,647 A | 7/1999 | Rock |
| 5,942,252 A | 8/1999 | Tice et al. |
| 5,955,077 A | 9/1999 | Andersen et al. |
| 5,985,287 A | 11/1999 | Tan et al. |
| 6,001,361 A | 12/1999 | Tan et al. |
| 6,034,218 A | 3/2000 | Reed et al. |
| 6,037,135 A | 3/2000 | Kubo et al. |
| 6,113,918 A | 9/2000 | Johnson et al. |
| 6,290,969 B1 | 9/2001 | Reed et al. |
| 6,338,852 B1 | 1/2002 | Reed et al. |
| 6,350,456 B1 | 2/2002 | Reed et al. |
| 6,355,257 B1 | 3/2002 | Johnson et al. |
| 6,458,366 B1 | 10/2002 | Reed et al. |
| 6,465,633 B1 | 10/2002 | Skeiky |
| 6,544,522 B1 | 4/2003 | Skeiky et al. |
| 6,555,653 B2 | 4/2003 | Alderson et al. |
| 6,592,877 B1 | 7/2003 | Reed et al. |

(Continued)

FOREIGN PATENT DOCUMENTS

EP 345242 12/1989

(Continued)

OTHER PUBLICATIONS

Orme, Preclinical testing of new vaccines for tuberculosis: A comprehensive review, Vaccine 24:2-19 (2006).

(Continued)

*Primary Examiner* — Rodney P. Swartz
(74) *Attorney, Agent, or Firm* — Convergent Law Group LLP

(57) ABSTRACT

The present invention relates to fusion proteins containing at least two *Mycobacterium* species antigens. In particular, it relates to nucleic acids encoding fusion proteins that include two or more individual *M. tuberculosis* antigens, which increase serological sensitivity of sera from individuals infected with tuberculosis, and methods for their use in the diagnosis, treatment, and prevention of tuberculosis infection.

9 Claims, 48 Drawing Sheets

U.S. PATENT DOCUMENTS

| | | | |
|---|---|---|---|
| 6,613,881 B1 | 9/2003 | Alderson et al. |
| 6,627,198 B2 | 9/2003 | Reed et al. |
| 6,949,246 B2 | 9/2005 | Reed et al. |
| 6,962,710 B2 | 11/2005 | Reed et al. |
| 6,977,069 B2 | 12/2005 | Reed et al. |
| 7,026,465 B2 | 4/2006 | Skeiky et al. |
| 7,064,195 B2 | 6/2006 | Skeiky et al. |
| 7,083,796 B2 | 8/2006 | Skeiky et al. |
| 7,087,713 B2 | 8/2006 | Campos-Neto et al. |
| 7,122,196 B2 | 10/2006 | Reed et al. |
| 7,186,412 B1 | 3/2007 | Skeiky et al. |
| 7,261,897 B2 | 8/2007 | Skeiky et al. |
| 7,311,922 B1 | 12/2007 | Skeiky et al. |
| 7,335,369 B2 | 2/2008 | Reed et al. |
| 7,678,375 B2 | 3/2010 | Skeiky et al. |
| 7,691,993 B2 | 4/2010 | Skeiky et al. |
| 2006/0193876 A1 | 8/2006 | Skeiky et al. |
| 2007/0054336 A1 | 3/2007 | Campos-Neto et al. |
| 2007/0141087 A1 | 6/2007 | Reed et al. |
| 2008/0176798 A1 | 7/2008 | Campos-Neto et al. |
| 2008/0199405 A1 | 8/2008 | Reed et al. |
| 2008/0269151 A1 | 10/2008 | Skeiky et al. |
| 2008/0317716 A1 | 12/2008 | Skeiky et al. |
| 2009/0017077 A1 | 1/2009 | Reed et al. |
| 2009/0018095 A1 | 1/2009 | Skeiky et al. |
| 2009/0022742 A1 | 1/2009 | Campos-Neto et al. |
| 2009/0281168 A1 | 11/2009 | Reed et al. |
| 2009/0306195 A1 | 12/2009 | Skeiky et al. |
| 2010/0015096 A1 | 1/2010 | Skeiky et al. |
| 2010/0183657 A1 | 7/2010 | Skeiky et al. |
| 2010/0183677 A1 | 7/2010 | Skeiky et al. |

FOREIGN PATENT DOCUMENTS

| | | |
|---|---|---|
| EP | 419355 | 3/1991 |
| EP | 519218 | 12/1992 |
| FR | 2244539 | 4/1975 |
| FR | 2265402 | 10/1975 |
| GB | 2200651 | 8/1988 |
| GB | 2298862 | 9/1996 |
| HU | 158035 | 3/1971 |
| RU | 2024021 | 11/1994 |
| WO | WO 88/05823 | 8/1988 |
| WO | WO 88/06591 | 9/1988 |
| WO | WO 89/01973 | 3/1989 |
| WO | WO 89/06280 | 7/1989 |
| WO | WO 91/02805 | 3/1991 |
| WO | WO 91/04272 | 4/1991 |
| WO | WO 91/14448 | 10/1991 |
| WO | WO 91/18926 | 12/1991 |
| WO | WO 92/04049 | 3/1992 |
| WO | WO 92/07243 | 4/1992 |
| WO | WO 92/14154 | 8/1992 |
| WO | WO 92/14823 | 9/1992 |
| WO | WO 92/16628 | 10/1992 |
| WO | WO 92/21697 | 12/1992 |
| WO | WO 92/21758 | 12/1992 |
| WO | WO 94/00153 | 1/1994 |
| WO | WO 94/00228 | 1/1994 |
| WO | WO 94/00492 | 1/1994 |
| WO | WO 94/00493 | 1/1994 |
| WO | WO 94/14069 | 6/1994 |
| WO | WO 94/20078 | 9/1994 |
| WO | WO 94/23701 | 10/1994 |
| WO | WO 95/01440 | 1/1995 |
| WO | WO 95/01441 | 1/1995 |
| WO | WO 95/14713 | 6/1995 |
| WO | WO 95/17210 | 6/1995 |
| WO | WO 95/17511 | 6/1995 |
| WO | WO 95/31216 | 11/1995 |
| WO | WO 96/02555 | 2/1996 |
| WO | WO 96/06638 | 3/1996 |
| WO | WO 96/15241 | 5/1996 |
| WO | WO 96/23885 | 8/1996 |
| WO | WO 96/28551 | 9/1996 |
| WO | WO 96/33739 | 10/1996 |
| WO | WO 96/38591 | 12/1996 |
| WO | WO 97/09248 | 3/1997 |
| WO | WO 97/09249 | 3/1997 |
| WO | WO 97/09428 | 3/1997 |
| WO | WO 97/09429 | 3/1997 |
| WO | WO 97/24447 | 10/1997 |
| WO | WO 98/07868 | 2/1998 |
| WO | WO 98/16645 | 4/1998 |
| WO | WO 98/16646 A1 | 4/1998 |
| WO | WO 98/44119 | 10/1998 |
| WO | WO 98/53075 | 11/1998 |
| WO | WO 98/53076 | 11/1998 |
| WO | WO 99/09186 | 2/1999 |
| WO | WO 99/33488 | 7/1999 |
| WO | WO 99/42076 | 8/1999 |
| WO | WO 99/42118 | 8/1999 |
| WO | WO 99/51748 | 10/1999 |
| WO | WO 99/52549 | 10/1999 |
| WO | WO 00/09159 | 2/2000 |
| WO | WO 01/24820 | 4/2001 |
| WO | WO 01/34802 | 5/2001 |
| WO | WO 01/34803 | 5/2001 |
| WO | WO 01/51633 | 7/2001 |
| WO | WO 01/62893 | 8/2001 |
| WO | WO 01/73032 | 10/2001 |
| WO | WO 01/90152 | 11/2001 |
| WO | WO 01/98460 | 12/2001 |
| WO | WO 2005/076101 | 8/2005 |
| WO | WO 2008/107370 | 9/2008 |

OTHER PUBLICATIONS

Girard, et al., A review of vacciine research and development: Tuberculosis, Vaccine 23:5725-31 (2006).

Office Action for U.S. Appl. No. 12/698,893, 2010.

Wang, et al., "Tuberculosis Vaccines: Past, Present and Future," Expert Rev. Vaccines 1(3):341-54 (2002).

Wang, et al., "A novel method for increasing the expression level of recombinant proteins," Protein Expression and Purification 30(1):124-133 (2003).

Webb, et al., "Molecular Cloning, Expression and Immunogenicity of MTB12," Infection & Immunity 66(9):4208-4214 (1998).

Wiegeshaus, et al., "Evaluation of the protective potency of new tuberculosis vaccines," Reviews of Infectious Diseases 11(Suppl. 2):S484-S490 (1989).

Wieles, et al., "Characterization of a *Mycobacterium leprae* Antigen Related to the Secreted *Mycobacterium tuberculosis* Protein MPT32," Infection and Immunity 62(1):252-258 (1994).

Wigler, et al., "Transformation of mammalian cells with an amplifiable dominant-acting gene," PNAS USA 77:3567-70 (1980).

Wiker and Harboe, "The Antigen 85 Complex: a Major Secretion Product of *Mycobacterium tuberculosis*," Microbiological Reviews 56(4):648-661 (1992).

Winter, "The Expression of Heat Shock Proteins and Cognate Genes During Plant Development," Results Probl. Cell Differ. 17: 85-105 (1991).

Yamaguchi, et al., "Cloning and Characterization of the Gene for Immunogenic Protein MPB64 of *Mycobacterium bovis* BDG," Infection and Immunity 57(1):283-288 (1989).

Young, et al., "Screening of a Recombinant Mycobacterial DNA Library with Polyclonal Antiserum and Molecular Weight Analysis of Expressed Antigens," Infection and Immunity 55(6):1421-1425 (1987).

Zitvogel, et al., "Eradiation of established murine tumors using a novel cell-free vaccine: dedritic cell-derived exosomes," Nature Med. 4:594-600 (1998).

Seq_NCBI_AF2122897, 1 page, 2000.

Seq_XP002416348_CDC1551, 2 pages, 2000.

Seq_NCBI AD000020 gi: 1717739 Dec. 10, 1996, 10 pages.

Seq_NCBI_AL021930.1, 2 pages, 2000.

Seq_NCBI_AL021930, 17 pages, 2000.

Seq_Database EMBL_U34848 "*Mycobacterium bovis* deletion region 1, 6kDa early secretory antigenic target (esat6) gene", 2000.

Seq_Accession No. O05907, Database:stpremb119, publiclly available Jul. 1, 1997.

Seq_Accession No. O05908, Database:stpremb119, publicly available Jul. 1, 1997.

Seq_EMBL_MTCY7H7Bc, Accession No. Z95557, May 20, 1997.
Seq_EMBL_MTCY24G1, Accession No. Z83858, Jan. 13, 1997.
Seq_EMBL_MTCY19G5, Accession No. Z77826, Jul. 31, 1996.
Seq_EMBL_MTCY261, Accession No. Z97559, Jul. 10, 1997.
Seq_Accession_No._AU077540, 2000.
Seq_EMBL_P15712, (Apr. 1, 1990) "PBP-1 from *M. tuberculosis*" XP002359448.
Seq_Uniprot _Q79FV1, 2000.
Seq_Uniprot _O06267, 2000.
Seq_Uniprot_P96364, 2000.
Seq_Uniprot_O05300, 2000.
Seq_Sequence Alignment_SEQ ID No. 163-*Mycobacterium smegmatis* (Cirillo et al.), 2000.
Seq_Sequence Alignment_*Corynebacterium glutamicum*, 2000.
Seq_Sequence alignment _*Mycobacterium segmatis*_P41403, created Nov. 1995.
Seq_NCBI_214801_Rv0287 [*Mycobacterium tuberculosisi* H37Rv]), 2000.
Seq_NCBI_CAA17362, 2000.
Seq_EMBL_Q7U0G8—Hypothetical Protein Mb1207c, Oct. 31, 2006 XP002416347.
Seq_EMBL_050430—Hypothetical Protein Mb1207c, Oct. 31, 2006, XP002416348.
Seq_Compugen_P95242, 1997.
Seq_Compugen_P96363, 1997.
Seq_Compugen_P95243, 1997.
Seq_Compugen_P96361, 1997.
Seq_Compugen_P95012, 1997.
Seq_Compugen_Q49722, 1996.
Seq_EMBL_X84741—Mycrobacteriumbovis BCG IS1081 DNA Sequence, Van Soolingen, D., 2000.
U.S. Appl. No. 09/724,685, filed Oct. 11, 1996.
First Office Action for U.S. Appl. No. 08/658,800, 1998.
Second Office Action for U.S. Appl. No. 08/658,800, 1998.
First Office Action for U.S. Appl. No. 08/659,683, 1997.
Second Office Action for U.S. Appl. No. 08/659,683, 1998.
First Office Action for U.S. Appl. No. 08/680,573, 1998.
Second Office Action for U.S. Appl. No. 08/680,573, 1998.
First Office Action for U.S. Appl. No. 08/680,574, 1997.
Second Office Action for U.S. Appl. No. 08/680,574, 1998.
First Office Action for U.S. Appl. No. 08/729,622, 1998.
Second Office Action for U.S. Appl. No. 08/729,622, 1998.
First Office Action for U.S. Appl. No. 08/730,510, 1998.
First Office Action for U.S. Appl. No. 08/818,111, 1998.
Second Office Action for U.S. Appl. No. 08/818,111, 1999.
First Office Action for U.S. Appl. No. 08/818,112, 1998.
Second Office Action for U.S. Appl. No. 08/818,112, 1998.
First Office Action for U.S. Appl. No. 08/858,998, 1998.
First Office Action for U.S. Appl. No. 08/859,381, 1998.
First Office Action for U.S. Appl. No. 08/942,341, 1998.
First Office Action for U.S. Appl. No. 09/056,556, 2000.
Second Office Action for U.S. Appl. No. 09/056,556, 2000.
First Office Action for U.S. Appl. No. 09/072,967, 2000.
First Office Action for U.S. Appl. No. 09/073,009, 1999.
Second Office Action for U.S. Appl. No. 09/073,009, 2000.
Third Office Action for U.S. Appl. No. 09/073,009, 2001.
Fourth Office Action for U.S. Appl. No. 09/073,009, 2001.
First Office Action for U.S. Appl. No. 09/073,010, 2000.
Second Office Action for U.S. Appl. No. 09/073,010, 2000.
Office Action for U.S. Appl. No. 08/730,510, 1998.
Office Action for U.S. Appl. No. 09/470,191, 2001.
First Office Action for U.S. Appl. No. 09/072,596, 2001.
Orme, "Prospects for new vaccines against tuberculosis," Trends in Microbiology 3(10):401-404 (1995).
Ortega, et al., "Single-step purification on DEAE-sephacel of recombinant polypeptides produced in *Escherichia coli*," Biotechnology 10:795-798 (1992).
Pal, et al., "Immunization with extracellular proteins of *Mycobacterium tuberculosis* induces cell-mediated immune responses and substantial protective immunity in a guinea pig model of pulmonary tuberculosis", Infection and Immunity 60(11):4781-4792 (1992).

Pancholi, et al., "Dendritic cells efficiently immunoselect mycobacterial-reactive T cells in human blood, including clonable antigen-reactive precursors," Immunology 76(2):217-224 (1992).
Parker, et al., "Targeted Gene Walking Polymerase Chain Reactions," Nuc. Acids Res. 19: 3055-60 (1991).
Paul, Fundamental Immunology, chap. 8, 243-247 (1993).
Philipp, et al., "An integrated map of the genome of the tubercle bacillus, *Mycobacterium tuberculosis* H37Rv, and comparison with *Mycobacterium leprae*," PNAS USA 93(7):3132-3137 (1996).
Porath, et al., "Immobilized Metal Ion Affinity Chromatography," Proto Exp. Purif. 3:263-281 (1992).
Pouthier, et al., "Anti-A60 immunoglobulin G in the serodiagnosis of tuberculosis in HIV-seropositive and seronegative patients," AIDS 8(9):1277-80 (1994).
Reed, et al., "Tuberculosis vaccine development: from mouse to man," Microbes and Infection 7(5-6):992-31 (2005).
Reed, et al., "Defined tuberculosis vaccine, Mtb72F/AS02A,evidence of protection in cynomolgus monkeys," PNAS 106(7):2301-06 (2009).
Rhodes, et al., "Transformations of Maize by the Electroporation of Embryos," Methods Mol. Biol. 55:121-131 (1995).
Rinke De Wit, et al., "A *Mycobacterium leprae*-specific gene encoding an immunologically recognized 45 kDa protein," Mol. Microbiol. 10(4):829-838 (1993).
Rinke De Wit, et al., "Mycobacteria contains two groEL genes: the second *Mycobacterium leprae* groEL gene is arranged in an operon with groES," Mol. Microbiol. 6(14):1995-2007 (1992).
Riveau, et al., "Synthetic peptide vaccines against peptides and biological mediators," Trends in Pharmacological Sciences 11:194-198 (1990).
Roberts, et al., "Prediction of HIV peptide epitopes by a novel algorithm," AIDS Research and Human Retroviruses 12:593-610 (1996).
Romain, et al., "Identification of a *Mycobacterium bovis* BCG 45/47-Kilodalton Antigen Complex, an Immunodominant Target for Antibody Response after Immunization with Living Bacteria," Infection and Immunity 61(2):742-750 (1993).
Romain, et al., "Isolation of a proline-rich mycobacterial protein eliciting delayed-type hypersensitivity reactions only in guinea pigs immunized with living mycobacteria," PNAS USA 90:5322-5326 (1993).
Romain, et al., "Preparation of Tuberculin Antigen L," Ann. Inst. Pasteur/Microbiol. 136B:235-248 (1985).
Romano, et al., "Immunogenicity and protective efficacy of tuberculosis subunit vaccines expression PPE44 (Rv2770c)," Vaccine, 26(48):6053-63 (2008).
Rolland, "From Genes to Gene Medicines: Recent Advances in Nonviral Gene Delivery," Crit. Rev. Therap. Drug Carrier Systems 15:143-198 (1998).
Rosenfeld, et al., "Adenovirus-Mediated Transfere of a Recombinant Alpha-1 Antitrypsin Gene to Lung Epithelium in Vivo," Science 252:431-434 (1991).
Rossolini, et al., "Use of deoxyinosine-containing primers versus degenerate primers," Mol. Cell. Probes 8:91-98 (1994).
Sanderson, et al., "Identification of a CD4+ T Cell-stimulating Antigen of Pathogenic Bacteria by Expression Cloning," J. Exp. Med. 182(6):1751-1757 (1995).
Sato, et al., "Immunostimulatory DNA Sequences Necessary for Effective Intradermal Gene Immunization," Science 273:352 (1996).
Scharf, et al., "Heat Stress Promoters and Transcription Factors," Results Probl. Cell Differ. 20:125-162 (1994).
Schorey, "A *Mycobacterium leprae* Gene Encoding a Fibronectin Binding Protein is Used for Efficient Invasion of Epithelial Cells and Schwann Cells," Infection and Immunity 63(7):2652-2657 (1995).
Shinnick, "The 65-Kilodalton Antigen of *Mycobacterioum tuberculosis*," J. of Bacteriology 169(3): 1080-1088 (1987).
Singh, et al., "In Vitro Characterization of T Cells from *Mycobacterium* W-Vaccinated Mice," Infection and Immunity 60(1):257-263 (1992).
Sinha, et al., "Immunological properties of a 30 Kda secretory protein of *Mycobacterium tuberculosis* H37RA," Vaccine 15(6-7): 689-99 (1997).
Simonney, et al., "Analysis of the immunological humoral response to *Mycobacterium tuberculosis* glycolipid antigens (DAT, PGLTb1)

for diagnosis of tuberculosis in HIV-seropositive and seronegative patients," Eur. J. of Clin. Microbiology and Infectious Disease 14(10):883-891 (1995).

Skeiky, et al., "Cloning Expression and Immunological Evaluation of Two Putative Secreted Serine Protease Antigens of *Mycrobactenum tuberculosis*," Infection and Immunity 67(8): 3998-4007 (1999).

Skeiky, et al., "LeIF:a recombinant leishmania protein that induces an IL-12 mediated Th cytokine profile," J. of Immunology 161: 6171-79 (1998).

Skeiky, et al., "Differential immune responses and protective efficacy induced by components of a tuberculosis polyprotein vaccine, Mtb72F, delivered as naked DNA or recombinant protein," J. of Immunology 172(12):7618-28 (2004).

Skorko-Glonek, "Comparison of the structure of wild-type HtrA heat shock protease and mutant HtrA proteins. A Fourier transform infrared spectroscopic study," JBC 270(19): 11140-11146 (1995).

Skuce, et al., "Discrimination of *M. tuberculosis* complex bacterial using novel VNTR-PCR targets," Microbiology 148(2):519-28 (2002).

Sorensen, et al., "Purification and characterization of a low-molecular-mass T-cell antigen secreted by *Mycobacterium tuberculosis*," Infection and Immunity 63(5): 1710-1717 (1995).

Stoute, et al., "A Preliminary Evaluation of a Recombinant Circumsporozoite Protein Vaccine Against Plasmodium Falciparum Malaria," New Engl. J. Med. 336:86-91 (1997).

St. Pierre, et al., "A refined vector system for the in vitro construction of single-copy transcriptional or translational fusions to lacZ," Gene169:65-68 (1996).

Timmerman and Levy, "Dendritic Cell Vaccines for Cancer Immunotherapy," Ann. Rev. Med 50: 507-529 (1999).

Triglia, et al., "A Procedure for in Vitro Amplification of DNA Sequences that Lie Outside the Boundaries of Known Sequences," Nucl. Acids Res. 16:8186 (1988).

Tsenova, et al. "Evaluation of the Mtb72F Polyprotein Vaccine in a Rabbit Model," Infection and Immunity 74(4):2922-401 (2006).

Ulmer, et al., "Heterologous Protection Against Influenze by Injection of DNA Encoding a Viral Protein," Science 259:1745-1749 (1993).

Van Pittius, et al., "Evolution and expansion of the *M. tuberculosis* PE and PPE multigene families and their association with the duplication of the ESAT-6 (esx) gene cluster regions," BML Evolutionary Biology 6(1):95 (2006).

Van Soolingen, et al., "Host-Mediated Modification of Pvull Restriction in *Mycobacterium tuberculosis*," J. of Bactreriology 178(1):78-84 (1996).

Vekemans et al., "Immune Responses to Mycobacterial Antigens in the Gambian Population,", Infection and Immunity 72(1):381-88 (2004).

Von Eschen, et al., "The candidate tuberculosis vaccine Mtb72F/AS02A," Human Vaccines 5(7):475-82 (2009).

Vega-Lopez, et al., "Sequence and immunological characterization of a serine-rich antigen from *Mycobacterium leprae*," Infection and Immunity 61(5):2145-2153 (1993).

Verbon, et al., "The 14,000-Molecular-Weight Antigen of *Mycobacterium tuberculosis* Is Related to the Alpha-Crystallin Family of Low-Molecular-Weight Heat Shock Proteins," J. of Bacteriology 174(4):1352-1359 (1992).

Wallis, et al., "Identification of Antigens of *Mycobacterium tuberculosis* Using Human Monoclonal Antibodies," J. Clin. Invest. 84:214-219 (1989).

Alderson, et al. "Expression cloning of an immunodominant family of *Mycobacterium tuberculosis* antigens using human CD4+ T cells," J. Exp. Med. 191(3):551-559 (Feb. 7, 2000).

Brandt, et al. "ESAT-6 subunit vaccination against *Mycobacterium tuberculosis*," Infect. Immun. 68(2):791-795 (Feb. 2000).

Coler, et al. "Molecular cloning and immunologic reactivity of a novel low molecular mass antigen of *Mycobacterium tuberculosis*," J. Immunol. 161(5):2356-2364 (Sep. 1, 1998).

Hendrickson, et al. "Mass Spectrometric Identification of Mtb81, A Novel Serological Marker for Tuberculosis," J. Clin. Microbiol 38(6):2354-2361 (Jun. 2000).

Leao, et al. "Immunological and functional characterization of proteins of the *Mycobacterium tuberculosis* antigen 85 complex using synthetic peptides," J. Gen. Microbiol. 139:1543-1549 (1993).

Lowrie, et al. "Progress towards a new tuberculosis vaccine," BioDrugs 10(3):201-213 (Sep. 1998).

Vordermeier, et al. "Synthetic delivery system for tuberculosis vaccines: immunological evaluation of the *M. tuberculosis* 38 kDa protein entrapped in biodegradable PLG microparticles," Vaccine 13(16):1576-1582 (1995).

Zimmerman, et al. "Immunization with peptide heteroconjugates primes a T helper cell type 1-associated antibody (IgG2a) response that recognizes the native epitope on the 38-kDa protein of *Mycobacterium tuberculosis*," Vaccine Res. 5(2):103-118 (1996).

Database EMBL [Online] accession No. Q50596, XP002224822, 2000.

Database EMBL [Online] accession No. Z78020, XP002224823, 2000.

Database EMBL [Online] accession No. P41403, XP002224824, 2000.

Database EMBL [Online] accession No. Z17372, XP002224825, 2000.

Database EMBL [Online] accession No. U90239, XP002224826, 2000.

Database EMBL [Online] accession No. P97048, XP002224827, 2000.

Cole et al., "Deciphering the biology of *Mycobacterium tuberculosis* from the complete genome sequence", Nature 393: 537-544 (1998).

Collins, F.M. "New Generation of Tuberculosis Vaccines," 2001, Clinical Microbiology Newsletter, vol. 23, No. 3, pp. 17-23.

First Office Action for U.S. Appl. No. 08/729,662, 1998.

First Office Action for U.S. Appl. No. 08/925,78, 1998.

Third Office Action for U.S. Appl. No. 09/073,010, 2001.

Altschul, et al., "Gapped BLAST and PSI-BLAST: a new generation of protein database search programs," Nuc. Acids Res. (25):3389-3402 (1977).

Andersen and Hansen, "Structure and Mapping of Antigenic Domains of Protein Antigen b, a 38,000-Molecular-Weight Protein of *Mycobacterium tuberculosis*," Infection and Immunity 37(8):2481-2488 (1989).

Andersen and Heron, "Specificity of a Protective Memory Immune Response against *Mycobacterium tuberculosis*," Infection and Immunity 61(3):844-851 (1993).

Andersen, "Effective Vaccination of Mice against *Mycobacterium tuberculosis* Infection with a Soluble Mixture of Secreted Mycobacterial Proteins," Infection and Immunity 62(6):2536-2544 (1994).

Andersen, et al., "Identification of Immunodominant Antigens of *Mycobacterium tuberculosis*," Scand. J. Immunol 6:823-831 (1992).

Andersen, et al, "The T Cell Response to Secreted Antigens and *Mycobacterium tuberculosis*," Immunobiol 191:537-547 (1994).

Arnon, "Synthetic Peptides as a Basis for Vaccine Design," Molecular Immunology 28(2):209-215 (1991).

Ausubel, et al., "Isolation of Proteins for Microsequence Analysis," Current Protocols in Molecular Biology, Wiley & Sons, NY, pp. 10.19.1-10.19.12 (1993).

Banchereau, et al. "Dendritic cells and the control of immunity," Nature 392:245-251 (1998).

Barnes, et al., "Immunoreactivity of a 10-kDa Antigen of *Mycobacterium tuberculosis*," J. of Immunology 148(6):1835-1840 (1992).

Barrera, et al., Humoral Response to *Mycobacterium tuberculosis* in Patients with Human Immunodeficiency Virus Infection Tuberde and Lung Disease 73(4):187-91 (1992).

Batzer, et al., "Enhances evolutionary PCR using oligonucleotides with inosine at the 3' terminus" Nuc. Acids Res. 19:5081 (1991).

Berkner, "Development of Adenovirus Vectors for the Expression of Heterologous Genes," Biotechniques 6:616-627 (1988).

Boesen et al., "Human T-Cell Responses to Secreted Antigen Fractions of *Mycobacterium tuberculosis*," Infection and Immunity 63(4):1491-1497 (1995).

Borremans et al., "Cloning, Sequencing Determination, and Expression of a 32-Kilodalton-Protein Gene of *Mycobacterium tuberculosis*," Infection and Immunity 57(10):3123-3130 (1989).

Bowie, et al., "Deciphering the Message of Protein Sequences: Tolerance to Amino Acid Substitutions" Science 257:1306-10 (1990).
Brandt, et al. "The Protective Effect of the *Mycobacterium bovis* BCG Vaccine is Increased by Coadministration with the *Mycobacterium tuberculosis* 72-Kilodalton Fusion Polyprotein Mtb72F in *M. tuberculosis*-Infected Guinea Pigs" Infection and Immunity 72(11):6622-32 (2004).
Burgess, et al. "Possible Dissociation of the Heparin-binding and Mitogenic Activities of Heparin-Binding (Acidic Fibroblast) Growth Factor-1 from its Receptor-binding Activities by Site-Directed Mutagenesis of a Single Lysine Residue" J. Cell. Biol. 111:2129-2138 (1990).
Cameron, et al., "Identification and characterization of a putative serine protease expressed in vivo by *Mycobacterium avium* subsp. *Paratuberculosisi*," Microbiology 140( 8):1977-1982 (1994).
Campos-Neto, et al., "Cutting Edge: CD40 Ligand Is Not Essential for the Development of Cell-Mediated Immunity and Resistance to *Mycobacterium tuberculosis*," J. Immunol.160(5): 2037-2041 (1988).
Carter and Wells, "Dissecting the catalytic triad of a serine protease," Nature 332: 564-568 (1988).
Carter, "Peptide Analysis Protocols," Methods in Molecular Biology, Chapter 1.1, 36:193-206 (1994).
Chaitra, et al., "Defining putative T cell epitopes from PE and PPE families of protein of *M. tuberculosis* with vaccine potential" Vaccine 23(10):1265-72 (2005).
Chaitra, et al., "HLAA0201-restricted cytotoxic T-cell epitopes in three PE/PPE family proteins of *M. tuberculosis*" Scand. J. of Immunology 67(4):411-17 (2008).
Chan and Kaufmann, Tuberculosis: Pathogenesis, Protection and Control, Chap. 24, ASM Press (1994).
Chen, et al., "T Cells for Tumor Therapy can be Obtained from Antigen-loaded Sponge Implants" Cancer Res. 54: 1065-1070 (1994).
Cirillo, et al., "Isolation and characterization of the aspartokinase and aspartate semialdehyde dehydrogenase operon from mycobacteria," Molecular Microbiology 11(4): 629-639 (1994).
Cohen, "Naked DNA Points Way to Vaccines" Science 259: 1691-1692 (1993).
Colbere-Garapin, et al., "A New Dominant Hybrid Selective Marker for Higher Eucaryotic Cells," J. Mol. Biol. 150:1-14 (1981).
Content, et al., "The Genes Coding for the Antigen 85 Complexes of *Mycobacterium tuberculosis* and *Mycobacterium bovis* BCG Are Members of a Gene Family: Cloning, Sequence Determination, and Genomic Orginization of the Gene Coding for Antigen 85-C of *M. tuberculosis*," Infection and Immunity 59:3205-3212 (1991).
Coombes, et al., "Single dose, polymeric, microparticle-based vaccines: the influence of formulation conditions on the magnitude and duration of the immune response to a protein antigen," Vaccine 14: 1429-1438 (1996).
Coruzzi, et al., "Tissue-specific and light-regulated expression of a pea nuclear gene encoding the small subunit of ribulose-1,5-biphosphate carboxylase," EMBO 3: 1671-1680 (1984).
Creighton, Protein Structure: A Practical Approach, pp. 184-186 (1989).
Creighton, Proteins: Structures and Molecular Properties, pp. 314-315 (1984).
Daleine, et al., "Preliminary evaluation of a *Mycobacterium tuberculosis* lipoligosaccharide (LOS) antigen in the serological diagnosis of tuberculosis in HIV seropositive and seronegative patients," Tuberde and Lung Disease, 76( 3): 234-39 (1995).
Devereaux, et al., "A Comprehensive System of Sequence Analysis Tools for the VAX," Nuc. Acids Res. 12: 387-395 (1984).
Dillon, et al., "Molecular Characterization and Human T-Cell Responses to a Member of Novel *Mycobacterium tuberculosis* mtb39 Gene Family," Infection and Immunity 67( 6): 2941-2950 (1999).
Doran, et al., "Characertisation of a Novel Repetitive DNA sequence from *Mycrobacerium bovis*," FEMS Microbiology Letters 96: 179-186 (1992).
Eiglmeier, et al., "Use of an ordered cosmid library to deduce the genomic organization of *Mycobacterium leprae*," Mol. Microbiol. 7(2):197-206 (1993).
Fifis, et al., "Purification and Characterization of Major Antigens from a *Mycobacterium bovis* Culture Filtrate," Infection and Immunity 59(3):800-807 (1991).
Fisher-Hoch, et al., "Protection of rhesus monkey from fatal Lassa fever by vaccination with a recombinant vaccinia virus containing the Lassa virus glycoprotein gene" PNAS USA 86: 317-321 (1989).
Flexner, et al., "Vaccinia Virus Expression Vectors" Vaccine 8:17-21 (1989).
Flexner, "Attenuation and immugenicity in primates of vaccinia virus recombinants expression human interleukin-2," Ann. NY. Acad. Sci. 569: 86-103 (1989).
Flynn, et al., "An essential Role for Interferon γ in Resistance to *Mycobacterium tuberculosis* Infection," J. of Experimental Medicine 178: 2249-2254 (1993).
Fsihi, et al. "The *Mycrobacterium Leprae* genome: systematic sequence ananlysis indentifies key catabolic enzymes, ATP-dependaent transport system and a novel PoIA locus associated with genomic variability," Molecular Microbiology 16(5):909-919 (1995).
Garcia, "Nucleotide Sequence and Expression of pneumococcal autolysin gene from its own promoter in *E. coli*," Gene (43):265-292 (1986).
Geysen, et al. "Cognitive features of continuous antigenic determinants," J. Mol. Recognition 1:32-41 (1988).
Goodman-Smitkoff, et al., "Defining minimal requirements for antibody production to peptide antigens," Vaccine 8: 257-262 (1990).
Grant, et al., "Expression and Secretion Vectors for Yeast,"Methods Enzymol. 153: 516-544 (1987).
Greenspan and Di Cera, "Defining epitopes: Its not as easy as it seems," Nature Biotechnology 17: 936-937 (1999).
Greenway, et al., "Enhancement of protective immune responses to Venezuelan equine encephalitis (VEE) virus with microencapsulated vaccine," Vaccine 13:1411-1420 (1995).
Griffin, et al., "Animal Models of Protective Immunity in Tuberculosis to Evaluate Candidate Vaccines;" Trends in Microbiology 3(11): 418-423 (1995).
Guzman, et al., "Efficient Gene Transfer into Myocardium by Direct Injection of Adenovirus," Cir. Res. 73: 1202-1207 (1993).
Harrison's Principles of Internal Medicine, vol. 1, pp. 1004-1014 (1998).
Harrison's Principles of Internal Medicine, vol. 1, pp. 1019-1023 (1998).
Hartman and Mulligan, "Two dominant-acting selectable markers for gene transfer studies in mammalian cells," PNAS USA 85: 8047-51 (1988).
Hendrickson, et al., "Mass Spectrometric Identification of Mtb81, a Novel Serological Marker for Tuberculosis," J. Clin. Microbiol 38(6):2354-2361 (2000).
Higgins and Sharp, "Fast and sensitive multiple sequence alignments on a microcomputer," Cabios 5:151-153 (1989).
Hobbs, McGraw Hill Yearbook of Science and Technology, pp. 191-96 (1992).
Horn, et al., "Synthesis of oligonucleotides on cellulose," Nucl. Acids Res. Symposia Series, pp. 225-232 (1980).
Horwitz et al., "Protective immunity against tuberculosis induced by vaccination with major extracellular proteins of *Mycobacterium tuberculosis*," PNAS USA 92:1530-1534 (1995).
Jacobs, "Advances in mycobacterial genetics: new promises for old diseases," Immunobiology 184(2-3):147-156 (1992).
Jurcevic, et al., "T cell responses to a mixture of *Mycobacterium tuberculosis* peptide with complementary HLA-DR binding profiles," Clinical and Experimental Immunology 105(3): 416-421 (1996).
Kadival, et al. "Radioimmunoassay of tuberculous antigen," Indian J. Med. Res. 75:765-770 (1982).
Kalinowski, et al., "Genetic and biochemical analysis of the aspartokinase from *Corynebacterium glutamicum*," Molecular Microbiology 5:1197-1204 (1991).
Kass-Eisler, et al., "Quantitative determination of Adenoviral-mediated gene delivery to rat cardiac myocytes in vitro and in vivo," PNAS USA 90:11498-11502 (1993).

Karlin and Altschul, "Applications and statistics for multiple high-scoring segments in molecular sequences," PNAS USA 90: 5873-5787 (1993).

Kaufmann, et al., "Vaccination against tuberculosis and leprosy," Immunobiology 184(2-3): 208-229 (1992).

Khanolkar-Young, et al., "Results of the Third Immunology of Tuberculosis Anitmycobacterial Monoclonal Antibody Workshop" Infection and Immunity 60(9):3925-927 (1992).

Kohler and Milstein, "Continuous cultures of fused cells secreting antibodies of predefined sequence," Nature 256:495-497 (1975).

Kolls, "Prolonged and effective blockade of TNF activity through Adenoviral-mediated gene transfer," PNAS USA 91: 215-219 (1994).

Kozak, "Comparison of Initiation of Protein Synthesis in Procaryotes, Eucaryotes, and Organelles;" Microbiological Review, pp. 1-45 (1983).

Kroll, et al., "A Multifunctional Prokaryotic Protein Expression System: Overproduction, Affinity Purification, and Selective Detection," DNA Cell Biol. 12:441-453 (1993).

Labouesse, et al., "Conformational changes in enzyme catalysis," Biochemistry 48:2137-2145 (1962).

Launois, et al., "T-Cell Epitope Mapping of the Major Secreted Mycobacterial Antigen AG85A in Tuberculosis and Leprosy," Infection and Immunity 62:3679-87 (1994).

Lazar, et al., "Transforming Growth Factor-alpha Mutation of Aspartic Acid 47 and Leucine 48 results in Different Biological Activities" Mol. Cell. Biol. 8(3):1247-1252 (1988).

Lee, et al. "Characterization of the Major Membrane Protein of Virulent *Mycobacterium tuberculosis*," Infection and Immunity 60:2066-2074 (1992).

Lerner, et al., "Cloning and structure of the *Bacillus subtilis* aspartate transcarbamylas gene (pyrB)," J. Biol. Chem. 261(24):11156-11165 (1986).

Lewin, Genes IV, Oxford University Press, pp. 124-126 (1990).

Lewinsohn, et al., "Characterization of HumanCD8+ T Cells Reactive with *Mycrobacterium tuberculosis*-infected Antigen-presenting Cells," J. Exp. Med. 187(10):1633-1640 (1998).

Li, et al., "Important Role of the Amino Acid Attached to tRNA in Formylation and in Initiation of Protein Synthesis in *Escherichia coli*," J. Biol. Chem., 271:1022-1028 (1996).

Ljungqvist, et al., "Antibody Responses Against *Mycobacterium tuberculosis* in 11 Strains of Inbred Mice Novel Monoclonal Antibody Specificities Generated by Fusions Using Spleens from BALB B10 and CBA-J Mice," Infections and Immunity 56(8):1994-98 (1988).

Logan and Shenk, "Advenovirus tripartite leader sequence enhances translation of mRNAs late after infection," PNAS USA 81: 365-3659 (1984).

Lowy, et al., "Isolation of transforming DNA: Cloning the Hamster aprt Gene," Cell 22:817-23 (1990).

Maddox, et al., "Elevated Serum Levels in Human Pregnancy of a Molecule Immunochemically similar to Eosinophil Granule Major Basic Protein," J. Exp. Med. 158:1211-1216 (1983).

Mahairas, et al., "Molecular Analysis of Genetic Differences Between *Mycrobacterium bovis* BCG and Virulent *M. bovis*," J. of Bacteriology 178(5): 1274-1282 (1996).

Mahvi, et al., "DNA Cancer Vaccines—A Gene Gun Approach," Imm. and Cell Bio. 75: 456-460 (1997).

Manca, et al., "Molecular cloning, purification, and serological characterization of MPT63, a novel antigen secreted by *Mycobacterium tuberculosis*," Infection and Immunity 65(1):16-23 (1997).

Maratea, et al., "Deletion and fusion analysis of phage phi-X-174 lysis gene E," Gene 40:39-46 (1985).

Mathur and Kolttukudy, "Molecular cloning and sequencing of the gene for mycocerosic acid synthase, a novel falty acid elongating multifunctional enzyme, from *Mycobacterium tuberculosis* var. bovis Bacillus Calmette-Guerin," J. Biol. Chem. 267:19388-19395 (1992).

Matsumoto, et al., "Cloning and Sequencing of a Unique Antigen MPT70 from *Mycobacterium tuberculosis* H37Rv and Expression in BCG Using *E. coli*—Mycobacteria Shuttle Vector," Scand. J. Immunol. 41:281-287 (1995).

Merrifield, "Solid Phase Peptide Synthesis," J. Am. Chem. Soc. 85:2149-2146 (1963).

Moos, Isolation of Proteins for Microsequence Analysis, Current Protocols in Molecular Biology, pp. 10.19.1-10.19.12 (2000).

Mosmann and Coffan, "Th1 and TH2 Cells: Different Patterns of Lymphokine Secretion Lead to Different Functional Properties," Ann. Rev. Immunol. 7:145-173 (1989).

Murphy, et al., "Genetic construction, expression and melanoma-selective cytotoxicity of a diphtheria toxin-related alpha-melanocyte stimulating hormone fusion protein," PNAS USA 83: 8258-8262 (1986).

Nagai, et al., "Isolation and Partial Characterization of Major Protein Antigens in the Culture Fluid of *Mycobacterium tuberculosis*," Infection and Immunity 59(1):372-382 (1991).

Needleman and Wunsch, "A General Method Applicable to the Search for Similarities in the Amino Acid Sequence of Two Proteins," J. Mol. Biol. 48:443 (1970).

Newport, et al., "A Mutation in the Interferon-γ-Receptor Gene and Susceptibility to Mycobacterial Infection," New Eng. J. of Medicine 335(26):1941-1949 (1996).

Nosoh, et al., Protein Stability and Stabilization through Protein Engineering, chap. 7, p. 197 (1991).

Oettinger, et al., "Cloning and B-cell-epitope mapping of MPT64 from *Mycobacterium tuberculosis* H37Rv," Infection and Immunity 62(5):2058-2064 (1994).

Wang, et al., "Tuberculosis Vaccines: Past, Present and Future," Expert Rev. Vaccines 1(3):341-54 (2002).

Wang, et al., "A novel method for increasing the expression level of recombinant proteins," Protein Expression and Purification 30(1):124-133 (2003).

Webb, et al., "Molecular Cloning, Expression and Immunogenicity of MTB12," Infection & Immunity 66(9):4208-4214 (1998).

Wiegeshaus, et al., "Evaluation of the protective potency of new tuberculosis vaccines," Reviews of Infectious Diseases 11(Suppl. 2):S484-S490 (1989).

Wieles, et al., "Characterization of a *Mycobacterium leprae* Antigen Related to the Secreted *Mycobacterium tuberculosis* Protein MPT32," Infection and Immunity 62(1):252-258 (1994).

Wigler, et al., "Transformation of mammalian cells with an amplifiable dominant-acting gene," PNAS USA 77:3567-70 (1980).

Wiker and Harboe, "The Antigen 85 Complex: a Major Secretion Product of *Mycobacterium tuberculosis*," Microbiological Reviews 56(4):648-661 (1992).

Winter, "The Expression of Heat Shock Proteins and Cognate Genes During Plant Development," Results Probl. Cell Differ. 17: 85-105 (1991).

Yamaguchi, et al., "Cloning and Characterization of the Gene for Immunogenic Protein MPB64 of *Mycobacterium bovis* BDG," Infection and Immunity 57(1):283-288 (1989).

Young, et al., "Screening of a Recombinant Mycobacterial DNA Library with Polyclonal Antiserum and Molecular Weight Analysis of Expressed Antigens," Infection and Immunity 55(6):1421-1425 (1987).

Zitvogel, et al., "Eradiation of established murine tumors using a novel cell-free vaccine: dedritic cell-derived exosomes," Nature Med. 4:594-600 (1998).

Seq_Database EMBL_U34848 "*Mycobacterium bovis* deletion region 1, 6kDa early secretory antigenic target (esat6) gene", 2000.

Seq_Accession No. O05907, Database:stpremb119, publicly available Jul. 1, 1997.

Seq_Accession No. O05908, Database:stpremb119, publicly available Jul. 1, 1997.

Seq_EMBL_MTCYH7Bc, Accession No. Z95557, May 20, 1997.

Seq_EMBL_MTCY24G1, Accession No. Z83858, Jan. 13, 1997.

Seq_EMBL_MTCY19G5, Accession No. Z77826, Jul. 31, 1996.

Seq_EMBL_MTCY261, Accession No. Z07559, Jul. 10, 1997.

Seq_EMBL_P15712, (Apr. 1, 1990) "PBP-1 from *M. tuberculosis*" XP002359448.

Seq_Uniprot_Q79FV1, 2000.

Seq_Uniprot_O06267, 2000.

Seq_Sequence Alignment_SEQ ID No. 163-Mycobacterium smegmatis (Cirillo et al.).

Seq_Sequence Alignment_*Corynebacterium glutamicum*, 2000.

Seq_Sequence alignment_*Mycobacterium segmatis*_P41403, created Nov. 1995.
Seq_NCBI_214801_Rv0287 [*Mycobacterium tuberculosisi* H37Rv]), 2000.
Seq_EMBL_Q7U0G8—Hypothetical Protein Mb1207c, Oct. 31, 2006 XP002416347.
Seq_EMBL_050430—Hypothetical Protein Mb1207c, Oct. 31, 2006, XP02416348.
Seq_Compugen _P95012, 1997.
Seq_EMBL_X84741—Mycrobacteriumbovis BCG IS1081 DNA Sequence, Van Soolingen, D., 2000.
U.S Appl. No. 09/724,685, filed Oct. 11, 1996.
Langermans, et al., "Protection of macaques against Mycobacterium tuberculosis infection by a subunit vaccine based on a fusion protein of antigen 85B and ESAT-6," Vaccine 23:2740-50 (2005).
Mustafa, et al., "Immunogenicity of Mycobacterium tuberculosis Antigens in Mycobacterium bovis BCG-Vaccinated and M. bovis-Infected Cattle," Infection and Immunity 74(8)4566-72 (2006).
Reece, et al., "Skin Text Performed with Highly Purified Mycobacterium tuberculosis Recombinant Protein Triggers Tuberculin Shock in Infected Guinea Pigs," Infection and Immunity 73(6):3301-06 (2005).
Tanghe, et al., "Improved Immunogenicity and protective Efficay of a Tuberculosis DNA Vaccine Encoding Ag85 by Protein Boosting," Infection and Immunity 69(5):3041-47 (2001).
Williams, et al., "Evaluation of vaccines in the EU TB Vaccine Cluster using a guinea pig aerosol infection model of tuberculosis," Tuberculosis 85:29-38 (2005).
Final Office Action for U.S. Appl. No. 11/801,112, Feb. 4, 2011.
Office Action for U.S. Appl. No. 11/927,566, Oct. 29, 2010.
Office Action for U.S. Appl. No. 11/978,786, Jan. 26, 2011.
Advisory Action for U.S. Appl. No. 11/981,459, Jan. 10, 1011.
Office Action for U.S. Appl. No. 12/490,272, Jan. 13, 2011.
Office Action for U.S. Appl. No. 12/490,272, Apr. 22, 2011.
Office Action for U.S. Appl. No. 12/698,893, Dec. 6, 2010.
Office Action for U.S. Appl. No. 12/698,976, Dec. 6, 2010.

```
FEATURES          Location/Qualifiers
    misc_feature  5072..5095
                  /note="His tag coding region"
    misc_feature  5096..7315
                  /note="MtB81 coding region"
    misc_feature  7316..8594
                  /note="Mo2 coding region"
```

TGGCGAATGGGACGCGCCCTGTAGCGGCGCATTAAGCGCGGCGGGTGTGGTGGTTACGCGCAGCGT
GACCGCTACACTTGCCAGCGCCCTAGCGCCCGCTCCTTTCGCTTTCTTCCCTTCCTTTCTCGCCAC
GTTCGCCGGCTTTCCCCGTCAAGCTCTAAATCGGGGGCTCCCTTTAGGGTTCCGATTTAGTGCTTT
ACGGCACCTCGACCCCAAAAAACTTGATTAGGGTGATGGTTCACGTAGTGGGCCATCGCCCTGATA
GACGGTTTTTCGCCCTTTGACGTTGGAGTCCACGTTCTTTAATAGTGGACTCTTGTTCCAAACTGG
AACAACACTCAACCCTATCTCGGTCTATTCTTTTGATTTATAAGGGATTTTGCCGATTTCGGCCTA
TTGGTTAAAAAATGAGCTGATTTAACAAAAATTTAACGCGAATTTTAACAAAATATTAACGTTTAC
AATTTCAGGTGGCACTTTTCGGGGAAATGTGCGCGGAACCCCTATTTGTTTATTTTTCTAAATACA
TTCAAATATGTATCCGCTCATGAATTAATTCTTAGAAAAACTCATCGAGCATCAAATGAAACTGCA
ATTTATTCATATCAGGATTATCAATACCATATTTTTGAAAAAGCCGTTTCTGTAATGAAGGAGAAA
ACTCACCGAGGCAGTTCCATAGGATGGCAAGATCCTGGTATCGGTCTGCGATTCCGACTCGTCCAA
CATCAATACAACCTATTAATTTCCCCTCGTCAAAAATAAGGTTATCAAGTGAGAAATCACCATGAG
TGACGACTGAATCCGGTGAGAATGGCAAAAGTTTATGCATTTCTTTCCAGACTTGTTCAACAGGCC
AGCCATTACGCTCGTCATCAAAATCACTCGCATCAACCAAACCGTTATTCATTCGTGATTGCGCCT
GAGCGAGACGAAATACGCGATCGCTGTTAAAAGGACAATTACAAACAGGAATCGAATGCAACCGGC
GCAGGAACACTGCCAGCGCATCAACAATATTTTCACCTGAATCAGGATATTCTTCTAATACCTGGA
ATGCTGTTTTCCCGGGGATCGCAGTGGTGAGTAACCATGCATCATCAGGAGTACGGATAAAATGCT
TGATGGTCGGAAGAGGCATAAATTCCGTCAGCCAGTTTAGTCTGACCATCTCATCTGTAACATCAT
TGGCAACGCTACCTTTGCCATGTTTCAGAAACAACTCTGGCGCATCGGGCTTCCCATACAATCGAT
AGATTGTCGCACCTGATTGCCCGACATTATCGCGAGCCCATTTATACCCATATAAATCAGCATCCA
TGTTGGAATTTAATCGCGGCCTAGAGCAAGACGTTTCCCGTTGAATATGGCTCATAACACCCCTTG
TATTACTGTTTATGTAAGCAGACAGTTTTATTGTTCATGACCAAAATCCCTTAACGTGAGTTTTCG
TTCCACTGAGCGTCAGACCCCGTAGAAAAGATCAAAGGATCTTCTTGAGATCCTTTTTTTCTGCGC
GTAATCTGCTGCTTGCAAACAAAAAAACCACCGCTACCAGCGGTGGTTTGTTTGCCGGATCAAGAG
CTACCAACTCTTTTTCCGAAGGTAACTGGCTTCAGCAGAGCGCAGATACCAAATACTGTCCTTCTA
GTGTAGCCGTAGTTAGGCCACCACTTCAAGAACTCTGTAGCACCGCCTACATACCTCGCTCTGCTA
ATCCTGTTACCAGTGGCTGCTGCCAGTGGCGATAAGTCGTGTCTTACCGGGTTGGACTCAAGACGA
TAGTTACCGGATAAGGCGCAGCGGTCGGGCTGAACGGGGGGTTCGTGCACACAGCCCAGCTTGGAG
CGAACGACCTACACCGAACTGAGATACCTACAGCGTGAGCTATGAGAAAGCGCCACGCTTCCCGAA
GGGAGAAAGGCGGACAGGTATCCGGTAAGCGGCAGGGTCGGAACAGGAGAGCGCACGAGGGAGCTT
CCAGGGGGAAACGCCTGGTATCTTTATAGTCCTGTCGGGTTTCGCCACCTCTGACTTGAGCGTCGA
TTTTTGTGATGCTCGTCAGGGGGGCGGAGCCTATGGAAAAACGCCAGCAACGCGGCCTTTTTACGG
TTCCTGGCCTTTTGCTGGCCTTTTGCTCACATGTTCTTTCCTGCGTTATCCCCTGATTCTGTGGAT
AACCGTATTACCGCCTTTGAGTGAGCTGATACCGCTCGCCGCAGCCGAACGACCGAGCGCAGCGAG
TCAGTGAGCGAGGAAGCGGAAGAGCGCCTGATGCGGTATTTTCTCCTTACGCATCTGTGCGGTATT
TCACACCGCATATATGGTGCACTCTCAGTACAATCTGCTCTGATGCCGCATAGTTAAGCCAGTATA

FIG. 1-1

Nucleotide Sequence of TbF14

```
CACTCCGCTATCGCTACGTGACTGGGTCATGGCTGCGCCCCGACACCCTCCAACACCCGCTGACGC
GCCCTGACGGGCTTGTCTGCTCCCGGCATCCGCTTACAGACAAGCTGTGACCGTCTCCGGGAGCTG
CATGTGTCAGAGGTTTTCACCGTCATCACCGAAACGCGCGAGGCAGCTGCGGTAAAGCTCATCAGC
GTGGTCGTGAAGCGATTCACAGATGTCTGCCTGTTCATCCGCGTCCAGCTCGTTGAGTTTCTCCAG
AAGCGTTAATGTCTGGCTTCTGATAAAGCGGGCCATGTTAAGGGCGGTTTTTTCCTGTTTGGTCAC
TGATGCCTCCGTGTAAGGGGGATTTCTGTTCATGGGGTAATGATACCGATGAAACGAGAGAGGAT
GCTCACGATACGGGTTACTGATGATGAACATGCCCGGTTACTGGAACGTTGTGAGGGTAAACAACT
GGCGGTATGGATGCGGCGGGACCAGAGAAAATCACTCAGGGTCAATGCCAGCGCTTCGTTAATAC
AGATGTAGGTGTTCCACAGGGTAGCCAGCAGCATCCTGCGATGCAGATCCGGAACATAATGGTGCA
GGGCGCTGACTTCCGCGTTTCCAGACTTTACGAAACACGGAAACCGAAGACCATTCATGTTGTTGC
TCAGGTCGCAGACGTTTTGCAGCAGCAGTCGCTTCACGTTCGCTCGCGTATCGGTGATTCATTCTG
CTAACCAGTAAGGCAACCCCGCCAGCCTAGCCGGGTCCTCAACGACAGGAGCACGATCATGCGCAC
CCGTGGGGCCGCCATGCCGGCGATAATGGCCTGCTTCTCGCCGAAACGTTTGGTGGCGGGACCAGT
GACGAAGGCTTGAGCGAGGGCGTGCAAGATTCCGAATACCGCAAGCGACAGGCCGATCATCGTCGC
GCTCCAGCGAAAGCGGTCCTCGCCGAAAATGACCCAGAGCGCTGCCGGCACCTGTCCTACGAGTTG
CATGATAAAGAAGACAGTCATAAGTGCGGCGACGATAGTCATGCCCCGCGCCCACCGGAAGGAGCT
GACTGGGTTGAAGGCTCTCAAGGGCATCGGTCGAGATCCCGGTGCCTAATGAGTGAGCTAACTTAC
ATTAATTGCGTTGCGCTCACTGCCCGCTTTCCAGTCGGGAAACCTGTCGTGCCAGCTGCATTAATG
AATCGGCCAACGCGCGGGGAGAGGCGGTTTGCGTATTGGGCGCCAGGGTGGTTTTTCTTTTCACCA
GTGAGACGGGCAACAGCTGATTGCCCTTCACCGCCTGGCCCTGAGAGAGTTGCAGCAAGCGGTCCA
CGCTGGTTTGCCCCAGCAGGCGAAAATCCTGTTTGATGGTGGTTAACGGCGGGATATAACATGAGC
TGTCTTCGGTATCGTCGTATCCCACTACCGAGATATCCGCACCAACGCGCAGCCCGGACTCGGTAA
TGGCGCGCATTGCGCCCAGCGCCATCTGATCGTTGGCAACCAGCATCGCAGTGGGAACGATGCCCT
CATTCAGCATTTGCATGGTTTGTTGAAAACCGGACATGGCACTCCAGTCGCCTTCCCGTTCCGCTA
TCGGCTGAATTTGATTGCGAGTGAGATATTTATGCCAGCCAGCCAGACGCAGACGCGCCGAGACAG
AACTTAATGGGCCCGCTAACAGCGCGATTTGCTGGTGACCCAATGCGACCAGATGCTCCACGCCCA
GTCGCGTACCGTCTTCATGGGAGAAAATAATACTGTTGATGGGTGTCTGGTCAGAGACATCAAGAA
ATAACGCCGGAACATTAGTGCAGGCAGCTTCCACAGCAATGGCATCCTGGTCATCCAGCGGATAGT
TAATGATCAGCCCACTGACGCGTTGCGCGAGAAGATTGTGCACCGCCGCTTTACAGGCTTCGACGC
CGCTTCGTTCTACCATCGACACCACCACGCTGGCACCCAGTTGATCGGCGCGAGATTTAATCGCCG
CGACAATTTGCGACGGCGCGTGCAGGGCCAGACTGGAGGTGGCAACGCCAATCAGCAACGACTGTT
TGCCCGCCAGTTGTTGTGCCACGCGGTTGGGAATGTAATTCAGCTCCGCCATCGCCGCTTCCACTT
TTTCCCGCGTTTTCGCAGAAACGTGGCTGGCCTGGTTCACCACGCGGGAAACGGTCTGATAAGAGA
CACCGGCATACTCTGCGACATCGTATAACGTTACTGGTTTCACATTCACCACCCTGAATTGACTCT
CTTCCGGGCGCTATCATGCCATACCGCGAAAGGTTTTGCGCCATTCGATGGTGTCCGGGATCTCGA
CGCTCTCCCTTATGCGACTCCTGCATTAGGAAGCAGCCCAGTAGTAGGTTGAGGCCGTTGAGCACC
GCCGCCGCAAGGAATGGTGCATGCAAGGAGATGGCGCCCAACAGTCCCCGGCCACGGGCCTGCC
ACCATACCCACGCCGAAACAAGCGCTCATGAGCCCGAAGTGGCGAGCCCGATCTTCCCCATCGGTG
ATGTCGGCGATATAGGCGCCAGCAACCGCACCTGTGGCGCCGGTGATGCCGGCCACGATGCGTCCG
GCGTAGAGGATCGAGATCTCGATCCCGCGAAATTAATACGACTCACTATAGGGGAATTGTGAGCGG
ATAACAATTCCCCTCTAGAAATAATTTTGTTTAACTTTAAGAAGGAGATATACATATGCAGCATCA
CCACCATCACCACACTGATCGCGTGTCGGTGGCAACTTGCGCATCGCTCGGGTGCTCTACGACTT
CGTGAACAATGAAGCCCTGCCTGGCACCGATATCGACCCGGACAGCTTCTGGGCGGGCGTCGACAA
```

*FIG. 1-2*

Nucleotide Sequence of TbF14

```
GTCGTCGCCGACCTGACCCCGCAGAACCAAGCTCTGTTGAACGCCCGCGACGAGCTGCAGGCGCAG
ATCGACAAGTGGCACCGGCGTCGGGTGATCGAGCCCATCGACATGGATGCCTACCGCCAGTTCCTC
ACCGAGATCGGCTACCTGCTTCCCGAACCTGATGACTTCACCATCACCACGTCCGGTGTCGACGCT
GAGATCACCACGACCGCCGGCCCCAGCTGGTGGTGCCGGTGCTCAACGCGCGGTTTGCTCTGAAC
GCGGCCAACGCTCGCTGGGCTCCCTCTACGACGCCTTGTATGGCACCGATGTCATCCCCGAGACC
GACGGCGCCGAAAAAGGCCCCACGTACAACAAGGTTCGTGGCGACAAGGTGATCGCGTATGCCCGC
AAGTTCCTCGACGACAGTGTTCCGCTGTCGTCGGGTTCCTTTGGCGACGCCACCGGTTTCACAGTG
CAGGATGGCCAGCTCGTGGTTGCCTTGCCGGATAAGTCCACCGGCCTGGCCAACCCCGGCCAGTTC
GCCGGCTACACCGGCGCAGCCGAGTCGCCGACATCGGTGCTGCTAATCAATCACGGTTTGCACATC
GAGATCCTGATCGATCCGGAGTCGCAGGTCGGCACCACCGACCGGGCCGGCGTCAAGGACGTGATC
CTGGAATCCGCGATCACCACGATCATGGACTTCGAGGACTCGGTGGCCGCCGTGGACGCCGCCGAC
AAGGTGCTGGGTTATCGGAACTGGCTCGGCCTGAACAAGGGCGACCTGGCAGCAGCGGTAGACAAG
GACGGCACCGCTTTCCTGCGGGTGCTCAATAGGGACCGGAACTACACCGCACCCGGCGGTGGCCAG
TTCACGCTGCCTGGACGCAGCCTCATGTTCGTCCGCAACGTCGGTCACTTGATGACGAATGACGCC
ATCGTCGACACTGACGGCAGCGAGGTGTTCGAAGGCATCATGGATGCCCTATTCACCGGCCTGATC
GCCATCCACGGGCTAAAGGCCAGCGACGTCAACGGGCCGCTGATCAACAGCCGCACCGGCTCCATC
TACATCGTCAAGCCGAAGATGCACGGTCCGGCCGAGGTGGCGTTTACCTGCGAACTGTTCAGCCGG
GTTGAAGATGTGCTGGGGTTGCCGCAAAACACCATGAAGATCGGCATCATGGACGAGGAACGCCGG
ACCACGGTCAACCTCAAGGCGTGCATCAAAGCTGCCGCGGACCGCGTGGTGTTCATCAACACCGGG
TTCCTGGACCGCACCGGCGATGAAATCCACACCTCGATGGAGGCCGGCCCGATGGTGCGCAAGGGC
ACCATGAAGAGCCAGCCGTGGATCTTGGCCTACGAGGACCACAACGTCGATGCCGGCCTGGCCGCC
GGGTTCAGCGGCCGAGCCCAGGTCGGCAAGGGCATGTGGACAATGACCGAGCTGATGGCCGACATG
GTCGAGACAAAAATCGCCCAGCCGCGCGCCGGGGCCAGCACCGCCTGGGTTCCCTCTCCCACTGCG
GCCACCCTGCATGCGCTGCACTACCACCAGGTCGACGTCGCCGCGGTGCAACAAGGACTGGCGGGG
AAGCGTCGCGCCACCATCGAACAATTGCTGACCATTCCGCTGGCCAAGGAATTGGCCTGGGCTCCC
GACGAGATCCGCGAAGAGGTCGACAACAACTGTCAATCCATCCTCGGCTACGTGGTTCGCTGGGTT
GATCAAGGTGTCGGCTGCTCGAAGGTGCCCGACATCCACGACGTCGCGCTCATGGAGGACCGGGCC
ACGCTGCGAATCTCCAGCCAATTGTTGGCCAACTGGCTGCGCCACGGTGTGATCACCAGCGCGGAT
GTGCGGGCCAGCTTGGAGCGGATGGCGCCGTTGGTCGATCGACAAAACGCGGGCGACGTGGCATAC
CGACCGATGGCACCCAACTTCGACGACAGTATCGCCTTCCTGGCCGCGCAGGAGCTGATCTTGTCC
GGGGCCCAGCAGCCCAACGGCTACACCGAGCCGATCCTGCACCGACGTCGTCGGGAGTTTAAGGCC
CGGGCCGCTGAGAAGCCGGCCCCATCGGACAGGGCCGGTGACGATGCGGCCAGGGTGCAGAAGTAC
GGCGGATCCTCGGTGGCCGACGCCGAACGGATTCGCCGCGTCGCCGAACGCATCGTCGCCACCAAG
AAGCAAGGCAATGACGTCGTCGTCGTCGTCTCTGCCATGGGGATACCACCGACGACCTGCTGGAT
CTGGCTCAGCAGGTGTGCCCGGCGCCGCCGCTCGGGAGCTGGACATGCTGCTTACCGCCGGTGAA
CGCATCTCGAATGCGTTGGTGGCCATGGCCATCGAGTCGCTCGGCGCGCATGCCCGGTCGTTCACC
GGTTCGCAGGCCGGGGTGATCACCACCGGCACCCACGGCAACGCCAAGATCATCGACGTCACGCCG
GGGCGGCTGCAAACCGCCCTTGAGGAGGGGCGGGTCGTTTTGGTGGCCGGATTCCAAGGGGTCAGC
CAGGACACCAAGGATGTCACGACGTTGGGCCGCGGCGGCTCGGACACCACCGCCGTCGCCATGGCC
GCCGCGCTGGGTGCCGATGTCTGTGAGATCTACACCGACGTGGACGGCATCTTCAGCGCCGACCCG
CGCATCGTGCGCAACGCCCGAAAGCTCGACACCGTGACCTTCGAGGAAATGCTCGAGATGGCGGCC
TGCGGCGCCAAGGTGCTGATGCTGCGCTGCGTGGAATACGCTCGCCGCCATAATATTCCGGTGCAC
GTCCGGTCGTCGTACTCGGACAGACCGGGCACCGTCGTTGTCGGATCGATCAAGGACGTACCCATG
```

FIG. 1-3

Nucleotide Sequence of TbF14

```
GAAGACCCCATCCTGACCGGAGTCGCGCACGACCGCAGCGAGGCCAAGGTGACCATCGTCGGGCTG
CCCGACATCCCCGGGTATGCGGCCAAGGTGTTTAGGGCGGTGGCCAGACGCCGACGTCAACATCGA
CATGGTGCTGCAGAACGTCTCCAAGGTCGAGGACGGCAAGACCGACATCACCTTCACCTGCTCCCG
CAGACGTCGGGCCCGCCGCCGTGGAAAAACTGGACTCGCTCAGAAACGAGATCGGCTTCTACACAG
CTGCTGTACGACGACCACATCGGCAAGGTATCGCTGATCGGTGCCGGCATGCGCAGCCACCCCGGG
GTCACCGCGACGTTCTGTGAGGCGCTGGCGGCGGTGGGGGTCAACATCGAGCTGATCTCCACCTCG
GAAGATCAGAGATCTCGGTGTTGTGCCGCGACACCGAACTGGACAAGGCCGTGGTCGCGCTGCATG
AAGCGTTCGGGCTCGGCGGCGACGAGGAGGCCACGGTGTACGCGGGGACGGGACGGTAGATGGGCC
TGTCAATAGTGAATTCATCGATGTGCAGATATCCATCACACTGGCGGCCGCTCGAGCACCACCACC
ACCACCACTGAGATCCGGCTGCTAACAAAGCCCGAAAGGAAGCTGAGTTGGCTGCTGCCACCGCTG
AGCAATAACTAGCATAACCCCTTGGGGCCTCTAAACGGGTCTTGAGGGGTTTTTTGCTGAAAGGAG
GAACTATATCCGGAT
```

FIG. 1-4

Nucleotide sequence of TbF15

```
FEATURES             Location/Qualifiers
     misc_feature    5072..5095
                     /note="His tag coding region"
     misc_feature    5096..5293
                     /note="Ra3 coding region"
     misc_feature    5294..6346
                     /note="38kD coding region"
     misc_feature    6347..6643
                     /note="38-1 coding region"
     misc_feature    6644..8023
                     /note="FL TbH4 coding region"
```

TGGCGAATGGGACGCGCCCTGTAGCGGCGCATTAAGCGCGGCGGGTGTGGTGGTTACGCGCAGCGT
GACCGCTACACTTGCCAGCGCCCTAGCGCCCGCTCCTTTCGCTTTCTTCCCTTCCTTTCTCGCCAC
GTTCGCCGGCTTTCCCCGTCAAGCTCTAAATCGGGGCTCCCTTTAGGGTTCCGATTTAGTGCTTT
ACGGCACCTCGACCCCAAAAAACTTGATTAGGGTGATGGTTCACGTAGTGGGCCATCGCCCTGATA
GACGGTTTTTCGCCCTTTGACGTTGGAGTCCACGTTCTTTAATAGTGGACTCTTGTTCCAAACTGG
AACAACACTCAACCCTATCTCGGTCTATTCTTTTGATTTATAAGGGATTTTGCCGATTTCGGCCTA
TTGGTTAAAAAATGAGCTGATTTAACAAAAATTTAACGCGAATTTTAACAAAATATTAACGTTTAC
AATTTCAGGTGGCACTTTTCGGGGAAATGTGCGCGGAACCCCTATTTGTTTATTTTTCTAAATACA
TTCAAATATGTATCCGCTCATGAATTAATTCTTAGAAAAACTCATCGAGCATCAAATGAAACTGCA
ATTTATTCATATCAGGATTATCAATACCATATTTTTGAAAAAGCCGTTTCTGTAATGAAGGAGAAA
ACTCACCGAGGCAGTTCCATAGGATGGCAAGATCCTGGTATCGGTCTGCGATTCCGACTCGTCCAA
CATCAATACAACCTATTAATTTCCCCTCGTCAAAAATAAGGTTATCAAGTGAGAAATCACCATGAG
TGACGACTGAATCCGGTGAGAATGGCAAAAGTTTATGCATTTCTTTCCAGACTTGTTCAACAGGCC
AGCCATTACGCTCGTCATCAAAATCACTCGCATCAACCAAACCGTTATTCATTCGTGATTGCGCCT
GAGCGAGACGAAATACGCGATCGCTGTTAAAAGGACAATTACAAACAGGAATCGAATGCAACCGGC
GCAGGAACACTGCCAGCGCATCAACAATATTTTCACCTGAATCAGGATATTCTTCTAATACCTGGA
ATGCTGTTTTCCCGGGGATCGCAGTGGTGAGTAACCATGCATCATCAGGAGTACGGATAAAATGCT
TGATGGTCGGAAGAGGCATAAATTCCGTCAGCCAGTTTAGTCTGACCATCTCATCTGTAACATCAT
TGGCAACGCTACCTTTGCCATGTTTCAGAAACAACTCTGGCGCATCGGGCTTCCCATACAATCGAT
AGATTGTCGCACCTGATTGCCCGACATTATCGCGAGCCCATTTATACCCATATAAATCAGCATCCA
TGTTGGAATTTAATCGCGGCCTAGAGCAAGACGTTTCCCGTTGAATATGGCTCATAACADDDDTTG
TATTACTGTTTATGTAAGCAGACAGTTTTATTGTTCATGACCAAAATCCCTTAACGTGAGTTTTCG
TTCCACTGAGCGTCAGACCCCGTAGAAAAGATCAAAGGATCTTCTTGAGATCCTTTTTTTCTGCGC
GTAATCTGCTGCTTGCAAACAAAAAAACCACCGCTACCAGCGGTGGTTTGTTTGCCGGATCAAGAG
CTACCAACTCTTTTTCCGAAGGTAACTGGCTTCAGCAGAGCGCAGATACCAAATACTGTCCTTCTA
GTGTAGCCGTAGTTAGGCCACCACTTCAAGAACTCTGTAGCACCGCCTACATACCTCGCTCTGCTA
ATCCTGTTACCAGTGGCTGCTGCCAGTGGCGATAAGTCGTGTCTTACCGGGTTGGACTCAAGACGA
TAGTTACCGGATAAGGCGCAGCGGTCGGGCTGAACGGGGGGTTCGTGCACACAGCCCAGCTTGGAG
CGAACGACCTACACCGAACTGAGATACCTACAGCGTGAGCTATGAGAAAGCGCCACGCTTCCCGAA
GGGAGAAAGGCGGACAGGTATCCGGTAAGCGGCAGGGTCGGAACAGGAGAGCGCACGAGGGAGCTT
CCAGGGGGAAACGCCTGGTATCTTTATAGTCCTGTCGGGTTTCGCCACCTCTGACTTGAGCGTCGA
TTTTTGTGATGCTCGTCAGGGGGCGGAGCCTATGGAAAAACGCCAGCAACGCGGCCTTTTTACGG

*FIG. 2-1*

Nucleotide sequence of TbF15

```
TTCCTGGCCTTTTGCTGGCCTTTTGCTCACATGTTCTTTCCTGCGTTATCCCCTGATTCTGTGGAT
AACCGTATTACCGCCTTTGAGTGAGCTGATACCGCTCGCCGCAGCCAACGACCGAGCGCAGCGAG
TCAGTGAGCGAGGAAGCGGAAGAGCGCCTGATGCGGTATTTTCTCCTTACGCATCTGTGCGGTATT
TCACACCGCATATATGGTGCACTCTCAGTACAATCTGCTCTGATGCCGCATAGTTAAGCCAGTATA
CACTCCGCTATCGCTACGTGACTGGGTCATGGCTGCGCCCCGACACCCGCCAACACCCGCTGACGC
GCCCTGACGGGCTTGTCTGCTCCCGGCATCCGCTTACAGACAAGCTGTGACCGTCTCCGGGAGCTG
CATGTGTCAGAGGTTTTCACCGTCATCACCGAAACGCGCGAGGCAGCTGCGGTAAAGCTCATCAGC
GTGGTCGTGAAGCGATTCACAGATGTCTGCCTGTTCATCCGCGTCCAGCTCGTTGAGTTTCTCCAG
AAGCGTTAATGTCTGGCTTCTGATAAAGCGGGCCATGTTAAGGGCGGTTTTTTCCTGTTTGGTCAC
TGATGCCTCCGTGTAAGGGGATTTCTGTTCATGGGGGTAATGATACCGATGAAACGAGAGAGGAT
GCTCACGATACGGGTTACTGATGATGAACATGCCCGGTTACTGGAACGTTGTGAGGGTAAACAACT
GGCGGTATGGATGCGGCGGGACCAGAGAAAAATCACTCAGGGTCAATGCCAGCGCTTCGTTAATAC
AGATGTAGGTGTTCCACAGGGTAGCCAGCAGCATCCTGCGATGCAGATCCGGAACATAATGGTGCA
GGGCGCTGACTTCCGCGTTTCCAGACTTTACGAAACACGGAAACCGAAGACCATTCATGTTGTTGC
TCAGGTCGCAGACGTTTTGCAGCAGCAGTCGCTTCACGTTCGCTCGCGTATCGGTGATTCATTCTG
CTAACCAGTAAGGCAACCCCGCCAGCCTAGCCGGGTCCTCAACGACAGGAGCACGATCATGCGCAC
CGTGGGGCCGCCATGCCGGCGATAATGGCCTGCTTCTCGCCGAAACGTTTGGTGGCGGGACCAGT
GACGAAGGCTTGAGCGAGGGCGTGCAAGATTCCGAATACCGCAAGCGACAGGCCGATCATCGTCGC
GCTCCAGCGAAAGCGGTCCTCGCCGAAAATGACCCAGAGCGCTGCCGGCACCTGTCCTACGAGTTC
CATGATAAAGAAGACAGTCATAAGTGCGGCGACGATAGTCATGCCCCGCGCCCACCGGAAGGAGCT
GACTGGGTTGAAGGCTCTCAAGGGCATCGGTCGAGATCCCGGTGCCTAATGAGTGAGCTAACTTAC
ATTAATTGCGTTGCGCTCACTGCCCGCTTTCCAGTCGGGAAACCTGTCGTGCCAGCTGCATTAATG
AATCGGCCAACGCGCGGGGAGAGGCGGTTTGCGTATTGGGCGCCAGGGTGGTTTTTCTTTTCACCA
GTGAGACGGGCAACAGCTGATTGCCCTTCACCGCCTGGCCCTGAGAGAGTTGCAGCAAGCGGTCCA
CGCTGGTTTGCCCCAGCAGGCGAAAATCCTGTTTGATGGTGGTTAACGGCGGGATATAACATGAGC
TGTCTTCGGTATCGTCGTATCCCACTACCGAGATATCCGCACCAACGCGCAGCCCGGACTCGGTAA
TGGCGCGCATTGCGCCCAGCGCCATCTGATCGTTGGCAACCAGCATCGCAGTGGGAACGATGCCCT
CATTCAGCATTTGCATGGTTTGTTGAAAACCGGACATGGCACTCCAGTCGCCTTCCCGTTCCGCTA
TCGGCTGAATTTGATTGCGAGTGAGATATTTATGCCAGCCAGCCAGACGCAGACGCGCCGAGACAG
AACTTAATGGGCCCGCTAACAGCGCGATTTGCTGGTGACCCAATGCGACCAGATGCTCCACGCCCA
GTCGCGTACCGTCTTCATGGGAGAAAATAATACTGTTGATGGGTGTCTGGTCAGAGACATCAAGAA
ATAACGCCGGAACATTAGTGCAGGCAGCTTCCACAGCAATGGCATCCTGGTCATCCAGCGGATAGT
TAATGATCAGCCCACTGACGCGTTGCGCGAGAAGATTGTGCACCGCCGCTTTACAGGCTTCGACGC
CGCTTCGTTCTACCATCGACACCACCACGCTGGCACCCAGTTGATCGGCGCGAGATTTAATCGCCG
CGACAATTTGCGACGGCGCGTGCAGGGCCAGACTGGAGGTGGCAACGCCAATCAGCAACGACTGTT
TGCCCGCCAGTTGTTGTGCCACGCGGTTGGGAATGTAATTCAGCTCCGCCATCGCCGCTTCCACTT
TTTCCCGCGTTTTCGCAGAAACGTGGCTGGCCTGGTTCACCACGCGGGAACGGTCTGATAAGAGA
CACCGGCATACTCTGCGACATCGTATAACGTTACTGGTTTCACATTCACCACCCTGAATTGACTCT
CTTCCGGGCGCTATCATGCCATACCGCGAAAGGTTTTGCTCCATTCGATGGTGTCCGGGATCTCGA
CGCTCTCCCTTATGCGACTCCTGCATTAGGAAGCAGCCCAGTAGTAGGTTGAGGCCGTTGAGCACC
GCCGCCGCAAGGAATGGTGCATGCAAGGAGATGGCGCCCAACAGTCCCCCGGCCACGGGGCCTGCC
ACCATACCCACGCCGAAACAAGCGCTCATGAGCCCGAAGTGGCGAGCCCGATCTTCCCCATCGGTG
ATGTCGGCGATATAGGCGCCAGCAACCGCACCTGTGGCGCCGGTGATGCCGGCCACGATGCGTCCG
```

FIG. 2-2

Nucleotide sequence of TbF15

```
GCGTAGAGGATCGAGATCTCGATCCCGCGAAATTAATACGACTCACTATAGGGGAATTGTGAGCGG
ATAACAATTCCCCTCTAGAAATAATTTTGTTTAACTTTAAGAAGGAGATATACATATGGGCCATCA
TCATCATCATCACGTGATCGACATCATCGGGACCAGCCCCACATCCTGGGAACAGGCGGCGGCGGA
GGCGGTCCAGCGGGCGCGGGATAGCGTCGATGACATCCGCGTCGCTCGGGTCATTGAGCAGGACAT
GGCCGTGGACAGCGCCGGCAAGATCACCTACCGCATCAAGCTCGAAGTGTCGTTCAAGATGAGGCC
GGCGCAACCGAGGTGTGGCTCGAAACCACCGAGCGGTTCGCCTGAAACGGGCGCCGGCGCCGGTAC
TGTCGCGACTACCCCGCGTCGTCGCCGGTGACGTTGGCGGAGACCGGTAGCACGCTGCTCTACCC
GCTGTTCAACCTGTGGGGTCCGGCCTTTCACGAGAGGTATCCGAACGTCACGATCACCGCTCAGGG
CACCGGTTCTGGTGCCGGGATCGCGCAGGCCGCCGCCGGGACGGTCAACATTGGGGCCTCCGACGC
CTATCTGTCGGAAGGTGATATGGCCGCGCACAAGGGGCTGATGAACATCGCGCTAGCCATCTCCGC
TCAGCAGGTCAACTACAACCTGCCCGGAGTGAGCGAGCACCTCAAGCTGAACGGAAAAGTCCTGGC
GGCCATGTACCAGGGCACCATCAAAACCTGGGACGACCCGCAGATCGCTGCGCTCAACCCCGGCGT
GAACCTGCCCGGCACCGCGGTAGTTCCGCTGCACCGCTCCGACGGGTCCGGTGACACCTTCTTGTT
CACCCAGTACCTCTCCAAGCAAGATCCCGAGGGCTGGGGCAAGTCGCCCGGCTTCGGCACCACCGT
CGACTTCCCGGCGGTGCCGGGTGCGCTGGGTGAGAACGGCAACGGCGGCATGGTGACCGGTTGCGC
CGAGACACCGGGCTGCGTGGCCTATATCGGCATCAGCTTCCTCGACCAGGCCAGTCAACGGGGACT
CGGCGAGGCCCAACTAGGCAATAGCTCTGGCAATTTCTTGTTGCCCGACGCGCAAAGCATTCAGGC
CGCGGCGGCTGGCTTCGCATCGAAAACCCCGGCGAACCAGGCGATTTCGATGATCGACGGGCCCGC
CCCGGACGGCTACCCGATCATCAACTACGAGTACGCCATCGTCAACAACCGGCAAAAGGACGCCGC
CACCGCGCAGACCTTGCAGGCATTTCTGCACTGGGCGATCACCGACGGCAACAAGGCCTCGTTCCT
CGACCAGGTTCATTTCCAGCCGCTGCCGCCCGCGGTGGTGAAGTTGTCTGACGCGTTGATCGCGAC
GATTTCCAGCGCTGAGATGAAGACCGATGCCGCTACCCTCGCGCAGGAGGCAGGTAATTTCGAGCG
GATCTCCGGCGACCTGAAAACCCAGATCGACCAGGTGGAGTCGACGGCAGGTTCGTTGCAGGGCCA
GTGGCGCGGCGCGGCGGGGACGGCCGCCCAGGCCGCGGTGGTGCGCTTCCAAGAAGCAGCCAATAA
GCAGAAGCAGGAACTCGACGAGATCTCGACGAATATTCGTCAGGCCGGCGTCCAATACTCGAGGGC
CGACGAGGAGCAGCAGCAGGCGCTGTCCTCGCAAATGGGCTTTACTCAGTCGCAGACCGTGACGGT
GGATCAGCAAGAGATTTTGAACAGGGCCAACGAGGTGGAGGCCCCGATGGCGGACCCACCGACTGA
TGTCCCCATCACACCGTGCGAACTCACGGCGGCTAAAAACGCCGCCCAACAGCTGGTATTGTCCGC
CGACAACATGCGGGAATACCTGGCGGCCGGTGCCAAAGAGCGGCAGCGTCTGGCGACCTCGCTGCG
CAACGCGGCCAAGGCGTATGGCGAGGTTGATGAGGAGGCTGCGACCGCGCTGGACAACGACGGCGA
AGGAACTGTGCAGGCAGAATCGGCCGGGGCCGTCGGAGGGGACAGTTCGGCCGAACTAACCGATAC
GCCGAGGGTGGCCACGGCCGGTGAACCCAACTTCATGGATCTCAAAGAAGCGGCAAGGAAGCTCGA
AACGGGCGACCAAGGCGCATCGCTCGCGCACTTTGCGGATGGGTGGAACACTTTCAACCTGACGCT
GCAAGGCGACGTCAAGCGGTTCCGGGGGTTTGACAACTGGGAAGGCGATGCGGCTACCGCTTGCGA
GGCTTCGCTCGATCAACAACGGCAATGGATACTCCACATGGCCAAATTGAGCGCTGCGATGGCCAA
GCAGGCTCAATATGTCGCGCAGCTGCACGTGTGGGCTAGGCGGGAACATCCGACTTATGAAGACAT
AGTCGGGCTCGAACGGCTTTACGCGGAAAACCCTTCGGCCCGCGACCAAATTCTCCCGGTGTACGC
GGAGTATCAGCAGAGGTCGGAGAAGGTGCTGACCGAATACAACAACAAGGCAGCCCTGGAACCGGT
AAACCCGCCGAAGCCTCCCCCGCCATCAAGATCGACCCGCCCCGCCTCCGCAAGAGCAGGGATT
GATCCCTGGCTTCCTGATGCCGCCGTCTGACGGCTCCGGTGTGACTCCCGGTACCGGGATGCCAGC
CGCACCGATGGTTCCGCCTACCGGATCGCCGGGTGGTGGCCTCCGGCTGACACGGCGGCGCAGCT
GACGTCGGCTGGGCGGGAAGCCGCAGCGCTGTCGGGCGACGTGGCGGTCAAAGCGGCATCGCTCGG
TGGCGGTGGAGGCGGCGGGGTGCCGTCGGCGCCGTTGGGATCCGCGATCGGGGGCGCCGAATCGGT
```

*FIG. 2-3*

Nucleotide sequence of TbF15

GCGGCCCGCTGGCGCTGGTGACATTGCCGGCTTAGGCCAGGGAAGGGCCGGCGGCGGCGCCGCGCT
GGGCGGCGGTGGCATGGGAATGCCGATGGGTGCCGCGCATCAGGGACAAGGGGGCGCCAAGTCCAA
GGGTTCTCAGCAGGAAGACGAGGCGCTCTACACCGAGGATCGGGCATGGACCGAGGCCGTCATTGG
TAACCGTCGGCGCCAGGACAGTAAGGAGTCGAAGTGAATTCTGCAGATATCCATCACACTGGCGGC
CGCTCGAGCACCACCACCACCACCACTGAGATCCGGCTGCTAACAAAGCCCGAAAGGAAGCTGAGT
TGGCTGCTGCCACCGCTGAGCAATAACTAGCATAACCCCTTGGGGCCTCTAAACGGGTCTTGAGGG
GTTTTTTGCTGAAAGGAGGAACTATATCCGGAT

*FIG. 2-4*

Amino Acid Sequence of MbF14

```
MQHHHHHHTDRVSVGNLRIARVLYDFVNNEALPGTDIDPDSFWAGVDKVVADLTPQNQALLNARDE
LQAQIDKWHRRRVIEPIDMDAYRQFLTEIGYLLPEPDDFTITTSGVDAEITTTAGPQLVVPVLNAR
FALNAANARWGSLYDALYGTDVIPETDGAEKGPTYNKVRGDKVIAYARKFLDDSVPLSSGSFGDAT
GFTVQDGQLVVALPDKSTGLANPGQFAGYTGAAESPTSVLLINHGLHIEILIDPESQVGTTDRAGV
KDVILESAITTIMDFEDSVAAVDAADKVLGYRNWLGLNKGDLAAAVDKDGTAFLRVLNRDRNYTAP
GGGQFTLPGRSLMFVRNVGHLMTNDAIVDTDGSEVFEGIMDALFTGLIAIHGLKASDVNGPLINSR
TGSIYIVKPKMHGPAEVAFTCELFSRVEDVLGLPQNTMKIGIMDEERRTTVNLKACIKAAADRVVF
INTGFLDRTGDEIHTSMEAGPMVRKGTMKSQPWILAYEDHNVDAGLAAGFSGRAQVGKGMWTMTEL
MADMVETKIAQPRAGASTAWVPSPTAATLHALHYHQVDVAAVQQGLAGKRRATIEQLLTIPLAKEL
AWAPDEIREEVDNNCQSILGYVVRWVDQGVGCSKVPDIHDVALMEDRATLRISSQLLANWLRHGVI
TSADVRASLERMAPLVDRQNAGDVAYRPMAPNFDDSIAFLAAQELILSGAQQPNGYTEPILHRRRR
EFKARAAEKPAPSDRAGDDAARVQKYGGSSVADAERIRRVAERIVATKKQGNDVVVVSAMGDTTD
DLLDLAQQVCPAPPPRELDMLLTAGERISNALVAMAIESLGAHARSFTGSQAGVITTGTHGNAKII
DVTPGRLQTALEEGRVVLVAGFQGVSQDTKDVTTLGRGGSDTTAVAMAAALGADVCEIYTDVDGIF
SADPRIVRNARKLDTVTFEEMLEMAACGAKVLMLRCVEYARRHNIPVHVRSSYSDRPGTVVVGSIK
DVPMEDPILTGVAHDRSEAKVTIVGLPDIPGYAAKVFRAVARRRRQHRHGAAERLQGRGRQDRHHL
HLLPQTSGPPPWKNWTRSETRSASTQLLYDDHIGKVSLIGAGMRSHPGVTATFCEALAAVGVNIEL
ISTSEDQRSRCCAATPNWTRPWSRCMKRSGSAATRRPRCTRGRDGRWACQ.
```

FIG. 3

Amino Acid Sequence of MbF15

```
MGHHHHHHVIDIIGTSPTSWEQAAAEAVQRARDSVDDIRVARVIEQDMAVDSAGKITYRIKLEVSF
KMRPAQPRCGSKPPSGSPETGAGAGTVATTPASSPVTLAETGSTLLYPLFNLWGPAFHERYPNVTI
TAQGTGSGAGIAQAAAGTVNIGASDAYLSEGDMAAHKGLMNIALAISAQQVNYNLPGVSEHLKLNG
KVLAAMYQGTIKTWDDPQIAALNPGVNLPGTAVVPLHRSDGSGDTFLFTQYLSKQDPEGWGKSPGF
GTTVDFPAVPGALGENGNGGMVTGCAETPGCVAYIGISFLDQASQRGLGEAQLGNSSGNFLLPDAQ
SIQAAAAGFASKTPANQAISMIDGPAPDGYPIINYEYAIVNNRQKDAATAQTLQAFLHWAITDGNK
ASFLDQVHFQPLPPAVVKLSDALIATISSAEMKTDAATLAQEAGNFERISGDLKTQIDQVESTAGS
LQGQWRGAAGTAAQAAVVRFQEAANKQKQELDEISTNIRQAGVQYSRADEEQQQALSSQMGFTQSQ
TVTVDQQEILNRANEVEAPMADPPTDVPITPCELTAAKNAAQQLVLSADNMREYLAAGAKERQRLA
TSLRNAAKAYGEVDEEAATALDNDGEGTVQAESAGAVGGDSSAELTDTPRVATAGEPNFMDLKEAA
RKLETGDQGASLAHFADGWNTFNLTLQGDVKRFRGFDNWEGDAATACEASLDQQRQWILHMAKLSA
AMAKQAQYVAQLHVWARREHPTYEDIVGLERLYAENPSARDQILPVYAEYQQRSEKVLTEYNNKAA
LEPVNPPKPPPAIKIDPPPPPQEQGLIPGFLMPPSDGSGVTPGTGMPAAPMVPPTGSPGGGLPADT
AAQLTSAGREAAALSGDVAVKAASLGGGGGGGVPSAPLGSAIGGAESVRPAGAGDIAGLGQGRAGG
GAALGGGGMGMPMGAAHQGQGGAKSKGSQQEDEALYTEDRAWTEAVIGNRRRQDSKESK.
```

*FIG. 4*

|  | Status | TbF15 | TbF6 |
|---|---|---|---|
| 5004 | TB | 0.926 | 1.045 |
| 7004 | TB | 0.928 | 1.184 |
| 9004 | TB | 1.102 | 1.365 |
| 11004 | TB | 0.856 | 1.629 |
| 15004 | TB | 2.035 | 2.099 |
| 17004 | TB | 2.893 | 2.867 |
| 18004 | TB | 0.477 | 0.414 |
| 21004 | TB | 1.062 | 1.635 |
| 23004 | TB | 0.429 | 0.501 |
| 26004 | TB | 0.299 | 0.392 |
| 27004 | TB | 0.244 | 0.207 |
| 28004 | TB | 2.236 | 2.04 |
| 30004 | TB | 2.058 | 1.508 |
| 32004 | TB | 2.324 | 1.927 |
| 33004 | TB | 1.600 | 1.578 |
| 34004 | TB | 1.059 | 1.136 |
| 36004 | TB | 0.546 | 1.105 |
| 37004 | TB | 1.446 | 1.989 |
| 39004 | TB | 2.021 | 2.782 |
| 41004 | TB | 0.511 | 0.652 |
| 43004 | TB | 0.855 | 0.483 |
| 44004 | TB | 0.731 | 0.66 |
| 53004 | TB | 1.100 | 1.317 |
| FD8-24 | Control | 0.183 | 0.314 |
| FD8-25 | Control | 0.061 | 0.063 |
| FD8-26 | Control | 0.066 | 0.142 |
| FD8-27 | Control | 0.021 | 0.115 |
| FD8-28 | Control | 0.053 | 0.289 |
| FD8-29 | Control | 0.114 | 0.238 |
| FD8-30 | Control | 0.105 | 0.146 |
| FD8-31 | Control | 0.101 | 0.237 |
| FD8-33 | Control | 0.080 | 0.071 |
| FD8-34 | Control | 0.140 | 0.117 |
| FD8-35 | Control | 0.088 | 0.072 |
| FD8-36 | Control | 0.081 | 0.089 |
| FD8-37 | Control | 0.057 | 0.06 |
| FD8-38 | Control | 0.104 | 0.111 |
| FD8-39 | Control | 0.221 | 0.241 |
| FD8-40 | Control | 0.257 | 0.265 |
| FD8-41 | Control | 0.056 | 0.093 |
| FD8-42 | Control | 0.184 | 0.273 |
| FD8-43 | Control | 0.126 | 0.126 |
| FD8-44 | Control | 0.193 | 0.092 |
| FD8-45 | Control | 0.058 | 0.057 |
| FD8-46 | Control | 0.183 | 0.23 |
| FD8-48 | Control | 0.062 | 0.085 |
| FD8-49 | Control | 0.134 | 0.247 |

|  | Status | TbF15 | TbF6 |
|---|---|---|---|
| Mean |  | 0.113 | 0.157 |
| SD |  | 0.061 | 0.086 |
| Mean +3SD |  | 0.298 | 0.414 |
| Sensitivity |  | 22/23 | 22/23 |

```
TCAAGGGCACCCTCGGAGAAGTGTGGAGTTCATCACAAACGGGCTCAACGGGCTCAAACGAGCTTTGGGACAAGCTCACGGGGTGGTGACCGGA  665
AGTTCCCGTGGGAGCCTCTTCACACCCTCAAGTAGTGTTTGCGCAGTGTTTCTCGAAACCCTGTTCGAGTGCCCCACTCTGGCCT          665
           -------HTCC-1 FL------------------------------------------------------------
  I  K  G  T  L  G  E  V  W  E  F  I  T  N  A  L  N  G  L  K  E  L  W  D  K  L  T  G  W  V  T  G

CTGTTCTCTCGAGGGTGGTCGAACCTGGAGTCCTTCTTTGGGGCGTCCCCGGCTTGACCGGCGCCAGCGGCTTTGTCGCAAGTGACTGGCTT    760
GACAAGAGAGCTCCCACCAGCTTGGACCTCAGGAAGAAACCCCGCAGGGCCGAACTGGCCGCGGTCGCCGAACAGCGTTCACTGACCGAA    760
           -------HTCC-1 FL------------------------------------------------------------
  L  F  S  R  G  W  S  N  L  E  S  F  F  A  G  V  P  G  L  T  G  A  T  S  G  L  S  Q  V  T  G  L

GTTCGGTGCGGGCCGGTCTGTCCGCATCGTCGGGCTTGGCTCACGCGGATAGCCTCAGCGAGCTCAGCCTTGCCCCGGCATTGGGG          855
CAAGCCACGCGCCGGCCAGAGACAGGCGTAGCAGCCCGAACGGCTCGAGTGCGCTATCGGAGTCGCTCGAGTCGAACGGCGGGACCGGCGTAACCCC  855
           -------HTCC-1 FL------------------------------------------------------------
  F  G  A  A  G  L  S  A  S  S  G  L  A  H  A  D  S  L  A  S  S  A  S  L  P  A  L  A  G  I  G

GCGGGTCCGGTTTTGGGGCTTGCCGAGCCTGGCTCAATCGGCAGGGCGCTACGGCCTCGAGCTGATGGCCCGGTCGGC                 950
CGCCCAGGCCAAAACCCCGAACGGCTCGACCGGAGTTCCAGGTCGGAGCCGTCGGCGAGCGTGAGCCCGATGGCCCGATACCGGGCCAGCCG    950
           -------HTCC-1 FL------------------------------------------------------------
  G  G  S  G  F  G  G  L  P  S  L  A  Q  V  H  A  A  S  T  R  Q  A  L  R  P  R  A  D  G  P  V  G

GCCGCTGCCGAGCCGGCAGGTCGGCGGGCCGGAGTCGCAGCTGGTCTCCGGCAGGGTTCCCAAGGTATGGGGGACCCGTAGGCATGCGGCATGCCACCC  1045
CGGCGACGGCTCGTCCAGCGCCCGCCGGCCCGTCCAGCGTCGACGAGGGCCGTCCATACCCGCTGGGCCGTTCCATACCCGCCGCCGTACGTGGG     1045
           -------HTCC-1 FL------------------------------------------------------------
  A  A  A  E  Q  V  G  G  Q  S  Q  L  V  S  A  Q  G  S  Q  G  M  G  G  P  V  G  M  G  G  M  H  P

CTCTTCGGGGGTCGAAAGGGACGAAGGACGACGACGAAGAAGTACTCGGAAGGCGCCACTGAAGACGCCGAGCCGCCAGTCGAAGCTG         1140
GAGAAGCCCCCGCAGCTTTCCCTGCTTCTGCTGCTGCTTCTTCATGAGCCTTCCGCGGTGACTTCTGACTTCGAGCTTCGAC              1140
           -------HTCC-1 FL------------------------------------------------------------
  S  S  G  A  S  K  G  I  T  T  K  K  Y  S  E  G  A  A  A  G  T  E  D  A  E  R  A  P  V  E  A
```

FIG. 6-2

ACTCGGGGCGGTGGGCAAAAGGTACGAAACGTCGTCTAACGGCATGGGCGAGCCAA
TGGCGCCCGCCACCCGTTTTCCACGACCATGCTTTGCAGCAGATTGCCGTACCGCTCGGTT
----HTCC-1 FL------------------→
D A G G G Q K V L V R N V V

FIG. 6-3

```
ATGCATCACCATCACCATCATGAGCAGAGCGTTCATCATCGATCCAACGATCAGTGCCATTGACGGCTTGTGTACGACCTTCTGGGGATTGGAAT    95
TACGTAGTGGTAGTGGTAGTACTCGTCGTCAAGTAGTAGCTAGGTTGCTAGTCACGTGCTGGAACATGCTGGAAGACCCCTAACCTTA          95
 M  H  H  H  H  H  H  M  S  R  A  F  I  I  D  P  T  I  S  A  I  D  G  L  Y  D  L  L  G  I  G  I

ACCCAACCAAGGGGGTATCCTTTACTCCTCACTAGAGTACTTCGAAAAAGCCCTGGAGGAGCTGGCAGCAGCGTTTCCGGTGATGGCTGGTTAG    190
TGGGTTGGTTCCCCATAGGAAATGAGGAGTGATCTCATGAAGCTTTTTCGGGACCTCGTCGCAAGGCCACTACGACCAATC                 190
 P  N  Q  G  G  I  L  Y  S  L  E  Y  F  F  K  A  L  E  E  L  A  A  A  F  P  G  D  G  W  L

GTTCGGGCCGCGGACAAATACGCCGGGCAAAAATACCGCAACGTGAATTTTTTCCAGGAACTCGATCGTCAGCTCATCAGCCTGATC          285
CAAGCCGGCCGCCTGTTTATGCGGCCCGTTTTTTATGGCGTTGCACTTAAAAAAGGTCCTTGAGCAGTCGAGTAGTCGGACTAG              285
 G  S  A  A  D  K  Y  A  G  K  N  R  N  H  V  N  F  F  Q  E  L  A  D  L  D  R  Q  L  I  S  L  I

CACGACCAGGCCAACGCGGTCCAGACGACCCGCGACATCCTGGAGGGGCGCCAAGAAAAGGTCTCGAGTTCGTGCGCCGGTGGCTGTGACCTGAC    380
GTGCTGGTCCGGTTGCGCCAGGTCTGCTGGGCGCTGTAGGACCTCCCGCGGTTCTTTCCAGAGCTCAAGCACGCGGCCACCGACACTGGACTG    380
 H  D  Q  A  N  A  V  Q  T  T  R  D  I  L  E  G  A  K  K  G  L  E  F  V  R  P  V  A  V  D  L  T

CTACATCCCGGTCGTGGGCCACGCCCTATCGGCCGCCTTCCAGGCGCCGTTTTGCGCGGGCCGTAGTGGCCGCTTGCCTACT               475
GATGTAGGGCCAGCACCCGGTGCGGGATAGCCGGCGGAAGGTCCGCGGCAAATGCTTCGCGGCAAAACGCGCCCGGCATCACCGCGAACGGATGA  475
 Y  I  P  V  V  G  H  A  L  S  A  A  F  Q  A  P  F  C  A  G  A  M  A  V  V  G  G  A  L  A  Y

TGGTCGTGAAAACGCTGATCAACGCTGATTCCTCGACTCAACTCCTCAAATTGCTTGCCAAATTGGCGGAGTTGGTCGCGCCATTGCGACATCATTTCG  570
ACCAGCACTTTTGCGACTAGTTGCGACTAAGGAGCTGAGTTGAGGAGTTTAACGAACGGTTCAACGCCGGTAACGCCTAGTAGAAAGC          570
 L  V  K  T  L  I  N  A  T  Q  L  K  L  L  A  K  L  A  E  L  V  A  A  A  I  A  D  I  I  S

GATGTGGCGGACATCATCAAGGGCATCCTCGAGGAAGTGTGGGAGTTCATCACAAACGCGCTCAACGGCCTGAAAGAGCTTTGGGACAAGCTCAC   665
CTACACCGCCTGTAGTAGTTCCCGTAGGAGCTCCTTCACACCCTCAAGTAGTGTTTGCGCGAGTTGCCGGACTTTCTCGAAACCCTGTTCGAGTG   665
 D  V  A  D  I  K  G  I  L  G  E  V  W  E  F  I  T  N  A  L  N  G  L  K  E  L  W  D  K  L  T

GGGGTGGGTGACCGGACTGTTCTCTCGAGGGTGGTGAACCTGGAGTCCTTCTAAGAATTC                                      726
CCCCACCCACTGGCCTGACAAGAGAGCTCCCACCACTTGGACCTCAGGAAGATTCTTAAG                                      726
 G  W  V  T  G  L  F  S  R  G  W  S  N  L  E  S  F  F
```

FIG. 7A

```
ATGCATCATCACCATCACCATCACGATGTGGCGGACATCATCAAGGGCATCCTCGGAGAAGTGTGGGAGTTCATCACAAACGGCCTGAA      95
TACGTAGTAGTGGTAGTGGTAGTGCTACACCGCCTGTAGTAGTTCCCGTAGGAGCCTCTTCACACCTCAAGTAGTGTTTGCCGGACTT      95
 M  H  H  H  H  H  H  D  V  A  D  I  I  K  G  I  L  G  E  V  W  E  F  I  T  N  A  L  N  G  L  K

AGAGCTTTGGAACAAGCTCACGGGGTCAAGTGTTCGAAGTGCCCCTGTTCTCTCGAGGGTGTCGAACCTGAGTCCTTCTTTGCGGGCTTGA    190
TCTCGAAACCTTGTTCGAGTGCCCCAGTTCACAAGCTTCACGGGGACAAGAGAGTCCCACAGCTTGGACTCAGGAAGAAACGCCCGAACT    190
 E  L  W  D  K  L  T  G  W  V  T  G  L  F  S  R  G  W  S  N  L  E  S  F  F  A  G  V  P  G  L

CCGGCGCGACCAGCGGCTTGCCCGGCCTTGTCGCAAGTGACTGGGGACTGGACCGGGTTCCGGTCATTGGGGCCGGCATTGGGCCGGATAGCCTGGCG    285
GGCCGCGCTGGTCGCCGAACGGCGTTCACTGACCCTGACCCTGGCGCCAAGGCCAGCAGCCGTAGCAGCCGAGTGCGCCTATCGGACCGC    285
 T  G  A  T  S  G  L  S  Q  V  T  G  L  F  G  A  A  G  L  S  A  S  S  G  L  A  H  A  D  S  L  A

AGCTCAGCCAGCCTTGCCCGGCCTTGCCGGAGCCTTGCCGAGCCGTCCAGGTCCAGGTACGGGGAGTTGAGC    380
TCGAGTCGGTCGGAACGGGCGGCATCCGGGACGAGTGTTCCAGGTCCAGTTCCAGGTCCAGGTCAATTGAGC    380
 S  S  A  S  L  P  A  L  A  G  I  G  G  S  F  G  G  L  P  S  L  A  Q  V  H  A  A  S  T  R

GCAGGCGGCTACGGCGGCCCGACCGGCTGATGGCCAAGCTGGTCGACGTGACCAGAGAGGCCGTGCTCCCAAGGGTTCCCAAG    475
CGTCCGCGATGCCGCCGGGGCTGGCCGACTACCGGGTTCGACCAGCTGCACTGGTCCTCAGCGTCCAGGCGTTCCCAAGGTTC    475
 Q  A  L  R  P  R  A  D  G  P  V  G  A  A  A  E  Q  V  G  G  Q  S  Q  L  V  S  A  Q  G  S  Q

GTATGGGGGCCAGGACCCCGTAGGAGGCGCCATGCCAGTCGAAGCTGAACGGCGGCGAAAGGGACGAAGAAGTACTCGGAAGGCGGCGCG    570
CATACCCCGGGTCCTGGGGCATCCTCCGCGGTAGGTTCGACTTCGACTTGCCGCCGCTTTCCCTGCTTCTTCATGAGCCTTCCGCCGCGC    570
 G  M  G  G  P  V  G  M  G  G  M  H  P  S  S  G  A  S  K  G  T  T  K  K  Y  S  E  G  A  A  A

GGCACTGAAGACGCCGAGACGCCAGTCGAAGCTGAACGTCGTCGTAACGGCGAATTC    661
CCGTGACTTCTGCGGCTCTGCGGTCAGCTTCGACTTGCAGCAGATTGCCGCTTAAG    661
 G  T  E  D  A  E  T  A  P  V  E  A  D  A  G  G  G  D  K  V  L  V  R  N  V  V  R  R  I

FIG. 7B
```

```
ATGCATCACCATCACCATCACATGAGCCAGAGCGTTCATCATCAGTGCCATTGACGGCTTGTACGACCTTCTGGGATTGGAAT    95
TACGTAGTGGTAGTGGTAGTGTACTCGGTCTCGCAAGTAGTAGTCACGGTAACTGCCAATGCTGGAAGACCCTAACCTTA       95
 M  H  H  H  H  H  H  M  S  R  A  F  I  I  D  P  T  I  S  A  I  D  G  L  Y  D  L  L  G  I  G  I

ACCCAACCAAGGGGTATCCTTTACTCCTCACTAGAGTACTTCGAAAAAGCCCTGGCAGCAGGCGTTCCGGGTGATGGCTGTGGTTAG   190
TGGGTTGGTTCCCCATAGGAAATGAGAGTGATCTCATGAAGCTTTTCGGACAGCCTCGTCGTCGCAAAGGCCCACTACCGACCAATC   190
 P  N  Q  G  G  I  L  Y  S  S  L  E  Y  F  E  K  A  L  E  E  L  A  A  A  F  P  G  D  G  W  L

GTTCGGCCGCGGACAAATACGCCGGTCCAACACGTGAATTTTTTCCAGGAACTGGCAGATCTCGATCGTCAGCTCATCAGCCTGATC   285
CAAGCCGGCCGCCTGTTTATGCGGCCAGGTTGTGCACTTAAAAAAGGTCCTTGACCGTCTAGAGTCGAGTAGTCGGACTAG         285
 G  S  A  D  K  Y  A  G  K  N  R  N  H  V  N  F  F  Q  E  L  A  D  L  D  R  Q  L  I  S  L  I

CACGACCAGGCGCCAAGCGCGGTTCCAGACGACCCGGTGCCCCGGGTGCGGTCTCGAGTTCGTGACCTGGACCTGGAC         380
GTGCTGGTCCGCGGTTCGCGCCAAGGTCTGCTGGGCGCCAGGTCGCTGCTGGGCGCACGGGCCACCGGACACCTGGACCTG       380
 H  D  Q  A  N  A  V  Q  T  T  R  D  I  L  E  G  A  K  K  G  L  E  F  V  R  P  V  A  V  D  L  T

CTACATCCCGGTCGTCGGGCACGCCCTATAG   411
GATGTAGGGCCAGCAGCCCGTGCGGGATATC  411
 Y  I  P  V  V  G  H  A  L
```

```
CTGGAGGAGCTGGCAGCAGCCGTTTCCGGGTGATGGCCTGGTTAGGTTCGGCAGCGGGACAAATACGCCGGACAAAACCGCAACCACGTGAATTTTT   665
GACCTCCTCGACCGTCGTCGGCAAAGGCCCACTACCGACCAATCCAAGCCGTGTTTATGCGGCCCTGTTTTTGGCGTTGGTGCACTTAAAAAAA      665
                                                                                     --hTCC1
 L  E  E  L  A  A  A  F  P  G  D  G  W  L  G  S  A  A  D  K  Y  A  G  K  N  R  N  H  V  N  F  F

CCAGGAACTGGCAGACCTTGATCGTCAGTCAGCTCATCAGCCTCAGTCAGCTTGATCAACGACCAGGGCCAACGCGGTTGCCGCCAGTCCCGGTTCCAGGTTCTGCTGGAGGGCGCCA   760
GGTCCTTGACCGTCTGGAGCTAGCAGTCGAGTAGTCGGAGTCAGTCGAACTAGTTGCTGGTCCCGGTTGCGCCAACGGCGGTCAGGGCCAAGACGACCTCCCGCGGT               760
                                                                                     --hTCC1
 Q  E  L  A  D  L  D  R  Q  L  I  S  L  I  H  D  Q  A  N  A  V  Q  T  T  R  D  I  L  E  G  A

AGAAAGGTCTCGAGAGTTCGTGTGCCGGGTTGCTGTGGACTTACACATCCCGTCGTCGGGCACGCCCTACATCCCGGGGCCAGGGCCGCTTCCAGGCGCCGTTT   855
TCTTTCCAGAGCTCAAGCACGCGGCAACGACACCTGGATGTAGGGCAGCAGCCCTGTGCGGGATAGGGCCCGGTCCCGGCGAAGGTCCGGCCAAA            855
                                                                                     --hTCC1
 K  K  G  L  E  F  V  R  P  V  A  V  D  L  F  Y  I  P  V  V  G  H  A  L  S  A  A  F  Q  A  P  E

TGGCGGGGGCGGAGTTGGTCGGCGGCGATGGCCGTAGTGGGCGCTTGCCTACTTGGTCGTGAAAAACGCTGATCAACGCAGCCATCATCAAGGGCATCCTCGAGAAGTGTGGAGTTCATCA   950
ACGCCCCGCGCCTCAACCAGCCGCCGCTACCGGCATCACCCGCGAACGGATGAACCAGCACTTTTGCGACTAGTTGCGTCGGTAGTAGTTCCCGTAGGAGCTCTTCACACCTCAAGTAGT   950
                                                                                     --hTCC1
 C  A  G  A  M  A  V  V  G  G  A  L  A  Y  L  V  V  K  T  L  I  N  A  T  Q  L  L  K  L  L  A  K

ATTGGCGGAGTTGGCGAAGCTCAACCAGCCGCCCGGCGGCCGGGGCTACCCGGTGTAACGCCCTGTAGTAGTCAAAGCCTGTTTCTCGAGGGTGACCGGACTGTTCTCGAGGGTCGAACCTTGGAGTTCATCA   1045
TAACCGCCTCAACCGCTTCGAGTTGGTCGGCGGGCCGCCGGCCCCGATGGGCCACATTGCGGGACATCATCAGTTTCGGACAAAGAGCTCCCACTGGCCTGACAAGAGCTCCCAGCTGGAGACTTGGAACCTCTTGAACAGTAGT    1045
                                                                                     --hTCC1
 L  A  E  L  V  A  A  A  I  A  Q  I  I  S  D  V  A  D  I  I  K  G  I  L  G  E  V  W  E  F  I

CAAACGCGCTCAACGGCCTCAAAGAGCTTTGGGACAAGCTCACGGGGGTGGGTGACCGGACTGTTGCGGTGGTGACCGGACGTCCTTC    1140
GTTTGCGCGAGTTGCCGGAGTTTCTCGAAACGCCTGTTCGAGTGCCCACCACTGGCTGCAAGACGCCACCACTGGCCTGCAGGAAG       1140
                                                                                     --hTCC1
 T  N  A  L  N  G  L  K  E  L  W  D  K  L  T  G  W  V  E  G  L  F  S  R  G  W  S  N  L  E  S  F
```

FIG. 8-2

```
TTTGCGGGCGGTCCCGGCTTGACCGGCGCGGACCAGCGGCTTGTGCAAGTGACTGGCTTGTCGGTCTGTCCGCATCGTCGGGCTTT  1235
AAACGCCCGCAGGGGCGGAACTGGCGCCGAGCTGGTCGCCGAACAGCGTTCACTGACGTTCGACAAGCCACAGGCGTAGCAGCCCGAA  1235
                                                                                    --hTCC1--

F  A  G  V  P  G  L  T  G  A  T  S  G  L  S  Q  V  T  G  L  F  G  A  A  G  L  S  A  S  S  G  L

GGCTCACGCGGGATAGCGCCTGGGCGAGCTCAGCGAGCTTGCCCGGCCCTGGGGGCGGGGTTTCCGGTTTGGGGGCGGCCTTGGGGCTC  1330
CCGAGTGCGCCCTATCGCGGACCCGCTCGAGTCGCTCGAACGGGCCGGGACTAACCCCGCCCCAAGGCCAAACCCCGCCGGAACCCGAG  1330
                                                                                    --hTCC1--

A  H  A  D  S  L  A  S  S  A  S  L  P  A  L  A  G  I  G  G  S  G  F  G  G  L  P  S  L  A

AGGTCCATGCCGGCTCAACTCGGGCCAGGGCTACGCGGCGCTGATGGCCCCGAGCTCGCGGCGCTGCCGAGCGTCGGCAGTCGCAGCTG  1425
TCCAGGTACGGCCGAGTTGAGCCCGGTCCCGATGCGCCGCGACTACCGGGGCTCGAGCGCCGCGACGGCTCGCAGCCGTCAGCGTCGAC  1425
                                                                                    --hTCC1--

Q  V  H  A  A  S  T  R  Q  A  L  R  P  R  A  D  G  P  V  G  A  A  A  E  Q  V  G  G  Q  S  Q  L

GTTCTCCGCGCGCAGGGTTCCAAGGTATGGGCGGACCCGTAGGCGGCATGCACCCCTCTTCGGGGGCGTGAAAGGGACGACGAGAAGAA  1520
CAAGAGGCGCGCGTCCCAAGGTTCCATACCCGCCTGGGCATCCGCCGTACGTGGGGAGAAGCCCCCGCAGCTTTCCCTGCTGCTTCTT  1520
                                                                                    --hTCC1--

V  S  A  Q  G  S  Q  G  M  G  G  P  V  G  M  G  G  M  H  P  S  S  G  A  S  K  G  T  T  K  K

CAGAGGCCTTCCGCGAAGGCGCGGGCCACTGAAGACGCCGAGCGCCGCAGTCGAAGCTGACTCGAGCTTCGACTGCGCGGTACGAAACG  1615
CATGAGCCTTCTGCGGCCCGCGCGCCGGCCCGCGGTCTGCGGCTCGCGCGAGACTTCTCGCGGCCGTGGGCCACCCGTTTCCACGACCATGCTTTGC  1615
                                                                                    --hTCC1--

Y  S  E  G  A  A  K  G  T  E  D  A  E  R  A  P  V  E  A  D  A  G  G  G  Q  K  V  L  V  R  N

TCGTCTAAGAATTC    1629
AGCAGATTCTTAAG    1629
--hTCC1--[EcoRI]
          E  F
```

```
GCGGACCCGTAGGCATGGGGGGCATGCACCCCTCTTCGGGGGGCGTCGAAAGGGACGACGAAGAAGTACTCGGAAGGCGGGGGGCACT    1140
CGCCTGGGCATCCGTACCCGCCGCTACCCTGTACGTGGGGAGAAGCCCCCGCAGCTTCCCTGCTGCTTCTTCATGAGCCTTCCGCCCGTGA   1140
                                    |-----hTCC1--------------------------------------|
 G  G  P  V  G  M  G  G  M  H  P  S  S  G  A  S  K  G  T  T  T  K  K  Y  S  E  G  A  A  A  G  T

GAAGACGCCGAGCGCGCCAGTCGAAGCTGGAAGGTGCTGGGCAAAAGGTGCTGGTACGAAACGTCGTCTAACGGCGAATTC              1225
CTTCTGCGGCTCGCGCGGTCAGCTTCGACCTTCCACGACCATGCTTTGCAGCAGATTGCCGGCTTAAC                          1225
|-----hTCC1---------------------------------------|                     |EcoRI|
 E  D  A  E  R  A  P  V  E  A  D  A  G  G  G  Q  K  V  L  V  R  N  V  V  R  R  I
```

*FIG. 9A-3*

ATGAGCAGAGCGTTCATCATCGATCCAACGATCAGTGCCATTGACGGGCTTGTACGACCTTCTGGGGACTGGAATACCCAACCAAGGGGGT  95
M  S  R  A  F  I  I  D  P  T  I  S  A  I  D  G  L  Y  D  L  L  G  I  P  N  Q  G  G

ATCCTTTACTCCTCACTAGAGTACTTCGAAAAAGCCCTGGAGGAGCTGGCAGCAGCCGTTTCCGGGTGATGGCTTAGGTTCGGCGCGACAA  190
I  L  Y  S  S  L  E  Y  F  E  K  A  L  E  E  L  A  A  A  F  P  G  D  G  W  L  G  S  A  A  D  K

ATACGGCCGCAAAAACCGCAACCACGTGAATTTTTTCCAGGAACTGGCAGACCTCGATCGTCAGCTCATCCACGACCAGGCCAACG  285
Y  A  G  K  N  R  N  H  V  N  F  F  Q  E  L  A  D  L  D  R  Q  L  I  H  D  Q  A  N

CGGTCCAGACGACCCGGCGACATCCTGGAGGGCGCCAAGAAAGGTTCGAGTTCGTGCGCCCGGTGGCTGTGGACCTGACCTACATCCCGGTCGTC  380
A  V  Q  T  T  R  D  I  L  E  G  A  K  K  G  L  E  F  V  R  P  V  A  V  D  L  T  Y  I  P  V  V

GGGCACGCGCCCTATCGGCCCTTCCAGGCGCGCCGTTTGCGCGGGCGCTAGTGGGCGGCGCGATGGCCGTAGTGGGCGCTTGCCTACTTGGTCGTGAAAACGCT  475
G  H  A  L  S  A  A  F  Q  A  P  F  C  A  G  A  M  A  V  V  G  G  A  L  A  Y  L  V  V  K  T  L

GATCAACGCGACTCAACTCCTCAAATTGCTTGCCAAATTGGCGGAGTTGGTCGCGGCGCCATTGCGGACATCATTTCGGATGTGGCGGACATCA  570
I  N  Q  L  L  K  L  L  A  K  L  A  E  L  V  A  A  A  I  A  D  I  I  S  D  V  A  D  I

ACTCGGGCGGTGGGCAAAAGGTGCTGGTACGAAACGTCGTCTAA
----PEPTIDE 29----|
              |----PEPTIDE 30------------------|
D   A   G   G   G   Q   K   V   L   V   R   N   V   V

FIG. 9B-3

```
CATATGCATCATCACCATCACATGAGCAGAGCGTTCATCATCGATCCAACGATCAGTGCCATTGACGGCTTGTACGACCTTCTGGGGATTGG    95
GTATACGTAGTAGTGGTAGTGTACTCGTCTCGCAAGTAGTAGCTAGTTGCACGTTGCCGAACATGCTGGAAGACCCCTAACC             95
 H  M  H  H  H  H  H  M  S  R  A  F  I  I  D  P  T  I  S  A  I  D  G  L  Y  D  L  L  G  I  G
                                  |---------------------------hTCC1---------------------------

AATACCCAACCAAGGGGTATATCCTTTACTCCTCACTAGAGTACTTCGAAAAAAGCCCTGAATTTTTTCCAGGAACTGGCAGCAGCGTTTCGGGTGATGGCTGGT   190
TTATGGGTTGGTTCCCCATAGAGGAAATGAGGAGTGATCTCATGAAGCTTTTTTCGGGACTTAAAAAAGGTCCTTGACCGTCGTCGCAAAGGCCCACTACCGACCA   190
 I  P  N  Q  G  I  L  Y  S  S  L  E  Y  F  E  K  A  L  E  E  L  A  A  A  F  P  G  D  G  W
 ----------------------------------------------hTCC1----------------------------------------

TAGGTTCGGCGCGGACAAATACGCCGGGCAAAAACCGTGAATTTTTTCCAGGAACCTGGCAGAGACCTCGATCGTCAGCTCATCAGCCTG   285
ATCCAAGCCGCGGCCCTGTTTATGCGGCCCGTTTTTTGGCACTTAAAAAAGGTCCTTGGACCGTCTCTGGAGCTAGCAGTCGAGTAGTCGGAC   285
 L  G  S  A  A  D  K  Y  A  G  K  N  R  N  H  V  N  F  F  Q  E  L  A  D  L  D  R  Q  L  I  S  L
 -----------------------------------------hTCC1-----------------------------

ATCCACGACCAGGCCAACGCGGTCCAGACGACCCGCGACAAGCTTATCCTGGAGGGCGCCAAGAAAGGTCTCGAGTTCGTGCGCCCGGTGGCTGT   380
TAGGTGCTGGTCCGGTTGCGCCAGGTCTGCTGGGCGCTGTTCGAATAGGACCTCCCGCGGTTCTTTCCAGAGCTCAAGCACGCGGGCCACCGACA   380
                              |Hind3|-------------------------DELETED-----------------------
 I  H  D  Q  A  N  A  V  Q  T  T  R  D  K  L  I  L  E  G  A  K  K  G  L  E  F  V  R  P  V  A  V GGACCTGACTGACTTACATCCCGGTCGTCGGGCACGCCCTATCGGGGCACGCCCGTTTGCGCCGGGCGATGGCCGTAGTGGGCGGCGC   475
CCTGGACTGGATGTAGGGCCAGCAGCCCGTGCGGGACAGCCCGTGCGGGCAAAGCGCGCGCGGCCCGCTACCGGCATCACCCGCCGCG   475
 D  L  T  Y  I  P  V  V  G  H  A  L  S  A  A  F  Q  A  P  F  C  A  G  A  M  A  V  V  G  G  A
 ----DELETED----

TTGCCTACTTGGTCGTGAAAAACGCTGATCAACGCGACTCCTCAAATTGCTTGCCAAATTGGCGAGTTGGTTGCGGCCCGCCATTGCGGAC   570
AACGGATGAACCAGCACTTTTTGCGACTAGTTGCGCTGAGTTTAACGAACGGTTTAAGGAGTTTAAGAACGCCGGGCGGTAACGCCCTG   570
                                              ----DELETED----
 L  A  Y  L  V  V  K  T  L  I  N  A  T  Q  L  L  K  L  L  A  K  L  A  E  L  V  A  A  A  I  A  D
```

FIG. 9D-1

```
ATCAATTTCGGATGTGGCGGACATCATCAAGGGCATCCTCGGAGAAGTGTGGGAGTTCATCACAAACGCGAAGCTTCTCAACGGCCTGAAAGAGCT  665
TAGTAAAGCCTACACCGCCTGTAGTAGTTCCCGTAGGAGCCTCTTCACACCCTCAAGTAGTGTTTGCGCTTCGAAGAGTTGCGACTTTCTCGA    665
-------------DELETED--------------       Hind3 ---------------------
 I  I  S  D  V  A  D  I  I  K  G  I  L  G  E  V  W  E  F  I  T  N  A  K  L  L  N  G  L  K  E  L TTGGGACAAGCTCACGGGGTGGGTGACCGGACTGTTCTCTCGAGTCCTTCTTTGCGGGCGTCCCCGGCTTCCCCGGCTTGACCGGGCG        760
AACCCTGTTCGAGTGCCCCACCCACTGGCCTGACAAGAGACTCAGGAACTTGGACCTCAGGAAGAAACGCCCCAGGGGGCCGAACTGGCCGC   760
---------------------hTCC1-------------------------
 W  D  K  L  T  G  W  V  T  G  L  F  S  R  G  W  S  N  L  E  S  F  F  A  G  V  P  G  L  T  G CGACCAGCGGCTTGTCGCAAGTGACTGGCTTGTTCGGTGCGGCCGGTCTCGCATCGTCCGGGCTTGGCTCACGCGGAGCTCA             855
GCTGGTCGCCGAACAGCGTTCACTGACCGAACAAGCCACGCCGGCCAGGCGTAGCAGGCCCGAACCGAGTGCGCCGCTCGACCGCTCGAGT    855
---------------------hTCC1-------------------------
 A  T  S  G  L  S  Q  V  T  G  L  F  G  A  A  G  L  S  A  S  S  G  L  A  H  A  D  S  L  A  S  S GCCAGCTTGCCCGGCGCCCTGGCCGGCATTGGGGGCGGCCGCGTCGGCCTGCCCAGCTCCATGCCGCCTCAACTCGGCAGGC             950
CGGTCGAACGGGCCGCGGGACCGGCCGTAACCCCCGCCGGCGCAGCCGGACGGGTCGAGTTGAGCCGTCGGAGTTGAGCCGTCCG          950
---------------------hTCC1-------------------------
 A  S  L  P  A  L  A  G  I  G  G  G  S  G  F  G  G  L  P  S  L  A  Q  V  H  A  A  S  T  R  Q  A GCTACGGCCCCGAGCTGATGGCCCGGGTCGGCGGAGCGGGCCAGGTCGGCAGTCGCAGCTGGTCTCCGGCAGGTTCCCAAGGTATGG        1045
CGATGCCGGGGCTCGACTACCGGGCCCAGCCGCCGCTCGCCGGTCCAGCCGTCAGCGTCGACCAGAGGCGCGTCAGGGTTCCATACC       1045
---------------------hTCC1-------------------------
 L  R  P  R  A  D  G  P  V  G  A  A  A  E  Q  V  G  G  Q  S  Q  L  V  S  A  Q  G  S  Q  Q  G  M
```

*FIG. 9D-2*

```
GCGGACCCGTAGGCATGGGCGGCATGCACCCCTCTTCGGGGGTCGAAAGGGACGACGAAGAAGTACTCGGAAGGCGCGGGGCACT  1140
CGCCTGGGCATCCGTACCCGCCGTACGTGGGGAGAAGCCCCCAGCTTTCCCTGCTGCTTCTTCATGAGCCTTCCGCGCCCCGTGA  1140
---------------------------------------hTCC1--------------------------------------
 G  G  P  V  G  M  G  G  M  H  P  S  S  G  A  S  K  G  T  T  K  K  Y  S  E  G  A  A  A  G  T

GAAGACGCCGAGCGCGCCCCAGTCGAAGCTGACGCGGGGCGGTGGGCAAAAGGTGCTGGTACGAAACGTCGTCTAACGGCGAATTC  1225
CTTCTGCGGCTCGCGCGGGTCAGCTTCGACTGCGCCCCGCCACCCGTTTTCCACGACCATGCTTTGCAGCAGATTGCCGCTTAAG  1225
---------------hTCC1---------------|                                     |EcoRI|
 E  D  A  E  R  A  P  V  E  A  D  A  G  G  G  Q  K  V  L  V  R  N  V  V  .  R  R  I
```

FIG. 9D-3

```
CATATGCATCACCATCACCATCACGATGTGGCGGACATCATCAAGGGCATCCTCGGAGAAGTGTGGGAGTTCATCAACAAACGCGCTCAACGGCCT    95
GTATACGTAGTGGTAGTGGTAGTGCTACACCGCCTGTAGTAGTTCCCGTAGGAGCCTCTTCACACCCTCAAGTAGTGTTTGCGCGAGTTGCCCGA    95
|----Met/HIS TAG----|                                              |----hTTC1 (184-392)----|
 H  M  H  H  H  H  H  H  D  V  A  D  I  I  K  G  I  L  G  E  V  W  E  F  I  N  A  L  N  G  L

GAAAGAGCTTTGGGACAAGCTCACGGGGTGGTCGCAAGTGACCGGACTGTTCTCTCGAGGGTGGTCGGAGTCCTTGCGGGCGTCCCCGGCT         190
CTTTCTCGAAACCCTGTTCGAGTGCCCCACCAGCGTTCACTGGCCTGACAAGAGAGAGCTCCCACCAGTTGGACCTCAGGAAGAAACGCCCCAGGGCCGA 190
                                          |----hTTC1 (184-392)----|
 K  E  L  W  D  K  L  T  G  W  V  T  G  L  F  S  R  G  W  S  N  L  E  S  F  F  A  G  V  P  G

TGACCGGCGCGACCAGCAGCTTGCTGTCGCAAGTGACTGGCTTGTTCCGGTCCCGTCTCTCCGCATCGTCGGGCTCACGCGGATAGCCTG         285
ACTGGCCGCGCTGGTCGTCGAACAGCAGCGTTCACTGACCGAACAGGCCCAGGGCAGAGAGGCGTAGCAGCGAGTGCGCCTATCGGAC         285
                                          |----hTTC1 (184-392)----|
 L  T  G  A  T  S  G  L  S  Q  V  T  G  L  F  G  A  A  G  L  S  A  S  S  G  L  A  H  A  D  S  L

GCGAGCTCAGCCAGCTTGCCGCCCGGACTGGCCCGGTCCGGTTTGGGGGCTTGCCGAGCTCAGTTCATGCCGCCTCAAC                    380
CGCTCGAGTCGGTCGAACGGCGGGCCCTGACCGGGCCAGGCCAAAACCCCCGAACGGCTCGGACCGACTCGAGTCAAGTACGGCGGAGTTG         380
                                          |----hTTC1 (184-392)----|
 A  S  S  A  S  L  P  A  L  A  G  I  G  G  G  S  F  G  G  L  P  S  L  A  Q  V  H  A  A  S  T

TCGGCAGGCGGCTACGGCCCCGAGCTGATGCCCGGTCGGCGGCGCCGAGCCAGTCGGCAGTCAGCTGGTCTCCCGGCCAGGGTTCCC             475
AGCCGTCCGCCGATGCCGGGGCTCGACTACGGGCCAGCAGCTCGTCAGCGTCAGTCGACCAGAGGGCGTGTTCCGCCCAAGG                 475
                                          |----hTTC1 (184-392)----|
 T  Q  A  L  R  P  R  A  D  G  P  V  G  A  A  A  E  Q  V  G  G  G  Q  S  Q  L  V  S  A  Q  G  S

AAGGTATGGGCGGACCCGGTAGGCATGGGCGGCATGCACCCTCTTCGGGGGCGTCGAAAGGGACGAAGGACGAAGAAGTACTCGAAGCCTTCCGGCGCG 570
TTCCATACCCGCCTGGGCCATCCGTACCGCCGTACGTGGGAGAAGCCCCCGCAGCTTTCCCTGCTGCTTCATGAGCCTCCGGCCGC             570
                                          |----hTTC1 (184-392)----|
 Q  G  M  G  G  P  V  G  M  G  G  M  H  P  S  S  G  A  S  K  G  T  T  K  K  Y  S  E  G  A  A
```

*FIG. 10-1*

```
GCGGGCACTGAAGACGCGAGCGCGCCAGTCGGAAGCTGACGCGCGGTGGGCAAAAGGTGCTGTGTACGAAGTCGTGATGGTGA  665
CGCCCGTGACTTCTGCGCGCTCGCGGCGGTCAGCGTGCGCGCGGCCACCCGTTTTCCACGACGTTTGCAGCAGCTTAAGTACCACCT  665
          ------hTCC1 (184-392)------                      |EcoRI|--TbH9--
 A  G  T  E  D  A  E  R  A  P  V  E  A  D  A  G  G  G  Q  K  V  L  V  R  N  V  V  E  F  M  V  D

TTTCGGGGCGTTACCACCGGAGATCAACTCCGCGGAGGATGTACCGCCCGGCCCGGTTCGGCGGCCCGCTCGTGTGGCGCCGCGGCTCAGATGTGGGACAGCG  760
AAAGCCCCGCAATGGTGGCCTCTAGTTGAGGCGCCTCCTACATGCGGGCCGGGCCAAGCCGCCGGGCCAAGCCGACCACCCGAGTCTACACCCTGTCGA     760
                                      ------TbH9------
 F  G  A  L  P  P  E  I  N  S  A  R  M  Y  A  G  P  G  S  A  S  L  V  A  A  Q  M  W  D  S

TGGCGAGTCGACCTGTTTTCGGCCGCTCGCCGTATGTGCGTCTGGATGAGCGTGTCACCGCGCTCACCGGTGCGTGATAGGTTCGTCGGCGGTCTCGATG    855
ACCGGCTCACTGGACAAAGCCGGCGCAGCCGCATACACGCGCCACCTACCTCGAGCAGCCGCCGCCAGGTCTGAGTCGCGGGTCTACCCCAGACTAC      855
                                  ------TbH9------
 V  A  S  D  L  F  S  A  A  A  S  A  F  Q  S  V  V  W  G  L  T  V  G  S  W  I  G  S  S  A  G  L  M

GTGGCGGGGGCCTCGCCGTATGGGCTGACGGTGCCCCCGCGGGTGACCGCGAGCTGACCGCGAGTCCGGGTTGCTGCGGGGCCCTA                  950
CACCGCCCCCGGAGCGGCATACCCGACTGCCACGGGGCGCCCACTGGCGCTCGACTGGCGCGCCAACGACGCCGCCGGGAT                       950
                                  ------TbH9------
 V  A  A  A  S  P  Y  V  A  W  M  S  V  T  A  G  Q  A  E  L  T  A  A  Q  V  R  V  A  A  A  A  Y

CGAGAGACGGCGTATGGGCTGACGGTGCCGCCGCCGGTGATCGCCGAGAACCGTGCTGAACTGATGATTCTGATAGCCGAACCAACCTCTTGGGCAAA     1045
GCTCTGCCGCATACCCGACTGCCACGGGGCGGCACTACCGGCGGCCACTACTGGCACGACTTGACTACTAAGACTATCGCTGGTTGGAGAACCCGTTT      1045
                                  ------TbH9------
 E  T  A  Y  G  L  T  V  P  P  P  V  I  A  E  N  R  A  E  L  M  I  L  I  A  T  N  L  L  G  Q

ACACCCCGGCGATCGCCGTCAACGAGGCCGAATACGGCGAGATGTGGGCCCAAGACGCCGCCGCCATGTTTGGCTACGCCGCGGCCGACGGCGACG       1140
TGTGGGGCCGCTAGCGGCAGTTGCTCCGGACAGTTGCTCCCGGCTTCTACACCCGGGTTCTGCGGCGGCGGCGGCTACAAACCGATGCGGCGCCGCTGC    1140
                                  ------TbH9------
 N  T  P  A  I  A  V  N  E  A  E  Y  G  E  M  W  A  Q  D  A  A  A  M  F  G  Y  A  A  A  T  A  T
```

*FIG. 10-2*

```
GCGACGGGCGACGTTGCTGCCGTTCGAGGAGGCGCCGGAGATGACCAGCGCGGGGCCCCGCGGTCGAGGAGGCCTCCGA  1235
CGCTGCCCGCTGCAACGACGGCAAGCTCCCTCGAGGAGCTCGTCGCGGCCCCGGCGGCGGCCAGCTCCTCCGAGGCT  1235
-------------------TbH9-----------------------------------------------------
 A  T  L  L  P  F  E  E  A  P  E  M  T  S  A  G  G  L  L  E  Q  A  A  A  V  E  E  A  S  D

CACCCGCGGCGGCAACCAGTTGATGAACAATGTGCCCCAGGCGCTGCAACAGCTGGCCCAGCCCACCCAGGGCACCACGCCTTCTTCCAAGCTGG  1330
GTGGGCGGCCGCCGTTGGTCAACTACTTGTTACACGGGGTCCGCGACGTTGTCGACCGGGTCGGGTGCGTCCCGGTGCTGGAAGAAGGTTCGACC  1330
-------------------TbH9-----------------------------------------------------
 T  A  A  A  N  Q  L  M  N  N  V  P  Q  A  L  Q  Q  L  A  Q  P  T  Q  G  T  T  P  S  S  K  L

GTGGCCTGTGGAAGACGGTCTCGCCATCGGTCGCCGATCAGCAACATGGTGTCGATGGCCAACAACCACATGTCGATGACCAACTCGGGTGTG  1425
CACCGGACACACCTTCTGCCAGAGCGGTAGCCAGCGGCTAGTCGTTGTACCACAGCTACTGGTTGTGTACAGCTACTGGTTGAGCCCACAC  1425
-------------------TbH9-----------------------------------------------------
 G  G  L  W  K  T  V  S  P  H  R  S  P  I  S  N  M  V  S  M  A  N  N  H  M  S  M  T  N  S  G  V

TCGATGACCAACACCCTTGAGCTCGCTTGAAGGGCTTCTTCGGGTTCTTTCGGGTCTCGGGTCGGGCGGCGGGGTCCGGGGC  1520
AGCTACTGGTTGTGTGGGAACTCGAGCTACGACTTCCCGAAGAAGAGCCCAAGAAAGCCCAAGAAAGCCCAGGCCCG  1520
-------------------TbH9-----------------------------------------------------
 S  M  T  N  T  L  S  S  M  L  K  G  F  A  P  A  A  A  A  Q  A  V  Q  T  A  A  Q  N  G  V  R  A

GATGAGCTCGCTGGGCTCTCGAGCGACGCCCAGACCCCAGAACCCGGTTGAACCACCGGGTTGAACCCGGCCAAGCAACAGCC  1615
CTACTCGAGCGACCCGAGAGCTCGCTGCGGGTCTGGGCCAACTTGGGTGGCCCAACTTGGTGGCCCAGTTCGTTGTCGG  1615
-------------------TbH9-----------------------------------------------------
 M  S  S  L  G  S  S  L  G  S  S  G  L  G  G  G  V  A  A  N  L  G  R  A  A  S  V  G  S  L  S

TGCCGCAGGCGTCCGGCGCGGGGCCGCAACCAGGCAGTCACCCGGCGCGAAAGAGGGCCC  1710
ACGGGCGTCCGGCAGCGCCCGGCGTTGGTCGTCAGTGGGGCGCCGGACTGGTCGCGGCCCTTCTCCCGGG  1710
-------------------TbH9-----------------------------------------------------
 V  P  Q  A  W  A  A  A  N  Q  A  V  T  P  A  A  R  A  L  P  L  T  S  L  T  S  A  A  E  R  G  P
```

```
CATATGCATCACCATCACCATCACATGAGCAGAGCGTTGCATCATCGATCCAACGATCAGTGCCATTGACGGCGTTGTACGACCTTCTGGGATTGG      95
GTATACGTAGTGGTAGTGGTAGTGTACTCGTCTCGCAAGTAGCTAGGTTGCTAGTCACGTAACTGCCGCAACATGCTGGAACATGCTGGAAGACCCCTAACC   95
|-----Met/HIS TAG-----||-----------------------------------------hTTC1 (1-149)--------------------
  H  M  H  H  H  H  H  M  S  R  A  F  I  I  D  P  T  I  S  A  I  D  G  L  Y  D  L  L  G  I  G

AATACCCAACCAAGGGGTATCCTTTACTCCTCACTAGAGTACTTCGAAAAAAGCCCTCGGACCGTCAGCAGCGTTTCCGGGTGATGGCTGGT            190
TTATGGGTTGGTTCCCCATAGGAAATGAGGAGTGATCTCATGAAGCTTTTTCGGGAGCCTGGCAGTCGTCGCAAGGCCCACTACCGACCA              190
------------------------------------------hTTC1 (1-149)---------------------------------------
   I  P  N  Q  G  G  I  L  Y  S  S  L  E  Y  F  E  K  A  L  E  E  L  A  A  A  F  P  G  D  G  W

TAGGTTCGGCCGCGGAGACAAATACGCCGGTCCAGAGACGACCCGGATGGCAGAGACCTCGAATTTTTTCCAGGAACTGGTGAATTCTGAGCTCATCAGCCTG   285
ATCCAAGCCGGCGCCCTGTTTATGCGGCCAGGTCTCTGCTGGGCCTACCGTCTCTGGAGCTTAAAAAAGGTCCTTGACACTTAAGACTCGAGTAGTCGGAC    285
-----------------------------------------hTTC1 (1-149)------------------------------------------
   L  G  S  A  A  D  K  Y  A  G  K  N  R  N  H  V  N  F  E  Q  E  L  A  D  L  D  R  Q  L  I  S  L

ATCCACGACCAGGCCAACGCGGTCCAGAGACGACCCGGTCCAGAGACGACCCTATCGGCCGCCCTTCCAGGCCCGTTTTGCGGGGCCGATGGGCCGTAGTGGGGCGCTTAAGC  380
TAGGTGCTGGTCCGGTTGCGCCAGGTCTCTGCTGGGCCAGGTCTCTGCTGGGATAGCCGGCGGGAAGGTCCGGGCAAAACGCCCCGGCTACCCGGCATCACCGGCATCACCTGGA  380
---------------------------------hTTC1 (1-149)---------------------------------
   I  H  D  Q  A  N  A  V  Q  T  T  R  D  I  L  E  G  A  K  K  G  L  E  F  V  R  P  V  A  V  D  L

GACCTACATCCGGAGGATCGTCGGGCACGCCCTATCGGCCGCCGAGGATGTACGCCGGAGCAGGGAGCGGCCGGGCCGAAGCCCCGGGTTCGGCGGTTCGGC   475
CTGGATGTAGGGCCTCCTAGCAGCCCGTGCGGGATAGCCGGCGGCTCCTACATGCGGCCTCGTCCCTCGCCGGCCCGGCTTCGGGGCCCAAGCCGCCAAGCCG  475
                                                                                    |Hind3
-------------------------------------------------hTTC1 (1-149)-------------
   T  Y  I  P  V  V  G  H  A  L  S  A  A  F  Q  A  P  F  C  A  G  A  M  A  V  V  G  G  A  L  K TTATGGTGGATTTCGGGGCGTTACCACCGGAGATCAACTCCGGCGGAGGATGTACGCCGGAGGATGTACGCCGGCTCAGATG                  570
AATACCACCTAAAGCCCCGCAATGGTGGCCTCTAGTTGAGGCCGCCTCCTACATGCGGCCTCCTACATGCGGCCGAGTCTAC                570
-------------------------------TbH9------------
   L  M  V  D  F  G  A  L  P  P  E  I  N  S  A  R  M  Y  A  G  P  G  S  A  S  L  V  A  A  A  Q  M
```

```
GCGGACACATCATTTCGGATGTGGGGACATCATCAAGGGCATCCTCCTGGAGACAACTGTGGGAGTTCATCACAAACGCGCTCAACGGCCTGAAAGAGCT  1805
CGCCTGTGTAGTAAAGCCTACACCGCCTGTAGTAGTTCCCGTAGGAGCCTCTTCACACCCTCAAGTAGTGTTTGCGCGAGTTGCCGGACTTTCTCGA    1805
                    --------hTCC1 (181-392)---------
                     A  D  I  I  S  D  V  A  D  I  I  K  G  I  L  G  E  V  F  I  T  N  A  L  N  G  L  K  E  L

TTGGGACAAGCTCACGGGGTGGGTGACCGGACTGTTCTCTCGAGGTGGTCGAACCTGGAGTCCTTCTTGGGGGTCCCGGCGTCCCGGCGTTGACCGGGCG   1900
AACCCTGTTCGAGTGCCCCACCCACTGGCCTGACAAGAGAGCTCCAGGAACTTGGACCTCAGGAAGAAGAAGAAACGCCCGACAGGGGCCGAACTGGCCGC  1900
                    --------hTCC1 (181-392)---------
                     W  D  K  L  T  G  W  V  T  G  L  F  S  R  G  W  S  N  L  E  S  F  F  A  G  V  P  G  L  T  G

CGACCAGCGGCTTGTCGCAAGTGACTGGCTTGTTCGGGTTCCGGCCGGGTCTTGGCCTCACGCGGATAGCCTGGCTCGGCGAGCTCA  1995
GCTGGTCGCCGAACAGCGTTCACTGACCGAACAGAGCCTTGGGCCGGAACACCGAGTGCGCTATCGGACCGCTCGAGT         1995
                    --------hTCC1 (181-392)---------
                     A  T  S  G  L  S  Q  V  T  G  L  F  G  A  A  G  L  S  A  S  S  G  L  A  H  A  D  S  L  A  S  S

GCCAGCTTGCCCGCCCTGGCCGGCATTGGGGGCGGTCGGTTTTGGGGGTTCGGTTCGCAGGCCTTGCCGAGCCTGGCTCCATGCCGCCTCAACTCGGCAGGC  2090
CGGTCGAACGGGCCGGGACCCGGTAACCCCCCGCCAGCCAGAAACCCCCCCCAAGCCGTCGGAACGCTGGACCGAGTCCAGTTGAGCGCGTCCG        2090
                    --------hTCC1 (181-392)---------
                     A  S  L  P  A  L  A  G  I  G  G  G  S  G  F  G  G  L  P  S  L  A  Q  V  H  A  A  S  T  R  Q  A

GCTACGGCCCCCGAGCTGATGCCCGTCGGAGCAGGTCGGGCGCCGCTGCCGAGCAGGAAGAAGTACTCGGAAGAAGTACTCGGAAGGTTCCAAGGTATGG   2185
CGATGCCGGGGCTCGACTACGGGCAGCCTCGTCCAGCTTCGTCTGCTTCTCATGAGCTTCTTCATGAGCCTTCCAAGGTTCCATACC                2185
                    --------hTCC1 (181-392)---------
                     L  R  P  R  A  D  G  P  V  G  A  A  E  Q  V  G  G  Q  S  C  L  V  S  A  Q  G  S  Q  G  M

GCGGACCCGTAGGCGGCATGGGGCGGCATGCACCCCTCTTCGGGCCGTCGAAAGGCGCGGGAAGGAGTACTCGAAGAAGTACTCGGAAGGCGGGGACT     2280
CGCCTGGGCATCCGCTACCGCCGTACGTGGGGAGAAGCCCCCAGCTTTCGCTGCTCTTCTTCATGAGCCTTCGAAGCCTTCCGCGCCCCCTGA          2280
                    --------hTCC1 (181-392)---------
                     G  G  P  V  G  M  G  G  M  H  P  S  S  G  A  S  K  G  T  T  K  K  Y  S  E  G  A  A  G  T
```

GAAGACGCCGAGCGGCCAGTCGAAGTCGACGCGGTGGGCAAAAGGTGCTGGTACGAAACGTCGTCTAACGGCGAATTC
CTTCTGCGGCTCGCCGGTCAGCTTCGACTGCGCCACCCGTTTCCACGACCATGCTTTGCAGCAGATTGCCCGGTTAAG
             hTCC1 (181-392)----------------------|  EcoRI
 E  D  A  E  R  A  P  V  E  A  D  A  G  G  G  Q  K  V  L  V  R  N  V  V  R  R  I
```

FIG. 11-5

```
CATATGCATCACCATCACCATCACGAGTGTGGGCGACATCATCAAGGGCATCCTCGGAGAAGTGTGGGAGTTCATCACAAACGCGCTCAACGGCCT    95
GTATACGTAGTGGTAGTGGTAGTGCTACACCGCTGTAGTAGGGCCTCTTCACACCCTCTTCACACCCTCAAGTAGTGTTTGCGCGAGTTGCCGGA    95
|-----Met/HIS TAG-----||--------------------------------hTTC1 (184-392)---------------------------
  H  M  H  H  H  H  H  H  D  V  A  D  I  I  K  G  I  L  G  E  V  W  E  F  I  T  N  A  L  N  G  L

GAAAGAGCTTTGGGACAAGCTCACGGGGTGGGTCGACCGGACTGTTCTCTCGAGGTGGTCGAACCTGGAGTCCTTCTTTGCGGGTCCCGCGCT    190
CTTTCTCGAAACCCTGTTCGACGTGCCCCACCCAGCTGGCCTGACAAGAGACGCTCCAAGCTTGGACCTCAGGAAGAAACGCCCAGGGGCCGA    190
-----------------------------------------hTTC1 (184-392)-----------------------------------------
  K  E  L  W  D  K  L  T  G  W  V  T  G  L  F  S  R  G  W  S  N  L  E  S  F  F  A  G  V  P  G

TGACCGGCGCGACCAGCGGCTTGTGCAAGTGACTGGCTGTTGTTCGGTCCGGTTCGCATCGTCCGGCTTGGCTCACGCGGATAGCCTG    285
ACTGGCCGCGCGCTGGTCGCCGAACAGCGTTCACTGACCGACAAGCAGCCCAGAGAGCTCCCAGAGTCGTAGCAGCGCCTATCGGAC    285
---------------------------------------hTTC1 (184-392)-------------------------------------
  L  T  G  A  T  S  G  L  S  Q  V  T  G  L  F  G  A  A  G  L  S  A  S  S  G  L  A  H  A  D  S  L

GCGAGCTCAGCCAGCTTGCCGCCGAGCTGCCCGCCCTGGCCCGGTTTTGGGGGGTCCGGCATTGGGGGGGCTCGGGCGTCCGGCGGTCGGGCGT    380
CGCTCGAGTCGGTCGAACGGCGCTCGACGGGCGGGACTCGACGGGCATAACCCCCAGCCGGGAGGCCGAGCCGCAGGCCGCAGCCCGCAGCCCGCA    380
------------------------------------------hTTC1 (184-392)-----------------------------------------
  A  S  S  A  S  L  P  A  L  A  G  I  G  G  S  G  F  G  G  L  P  S  L  A  Q  V  H  A  A  S  T

TCGGGCAGGCGCTACGGCCCCGAGCTGATGGCCCGGCTGATGGCCCGTGACTACCGGGGCCCCAGCGTCGTTCAGCGCGGTGGCGTCGAGTTG    475
AGCCCGTCCGCGATGCCGGGGCTCGACTACCGGGCAGCTGATGGCCCCGGGCACTGATGGCCCACTGATGGCGCCACCGCAGCAAGTCGCGCCAAGG    475
-----------------------------------------hTTC1 (184-392)-------------------------------------------
  T  Q  A  L  R  P  R  A  D  G  P  V  G  A  A  A  E  Q  V  G  G  Q  S  Q  L  V  S  A  Q  G  S

AAGGTATGGGGGCGGACCCGTAGGCATGGGCATGCACCCCTCTTCGGGGGCGTCGAAAGGGACGAAGAAGTACTCGGAAGGCGCGGGCG    570
TTCCATACCCCGCTGGGCATCCGTACCCGTACGTGGGGAGAAGCCCCCGCAGCTTTCCCTGCTTCTTCATGAGCCTTCCGCGCCCGC    570
---------------------------------------hTTC1 (184-392)----------------------------------------
  Q  G  M  G  G  P  V  G  M  G  G  M  H  P  S  S  G  A  S  K  G  T  T  K  K  Y  S  E  G  A  A
```

FIG.12-1

```
GCGGGCACTGAAGACGCCGAGCGCGCCGAGTCGAAGCGCGGGGCGGTGGGCGGTGTACAAAGTCGTCGTCGAATTCATGGTTGGA  665
CGCCCGTGACTTCTGCGGCCTCGCGCCGGGGCCCCGTTTTCCACGACCAGCTTGCAGCAGTTAAGTTACCACCT  665
         ------hTCC1 (184-392)------|EcoRI|--TbH9---
 A  G  T  E  D  A  E  R  A  P  V  E  A  D  A  G  G  G  Q  K  V  L  V  R  N  V  E  F  M  V  D

TTTCGGGGGCGTTACCACCGGAGATCAACTCCGGAGGATGTACGCGAGCCGGGTTCGGCGGCTCAGATGTGGGACAGCG  760
AAAGCCCCGCAATGGTGGCCTCTAGTTGAGGCCTCCTACATGCGCGTCGGCCCAAGCCGCCGAGTCTACACCCTGTCGA  760
                                     ------TbH9-------
 F  G  A  L  P  P  E  I  N  S  A  R  M  Y  A  G  P  G  S  A  S  L  V  A  A  A  Q  M  W  D  S

TGGCGAGTGACCTGTTTTCGGCCGCGTTTCAGTCGGTGGATGAGCGTCACCGCGGGCAGGCCCAGTCCGAGCTGACGGGTGCTCGCGGCCTA  855
ACCGCTCACTGGACAAAGCCGGCGCAGCGGCATACACCGACCTACTCGCAGTGGCGCCCGTCCGGGTCAGGCTCGACTGCCCACGAGCGCCGGAT  855
                                     ------TbH9-------
 V  A  S  D  L  F  S  A  A  S  A  F  Q  S  V  V  W  G  L  T  V  G  S  W  M  I  G  S  S  A  G  L  M

GTGGCGGCGGCCTCGCCGTATGTGGCCTGGATGAGCGTGGAGCTGACCGCGGGGCAGGCCGAGCTGACGGCTGCTCGCGGGCCGGATGATTCGAGAACCGTGCTGAACTGATGATTCTGATAGCGACCAACTCTTGGGCAAA  1045
CACCGCCGCCGGAGCGGCATACACCGGACCTACTCGCACCTCGACCTCGACGAGCGCCCCGTCCGGCTCGACTGCCGACGAGCGCCCCGGCCTACTAAGCTCTTGGCACGACTTGACTACTAAGACTATCGCTGGTTGGAGAACCCGTTT  1045
                                     ------TbH9-------
 V  A  A  A  S  P  Y  V  A  W  M  S  V  T  A  G  Q  A  E  L  T  A  A  Q  V  R  V  A  A  A  A  Y

CGAGACGGGCTATGGGCTGACGGTGCCGCCGCCGGTGATCGCCGAGAACCGTGCTGAACTGATGATTCTGATAGCGACCAACTCTTGGGCAAA  1045
GCTCTGCCCGATACCCGACTGCCAGGCGGCCACTAGCGCCTTGGCACGACTTGACTACTAAGACTATCGCTGATAGCGTGGTTGGAGAACCCGTTT  1045
                                     ------TbH9-------
 E  T  A  Y  G  L  T  V  P  P  P  V  I  A  E  N  R  A  E  L  M  I  L  I  A  T  N  L  L  G  Q

ACACCCCGGCGATCGGGTCAACGAGGCCGAATACGGCGAGATGTGGGCCCAAGACGTGGGGCCGATGTTTGGCTACGCCGGCGCCGACGGCGACG  1140
TGTGGGGCCGCTAGCCCAGTTGCTCCGGCTTATGCCGCTCTACACCCGGGTTCTGCACGAGCGCGGCGCCATGCGGCCGCGCTGCCGCTGC  1140
                                     ------TbH9-------
 N  T  P  A  I  A  V  N  E  A  E  Y  G  E  M  W  A  Q  D  A  A  A  M  F  G  Y  A  A  A  T  A  T
```

*FIG. 12-2*

```
GCGACGGGGACGTTGCTGCCGTTCGAGGAGGGCGCCGGGGTGGGCTCCTCGAGCAGGCCGGGGTCGAGGAGGCCTCCGA  1235
CGCTGCCCGCTGCAACGACGGCAAGCTCCTCCGGGCCTCTACTGGTCGTCCGAGGAGCTCGTCGCGCCCAGCTCCTCCCGGAGGCT  1235
                                        ---TbH9---
 A  T  A  T  L  L  P  F  F  E  E  A  P  E  M  T  S  A  G  G  L  L  E  Q  A  A  A  V  E  E  A  S  D

CACCGCGCGGGGCGAACCAGTTGATGAACAATGTGCCCCAGCTGCAACAGCTGGCCCAGCCCACGCAGGCCTTCTTCCAAGCTGG  1330
GTGGCGCGCCCCGCTTGGTCAACTACTTGTTACACGGGGTCGGACGTTGTCGACGGTCCGCGGGTGCGGTCCCGTGGTGCGGAAGAAGGTTCGACC  1330
                                        ---TbH9---
 T  A  A  N  Q  L  M  N  N  V  P  Q  A  L  Q  Q  L  A  Q  P  T  Q  G  T  T  P  S  S  K  L

GTGGCCCTGTGGAAGACGGTCTCGCCGCATCGGTCTGAGCTCGATGTTGAAGGCTTTGCTCCTGGGGTCTGGGGTTCTTCGGGC  1425
CACCGGACACCTTCTGCCAGAGCGGCGTAGCCAGACTCGAACTGAGCTACAACTTCCGAAACGAGACCCAAGAGTTGGAACCCAGAAGAAGCCC  1425
                                        ---TbH9---
 G  G  L  W  K  T  V  S  P  H  R  S  P  I  S  N  M  V  S  M  A  N  N  H  M  S  M  T  N  S  G  V

TCGATGACCAACACCTTGAGCTCGATGTTGAAGGCTTTGCTCCTGGGGTCTGGGGTTCTTCGGGCCAAAACGGGGTCCGGGC  1520
AGCTACTGGTTGTGGAACTCGAGCTCAAGCTACAAGTTCCCGAAACGAGGACCCCAGAGCCGGTTGAACCCAGCAGCAACAGCC  1520
                                        ---TbH9---
 S  M  T  N  T  L  S  S  M  L  K  G  F  A  P  A  A  A  A  Q  A  V  Q  T  A  A  Q  N  G  V  R  A

GATGAGCTCGCTGGGCAGCCTCGCTGGGTTCTTCGGGGGTGTAGCCGCCAACTTGGGTCGGTCGGTCTTCGTTGTCGG  1615
CTACTCGAGCGACCCGTCGGAGCAGCCCGTCGGAGCGACCCAAGAAGCCCCACATCGGCGGTTGAACCAGCAGCCAAGCAACAGCC  1615
                                        ---TbH9---
 M  S  S  L  G  S  S  L  G  S  S  G  L  G  G  G  V  A  A  N  L  G  R  A  A  S  V  G  S  L  S

TGCCCGCAGGCCTGGGCGGCCGGGCGCAACCAGGCAGTCACCCCGGCAGCCTGCCGCTGACCAGCCTGGGGAAAGAGGCCC  1710
ACGGGCGTCCGGACCCGGACCCCGGCGCCGGTCGGCCGTCAGTGGCCGTCAGTGGTCGCGGCAGTGGTCGCGGCCTTTCTCCCGGG  1710
                                        ---TbH9---
 V  P  Q  A  W  A  A  A  N  Q  A  V  T  P  A  A  R  A  L  P  L  T  S  L  T  S  A  A  E  R  G  P
```

```
CTTGCCTACTTGGTCGTGAAAACGCTGATCAACGCGACTCAACTCCTCAAATTGCTTGCCAAATTGGCGGAGTTGGTCGCGGCGCCATTGCGGA  2375
GAACGGATGAACCAGCACTTTGCGACTAGTTGCGCTGAGTTGAAGGAGTTGAGGAGTTTAACGAACGGTTTAACCGCCTCAACCAGCGCCGGGCGGGTAACGCCT  2375
---------------hTTC1 (1-200)----------------
 L  A  Y  L  V  V  K  T  L  I  N  A  T  Q  L  L  K  L  L  A  K  L  A  E  L  V  A  A  I  A  D

CATCATTTCGGATGTGGCGGACATCATCAAGGGACATCAAGGGCATCCTCGGAGAAGTGTGGGAGTTCATCTAAGATATC  2445
GTAGTAAAGCCTACACCGCCTGTAGTAGTTCCCGCCTAGGAGCCCTCTTCACACCCTCAAGTTCTATAG  2445
                                                                 ┌──┐
---------------hTCC1 (1-200)-------------------------------------i│RV│
                                                                 └──┘
 I  I  S  D  V  A  D  I  I  K  G  I  L  G  E  V  W  E  F  I     D  I
```

FIG. 12.5

Nucleotide sequence of MTb59 cacgactgcccgactgaacccgaactagtcagcacaaaccgaagtaggaagacgaaaagctatggc
tgagttgacaatccccgctgatgacatccagagcgcaatcgaagagtacgtaagctctttcaccgc
cgacaccagtagagaggaagtcggtaccgtcgtcgacgccggggacggcatcgcacacgtcgaggg
tttgccatcggtgatgacccaagagctgctcgaattcccgggcggaatcctcggcgtcgccctcaa
cctcgacgagcacagcgtcggcgcggtgatcctcggtgacttcgagaacatcgaagaaggtcagca
ggtcaagcgcaccggcgaagtcttatcggttccggttggcgacgggtttttggggcgggtggttaa
cccgctcggccagccgatcgacgggcgcggagacgtcgactccgatacttggcgcgcgctggagct
ccaggcgccctcggtggtgcaccggcaaggcgtgaaggagccgttgcagaccgggatcaaggcgat
tgacgcgatgaccccgatcggccgcggccagcgccagctgatcatcggcgaccgcaagaccggcaa
aaccgccgtctgcgtcgacaccatcctcaaccagcggcagaactgggagtccggtgatcccaagaa
gcaggtgcgctgtgtatacgtggccatcgggcagaagggaactaccatcgccgcggtacgccgcac
actggaagagggcggtgcgatggactacaccaccatcgtcgcggccgcggcgtcggagtccgccgg
tttcaaatggcttgcgccgtacaccggttcggcgatcgcccagcactggatgtacgagggcaagca
tgtgctgatcatcttcgacgacctgactaagcaggccgaggcataccgggcgatctcgctgctgct
gcgccgtccgcccggccgtgaggcctaccccggcgatgtgttctatctgcattcgcggcttttgga
caaggccaacgacatctcggcctacatcccgaccaacgtcatctcgatcaccgacgggcaatgttt
cctggaaaccgacctgttcaaccagggcgtccggccggccatcaacgtcggtgtgtcggtgtcccg
agtcggcggcgcggcgcagatcaaggctatgaaagaggtcgccggaagcctccgcttggacctttc
gcaataccgcgagctagaagctttcgccgctttcgcttctgatttggacgccgcatcgaaggcgca
gttggagcgcggcgcccggctggtcgagctgctcaagcagccgcaatcccagcccatgcccgttga
ggagcaagtggtttcgatcttcctgggcaccggcggtcacctggactcggtgcccgtcgaggacgt
ccggcggttcgaaaccgaattactggaccacatgcgggcctccgaagaagagattttgactgagat
ccgggacagccaaaagctcaccgaggaggccgccgacaagctcaccgaggtcatcaagaacttcaa
gaagggcttcgcggccaccggtggcggctctgtggtgcccgacgaacatgtcgaggccctcgacga
ggataagctcgccaaggaagccgtgaaggtcaaaaagccggcgccgaagaagaagaaatagctaac
catggctgccacacttcgcgaactacgcgggcggatccgctcggcagggtcgatcaaaaagatcac
caaggcccaggagatgattgcgacatcgcgcatcgccagggcgcaggctcggctcgagtccgctcg
gccctacgcttttgagatcacccggatgcttaccaccctggccgctgaagccgcactggaccatcc
gttgct

*FIG. 13*

Amino acid sequence of MTb59

MAELTIPADDIQSAIEEYVSSFTADTSREEVGTVVDAGDGIAHVEGLPSVMTQELLEFPGGILGVA
LNLDEHSVGAVILGDFENIEEGQQVKRTGEVLSVPVGDGFLGRVVNPLGQPIDGRGDVDSDTRRAL
ELQAPSVVHRQGVKEPLQTGIKAIDAMTPIGRGQRQLIIGDRKTGKTAVCVDTILNQRQNWESGDP
KKQVRCVYVAIGQKGTTIAAVRRTLEEGGAMDYTTIVAAAASESAGFKWLAPYTGSAIAQHWMYEG
KHVLIIFDDLTKQAEAYRAISLLLRRPPGREAYPGDVFYLHSRLLERCAKLSDDLGGGSLTGLPII
ETKANDISAYIPTNVISITDGQCFLETDLFNQGVRPAINVGVSVSRVGGAAQIKAMKEVAGSLRLD
LSQYRELEAFAAFASDLDAASKAQLERGARLVELLKQPQSQPMPVEEQVVSIFLGTGGHLDSVPVE
DVRRFETELLDHMRASEEEILTEIRDSQKLTEEAADKLTEVIKNFKKGFAATGGGSVVPDEHVEAL
DEDKLAKEAVKVKKPAPKKKK

*FIG. 14*

Nucleotide sequence of MTb82 ccagccccgccccgcccacgccgaggtatgtggactgatggccaaagcgttagagaccgaacgtt
cgggccccggcacccaaccggcggacgcccagaccgcgacgtccgcgacggttcgacccctgagca
cccaggcggtgttccgccccgatttcggcgatgaggacaacttcccccatccgacgctcggcccgg
acaccgagccgcaagaccggatggccaccaccagccgggtgcgcccgccggtcagacggctgggcg
gcggcctggtggaaatcccgcgggcgcccgatatcgatccgcttgaggccctgatgaccaacccgg
tggtgccggagtccaagcggttctgctggaactgtggacgtcccgtcggccggtccgactcggaga
ccaagggagcttcagagggctggtgtccctattgcggcagcccgtattcgttcctgccgcagctaa
atcccggggacatcgtcgccggccagtacgaggtcaaaggctgcatcgcgcacggcggactgggct
ggatctacctcgctctcgaccgcaatgtcaacggccgtccggtggtgctcaagggcctggtgcatt
ccggtgatgccgaagcgcaggcaatggcgatggccgaacgccagttcctggccgaggtggtgcacc
cgtcgatcgtgcagatcttcaactttgtcgagcacaccgacaggcacggggatccggtcggctaca
tcgtgatggaatacgtcggcgggcaatcgctcaaacgcagcaagggtcagaaactgcccgtcgcgg
aggccatcgcctacctgctggagatcctgccggcgctgagctacctgcattccatcggcttggtct
acaacgacctgaagccggaaaacatcatgctgaccgaggaacagctcaagctgatcgacctgggcg
cggtatcgcggatcaactcgttcggctacctctacgggacccaggcttccaggcgcccgagatcg
tgcggaccggtccgacggtggccaccgacatctacaccgtgggacgcacgctcgcggcgctcacgc
tggacctgcccaccgcaatggccgttatgtggatgggctacccgaagacgacccggtgctgaaaa
cctacgactcttacggccggttgctgcgcagggccatcgacccgatccgcggcaacggttcacca
ccgccgaagagatgtccgcgcaattgacgggcgtgttgcgggaggtggtcgcccaggacaccgggg
tgccgcggccagggctatcaacgatcttcagtcccagtcggtcgacatttggagtggacctgctgg
tggcgcacaccgacgtgtatctggacgggcaggtgcacgcggagaagctgaccgccaacgagatcg
tgaccgcgctgtcggtgccgctggtcgatccgaccgacgtcgcagcttcggtcctgcaggccacgg
tgctctcccagccggtgcagaccctagactcgctgcgcgcggcccgccacggtgcgctggacgccg
acggcgtcgacttctccgagtcagtggagctgccgctaatggaagtccgcgcgctgctggatctcg
gcgatgtggccaaggccacccgaaaactcgacgatctggccgaacgcgttggctggcgatggcgat
tggtctggtaccgggccgtcgccgagctgctcaccggcgactatgactcggccaccaaacatttca
ccgaggtgctggataccttcccggcgagctggcgcccaagctcgccctggccgccaccgccgaac
tagccggcaacaccgacgaacacaagttctatcagacggtgtggagcaccaacgacggcgtgatct
cggcggctttcggactggccagagcccggtcggccgaaggtgatcgggtcggcgccgtgcgcacgc
tcgacgaggtaccgcccacttctcggcatttcaccacggcacggctgaccagcgcggtgactctgt
tgtccggccggtcaacgagtgaagtcaccgaggaacagatccgcgacgccgcccgaagagtggagg
cgctgccccgaccgaaccacgcgtgctgcagatccgcgcccctggtgctgggtggcgcgctggact
ggctgaaggacaacaaggccagcaccaaccacatcctcggtttcccgttcaccagtcacgggctgc
ggctgggtgtcgaggcgtcactgcgcagcctggcccgggtagctcccactcaacggcatcgctaca
cgctggtggacatggccaacaaggtccggcccaccagcacgttctaagccgcccgagtgtgaatcg

FIG. 15

Amino acid sequence of MTb82

MAKASETERSGPGTQPADAQTATSATVRPLSTQAVFRPDFGDEDNFPHPTLGPDTEPQDRMATTSR
VRPPVRRLGGGLVEIPRAPDIDPLEALMTNPVVPESKRFCWNCGRPVGRSDSETKGASEGWCPYCG
SPYSFLPQLNPGDIVAGQYEVKGCIAKGGLGWIYLALDRNVNGRPVVLKGLVHSGDAEAQAMAMAE
RQFLAEVVHPSIVQIFNFVEHTDRHGDPVGYIVMEYVGGQSLKRSKGQKLPVAEAIAYLLEILPAL
SYLHSIGLVYNDLKPENIMLTEEQLKLIDLGAVSRINSFGYLYGTPGFQAPEIVRTGPTVATDIYT
VGRTLAALTLDLPTRNGRYVDGLPEDDPVLKTYDSYGRLLRRAIDPDPRQRFTTAEEMSAQLTGVL
REVVAQDTGVPRPGLSTIFSPSRSTFGVDLLVAHTDVYLDGQVHAEKLTANEIVTALSVPLVDPTD
VAASVLQATVLSQPVQTLDSLRAARHGALDADGVDFSESVELPLMEVRALLDLGDVAKATRKLDDL
AERVGWRWRLVWYRAVAELLTGDYDSATKHFTEVLDTFPGELAPKLALAATAELAGNTDEHKFYQT
VWSTNDGVISAAFGLARARSAEGDRVGAVRTLDEVPPTSRHFTTARLTSAVTLLSGRSTSEVTEEQ
IRDAARRVEALPPTEPRVLQIRALVLGGALDWLKDNKASTNHILGFPFTSHGLRLGVEASLRSLAR
VAPTQRHRYTLVDMANKVRPTSTF

FIG. 16

Amino Acid Sequence of secreted DPPD

DPPDPHQPDMTKGYCPGGRWGFGDLAVCDGEKYPDGSFWHQWMQTWFTGPQFYFDCVSGGEPLP
GPPPPGGCGGAIPSEQPNAP

FIG. 17

FUSION PROTEINS OF *MYCOBACTERIUM TUBERCULOSIS*

CROSS-REFERENCES TO RELATED APPLICATIONS

This application is a Continuation of U.S. application Ser. No. 11/809,102, filed May 30, 2007, which is a Divisional of U.S. application Ser. No. 09/688,672, filed Oct. 10, 2000 (now U.S. Pat. No. 7,311,922), and claims priority to U.S. Provisional Application No. 60/158,338, filed Oct. 7, 1999, and U.S. Provisional Application No. 60/158,425, filed Oct. 7, 1999, herein each incorporated by reference in its entirety.

This application is also related to U.S. application Ser. No. 09/056,556, filed Apr. 7, 1998 (now U.S. Pat. No. 6,350,456); U.S. application Ser. No. 09/223,040, filed Dec. 30, 1998 (now U.S. Pat. No. 6,544,522); U.S. application Ser. No. 09/287,849, filed Apr. 7, 1999 (now U.S. Pat. No. 6,627,198); and published PCT Application No. WO99/51748, filed Apr. 7, 1999 (PCT/US99/07717), herein each incorporated by reference in its entirety.

BACKGROUND OF THE INVENTION

Tuberculosis is a chronic infectious disease caused by infection with *M. tuberculosis* and other *Mycobacterium* species. It is a major disease in developing countries, as well as an increasing problem in developed areas of the world, with about 8 million new cases and 3 million deaths each year. Although the infection may be asymptomatic for a considerable period of time, the disease is most commonly manifested as an acute inflammation of the lungs, resulting in fever and a nonproductive cough. If untreated, serious complications and death typically result.

Although tuberculosis can generally be controlled using extended antibiotic therapy, such treatment is not sufficient to prevent the spread of the disease. Infected individuals may be asymptomatic, but contagious, for some time. In addition, although compliance with the treatment regimen is critical, patient behavior is difficult to monitor. Some patients do not complete the course of treatment, which can lead to ineffective treatment and the development of drug resistance.

In order to control the spread of tuberculosis, effective vaccination and accurate early diagnosis of the disease are of utmost importance. Currently, vaccination with live bacteria is the most efficient method for inducing protective immunity. The most common mycobacterium employed for this purpose is *Bacillus* Calmette-Guerin (BCG), an avirulent strain of *M. bovis*. However, the safety and efficacy of BCG is a source of controversy and some countries, such as the United States, do not vaccinate the general public with this agent.

Diagnosis of tuberculosis is commonly achieved using a skin test, which involves intradermal exposure to tuberculin PPD (protein-purified derivative). Antigen-specific T cell responses result in measurable induration at the injection site by 48-72 hours after injection, which indicates exposure to mycobacterial antigens. Sensitivity and specificity have, however, been a problem with this test, and individuals vaccinated with BCG cannot be distinguished from infected individuals.

While macrophages have been shown to act as the principal effectors of *Mycobacterium* immunity, T cells are the predominant inducers of such immunity. The essential role of T cells in protection against *Mycobacterium* infection is illustrated by the frequent occurrence of *Mycobacterium* infection in AIDS patients, due to the depletion of CD4$^+$ T cells associated with human immunodeficiency virus (HIV) infection. *Mycobacterium* reactive CD4$^+$ T cells have been shown to be potent producers of γ-interferon (IFN-γ), which, in turn, has been shown to trigger the anti-mycobacterial effects of macrophages in mice. While the role of IFN-γ in humans is less clear, studies have shown that 1,25-dihydroxy-vitamin D3, either alone or in combination with IFN-γ or tumor necrosis factor-alpha, activates human macrophages to inhibit *M. tuberculosis* infection. Furthermore, it is known that IFN-γ stimulates human macrophages to make 1,25-dihydroxy-vitamin D3. Similarly, interleukin-12 (IL-12) has been shown to play a role in stimulating resistance to *M. tuberculosis* infection. For a review of the immunology of *M. tuberculosis* infection, see Chan & Kaufmann, Tuberculosis: Pathogenesis, Protection and Control (Bloom ed., 1994), and Harrison's Principles of Internal Medicine, volume 1, pp. 1004-1014 and 1019-1023 (14th ed., Fauci et al., eds., 1998).

Accordingly, there is a need for improved diagnostic reagents, and improved methods for diagnosis, preventing and treating tuberculosis.

SUMMARY OF THE INVENTION

The present invention provides pharmaceutical compositions comprising at least two heterologous antigens, fusion proteins comprising the antigens, and nucleic acids encoding the antigens, where the antigens are from a *Mycobacterium* species from the tuberculosis complex and other *Mycobacterium* species that cause opportunistic infections in immune compromised patients. The present invention also relates to methods of using the polypeptides and polynucleotides in the diagnosis, treatment and prevention of *Mycobacterium* infection.

The present invention is based, in part, on the inventors' discovery that fusion polynucleotides, fusion polypeptides, or compositions that contain at least two heterologous *M. tuberculosis* coding sequences or antigens are highly antigenic and upon administration to a patient increase the sensitivity of tuberculosis sera. In addition, the compositions, fusion polypeptides and polynucleotides are useful as diagnostic tools in patients that may have been infected with *Mycobacterium*.

In one aspect, the compositions, fusion polypeptides, and nucleic acids of the invention are used in in vitro and in vivo assays for detecting humoral antibodies or cell-mediated immunity against *M. tuberculosis* for diagnosis of infection or monitoring of disease progression. For example, the polypeptides may be used as an in vivo diagnostic agent in the form of an intradermal skin test. The polypeptides may also be used in in vitro tests such as an ELISA with patient serum. Alternatively, the nucleic acids, the compositions, and the fusion polypeptides may be used to raise anti-*M. tuberculosis* antibodies in a non-human animal. The antibodies can be used to detect the target antigens in vivo and in vitro.

In another aspect, the compositions, fusion polypeptides and nucleic acids may be used as immunogens to generate or elicit a protective immune response in a patient. The isolated or purified polynucleotides are used to produce recombinant fusion polypeptide antigens in vitro, which are then administered as a vaccine. Alternatively, the polynucleotides may be administered directly into a subject as DNA vaccines to cause antigen expression in the subject, and the subsequent induction of an anti-*M. tuberculosis* immune response. Thus, the isolated or purified *M. tuberculosis* polypeptides and nucleic acids of the invention may be formulated as pharmaceutical compositions for administration to a subject in the prevention and/or treatment of *M. tuberculosis* infection. The immunogenicity of the fusion proteins or antigens may be enhanced by the inclusion of an adjuvant, as well as additional fusion polypeptides, from *Mycobacterium* or other organisms, such as bacterial, viral, mammalian polypeptides. Additional polypeptides may also be included in the compositions, either linked or unlinked to the fusion polypeptide or compositions.

BRIEF DESCRIPTION OF THE DRAWINGS

FIG. 1 shows the nucleic acid sequence of a vector encoding TbF14 (SEQ ID NO:89). Nucleotides 5096 to 8594 encode TbF14 (SEQ ID NO:51). Nucleotides 5072 to 5095 encode the eight amino acid His tag (SEQ ID NO:90); nucleotides 5096 to 7315 encode the Mtb81 antigen (SEQ ID NO:1); and nucleotides 7316 to 8594 encode the Mo2 antigen (SEQ ID NO:3).

FIG. 2 shows the nucleic acid sequence of a vector encoding TbF15 (SEQ ID NO:91). Nucleotides 5096 to 8023 encode the TbF15 fusion protein (SEQ ID NO:53). Nucleotides 5072 to 5095 encode the eight amino acid His tag region (SEQ ID NO:90); nucleotides 5096 to 5293 encode the Ra3 antigen (SEQ ID NO:5); nucleotides 5294 to 6346 encode the 38 kD antigen (SEQ ID NO:7); nucleotides 6347 to 6643 encode the 38-1 antigen (SEQ ID NO:9); and nucleotides 6644 to 8023 encode the FL TbH4 antigen (SEQ ID NO:11).

FIG. 3 shows the amino acid sequence of TbF14 (SEQ ID NO:52), including the amino acid His tag at the N-terminus.

FIG. 4 shows the amino acid sequence of TbF15 (SEQ ID NO:54), including the amino acid His tag at the N-terminus.

FIG. 5 shows ELISA results using fusion proteins of the invention.

FIG. 6 shows the nucleic acid and the predicted amino acid sequences of the entire open reading frame of HTCC#1 FL (SEQ ID NO:13 and 14, respectively).

FIG. 7 shows the nucleic acid and predicted amino acid sequences of three fragments of HTCC#1. (a) and (b) show the sequences of two overlapping fragments: an amino terminal half fragment (residues 1 to 223), comprising the first trans-membrane domain (a) and a carboxy terminal half fragment (residues 184 to 392), comprising the last two trans-membrane domains (b); (c) shows a truncated amino-terminal half fragment (residues 1 to 128) devoid of the trans-membrane domain.

FIG. 8 shows the nucleic acid and predicted amino acid sequences of a TbRa12-HTCC#1 fusion protein (SEQ ID NO:63 and 64, respectively).

FIG. 9a shows the nucleic acid and predicted amino acid sequences of a recombinant HTCC#1 lacking the first trans-membrane domain (deleted of the amino acid residues 150 to 160). FIG. 9b shows the nucleic acid and predicted amino acid sequences of 30 overlapping peptides of HTCC#1 used for the T-cell epitope mapping. FIG. 9d shows the nucleic acid and predicted amino acid sequences of a deletion construct of HTCC#1 lacking all the trans-membrane domains (deletion of amino acid residues 101 to 203).

FIG. 10 shows the nucleic acid and predicted amino acid sequences of the fusion protein HTCC#1 (184-392)-TbH9-HTCC#1 (1-129) (SEQ ID NO:57 and 58, respectively).

FIG. 11 shows the nucleic acid and predicted amino acid sequences of the fusion protein HTCC#1(1-149)-TbH9-HTCC#1(161-392) (SEQ ID NO:59 and 60, respectively).

FIG. 12 shows the nucleic acid and predicted amino acid sequences of the fusion protein HTCC#1(184-392)-TbH9-HTCC#1(1-200) (SEQ ID NO:61 and 62, respectively).

FIG. 13 shows the nucleotide sequence of *Mycobacterium tuberculosis* antigen Mtb59 (SEQ ID NO:49).

FIG. 14 shows the amino acid sequence of *Mycobacterium tuberculosis* antigen Mtb59 (SEQ ID NO:50).

FIG. 15 shows the nucleotide sequence of *Mycobacterium tuberculosis* antigen Mtb82 (SEQ ID NO:47).

FIG. 16 shows the amino acid sequence of *Mycobacterium tuberculosis* antigen Mtb82 (SEQ ID NO:48).

FIG. 17 shows the amino acid sequence of *Mycobacterium tuberculosis* the secreted form of antigen DPPD (SEQ ID NO:44).

DESCRIPTION OF SEQUENCES

Figure 9C:
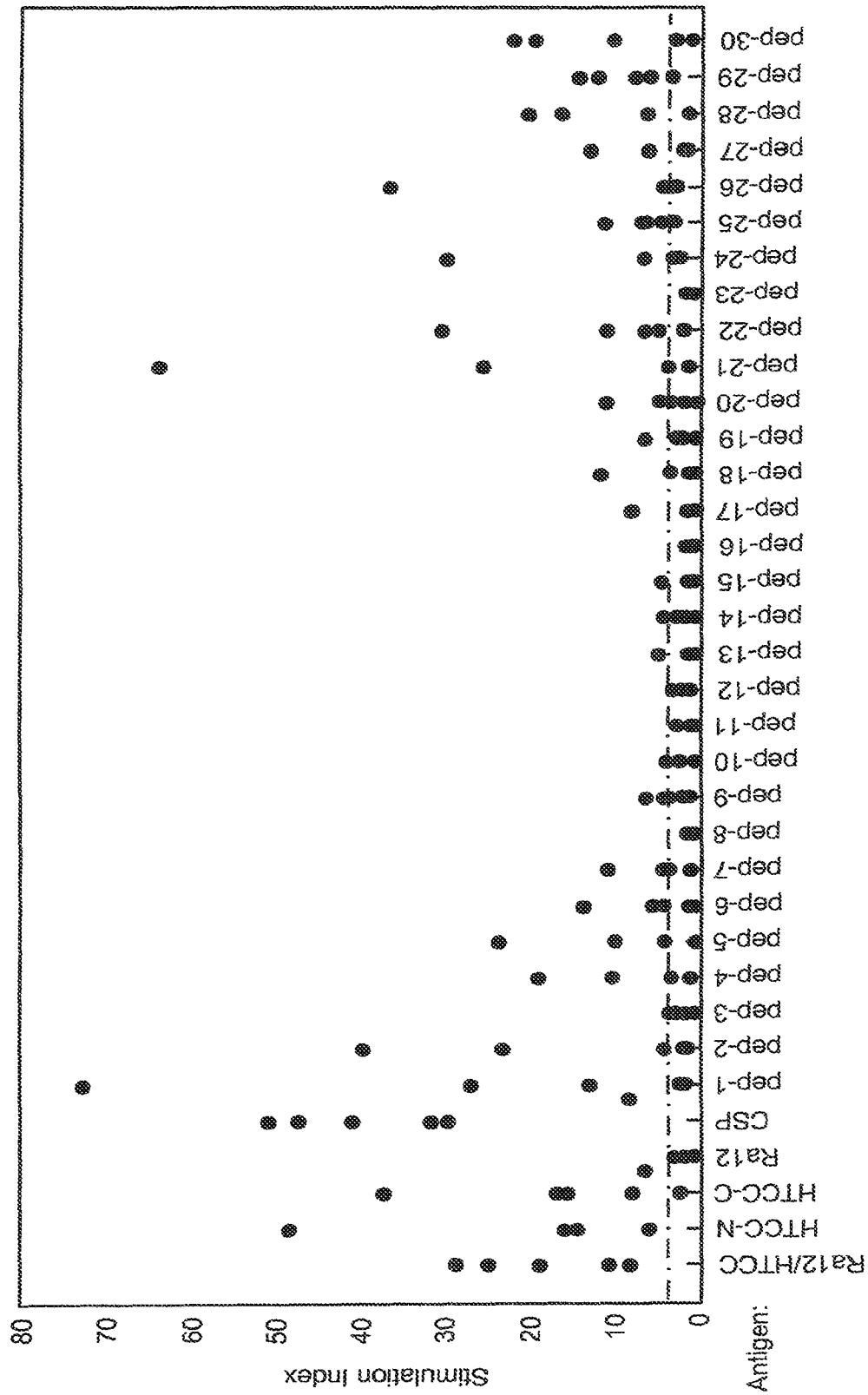
FIG. 9c illustrates the results of the T-cell epitope mapping of HTCC#1.

SEQ ID NO:1 is the nucleic acid sequence encoding the Mtb81 antigen.

SEQ ID NO:2 is the amino acid sequence of the Mtb81 antigen.

SEQ ID NO:3 is the nucleic acid sequence encoding the Mo2 antigen.

SEQ ID NO:4 is the amino acid sequence of the Mo2 antigen.

SEQ ID NO:5 is the nucleic acid sequence encoding the TbRa3 antigen.

SEQ ID NO:6 is the amino acid sequence of the TbRa3 antigen.

SEQ ID NO:7 is the nucleic acid sequence encoding the 38 kD antigen.

SEQ ID NO:8 is the amino acid sequence of the 38 kD antigen.

SEQ ID NO:9 is the nucleic acid sequence encoding the Tb38-1 antigen.

SEQ ID NO:10 is the amino acid sequence of the Tb38-1 antigen.

SEQ ID NO:11 is the nucleic acid sequence encoding the full-length (FL) TbH4 antigen.

SEQ ID NO:12 is the amino acid sequence of the FL TbH4 antigen.

SEQ ID NO:13 is the nucleic acid sequence encoding the HTCC#1 (Mtb40) antigen.

SEQ ID NO:14 is the amino acid sequence of the HTCC#1 antigen.

SEQ ID NO:15 is the nucleic acid sequence of an amino terminal half fragment (residues 1 to 223) of HTCC#1, comprising the first trans-membrane domain, with an N-terminal His Tag.

SEQ ID NO:16 is the predicted amino acid sequence of an amino terminal half fragment (residues 1 to 223) of HTCC#1 with an N-terminal His Tag.

SEQ ID NO:17 is the nucleic acid sequence of a carboxy terminal half fragment (residues 184 to 392) of HTCC#1, comprising the last two trans-membrane domains.

SEQ ID NO:18 is the predicted amino acid sequence of a carboxy terminal half fragment (residues 184 to 392) of HTCC#1.

SEQ ID NO:19 is the nucleic acid sequence of a truncated amino-terminal half fragment (residues 1 to 128) of HTCC#1, devoid of the trans-membrane domain, with an N-terminal His Tag.

SEQ ID NO:20 is the predicted amino acid sequence of a truncated amino-terminal half fragment (residues 1 to 128) of HTCC#1 with an N-terminal His Tag.

SEQ ID NO:21 is the nucleic acid sequence of a recombinant HTCC#1 lacking the first trans-membrane domain (deleted of the amino acid residues 150 to 160), with an N-terminal His Tag.

SEQ ID NO:22 is the predicted amino acid sequence of a recombinant HTCC#1 lacking the first trans-membrane domain (deleted of the amino acid residues 150 to 160), with an N-terminal His Tag.

SEQ ID NO:23 is the nucleic acid sequence of a deletion construct of HTCC#1 lacking all the trans-membrane domains (deletion of amino acid residues 101 to 203), with an N-terminal His Tag.

SEQ ID NO:24 is the predicted amino acid sequence of a deletion construct of HTCC#1 lacking all the trans-membrane domains (deletion of amino acid residues 101 to 203) with an N-terminal His Tag.

SEQ ID NO:25 is the nucleic acid sequence encoding the TbH9 (Mtb39A) antigen.

SEQ ID NO:26 is the amino acid sequence of the TbH9 antigen.

SEQ ID NO:27 is the nucleic acid sequence encoding the TbRa12 antigen.

SEQ ID NO:28 is the amino acid sequence of the TbRa12 antigen.

SEQ ID NO:29 is the nucleic acid sequence encoding the TbRa35 (Mtb32A) antigen.

SEQ ID NO:30 is the amino acid sequence of the TbRa35 antigen.

SEQ ID NO:31 is the nucleic acid sequence encoding the MTCC#2 (Mtb41) antigen.

SEQ ID NO:32 is the amino acid sequence of the MTCC#2 antigen.

SEQ ID NO:33 is the nucleic acid sequence encoding the MTI (Mtb9.9A) antigen.

SEQ ID NO:34 is the amino acid sequence of the MTI antigen.

SEQ ID NO:35 is the nucleic acid sequence encoding the MSL (Mtb9.8) antigen.

SEQ ID NO:36 is the amino acid sequence of the MSL antigen.

SEQ ID NO:37 is the nucleic acid sequence encoding the DPV (Mtb8.4) antigen.

SEQ ID NO:38 is the amino acid sequence of the DPV antigen.

SEQ ID NO:39 is the nucleic acid sequence encoding the DPEP antigen with an N-terminal His Tag.

SEQ ID NO:40 is the amino acid sequence of the DPEP antigen with an N-terminal His Tag.

SEQ ID NO:41 is the nucleic acid sequence encoding the Erd14 (Mtb16) antigen.

SEQ ID NO:42 is the amino acid sequence of the Erd14 antigen.

SEQ ID NO:43 is the nucleic acid sequence encoding the DPPD antigen.

SEQ ID NO:44 is the amino acid sequence of the DPPD antigen.

SEQ ID NO:45 is the nucleic acid sequence encoding the ESAT-6 antigen.

SEQ ID NO:46 is the amino acid sequence of the ESAT-6 antigen.

SEQ ID NO:47 is the nucleic acid sequence encoding the Mtb82 (Mtb867) antigen.

SEQ ID NO:48 is the amino acid sequence of the Mtb82 antigen.

SEQ ID NO:49 is the nucleic acid sequence encoding the Mtb59 (Mtb403) antigen.

SEQ ID NO:50 is the amino acid sequence of the Mtb59 antigen.

SEQ ID NO:51 is the nucleic acid sequence encoding the TbF14 fusion protein.

SEQ ID NO:52 is the amino acid sequence of the TbF14 fusion protein.

SEQ ID NO:53 is the nucleic acid sequence encoding the TbF15 fusion protein.

SEQ ID NO:54 is the amino acid sequence of the TbF15 fusion protein.

SEQ ID NO:55 is the nucleic acid sequence of the fusion protein HTCC#1(FL)-TbH9(FL).

SEQ ID NO:56 is the amino acid sequence of the fusion protein HTCC#1 (FL)-TbH9(FL).

SEQ ID NO:57 is the nucleic acid sequence of the fusion protein HTCC#1(184-392)-TbH9-HTCC#1(1-129).

SEQ ID NO:58 is the predicted amino acid of the fusion protein HTCC#1(184-392)-TbH9-HTCC#1(1-129).

SEQ ID NO:59 is the nucleic acid sequence of the fusion protein HTCC#1(1-149)-TbH9-HTCC#1 (161-392).

SEQ ID NO:60 is the predicted amino acid sequence of the fusion protein HTCC#1(1-149)-TbH9-HTCC#1 (161-392).

SEQ ID NO:61 is the nucleic acid sequence of the fusion protein HTCC#1 (184-392)-TbH9-HTCC#1(1-200).

SEQ ID NO:62 is the predicted amino acid sequence of the fusion protein HTCC#1 (184-392)-TbH9-HTCC#1 (1-200).

SEQ ID NO:63 is the nucleic acid sequence of the TbRa12-HTCC#1 fusion protein.

SEQ ID NO:64 is the predicted amino acid sequence of the TbRa12-HTCC#1 fusion protein.

SEQ ID NO:65 is the nucleic acid sequence of the TbF (TbRa3, 38 kD, Tb38-1) fusion protein.

SEQ ID NO:66 is the predicted amino acid sequence of the TbF fusion protein.

SEQ ID NO:67 is the nucleic acid sequence of the TbF2 (TbRa3, 38 kD, Tb38-1, DPEP) fusion protein.

SEQ ID NO:68 is the predicted amino acid sequence of the TbF2 fusion protein.

SEQ ID NO:69 is the nucleic acid sequence of the TbF6 (TbRa3, 38 kD, Tb38-1, TbH4) fusion protein.

SEQ ID NO:70 is the predicted amino acid sequence of the TbF6 fusion protein.

SEQ ID NO:71 is the nucleic acid sequence of the TbF8 (38 kD-linker-DPEP) fusion protein.

SEQ ID NO:72 is the predicted amino acid sequence of the TbF8 fusion protein.

SEQ ID NO:73 is the nucleic acid sequence of the Mtb36F (Erd14-DPV-MTI) fusion protein.

SEQ ID NO:74 is the predicted amino acid sequence of the Mtb36F fusion protein.

SEQ ID NO:75 is the nucleic acid sequence of the Mtb88F (Erd14-DPV-MTI-MSL-MTCC#2) fusion protein.

SEQ ID NO:76 is the predicted amino acid sequence of the Mtb88F fusion protein.

SEQ ID NO:77 is the nucleic acid sequence of the Mtb46F (Erd14-DPV-MTI-MSL) fusion protein.

SEQ ID NO:78 is the predicted amino acid sequence of the Mtb46F fusion protein.

SEQ ID NO:79 is the nucleic acid sequence of the Mtb71F (DPV-MTI-MSL-MTCC#2) fusion protein.

SEQ ID NO:80 is the predicted amino acid sequence of the Mtb71F fusion protein.

SEQ ID NO:81 is the nucleic acid sequence of the Mtb31F (DPV-MTI-MSL) fusion protein.

SEQ ID NO:82 is the predicted amino acid sequence of the Mtb31F fusion protein.

SEQ ID NO:83 is the nucleic acid sequence of the Mtb61F (TbH9-DPV-MTI) fusion protein.

SEQ ID NO:84 is the predicted amino acid sequence of the Mtb61F fusion protein.

SEQ ID NO:85 is the nucleic acid sequence of the Ra12-DPPD (Mtb24F) fusion protein.

SEQ ID NO:86 is the predicted amino acid sequence of the Ra12-DPPD fusion protein.

SEQ ID NO:87 is the nucleic acid sequence of the Mtb72F (TbRa12-TbH9-TbRa35) fusion protein.

SEQ ID NO:88 is the predicted amino acid sequence of the Mtb72F fusion protein.

SEQ ID NO:89 is the nucleic acid sequence of the Mtb59F (TbH9-TbRa35) fusion protein.

SEQ ID NO:90 is the predicted amino acid sequence of the Mtb59F fusion protein.

SEQ ID NO:91 is the nucleic acid sequence of a vector encoding TbF14.

SEQ ID NO:92 is the nucleotide sequence of the region spanning nucleotides 5072 to 5095 of SEQ ID NO:91 encoding the eight amino acid His tag.

SEQ ID NO:93 is the nucleic acid sequence of a vector encoding TbF15.

SEQ ID NO:94-123 are the nucleic acid sequences of 30 overlapping peptides of HTCC#1 used for the T-cell epitope mapping.

SEQ ID NO:124-153 are the predicted amino acid sequences of 30 overlapping peptides of HTCC#1 used for the T-cell epitope mapping.

SEQ ID NO:154 is the amino acid sequence of the secreted form of DPPD.

SEQ ID NO: 155 is the nucleic acid sequence of the Mtb9.9A (MTI-A) open reading frame (ORF).

SEQ ID NO:156-171 are the predicted amino acid sequences of 16 overlapping peptides of Mtb9.9A (MTI-A) open reading frame (ORF).

SEQ ID NO:172-186 are the predicted amino acid sequences of 15 overlapping peptides of the Mtb9.8 open reading frame (ORF).

SEQ ID NO:187-204 are nucleic acid sequences of oligonucleotides used in amplification of different *Mycobacterium tuberculosis* nucleic acids.

DETAILED DESCRIPTION OF THE INVENTION

I. Introduction

The present invention relates to compositions comprising antigen compositions and fusion polypeptides useful for the diagnosis and treatment of *Mycobacterium* infection, polynucleotides encoding such antigens, and methods for their use. The antigens of the present invention are polypeptides or fusion polypeptides of *Mycobacterium* antigens and immunogenic fragments thereof. More specifically, the compositions of the present invention comprise at least two heterologous polypeptides of a *Mycobacterium* species of the tuberculosis complex, e.g., a species such as *M. tuberculosis, M. bovis*, or *M. africanum*, or a *Mycobacterium* species that is environmental or opportunistic and that causes opportunistic infections such as lung infections in immune compromised hosts (e.g., patients with AIDS), e.g., BCG, *M. avium, M. intracellulare, M. celatum, M. genavense, M. haemophilum, M. kansasii, M. simiae, M. vaccae, M. fortuitum*, and *M. scrofulaceum* (see, e.g., *Harrison's Principles of Internal Medicine*, volume 1, pp. 1004-1014 and 1019-1023 (14$^{th}$ ed., Fauci et al., eds., 1998). The inventors of the present application surprisingly discovered that compositions and fusion proteins comprising at least two heterologous *Mycobacterium* antigens, or immunogenic fragments thereof, where highly antigenic. These compositions, fusion polypeptides, and the nucleic acids that encode them are therefore useful for eliciting protective response in patients, and for diagnostic applications.

The antigens of the present invention may further comprise other components designed to enhance the antigenicity of the antigens or to improve these antigens in other aspects, for example, the isolation of these antigens through addition of a stretch of histidine residues at one end of the antigen. The compositions, fusion polypeptides, and nucleic acids of the invention can comprise additional copies of antigens, or additional heterologous polypeptides from *Mycobacterium* species, such as, e.g., Mtb81, Mo2, TbRa3, 38 kD (with the N-terminal cysteine residue), Tb38-1, FL TbH4, HTCC#1, TbH9, MTCC#2, MTI, MSL, TbRa35, DPV, DPEP, Erd14, TbRa12, DPPD, Mtb82, Mtb59, ESAT-6, Mtb85 complex, or α-crystalline. Such fusion polypeptides are also referred to as polyproteins. The compositions, fusion polypeptides, and nucleic acids of the invention can also comprise additional polypeptides from other sources. For example, the compositions and fusion proteins of the invention can include polypeptides or nucleic acids encoding polypeptides, wherein the polypeptide enhances expression of the antigen, e.g., NS1, an influenza virus protein, or an immunogenic portion thereof (see, e.g., WO99/40188 and WO93/04175). The nucleic acids of the invention can be engineered based on codon preference in a species of choice, e.g., humans.

The compositions of the invention can be naked DNA, or the compositions, e.g., polypeptides, can also comprise adjuvants such as, for example, AS2, AS2', AS2", AS4, AS6, ENHANZYN (Detox), MPL, QS21, CWS, TDM, AGPs, CPG, Leif, saponin, and saponin mimetics, and derivatives thereof.

In one aspect, the compositions and fusion proteins of the invention are composed of at least two antigens selected from the group consisting of an Mtb81 antigen or an immunogenic fragment thereof from a *Mycobacterium* species of the tuberculosis complex, and an Mo2 antigen or an immunogenic fragment thereof from a *Mycobacterium* species of the tuberculosis complex. In one embodiment, the compositions of the invention comprise the TbF14 fusion protein. The complete nucleotide sequence encoding TbF14 is set forth in SEQ ID NO:51, and the amino acid sequence of TbF14 is set forth in SEQ ID NO:52.

In another aspect, the compositions and fusion proteins of the invention are composed of at least four antigens selected from the group consisting of a TbRa3 antigen or an immunogenic fragment thereof from a *Mycobacterium* species of the tuberculosis complex, a 38 kD antigen or an immunogenic fragment thereof from a *Mycobacterium* species of the tuberculosis complex, a Tb38-1 antigen or an immunogenic fragment thereof from a *Mycobacterium* species of the tuberculosis complex, and a FL TbH4 antigen or an immunogenic fragment thereof from a *Mycobacterium* species of the tuberculosis complex. In one embodiment, the compositions of the invention comprise the TbF15 fusion protein. The nucleic acid and amino acid sequences of TbF15 are set forth in SEQ ID NO:53 and 54, respectively.

In another aspect, the compositions and fusion proteins of the invention are composed of at least two antigens selected from the group consisting of an HTCC#1 antigen or an immunogenic fragment thereof from a *Mycobacterium* species of the tuberculosis complex, and a TbH9 antigen or an immunogenic fragment thereof from a *Mycobacterium* species of the tuberculosis complex. In one embodiment, the compositions of the invention comprise the HTCC#1(FL)-TbH9(FL) fusion protein. The nucleic acid and amino acid sequences of HTCC#1-TbH9 are set forth in SEQ ID NO:55 and 56, respectively. In another embodiment, the compositions of the invention comprise the fusion protein HTCC#1(184-392)/TbH9/HTCC#1(1-129). The nucleic acid and amino acid sequences of HTCC#1(184-392)/TbH9/HTCC#1(1-129) are set forth in SEQ ID NO:57 and 58, respectively. In yet another embodiment, the compositions of the invention comprise the fusion protein HTCC#1(1-149)/TbH9/HTCC#1(161-392), having the nucleic acid and amino acid sequences set forth in SEQ ID NO:59 and 60, respectively. In still another embodiment, the compositions of the invention comprise the fusion protein HTCC# 1(184-392)/TbH9/HTCC#1(1-200), having the nucleic acid and amino acid sequences set forth in SEQ ID NO:61 and 62, respectively.

In a different aspect, the compositions and fusion proteins of the invention are composed of at least two antigens selected from the group consisting of an HTCC#1 antigen or an immunogenic fragment thereof from a *Mycobacterium* species of the tuberculosis complex, and a TbRa12 antigen or an immunogenic fragment thereof from a *Mycobacterium* species of the tuberculosis complex. In one embodiment, the compositions of the invention comprise the fusion protein TbRa12-HTCC#1. The nucleic acid and amino acid sequences of the TbRa12-HTCC#1 fusion protein are set forth in SEQ ID NO:63 and 64, respectively.

In yet another aspect, the compositions and fusion proteins of the invention are composed of at least two antigens selected from the group consisting of a TbH9 (MTB39) antigen or an immunogenic fragment thereof from a *Mycobacterium* species of the tuberculosis complex, and a TbRa35 (MTB32A) antigen or an immunogenic fragment thereof from a *Mycobacterium* species of the tuberculosis complex. In one embodiment, the antigens are selected from the group consisting of a TbH9 (MTB39) antigen or an immunogenic fragment thereof from a *Mycobacterium* species of the tuberculosis complex, and a polypeptide comprising at least 205 amino acids of the N-terminus of a TbRa35 (MTB32A) antigen from a *Mycobacterium* species of the tuberculosis complex. In another embodiment, the antigens are selected from the group consisting of a TbH9 (MTB39) antigen or an immunogenic fragment thereof from a *Mycobacterium* species of the tuberculosis complex, a polypeptide comprising at least 205 amino acids of the N-terminus of a TbRa35 (MTB32A) antigen from a *Mycobacterium* species of the tuberculosis complex, and a polypeptide comprising at least about 132 amino acids from the C-terminus of a TbRa35 (MTB32A) antigen from a *Mycobacterium* species of the tuberculosis complex.

In yet another embodiment, the compositions of the invention comprise the Mtb59F fusion protein. The nucleic acid and amino acid sequences of the Mtb59F fusion protein are set forth in SEQ ID NO:89 and 90, respectively, as well as in the U.S. patent application Ser. No. 09/287,849 (now U.S. Pat. No. 6,627,198) and in the PCT/US99/07717 application. In another embodiment, the compositions of the invention comprise the Mtb72F fusion protein having the nucleic acid and amino acid sequences set forth in SEQ ID NO:87 and 88, respectively. The Mtb72F fusion protein is also disclosed in the U.S. patent application Ser. No. 09/223,040 (now U.S. Pat. No. 6,544,522) and; in the PCT/US99/07717 application.

In yet another aspect, the compositions and fusion proteins of the invention comprise at least two antigens selected from the group consisting of Mtb81, Mo2, TbRa3, 38 kD, Tb38-1 (MTb11), FL TbH4, HTCC#1 (Mtb40), TbH9, MTCC#2 (Mtb41), DPEP, DPPD, TbRa35, TbRa12, Mtb59, Mtb82, Erd14 (Mtb16), FL TbRa35 (Mtb32A), DPV (Mtb8.4), MSL (Mtb9.8), MTI (Mtb9.9A, also known as MTI-A), ESAT-6, .alpha.-crystalline, and 85 complex, or an immunogenic fragment thereof from a *Mycobacterium* species of the tuberculosis complex.

In another aspect, the fusion proteins of the invention are:
TbRa3-38 kD-Tb38-1 (TbF), the sequence of which is disclosed in SEQ ID NO:65 (DNA) and SEQ ID NO:66 (protein), as well as in the U.S. patent application Ser. No. 08/818,112 (now U.S. Pat. No. 6,290,969); Ser. No. 08/818,111 now U.S. Pat. No. 6,338,852); and Ser. No. 09/056,556 (now U.S. Pat. No. 6,350,456); and in the WO98/16646 and WO98/16645 applications;

TbRa3-38 kD-Tb38-1-DPEP (TbF2), the sequence of which is disclosed in SEQ ID NO:67 (DNA) and SEQ ID NO:68 (protein), and in the U.S. patent application Ser. No. 08/942,578 (now abandoned); Ser. No. 08/942,341 (now abandoned); Ser. No. 09/056,556 (now U.S. Pat. No. 6,350,456); and in the WO98/16646 and WO98/16645 applications;

TbRa3-38 kD-Tb38-1-TBH4 (TbF6), the sequence of which is disclosed in SEQ ID NO:69 (DNA) and SEQ ID NO:70 (protein) in the U.S. patent application Ser. No. 08/072,967 (now U.S. Pat. No. 6,592,877); Ser. No. 09/072,596 (now U.S. Pat. No. 6,458,366); and in the PCT/US99/03268 and PCT/US99/03265 applications;

38 kD-Linker-DPEP (TbF8), the sequence of which is disclosed in SEQ ID NO:71 (DNA) and SEQ ID NO:72 (protein), and in the U.S. patent application Ser. No. 09/072,967 (now U.S. Pat. No. 6,592,877) and Ser. No. 09/072,596 (now U.S. Pat. No. 6,458,366); as well as in the PCT/US99/03268 and PCT/US99/03265 applications;

Erd14-DPV-MTI (FMtb36F), the sequence of which is disclosed in SEQ ID NO:73 (DNA), SEQ ID NO:74 (protein), as well as in the U.S. patent application Ser. No. 09/223,040 (now U.S. Pat. No. 6,544,522) and Ser. No. 09/287,849 (now U.S. Pat. No. 6,627,198); and in the PCT/US99/07717 application;

Erd14-DPV-MTI-MSL-MTCC#2 (Mtb88f), the sequence of which is disclosed in SEQ ID NO:75 (cDNA) and SEQ ID NO:76 (protein), as well as in the U.S. patent application Ser. No. 09/287,849 (now U.S. Pat. No. 6,627,198) and in the PCT/US99/07717 application;

Erd14-DPV-MTI-MSL (FMtb46F), the sequence of which is disclosed in SEQ ID NO:77 (cDNA) and SEQ ID NO:78 (protein), and in the U.S. patent application Ser. No. 09/287,849 (now U.S. Pat. No. 6,627,198) and in the PCT/US99/07717 application;

DPV-MTI-MSL-MTCC#2 (Mtb71F), the sequence of which is disclosed in SEQ ID NO:79 (cDNA) and SEQ ID NO:80 (protein), as well as in the U.S. patent application Ser. No. 09/287,849 (now U.S. Pat. No. 6,627,198) and in the PCT/US99/07717 application;

DPV-MTI-MSL (FMtb31F), the sequence of which is disclosed in SEQ ID NO:81 (cDNA) and SEQ ID NO:82 (protein), and in the U.S. patent application Ser. No. 09/287,849 (now U.S. Pat. No. 6,627,198) and in the PCT/US99/07717 application;

TbH9-DPV-MTI (FMtb61F), the sequence of which is disclosed in SEQ ID NO:83 (cDNA) and SEQ ID NO:84 (protein) (see, also, U.S. patent application Ser. No. 09/287,849 (now U.S. Pat. No. 6,627,198) and PCT/US99/07717 application);

Ra12-DPPD (MTb24F), the sequence of which is disclosed in SEQ ID NO:85 (cDNA) and SEQ ID NO:86 (protein), as well as in the U.S. patent application Ser. No. 09/287,849 (now U.S. Pat. No. 6,627,198) and in the PCT/US99/07717 application.

In the nomenclature of the application, TbRa35 refers to the N-terminus of MTB32A (TbRa35FL), comprising at least about the first 205 amino acids of MTB32A from *M. tuberculosis*, or the corresponding region from another *Mycobacterium* species. TbRa12 refers to the C-terminus of MTB32A (TbRa35FL), comprising at least about the last 132 amino acids from MTB32A from *M. tuberculosis*, or the corresponding region from another *Mycobacterium* species.

The following provides sequences of some individual antigens used in the compositions and fusion proteins of the invention:

Mtb81, the sequence of which is disclosed in SEQ ID NO:1 (DNA) and SEQ ID NO:2 (predicted amino acid).

Mo2, the sequence of which is disclosed in SEQ ID NO:3 (DNA) and SEQ ID NO:4 (predicted amino acid).

Tb38-1 or 38-1 (Mtb11), the sequence of which is disclosed in SEQ ID NO:9 (DNA) and SEQ ID NO:10 (predicted amino acid), and is also disclosed in the U.S. patent application Ser. No. 09/072,96 (now U.S. Pat. No. 6,592,877); Ser. No. 08/523,436; (now abandoned); Ser. No. 08/523,435 (now abandoned); Ser. No. 08/818,112 (now U.S. Pat. No. 6,290, 969); and Ser. No. 08/818,111 (now U.S. Pat. No. 6,338,852); and in the WO97/09428 and WO97/09429 applications;

TbRa3, the sequence of which is disclosed in SEQ ID NO:5 (DNA) and SEQ ID NO:6 (predicted amino acid sequence) (see, also, WO 97/09428 and WO97/09429 applications);

38 kD, the sequence of which is disclosed in SEQ ID NO:7 (DNA) and SEQ ID NO:8 (predicted amino acid sequence), as well as in the U.S. patent application Ser. No. 09/072,967 (now U.S. Pat. No. 6,592,877)—. 38 kD has two alternative forms, with and without the N-terminal cysteine residue;

DPEP, the sequence of which is disclosed in SEQ ID NO:39 (DNA) and SEQ ID NO:40 (predicted amino acid sequence), and in the WO97/09428 and WO97/09429 publications;

TbH4, the sequence of which is disclosed as SEQ ID NO:11 (DNA) and SEQ ID NO:12 (predicted amino acid sequence) (see, also, WO97/09428 and WO97/09429 publications);

Erd14 (Mtb16), the cDNA and amino acids sequences of which are disclosed in SEQ ID NO:41 (DNA) and 42 (predicted amino acid), and in Verbon et al., J. Bacteriology 174:1352-1359 (1992);

DPPD, the sequence of which is disclosed in SEQ ID NO:43 (DNA) and SEQ ID NO:44 (predicted amino acid sequence), and in the PCT/US99/03268 and PCT/US99/03265 applications. The secreted form of DPPD is shown herein in FIG. 12;

Mtb82 (Mtb867), the sequence of which is disclosed in SEQ ID NO:47 (DNA) and SEQ ID NO:48 (predicted amino acid sequence), and in FIGS. 8 (DNA) and 9 (amino acid);

Mtb59 (Mtb403), the sequence of which is disclosed in SEQ ID NO:49 (DNA) and SEQ ID NO:50 (predicted amino acid sequence), and in FIGS. 10 (DNA) and 11 (amino acid);

TbRa35FL (Mtb32A), the sequence of which is disclosed as SEQ ID NO:29 (cDNA) and SEQ ID NO:30 (protein), and in the U.S. patent application Ser. No. 08/523,436 (now abandoned), Ser. No. 08/523,435 (now abandoned); Ser. No. 08/658,800 (now (now U.S. Pat. No. abandoned); Ser. No. 08/659,683 (now abandoned); Ser. No. 08/818,112 (now U.S. Pat. No. 6,290,969); Ser. No. 09/056,556 (now U.S. Pat. No. 6,350,456); and Ser. No. 08/818,111 (now U.S. Pat. No. 6,338,852); as well as in the WO97/09428 and WO97/09429 applications; see also Skeiky et al., Infection and Immunity 67:3998-4007 (1999);

TbRa12, the C-terminus of Mtb32A (TbRa35FL), comprising at least about the last 132 amino acids from Mtb32A from *M. tuberculosis*, the sequence of which is disclosed as SEQ ID NO:27 (DNA) and SEQ ID NO:28 (predicted amino acid sequence) (see, also, U.S. patent application Ser. No. 09/072,967 (now U.S. Pat. No. 6,592,877); and WO97/09428 and WO97/09429 publications);

TbRa35, the N-terminus of Mtb32A (TbRa35FL), comprising at least about the first 205 amino acids of Mtb32A from *M. tuberculosis*, the nucleotide and amino acid sequence of which is disclosed in FIG. 4;

TbH9 (Mtb39), the sequence of which is disclosed in SEQ ID NO:25 (cDNA full length) and SEQ ID NO:26 (protein full length), as well as in the U.S. patent application Ser. No. 08/658,800 (now abandoned); Ser. No. 08/659,683 (now abandoned); Ser. No. 08/818,112 (now U.S. Pat. No. 6,290, 969); Ser. No. 08/818,111 (now U.S. Pat. No. 6,338,852); and Ser. No. 09/056,556 (now U.S. Pat. No. 6,350,456); and in the WO97/09428 and WO97/09429 applications.

HTCC#1 (Mtb40), the sequence of which is disclosed in SEQ ID NO:13 (DNA) and SEQ ID NO:14 (amino acid), as well as in the U.S. patent application Ser. No. 09/073,010 (now U.S. Pat. No. 6,613,881); and Ser. No. 09/073,009 (now U.S. Pat. No. 6,555,653); and in the PCT/US98/10407 and PCT/US98/10514 applications;

MTCC#2 (MTB41), the sequence of which is disclosed in SEQ ID NO:31 (DNA) and SEQ ID NO:32 (amino acid), as well as in the U.S. patent application Ser. No. 09/073,010 (now U.S. Pat. No. 6,613,881); and Ser. No. 09/073,009 (now U.S. Pat. No. 6,555,653); and in the WO98/53075 and WO98/53076 publications;

MTI (Mtb9.9A), the sequence of which is disclosed in SEQ ID NO:33 (DNA) and SEQ ID NO:34 (amino acid), as well as in the U.S. patent application Ser. Nos. 09/073,010 (now U.S. Pat. No. 6,613,881); and 09/073,009 (now U.S. Pat. No. 6,555,653); and in the WO98/53075 and WO98/53076 publications;

MSL (Mtb9.8), the sequence of which is disclosed in SEQ ID NO:35 (DNA) and SEQ ID NO:36 (amino acid), as well as in the U.S. patent application Ser. Nos. 09/073,010 (now U.S. Pat. No. 6,613,881); and 09/073,009 (now U.S. Pat. No. 6,555,653); and in the WO98/53075 and WO98/53076 publications;

DPV (Mtb8.4), the sequence of which is disclosed in SEQ ID NO:37 (DNA) and SEQ ID NO:38 (amino acid), and in the U.S. patent application Ser. Nos. 08/658,800 (now abandoned); 08/659,683 (now abandoned); 08/818,111 (now U.S. Pat. No. 6,338,852); 08/818,112 (now U.S. Pat. No. 6,290, 969); as well as in the WO97/09428 and WO97/09429 publications;

ESAT-6 (Mtb8.4), the sequence of which is disclosed in SEQ ID NO:45 (DNA) and SEQ ID NO:46 (amino acid), and in the U.S. patent application Ser. No. 08/658,800 (now abandoned); Ser. No. 08/659,683 (now abandoned); Ser. No. 08/818,111 (now U.S. Pat. No. 6,338,852); Ser. No. 08/818, 112 (now U.S. Pat. No. 6,290,969); as well as in the WO97/09428 and WO97/09429 publications;

The following provides sequences of some additional antigens used in the compositions and fusion proteins of the invention:

α-crystalline antigen, the sequence of which is disclosed in Verbon et al., *J. Bact.* 174:1352-1359 (1992);

85 complex antigen, the sequence of which is disclosed in Content et al., *Infect.& Immunol.* 59:3205-3212 (1991).

Each of the above sequences is also disclosed in Cole et al. Nature 393:537 (1998).

The above sequences are disclosed in U.S. patent applications No. 08/523,435 (now abandoned); Ser. No. 08/523,436 (now abandoned); Ser. No. 08/658,800 (now abandoned); Ser. No. 08/659,683 (now abandoned); Ser. No. 08/818,111 (now U.S. Pat. No. 6,338,852); Ser. No. 08/818,112 (now U.S. Pat. No. 6,290,969); Ser. No. 08/942,341 (now abandoned); Ser. No. 08/942,578 (now abandoned); Ser. No. 08/858,998 (now abandoned); Ser. No. 08/859,381 (now abandoned); Ser. No. 09/056,556 (now U.S. Pat. No. 6,350,456); Ser. No. 09/072,596 (now U.S. Pat. No. 6,458,366); Ser. No. 09/072,967 (now U.S. Pat. No. 6,592,877); Ser. No. 09/073,009 (now U.S. Pat. No. 6,555,653); Ser. No. 09/073,010 (now U.S. Pat. No. 6,613,881); Ser. No. 09/223,040 (now U.S. Pat. No. 6,544,522); Ser. No. 09/287,849 (now U.S. Pat. No. 6,627,198); and in PCT patent applications PCT/US99/03265, PCT/US99/03268; PCT/US99/07717; WO97/09428; WO97/09429; WO98/16645; WO98/16646; WO98/53075; and WO98/53076, each of which is herein incorporated by reference.

The antigens described herein include polymorphic variants and conservatively modified variations, as well as interstrain and interspecies *Mycobacterium* homologs. In addition, the antigens described herein include subsequences or truncated sequences. The fusion proteins may also contain additional polypeptides, optionally heterologous peptides from *Mycobacterium* or other sources. These antigens may be modified, for example, by adding linker peptide sequences as described below. These linker peptides may be inserted between one or more polypeptides which make up each of the fusion proteins.

II. Definitions

"Fusion polypeptide" or "fusion protein" refers to a protein having at least two heterologous *Mycobacterium* sp. polypeptides covalently linked, either directly or via an amino acid linker. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order. This term also refers to conservatively modified variants, polymorphic variants, alleles, mutants, subsequences, and interspecies homologs of the antigens that make up the fusion protein. *Mycobacterium tuberculosis* antigens are described in Cole et al., Nature 393:537 (1998), which discloses the entire *Mycobacterium tuberculosis* genome. Antigens from other *Mycobacterium* species that correspond to *M. tuberculosis* antigens can be identified, e.g., using sequence comparison algorithms, as described herein, or other methods known to those of skill in the art, e.g., hybridization assays and antibody binding assays.

The term "TbF14" refers to a fusion protein having at least two antigenic, heterologous polypeptides from *Mycobacterium* fused together. The two peptides are referred to as Mtb81 and Mo2. This term also refers to a fusion protein having polymorphic variants, alleles, mutants, fragments, and interspecies homologs of Mtb81 and Mo2. A nucleic acid encoding TbF14 specifically hybridizes under highly stringent hybridization conditions to SEQ ID NO:1 and 3, which individually encode the Mtb81 and Mo2 antigens, respectively, and alleles, polymorphic variants, interspecies homologs, subsequences, and conservatively modified variants thereof. A TbF14 fusion polypeptide specifically binds to antibodies raised against Mtb81 and Mo2, and alleles, polymorphic variants, interspecies homologs, subsequences, and conservatively modified variants thereof (optionally including an amino acid linker). The antibodies are polyclonal or monoclonal. Optionally, the TbF14 fusion polypeptide specifically binds to antibodies raised against the fusion junction of Mtb81 and Mo2, which antibodies do not bind to Mtb81 or Mo2 individually, i.e., when they are not part of a fusion protein. The individual polypeptides of the fusion protein can be in any order. In some embodiments, the individual polypeptides are in order (N- to C-terminus) from large to small. Large antigens are approximately 30 to 150 kD in size, medium antigens are approximately 10 to 30 kD in size, and small antigens are approximately less than 10 kD in size. The sequence encoding the individual polypeptide may be, e.g., a fragment such as an individual CTL epitope encoding about 8 to 9 amino acids. The fragment may also include multiple epitopes. The fragment may also represent a larger part of the antigen sequence, e.g., about 50% or more of Mtb81 and Mo2.

TbF14 optionally comprises additional polypeptides, optionally heterologous polypeptides, fused to Mtb81 and Mo2, optionally derived from *Mycobacterium* as well as other sources, such as viral, bacterial, eukaryotic, invertebrate, vertebrate, and mammalian sources. As described herein, the fusion protein can also be linked to other molecules, including additional polypeptides.

The term "TbF15" refers to a fusion protein having at least four antigenic, heterologous polypeptides from *Mycobacterium* fused together. The four peptides are referred to as TbRa3, 38 kD, Tb38-1 (with the N-terminal cysteine), and FL TbH4. This term also refers to a fusion protein having polymorphic variants, alleles, mutants, and interspecies homologs of TbRa3, 38 kD, Tb38-1, and FL TbH4. A nucleic acid encoding TbF15 specifically hybridizes under highly stringent hybridization conditions to SEQ ID NO:5, 7, 9 and 11, individually encoding TbRa3, 38 kD, Tb38-1 and FL TbH4, respectively, and alleles, fragments, polymorphic variants, interspecies homologs, subsequences, and conservatively modified variants thereof. A TbF15 fusion polypeptide specifically binds to antibodies raised against TbRa3, 38 kD, Tb38-1, and FL TbH4 and alleles, polymorphic variants, interspecies homologs, subsequences, and conservatively modified variants thereof (optionally including an amino acid linker). The antibodies are polyclonal or monoclonal. Optionally, the TbF15 fusion polypeptide specifically binds to antibodies raised against the fusion junction of TbRa3, 38 kD, Tb38-1, and FL TbH4, which antibodies do not bind to TbRa3, 38 kD, Tb38-1, and FL TbH4 individually, i.e., when they are not part of a fusion protein. The polypeptides of the fusion protein can be in any order. In some embodiments, the individual polypeptides are in order (N- to C-terminus) from large to small. Large antigens are approximately 30 to 150 kD in size, medium antigens are approximately 10 to 30 kD in size, and small antigens are approximately less than 10 kD in size. The sequence encoding the individual polypeptide may be as small as, e.g., a fragment such as an individual CTL epitope encoding about 8 to 9 amino acids. The fragment may also include multiple epitopes. The fragment may also represent a larger part of the antigen sequence, e.g., about 50% or more of TbRa3, 38 kD, Tb38-1, and FL TbH4.

TbF15 optionally comprises additional polypeptides, optionally heterologous polypeptides, fused to TbRa3, 38 kD, Tb38-1, and FL TbH4, optionally derived from *Mycobacterium* as well as other sources such as viral, bacterial, eukaryotic, invertebrate, vertebrate, and mammalian sources. As described herein, the fusion protein can also be linked to other molecules, including additional polypeptides. The compositions of the invention can also comprise additional polypeptides that are unlinked to the fusion proteins of the invention. These additional polypeptides may be heterologous or homologous polypeptides.

The "HTCC# 1 (FL)-TbH9(FL)," "HTCC#1 (184-392)/TbH9/HTCC#1 (1-129)," "HTCC#1 (1-149)/TbH9/HTCC#1 (161-392)," and "HTCC#1 (184-392)/TbH9/

HTCC#1 (1-200)" fusion proteins refer to fusion proteins comprising at least two antigenic, heterologous polypeptides from *Mycobacterium* fused together. The two peptides are referred to as HTCC#1 and TbH9. This term also refers to fusion proteins having polymorphic variants, alleles, mutants, and interspecies homologs of HTCC#1 and TbH9. A nucleic acid encoding HTCC#1-TbH9, HTCC#1(184-392)/TbH9/HTCC#1(1-129), HTCC#(1-149)/TbH9/HTCC#1 (161-392), or HTCC#1 (184-392)/TbH9/HTCC#1 (1-200) specifically hybridizes under highly stringent hybridization conditions to SEQ ID NO:13 and 25, individually encoding HTCC#1 and TbH9, respectively, and alleles, fragments, polymorphic variants, interspecies homologs, subsequences, and conservatively modified variants thereof. A HTCC#1 (FL)-TbH9(FL), HTCC#1 (184-392)/TbH9/HTCC#1 (1-129), HTCC#1 (1-149)/TbH9/HTCC#1 (161-392), or HTCC#1 (184-392)/TbH9/HTCC#1 (1-200) fusion polypeptide specifically binds to antibodies raised against HTCC#1 and TbH9, and alleles, polymorphic variants, interspecies homologs, subsequences, and conservatively modified variants thereof (optionally including an amino acid linker). The antibodies are polyclonal or monoclonal. Optionally, the HTCC#1(FL)-TbH9(FL), HTCC#1(184-392)/TbH9/HTCC#1(1-129), HTCC#1(1-149)/TbH9/HTCC#1(161-392), or HTCC#1(184-392)/TbH9/HTCC#1(1-200) fusion polypeptide specifically binds to antibodies raised against the fusion junction of the antigens, which antibodies do not bind to the antigens individually, i.e., when they are not part of a fusion protein. The polypeptides of the fusion protein can be in any order. In some embodiments, the individual polypeptides are in order (N- to C-terminus) from large to small. Large antigens are approximately 30 to 150 kD in size, medium antigens are approximately 10 to 30 kD in size, and small antigens are approximately less than 10 kD in size. The sequence encoding the individual polypeptide may be as small as, e.g., a fragment such as an individual CTL epitope encoding about 8 to 9 amino acids. The fragment may also include multiple epitopes. The fragment may also represent a larger part of the antigen sequence, e.g., about 50% or more (e.g., full-length) of HTCC#1 and TbH9.

HTCC#1 (FL)-TbH9(FL), HTCC#1(184-392)/TbH9/HTCC#1(1-129), HTCC#1(1-149)/TbH9/HTCC#1(161-392), and HTCC#1(184-392)/TbH9/HTCC#1(1-200) optionally comprise additional polypeptides, optionally heterologous polypeptides, fused to HTCC#1 and TbH9, optionally derived from *Mycobacterium* as well as other sources such as viral, bacterial, eukaryotic, invertebrate, vertebrate, and mammalian sources. As described herein, the fusion protein can also be linked to other molecules, including additional polypeptides. The compositions of the invention can also comprise additional polypeptides that are unlinked to the fusion proteins of the invention. These additional polypeptides may be heterologous or homologous polypeptides.

The term "TbRa12-HTCC#1" refers to a fusion protein having at least two antigenic, heterologous polypeptides from *Mycobacterium* fused together. The two peptides are referred to as TbRa12 and HTCC#1. This term also refers to a fusion protein having polymorphic variants, alleles, mutants, and interspecies homologs of TbRa12 and HTCC#1. A nucleic acid encoding "TbRa12-HTCC#1" specifically hybridizes under highly stringent hybridization conditions to SEQ ID NO:27 and 13, individually encoding TbRa12 and HTCC#1, respectively, and alleles, fragments, polymorphic variants, interspecies homologs, subsequences, and conservatively modified variants thereof. A "TbRa12-HTCC#1" fusion polypeptide specifically binds to antibodies raised against TbRa12 and HTCC#1 and alleles, polymorphic variants, interspecies homologs, subsequences, and conservatively modified variants thereof (optionally including an amino acid linker). The antibodies are polyclonal or monoclonal. Optionally, the "TbRa12-HTCC#1" fusion polypeptide specifically binds to antibodies raised against the fusion junction of TbRa12 and HTCC#1, which antibodies do not bind to TbRa12 and HTCC#1 individually, i.e., when they are not part of a fusion protein. The polypeptides of the fusion protein can be in any order. In some embodiments, the individual polypeptides are in order (N- to C-terminus) from large to small. Large antigens are approximately 30 to 150 kD in size, medium antigens are approximately 10 to 30 kD in size, and small antigens are approximately less than 10 kD in size. The sequence encoding the individual polypeptide may be as small as, e.g., a fragment such as an individual CTL epitope encoding about 8 to 9 amino acids. The fragment may also include multiple epitopes. The fragment may also represent a larger part of the antigen sequence, e.g., about 50% or more of TbRa12 and HTCC#1.

"TbRa12-HTCC#1" optionally comprises additional polypeptides, optionally heterologous polypeptides, fused to TbRa12 and HTCC#1, optionally derived from *Mycobacterium* as well as other sources such as viral, bacterial, eukaryotic, invertebrate, vertebrate, and mammalian sources. As described herein, the fusion protein can also be linked to other molecules, including additional polypeptides. The compositions of the invention can also comprise additional polypeptides that are unlinked to the fusion proteins of the invention. These additional polypeptides may be heterologous or homologous polypeptides.

The term "Mtb72F" and "Mtb59F" refer to fusion proteins of the invention which hybridize under stringent conditions to at least two nucleotide sequences set forth in SEQ ID NO:25 and 29, individually encoding the TbH9 (MTB39) and Ra35 (MTB32A) antigens. The polynucleotide sequences encoding the individual antigens of the fusion polypeptides therefore include conservatively modified variants, polymorphic variants, alleles, mutants, subsequences, and interspecies homologs of TbH9 (MTB39) and Ra35 (MTB32A). The polynucleotide sequence encoding the individual polypeptides of the fusion proteins can be in any order. In some embodiments, the individual polypeptides are in order (N- to C-terminus) from large to small. Large antigens are approximately 30 to 150 kD in size, medium antigens are approximately 10 to 30 kD in size, and small antigens are approximately less than 10 kD in size. The sequence encoding the individual polypeptide may be as small as, e.g., a fragment such as an individual CTL epitope encoding about 8 to 9 amino acids. The fragment may also include multiple epitopes. The fragment may also represent a larger part of the antigen sequence, e.g., about 50% or more of TbH9 (MTB39) and Ra35 (MTB32A), e.g., the N- and C-terminal portions of Ra35 (MTB32A).

An "Mtb72F" or "Mtb59F" fusion polypeptide of the invention specifically binds to antibodies raised against at least two antigen polypeptides, wherein each antigen polypeptide is selected from the group consisting of TbH9 (MTB39) and Ra35 (MTB32A). The antibodies can be polyclonal or monoclonal. Optionally, the fusion polypeptide specifically binds to antibodies raised against the fusion junction of the antigens, which antibodies do not bind to the antigens individually, i.e., when they are not part of a fusion protein. The fusion polypeptides optionally comprise additional polypeptides, e.g., three, four, five, six, or more polypeptides, up to about 25 polypeptides, optionally heterologous polypeptides or repeated homologous polypeptides, fused to the at least two heterologous antigens. The additional polypeptides of the fusion protein are optionally derived from *Mycobacterium* as well as other sources, such as other bacterial, viral, or invertebrate, vertebrate, or mammalian sources. The individual polypeptides of the fusion protein can be in any order. As described herein, the fusion protein can also be linked to other molecules, including additional polypeptides. The compositions of the invention can also comprise additional polypeptides that are unlinked to the fusion proteins of the invention. These additional polypeptides may be heterologous or homologous polypeptides.

A polynucleotide sequence comprising a fusion protein of the invention hybridizes under stringent conditions to at least two nucleotide sequences, each encoding an antigen polypeptide selected from the group consisting of Mtb81, Mo2, TbRa3, 38 kD, Tb38-1, TbH4, HTCC#1, TbH9, MTCC#2, MTI, MSL, TbRa35, DPV, DPEP, Erd14, TbRa12, DPPD, ESAT-6, Mtb82, Mtb59, Mtb85 complex, and α-crystalline. The polynucleotide sequences encoding the individual antigens of the fusion polypeptide therefore include conservatively modified variants, polymorphic variants, alleles, mutants, subsequences, and interspecies homologs of Mtb81, Mo2, TbRa3, 38 kD, Tb38-1, TbH4, HTCC#1, TbH9, MTCC#2, MTI, MSL, TbRa35, DPV, DPEP, Erd14, TbRa12, DPPD, ESAT-6, Mtb82, Mtb59, Mtb85 complex, and α-crystalline. The polynucleotide sequence encoding the individual polypeptides of the fusion protein can be in any order. In some embodiments, the individual polypeptides are in order (N- to C-terminus) from large to small. Large antigens are approximately 30 to 150 kD in size, medium antigens are approximately 10 to 30 kD in size, and small antigens are approximately less than 10 kD in size. The sequence encoding the individual polypeptide may be as small as, e.g., a fragment such as an individual CTL epitope encoding about 8 to 9 amino acids. The fragment may also include multiple epitopes. The fragment may also represent a larger part of the antigen sequence, e.g., about 50% or more of Mtb81, Mo2, TbRa3, 38 kD, Tb38-1, TbH4, HTCC#1, TbH9, MTCC#2, MTI, MSL, TbRa35, DPV, DPEP, Erd14, TbRa12, DPPD, ESAT-6, MTb82, MTb59, Mtb85 complex, and α-crystalline.

A fusion polypeptide of the invention specifically binds to antibodies raised against at least two antigen polypeptides, wherein each antigen polypeptide is selected from the group consisting of Mtb81, Mo2, TbRa3, 38 kD, Tb38-1, TbH4, HTCC#1, TbH9, MTCC#2, MTI, MSL, TbRa35, DPV, DPEP, Erd14, TbRa12, DPPD, ESAT-6, Mtb82, Mtb59, Mtb85 complex, and α-crystalline. The antibodies can be polyclonal or monoclonal. Optionally, the fusion polypeptide specifically binds to antibodies raised against the fusion junction of the antigens, which antibodies do not bind to the antigens individually, i.e., when they are not part of a fusion protein. The fusion polypeptides optionally comprise additional polypeptides, e.g., three, four, five, six, or more polypeptides, up to about 25 polypeptides, optionally heterologous polypeptides or repeated homologous polypeptides, fused to the at least two heterologous antigens. The additional polypeptides of the fusion protein are optionally derived from *Mycobacterium* as well as other sources, such as other bacterial, viral, or invertebrate, vertebrate, or mammalian sources. The individual polypeptides of the fusion protein can be in any order. As described herein, the fusion protein can also be linked to other molecules, including additional polypeptides. The compositions of the invention can also comprise additional polypeptides that are unlinked to the fusion proteins of the invention. These additional polypeptides may be heterologous or homologous polypeptides.

The term "fused" refers to the covalent linkage between two polypeptides in a fusion protein. The polypeptides are typically joined via a peptide bond, either directly to each other or via an amino acid linker. Optionally, the peptides can be joined via non-peptide covalent linkages known to those of skill in the art.

"FL" refers to full-length, i.e., a polypeptide that is the same length as the wild-type polypeptide.

The term "immunogenic fragment thereof" refers to a polypeptide comprising an epitope that is recognized by cytotoxic T lymphocytes, helper T lymphocytes or B cells.

The term "*Mycobacterium* species of the tuberculosis complex" includes those species traditionally considered as causing the disease tuberculosis, as well as *Mycobacterium* environmental and opportunistic species that cause tuberculosis and lung disease in immune compromised patients, such as patients with AIDS, e.g., *M. tuberculosis, M. bovis*, or *M. africanum*, BCG, *M. avium, M. intracellulare, M. celatum, M. genavense, M. haemophilum, M. kansasii, M. simiae, M. vaccae, M. fortuitum*, and *M. scrofulaceum* (see, e.g., *Harrison's Principles of Internal Medicine*, volume 1, pp. 1004-1014 and 1019-1023 (14$^{th}$ ed., Fauci et al., eds., 1998).

An adjuvant refers to the components in a vaccine or therapeutic composition that increase the specific immune response to the antigen (see, e.g., Edelman, *AIDS Res. Hum Retroviruses* 8:1409-1411 (1992)). Adjuvants induce immune responses of the Th1-type and Th-2 type response. Th1-type cytokines (e.g., IFN-γ, IL-2, and IL-12) tend to favor the induction of cell-mediated immune response to an administered antigen, while Th-2 type cytokines (e.g., IL-4, IL-5, IL-6, IL-10 and TNF-β) tend to favor the induction of humoral immune responses.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology-Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$—$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of monoclonal or polyclonal antibodies, any technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy* (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)).

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to fusion proteins can be selected to obtain only those polyclonal antibodies that are specifically immunoreactive with fusion protein and not with individual components of the fusion proteins. This selection may be achieved by subtracting out antibodies that cross-react with the individual antigens. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

Polynucleotides may comprise a native sequence (i.e., an endogenous sequence that encodes an individual antigen or a portion thereof) or may comprise a variant of such a sequence. Polynucleotide variants may contain one or more substitutions, additions, deletions and/or insertions such that the biological activity of the encoded fusion polypeptide is not diminished, relative to a fusion polypeptide comprising native antigens. Variants preferably exhibit at least about 70% identity, more preferably at least about 80% identity and most preferably at least about 90% identity to a polynucleotide sequence that encodes a native polypeptide or a portion thereof.

The terms "identical" or percent "identity," in the context of two or more nucleic acids or polypeptide sequences, refer to two or more sequences or subsequences that are the same or have a specified percentage of amino acid residues or nucleotides that are the same (i.e., 70% identity, optionally 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Optionally, the identity exists over a region that is at least about 25 to about 50 amino acids or nucleotides in length, or optionally over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 25 to 500, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395 (1984).

Another example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

III. Polynucleotide Compositions

As used herein, the terms "DNA segment" and "polynucleotide" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the DNA segments of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

"Isolated," as used herein, means that a polynucleotide is substantially away from other coding sequences, and that the DNA segment does not contain large portions of unrelated coding DNA, such as large chromosomal fragments or other functional genes or polypeptide coding regions. Of course, this refers to the DNA segment as originally isolated, and does not exclude genes or coding regions later added to the segment by the hand of man.

As will be recognized by the skilled artisan, polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a *Mycobacterium* antigen or a portion thereof) or may comprise a variant, or a biological or antigenic functional equivalent of such a sequence. Polynucleotide variants may contain one or more substitutions, additions, deletions and/or insertions, as further described below, preferably such that the immunogenicity of the encoded polypeptide is not diminished, relative to a native tumor protein. The effect on the immunogenicity of the encoded polypeptide may generally be assessed as described herein. The term "variants" also encompasses homologous genes of xenogenic origin.

In additional embodiments, the present invention provides isolated polynucleotides and polypeptides comprising various lengths of contiguous stretches of sequence identical to or complementary to one or more of the sequences disclosed herein. For example, polynucleotides are provided by this invention that comprise at least about 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000; and the like.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative DNA segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

Moreover, it will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention, for example polynucleotides that are optimized for human and/or primate codon selection. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

IV. Polynucleotide Identification and Characterization

Polynucleotides may be identified, prepared and/or manipulated using any of a variety of well established techniques. For example, a polynucleotide may be identified, as described in more detail below, by screening a microarray of cDNAs for tumor-associated expression (i.e., expression that is at least two fold greater in a tumor than in normal tissue, as determined using a representative assay provided herein). Such screens may be performed, for example, using a Synteni microarray (Palo Alto, Calif.) according to the manufacturer's instructions (and essentially as described by Schena et al., *Proc. Natl. Acad. Sci. USA* 93:10614-10619 (1996) and Heller et al., *Proc. Natl. Acad. Sci. USA* 94:2150-2155 (1997)). Alternatively, polynucleotides may be amplified from cDNA prepared from cells expressing the proteins described herein, such as *M. tuberculosis* cells. Such polynucleotides may be amplified via polymerase chain reaction (PCR). For this approach, sequence-specific primers may be designed based on the sequences provided herein, and may be purchased or synthesized.

An amplified portion of a polynucleotide of the present invention may be used to isolate a full length gene from a suitable library (e.g., a *M. tuberculosis* cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then generally screened by hybridizing filters containing denatured bacterial colonies (or lawns containing phage plaques) with the labeled probe (see Sambrook et al., *Molecular Cloning. A Laboratory Manual* (1989)). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences can then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22-30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186 (1988)), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1:111-19 (1991)) and walking PCR (Parker et al., *Nucl. Acids. Res.* 19:3055-60 (1991)). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

V. Polynucleotide Expression in Host Cells

In other embodiments of the invention, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognized by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesized, in whole or in part, using chemical methods well known in the art (see Caruthers, M. H. et al., *Nucl. Acids Res. Symp. Ser. pp.* 215-223 (1980), Horn et al., *Nucl. Acids Res. Symp. Ser. pp.* 225-232 (1980)). Alternatively, the protein itself may be produced using chemical methods to synthesize the amino acid sequence of a polypeptide, or a portion thereof. For example, peptide synthesis can be performed using various solid-phase techniques (Roberge et al., *Science* 269:202-204 (1995)) and automated synthesis may be achieved, for example, using the ABI 431A Peptide Synthesizer (Perkin Elmer, Palo Alto, Calif.).

A newly synthesized peptide may be substantially purified by preparative high performance liquid chromatography (e.g., Creighton, *Proteins, Structures and Molecular Principles* (1983)) or other comparable techniques available in the art. The composition of the synthetic peptides may be confirmed by amino acid analysis or sequencing (e.g., the Edman degradation procedure). Additionally, the amino acid sequence of a polypeptide, or any part thereof, may be altered during direct synthesis and/or combined using chemical methods with sequences from other proteins, or any part thereof, to produce a variant polypeptide.

In order to express a desired polypeptide, the nucleotide sequences encoding the polypeptide, or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., *Molecular Cloning, A Laboratory Manual* (1989), and Ausubel et al., *Current Protocols in Molecular Biology* (1989).

A variety of expression vector/host systems may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector-enhancers, promoters, 5' and 3' untranslated regions-which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of β-galactosidase so that a hybrid protein is produced; pIN vectors (Van Heeke &Schuster, *J. Biol. Chem.* 264:5503-5509 (1989)); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al., *Methods Enzymol.* 153:516-544 (1987).

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, *EMBO J.* 6:307-311 (1987)). Alternatively, plant promoters such as the small subunit of RUBISCO or heat shock promoters may be used (Coruzzi et al., *EMBO J.* 3:1671-1680 (1984); Broglie et al., *Science* 224:838-843 (1984); and Winter et al., *Results Probl. Cell Differ.* 17:85-105 (1991)). These constructs can be introduced into plant cells by direct DNA transformation or pathogen-mediated transfection. Such techniques are described in a number of generally available reviews (see, e.g., Hobbs in *McGraw Hill Yearbook of Science and Technology* pp. 191-196 (1992)).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia larvae*. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia larvae* in which the polypeptide of interest may be expressed (Engelhard et al., *Proc. Natl. Acad. Sci. U.S.A.* 91:3224-3227 (1994)).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan & Shenk, *Proc. Natl. Acad. Sci. U.S.A.* 81:3655-3659 (1984)). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf. et al., *Results Probl. Cell Differ.* 20:125-162 (1994)).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler et al., Cell 11:223-32 (1977)) and adenine phosphoribosyltransferase (Lowy et al., Cell 22:817-23 (1990)) genes which can be employed in tk⁻ or aprt⁻ cells, respectively. Also, antimetabolite, antibiotic or herbicide resistance can be used as the basis for selection; for example, dhfr which confers resistance to methotrexate (Wigler et al., Proc. Natl. Acad. Sci. U.S.A. 77:3567-70 (1980)); npt, which confers resistance to the aminoglycosides, neomycin and G-418 (Colbere-Garapin et al., J. Mol. Biol. 150:1-14 (1981)); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman & Mulligan, Proc. Natl. Acad. Sci. U.S.A. 85:8047-51 (1988)). Recently, the use of visible markers has gained popularity with such markers as anthocyanins, β-glucuronidase and its substrate GUS, and luciferase and its substrate luciferin, being widely used not only to identify transformants, but also to quantify the amount of transient or stable protein expression attributable to a specific vector system (Rhodes et al., Methods Mol. Biol. 55:121-131 (1995)).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells which contain and express a desired polynucleotide sequence may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton et al., *Serological Methods, a Laboratory Manual* (1990) and Maddox et al., *J. Exp. Med.* 158:1211-1216 (1983).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath et al., *Prot. Exp. Purif.* 3:263-281 (1992) while the enterokinase cleavage site provides a means for purifying the desired polypeptide from the fusion protein. A discussion of vectors which contain fusion proteins is provided in Kroll et al., *DNA Cell Biol.* 12:441-453 (1993).

In addition to recombinant production methods, polypeptides of the invention, and fragments thereof, may be produced by direct peptide synthesis using solid-phase techniques (Merrifield, *J. Am. Chem. Soc.* 85:2149-2154 (1963)). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

VI. In Vivo Polynucleotide Delivery Techniques

In additional embodiments, genetic constructs comprising one or more of the polynucleotides of the invention are introduced into cells in vivo. This may be achieved using any of a variety or well known approaches, several of which are outlined below for the purpose of illustration.

1. Adenovirus

One of the preferred methods for in vivo delivery of one or more nucleic acid sequences involves the use of an adenovirus expression vector. "Adenovirus expression vector" is meant to include those constructs containing adenovirus sequences sufficient to (a) support packaging of the construct and (b) to express a polynucleotide that has been cloned therein in a sense or antisense orientation. Of course, in the context of an antisense construct, expression does not require that the gene product be synthesized.

The expression vector comprises a genetically engineered form of an adenovirus. Knowledge of the genetic organization of adenovirus, a 36 kb, linear, double-stranded DNA virus, allows substitution of large pieces of adenoviral DNA with foreign sequences up to 7 kb (Grunhaus & A, et al., *Virology*, 1994 May 1; 200(2):535-46). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target-cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, *Radiother Oncol.* 1990 November; 19(3):197-218.). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., *Adv Cancer Res.* 1977; 25:1-51). Since the E3 region is dispensable from the adenovirus genome (Jones & Shenk, *Cell.* 1978 January; 13(1):181-8.), the current adenovirus vectors, with the help of 293 cells, carry foreign DNA in either the E1, the D3 or both regions (Prevec et al. *J Acquir Immune Defic Syndr.* 1991; 4(6):568-76). In nature, adenovirus can package approximately 105% of the wild-type genome (Ghosh-Choudhury et al., *Biochem Biophys Res Commun.* 1987 Sep. 30; 147(3):964-73), providing capacity for about 2 extra kB of DNA. Combined with the approximately 5.5 kB of DNA that is replaceable in the E1 and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, *Science.* 1993 May 14; 260(5110):926-32).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the currently preferred helper cell line is 293.

Recently, Griffiths and Racher (*Cytotechnology.* 1994; 15(1-3):3-9) disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stifling at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlemneyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain a conditional replication-defective adenovirus vector for use in the present invention, since Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (*EMBO J.* 1986 September; 5(9):2377-85) or in the E4 region where a helper cell line or helper virus complements the E4 defect.

Adenovirus is easy to grow and manipulate and exhibits broad host range in vitro and in vivo. This group of viruses can be obtained in high titers, e.g., $10.\text{sup}.9\text{-}10.\text{sup}.11$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch R B et al., *Am Rev Respir Dis.* 1963 September; 88:SUPPL 394-403; Top et al., *J Infect Dis.* 1971 August; 124(2):155-60), demonstrating their safety and therapeutic potential as in vivo gene transfer vectors.

Adenovirus vectors have been used in eukaryotic gene expression (Levrero et al., *Gene.* 1991 May 30; 101(2):195-202; Gomez-Foix et al., *J Biol Chem.* 1992 Dec. 15; 267(35):25129-34) and vaccine development (Grunhaus & Horwitz, *Virology,* 1994 May 1; 200(2):535-6; Prevec et al. *J Acquir Immune Defic Syndr.* 1991; 4(6):568-76, 1992). Recently, animal studies suggested that recombinant adenovirus could be used for gene therapy (Rosenfeld et al., *Science.* 1991 Apr. 19; 252(5004):431-4; Stratford-Perricaudet et al., *Hum Gene Ther.* 1990 Fall; 1(3):241-56; Rich et al. *Hum Gene Ther.* 1993 August; 4(4):461-76). Studies in administering recombinant adenovirus to different tissues include trachea instillation (Rosenfeld et al., 1991, supra; Rosenfeld et al., *Cell.* 1992 Jan. 10; 68(1):143-55), muscle injection (Ragot *Nature.* 1993 Feb. 18; 361(6413):647-50), peripheral intravenous injections (Herz & Gerard, *Proc Natl Acad Sci USA.* 1993 Apr. 1; 90(7):2812-6) and stereotactic inoculation into the brain (Le Gal La Salle et al., *Gene Ther.* 1994; 1 Suppl 1:S52).

B. Retroviruses

The retroviruses are a group of single-stranded RNA viruses characterized by an ability to convert their RNA to double-stranded DNA in infected cells by a process of reverse-transcription (Coffin, *J Med Virol.* 1990 May; 31(1):43-9). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990, supra).

In order to construct a retroviral vector, a nucleic acid encoding one or more oligonucleotide or polynucleotide sequences of interest is inserted into the viral genome in the place of certain viral sequences to produce a virus that is replication-defective. In order to produce virions, a packaging cell line containing the gag, pol, and env genes but without the LTR and packaging components is constructed (Mann et al., Cell. 1983 May; 33(1):153-9). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas & Rubenstein, Biotechnology 1988; 10:493-513; Temin H M, Cell Biophys. 1986 December; 9(1-2):9-16; Mann et al., 1983, supra). The media containing the recombinant retroviruses is then collected, optionally concentrated, and used for gene transfer. Retroviral vectors are able to infect a broad variety of cell types. However, integration and stable expression require the division of host cells (Paskind et al., Virology. 1975 September; 67(1):242-8).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., Proc Natl Acad Sci USA. 1989 December; 86(23):9079-83). Using antibodies against major histocompatibility complex class I and class II antigens, they demonstrated the infection of a variety of human cells that bore those surface antigens with an ecotropic virus in vitro (Roux et al., 1989, supra).

C. Adeno-Associated Viruses

AAV (Ridgeway, 1988; Hermonat & Muzyczka, Proc Natl Acad Sci USA. 1984 October; 81(20):6466-70) is a parvovirus, discovered as a contamination of adenoviral stocks. It is a ubiquitous virus (antibodies are present in 85% of the US human population) that has not been linked to any disease. It is also classified as a dependovirus, because its replications is dependent on the presence of a helper virus, such as adenovirus. Five serotypes have been isolated, of which AAV-2 is the best characterized. AAV has a single-stranded linear DNA that is encapsidated into capsid proteins VP1, VP2 and VP3 to form an icosahedral virion of 20 to 24 nm in diameter (Muzyczka & McLaughlin, J. Virol. 1988 June; 62(6):1963-73).

The AAV DNA is approximately 4.7 kilobases long. It contains two open reading frames and is flanked by two ITRs. There are two major genes in the AAV genome: rep and cap. The rep gene codes for proteins responsible for viral replications, whereas cap codes for capsid protein VP1-3. Each ITR forms a T-shaped hairpin structure. These terminal repeats are the only essential cis components of the AAV for chromosomal integration. Therefore, the AAV can be used as a vector with all viral coding sequences removed and replaced by the cassette of genes for delivery. Three viral promoters have been identified and named p5, p19, and p40, according to their map position. Transcription from p5 and p19 results in production of rep proteins, and transcription from p40 produces the capsid proteins (Hermonat & Muzyczka, 1984, supra).

There are several factors that prompted researchers to study the possibility of using rAAV as an expression vector One is that the requirements for delivering a gene to integrate into the host chromosome are surprisingly few. It is necessary to have the 145-bp ITRs, which are only 6% of the AAV genome. This leaves room in the vector to assemble a 4.5-kb DNA insertion. While this carrying capacity may prevent the AAV from delivering large genes, it is amply suited for delivering the antisense constructs of the present invention.

AAV is also a good choice of delivery vehicles due to its safety. There is a relatively complicated rescue mechanism: not only wild type adenovirus but also AAV genes are required to mobilize rAAV. Likewise, AAV is not pathogenic and not associated with any disease. The removal of viral coding sequences minimizes immune reactions to viral gene expression, and therefore, rAAV does not evoke an inflammatory response.

D. Other Viral Vectors as Expression Constructs

Other viral vectors may be employed as expression constructs in the present invention for the delivery of oligonucleotide or polynucleotide sequences to a host cell. Vectors derived from viruses such as vaccinia virus (Ridgeway, Biotechnology 1988; 10:467-92; Coupar et al., Gene. 1988 Aug. 15; 68(1):1-10), lentiviruses, polio viruses and herpes viruses may be employed. They offer several attractive features for various mammalian cells (Friedmann, Mol Biol Med. 1989 April; 6(2):117-25; Ridgeway, 1988, supra; Coupar et al., 1988, supra; Summers J, Smith P M, and Horwich A L, J Virol. 1990 June; 64(6):2819-24).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al, J Virol. 1990 February; 64(2):642-50). This suggested that large portions of the genome could be replaced with foreign genetic material. The hepatotropism and persistence (integration) were particularly attractive properties for liver-directed gene transfer. Chang et al. (Hepatology, 14:124 A, 1991) introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991, supra).

E. Non-Viral Vectors

In order to effect expression of the oligonucleotide or polynucleotide sequences of the present invention, the expression construct must be delivered into a cell. This delivery may be accomplished in vitro, as in laboratory procedures for transforming cells lines, or in vivo or ex vivo, as in the treatment of certain disease states. As described above, one preferred mechanism for delivery is via viral infection where the expression construct is encapsulated in an infectious viral particle.

Once the expression construct has been delivered into the cell the nucleic acid encoding the desired oligonucleotide or polynucleotide sequences may be positioned and expressed at different sites. In certain embodiments, the nucleic acid encoding the construct may be stably integrated into the genome of the cell. This integration may be in the specific location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In certain embodiments of the invention, the expression construct comprising one or more oligonucleotide or polynucleotide sequences may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (*Proc. Nat. Acad. Sci. USA*, 81:7529-7533, 1984) successfully injected polyomavirus DNA in the form of calcium phosphate precipitates into liver and spleen of adult and newborn mice demonstrating active viral replication and acute infection. Benvenisty & Reshef (*Proc. Nat. Acad. Sci. USA*, 83:9551-9555, 1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., *Nature* 1987 327:70-73). Several devices for accelerating small particles have been developed. One such device relies on a high voltage discharge to generate an electrical current, which in turn provides the motive force (Yang et al., *Proc. Natl. Acad. Sci. USA*, 1990 87:9568-9572). The microprojectiles used have consisted of biologically inert substances such as tungsten or gold beads.

Selected organs including the liver, skin, and muscle tissue of rats and mice have been bombarded in vivo (Yang et al, 1990, supra; Zelenin et al., *FEBS Lett.,* 1991 280:94-96). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

VII. Polypeptide Compositions

The present invention, in other aspects, provides polypeptide compositions. Generally, a polypeptide of the invention will be an isolated polypeptide (or an epitope, variant, or active fragment thereof) derived from a mammalian species. Preferably, the polypeptide is encoded by a polynucleotide sequence disclosed herein or a sequence which hybridizes under moderately stringent conditions to a polynucleotide sequence disclosed herein. Alternatively, the polypeptide may be defined as a polypeptide which comprises a contiguous amino acid sequence from an amino acid sequence disclosed herein, or which polypeptide comprises an entire amino acid sequence disclosed herein.

Immunogenic portions may generally be identified using well known techniques, such as those summarized in Paul, *Fundamental Immunology*, 3rd ed., 243-247 (1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well known techniques. An immunogenic portion of a *Mycobacterium* sp. protein is a portion that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using methods well known to those of ordinary skill in the art, such as those described in Harlow & Lane, *Antibodies. A Laboratory Manual* (1988). For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast, and higher eukaryotic cells, such as mammalian cells and plant cells. Preferably, the host cells employed are *E. coli*, yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Polypeptides of the invention, immunogenic fragments thereof, and other variants having less than about 100 amino acids, and generally less than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149-2146 (1963). Equipment for automated synthesis of polypeptides is commercially available from suppliers such as Perkin Elmer/Applied BioSystems Division (Foster City, Calif.), and may be operated according to the manufacturer's instructions.

Within certain specific embodiments, a polypeptide may be a fusion protein that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46 (1985); Murphy et al., *Proc. Natl. Acad. Sci. USA* 83:8258-8262 (1986); U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided. Such proteins comprise a polypeptide as described herein together with an unrelated immunogenic protein. Preferably the immunogenic protein is capable of eliciting a recall response. Examples of such proteins include tetanus, tuberculosis and hepatitis proteins (see, e.g., Stoute et al., *New Engl. J. Med.* 336:86-91 (1997)).

Within preferred embodiments, an immunological fusion partner is derived from protein D, a surface protein of the gram-negative bacterium *Haemophilus influenza* B (WO 91/18926). Preferably, a protein D derivative comprises approximately the first third of the protein (e.g., the first N-terminal 100-110 amino acids), and a protein D derivative may be lipidated. Within certain preferred embodiments, the first 109 residues of a lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265-292 (1986)). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795-798 (1992)). Within a preferred embodiment, a repeat portion of LYTA may be incorporated into a fusion protein. A repeat portion is found in the C-terminal region starting at residue 178. A particularly preferred repeat portion incorporates residues 188-305.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

VIII. T Cells

Immunotherapeutic compositions may also, or alternatively, comprise T cells specific for a *Mycobacterium* antigen. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the Isolex™ System, available from Nexell Therapeutics, Inc. (Irvine, Calif.; see also U.S. Pat. No. 5,240,856; U.S. Pat. No. 5,215,926; WO 89/06280; WO 91/16116 and WO 92/07243). Alternatively, T cells may be derived from related or unrelated humans, non-human mammals, cell lines or cultures.

T cells may be stimulated with a polypeptide of the invention, polynucleotide encoding such a polypeptide, and/or an antigen presenting cell (APC) that expresses such a polypeptide. Such stimulation is performed under conditions and for a time sufficient to permit the generation of T cells that are specific for the polypeptide. Preferably, the polypeptide or polynucleotide is present within a delivery vehicle, such as a microsphere, to facilitate the generation of specific T cells.

T cells are considered to be specific for a polypeptide of the invention if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065-1070 (1994)). Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a polypeptide of the invention (100 ng/ml-100 µg/ml, preferably 200 ng/ml-25 µg/ml) for 3-7 days should result in at least a two fold increase in proliferation of the T cells. Contact as described above for 2-3 hours should result in activation of the T cells, as measured using standard cytokine assays in which a two fold increase in the level of cytokine release (e.g., TNF or IFN-γ) is indicative of T cell activation (see Coligan et al., *Current Protocols in Immunology*, vol. 1 (1998)). T cells that have been activated in response to a polypeptide, polynucleotide or polypeptide-expressing APC may be $CD4^+$ and/or $CD8^+$. Protein-specific T cells may be expanded using standard techniques. Within preferred embodiments, the T cells are derived from a patient, a related donor or an unrelated donor, and are administered to the patient following stimulation and expansion.

For therapeutic purposes, $CD4^+$ or $CD8^+$ T cells that proliferate in response to a polypeptide, polynucleotide or APC can be expanded in number either in vitro or in vivo. Proliferation of such T cells in vitro may be accomplished in a variety of ways. For example, the T cells can be re-exposed to a polypeptide, or a short peptide corresponding to an immunogenic portion of such a polypeptide, with or without the addition of T cell growth factors, such as interleukin-2, and/or stimulator cells that synthesize a r polypeptide. Alternatively, one or more T cells that proliferate in the presence of ar protein can be expanded in number by cloning. Methods for cloning cells are well known in the art, and include limiting dilution.

IX. Pharmaceutical Compositions

In additional embodiments, the present invention concerns formulation of one or more of the polynucleotide, polypeptide, T-cell and/or antibody compositions disclosed herein in pharmaceutically-acceptable solutions for administration to a cell or an animal, either alone, or in combination with one or more other modalities of therapy.

It will also be understood that, if desired, the nucleic acid segment, RNA, DNA or PNA compositions that express a polypeptide as disclosed herein may be administered in combination with other agents as well, such as, e.g., other proteins or polypeptides or various pharmaceutically-active agents. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein. Likewise, such compositions may further comprise substituted or derivatized RNA or DNA compositions.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

A. Oral Delivery

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (Mathiowitz et al., *Nature*. 1997 Mar. 27; 386 (6623):410; Gupta S K, Hwang et al., *J Clin Pharmacol*. 1998 January; 38(1):60-7; U.S. Pat. No. 5,641,515; U.S. Pat. No. 5,580,579 and U.S. Pat. No. 5,792,451, each specifically incorporated herein by reference in its entirety). The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Typically, these formulations may contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

B. Injectable Delivery

In certain circumstances it will be desirable to deliver the pharmaceutical compositions disclosed herein parenterally, intravenously, intramuscularly, or even intraperitoneally as described in U.S. Pat. No. 5,543,158; U.S. Pat. No. 5,641,515 and U.S. Pat. No. 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., *Remington's Pharmaceutical Sciences,* 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

C. Nasal Delivery

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described e.g., in U.S. Pat. No. 5,756,353 and U.S. Pat. No. 5,804,212 (each specifically incorporated herein by reference in its entirety) Likewise, the delivery of drugs using intranasal microparticle resins (Takenaga et al., J Control Release. 1998 Mar. 2; 52(1-2):81-7) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

D. Liposome-, Nanocapsule-, and Microparticle-Mediated Delivery

In certain embodiments, the inventors contemplate the use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, or a nanoparticle or the like.

Such formulations may be preferred for the introduction of pharmaceutically-acceptable formulations of the nucleic acids or constructs disclosed herein. The formation and use of liposomes is generally known to those of skill in the art (see for example, Couvreur et al., *FEBS Lett.* 1977 Dec. 15; 84(2): 323-6; Couvreur, *Crit Rev Ther Drug Carrier Syst.* 1988; 5(1):1-20; Lasic, *Trends Biotechnol.* 1998 July; 16(7):307-21; which describes the use of liposomes and nanocapsules in the targeted antibiotic therapy for intracellular bacterial infections and diseases). Recently, liposomes were developed with improved serum stability and circulation half-times (Gabizon & Papahadjopoulos, *Proc Natl Acad Sci USA.* 1988 September; 85(18):6949-53; Allen and Chonn, FEBS Lett. 1987 Oct. 19; 223(1):42-6; U.S. Pat. No. 5,741,516, specifically incorporated herein by reference in its entirety). Further, various methods of liposome and liposome like preparations as potential drug carriers have been reviewed (Takakura, *Nippon Rinsho,* 1998 March; 56(3):691-5; Chandran et al., *Indian J Exp Biol.* 1997 August; 35(8):801-9; Margalit, *Crit Rev Ther Drug Carrier Syst.* 1995; 12(2-3):233-61; U.S. Pat. No. 5,567,434; U.S. Pat. No. 5,552,157; U.S. Pat. No. 5,565,213; U.S. Pat. No. 5,738,868 and U.S. Pat. No. 5,795,587, each specifically incorporated herein by reference in its entirety).

Liposomes have been used successfully with a number of cell types that are normally resistant to transfection by other procedures including T cell suspensions, primary hepatocyte cultures and PC 12 cells (Renneisen et al., *J Biol Chem.* 1990 Sep. 25; 265(27):16337-42; Muller et al., *Chem Phys Lipids.* 1990 January; 52(2):111-27). In addition, liposomes are free of the DNA length constraints that are typical of viral-based delivery systems. Liposomes have been used effectively to introduce genes, drugs (Heath & Martin, *Chem Phys Lipids.* 1986 June-July; 40(2-4):347 58; Heath et al., Biochim Biophys Acta. 1986 Nov. 6; 862(1):72 80; Balazsovits et al., 1989; *Cancer Chemother Pharmacol.* 1989; 23(2):81-6; Fresta and Puglisi, *Biomaterials.* 1996 April; 17(8):751-8), radiotherapeutic agents (Pikul et al., *Arch Surg.* 1987 December; 122(12):1417-20), enzymes (Imaizumi et al., *Acta Neurochir Suppl* (*Wien*). 1990; 51:236-8; Imaizumi et al., *Stroke.* 1990 September; 21(9):1312-7), viruses (Faller & Baltimore, *J Virol.* 1984 January; 49(1):269-72), transcription factors and allosteric effectors (Nicolau & Gersonde, *Blut.* 1979 July; 39(1):1-7) into a variety of cultured cell lines and animals. In addition, several successful clinical trails examining the effectiveness of liposome-mediated drug delivery have been completed (Lopez-Berestein et al., *J Infect Dis.* 1985 April; 151(4):704-10; Lopez-Berestein et al., Cancer Drug Deliv. 1985 Summer; 2(3):183-9; Coune, Infection. 1988 May-June; 16(3):141-7; Sculier et al., *Eur J Cancer Clin Oncol.* 1988 March; 24(3):527-38). Furthermore, several studies suggest that the use of liposomes is not associated with autoimmune responses, toxicity or gonadal localization after systemic delivery (Mori & Fukatsu, *Epilepsia.* 1992 November-December; 33(6):994-1000).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Liposomes bear resemblance to cellular membranes and are contemplated for use in connection with the present invention as carriers for the peptide compositions. They are widely suitable as both water- and lipid-soluble substances can be entrapped, i.e. in the aqueous spaces and within the bilayer itself, respectively. It is possible that the drug-bearing liposomes may even be employed for site-specific delivery of active agents by selectively modifying the liposomal formulation.

In addition to the teachings of Couvreur et al. *FEBS Lett.* 1977 Dec. 15; 84(2):323-6; and Couvreur et al., *Crit Rev Ther Drug Carrier Syst.* 1988; 5(1):1-20, the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

In addition to temperature, exposure to proteins can alter the permeability of liposomes. Certain soluble proteins, such as cytochrome c, bind, deform and penetrate the bilayer, thereby causing changes in permeability. Cholesterol inhibits this penetration of proteins, apparently by packing the phospholipids more tightly. It is contemplated that the most useful liposome formations for antibiotic and inhibitor delivery will contain cholesterol.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

In addition to liposome characteristics, an important determinant in entrapping compounds is the physicochemical properties of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

Liposomes interact with cells via four different mechanisms: endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

The fate and disposition of intravenously injected liposomes depend on their physical properties, such as size, fluidity, and surface charge. They may persist in tissues for h or days, depending on their composition, and half lives in the blood range from min to several h. Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow, and lymphoid organs.

Targeting is generally not a limitation in terms of the present invention. However, should specific targeting be desired, methods are available for this to be accomplished. Antibodies may be used to bind to the liposome surface and to direct the antibody and its drug contents to specific antigenic receptors located on a particular cell-type surface. Carbohydrate determinants (glycoprotein or glycolipid cell-surface components that play a role in cell-cell recognition, interaction and adhesion) may also be used as recognition sites as they have potential in directing liposomes to particular cell types. Mostly, it is contemplated that intravenous injection of liposomal preparations would be used, but other routes of administration are also conceivable.

Alternatively, the invention provides for pharmaceutically-acceptable nanocapsule formulations of the compositions of the present invention. Nanocapsules can generally entrap compounds in a stable and reproducible way (Henry-Michelland et al., *J Pharm Pharmacology*. 1987 December; 39(12):973-7; Quintanar-Guerrero et al., *Drug Dev Ind Pharm*. 1998 December; 24(12):1113-28; Douglas et al., *Crit Rev Ther Drug Carrier Syst*. 1987; 3(3):233-61). To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use in the present invention. Such particles may be are easily made, as described (Couvreur et al., 1980 supra and 1988, supra; zur Muhlen et al., *Eur J Pharm Biopharm*. 1998 March; 45(2):149-55; Zambaux et al. *J Control Release*. 1998 Jan. 2; 50(1-3):31-40; Pinto-Alphandry et al., 1995 *J Drug Target*. 1995; 3(2):167-9 and U.S. Pat. No. 5,145,684, specifically incorporated herein by reference in its entirety).

X. Vaccines

In certain preferred embodiments of the present invention, vaccines are provided. The vaccines will generally comprise one or more pharmaceutical compositions, such as those discussed above, in combination with an immunostimulant. An immunostimulant may be any substance that enhances or potentiates an immune response (antibody and/or cell-mediated) to an exogenous antigen. Examples of immunostimulants include adjuvants, biodegradable microspheres (e.g., polylactic galactide) and liposomes (into which the compound is incorporated; see, e.g., Fullerton, U.S. Pat. No. 4,235,877). Vaccine preparation is generally described in, for example, Powell & Newman, eds., *Vaccine Design* (the subunit and adjuvant approach) (1995). Pharmaceutical compositions and vaccines within the scope of the present invention may also contain other compounds, which may be biologically active or inactive. For example, one or more immunogenic portions of other tumor antigens may be present, either incorporated into a fusion polypeptide or as a separate compound, within the composition or vaccine.

Illustrative vaccines may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, *Crit. Rev. Therap. Drug Carrier Systems* 15:143-198 (1998), and references cited therein. Appropriate nucleic acid expression systems contain the necessary DNA sequences for expression in the patient (such as a suitable promoter and terminating signal). Bacterial delivery systems involve the administration of a bacterium (such as *Bacillus*-Calmette-Guerrin) that expresses an immunogenic portion of the polypeptide on its cell surface or secretes such an epitope. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *Proc. Natl. Acad. Sci. USA* 86:317-321 (1989); Flexner et. al., *Ann. N. Y. Acad. Sci.* 569:86-103 (1989); Flexner et al., *Vaccine* 8:17-21 (1990); U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616-627 (1988); Rosenfeld et al., *Science* 252:431-434 (1991); Kolls et al., *Proc. Natl. Acad. Sci. USA* 91:215-219 (1994); Kass-Eisler et al., *Proc. Natl. Acad. Sci. USA* 90:11498-11502 (1993); Guzman et al., *Circulation* 88:2838-2848 (1993); and Guzman et al., *Cir. Res.* 73:1202-1207 (1993). Techniques for incorporating DNA into such expression systems are well known to those of ordinary skill in the art. The DNA may also be "naked," as described, for example, in Ulmer et al., *Science* 259:1745-1749 (1993) and reviewed by Cohen, *Science* 259:1691-1692 (1993). The uptake of naked DNA may be increased by coating the DNA onto biodegradable beads, which are efficiently transported into the cells. It will be apparent that a vaccine may comprise both a polynucleotide and a polypeptide component. Such vaccines may provide for an enhanced immune response.

It will be apparent that a vaccine may contain pharmaceutically acceptable salts of the polynucleotides and polypeptides provided herein. Such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

While any suitable carrier known to those of ordinary skill in the art may be employed in the vaccine compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268; 5,075,109; 5,928,647;

5,811,128; 5,820,883; 5,853,763; 5,814,344 and 5,942,252. One may also employ a carrier comprising the particulate-protein complexes described in U.S. Pat. No. 5,928,647, which are capable of inducing a class I-restricted cytotoxic T lymphocyte responses in a host.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate. Compounds may also be encapsulated within liposomes using well known technology.

Any of a variety of immunostimulants may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A. Bortadella pertussis or *Mycobacterium* species or *Mycobacterium* derived proteins. For example, delipidated, deglycolipidated *M. vaccae* ("pVac") can be used. In another embodiment, BCG is used. In addition, the vaccine can be administered to a subject previously exposed to BCG. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 and derivatives thereof (SmithKline Beecham, Philadelphia, Pa.); CWS, TDM, Leif, aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th 1-type, the level of Th 1-type cytokines will increase to a greater extent than the level of Th2-type cytokines. The levels of these cytokines may be readily assessed using standard assays. For a review of the families of cytokines, see Mosmann & Coffman, *Ann. Rev. Immunol.* 7:145-173 (1989).

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Corixa Corporation (Seattle, Wash.; see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352 (1996). Another preferred adjuvant comprises a saponin, such as Quil A, or derivatives thereof, including QS21 and QS7 (Aquila Biopharmaceuticals Inc., Framingham, Mass.); Escin; Digitonin; or *Gypsophila* or *Chenopodium quinoa* saponins. Other preferred formulations include more than one saponin in the adjuvant combinations of the present invention, for example combinations of at least two of the following group comprising QS21, QS7, Quil A, β-escin, or digitonin.

Alternatively the saponin formulations may be combined with vaccine vehicles composed of chitosan or other polycationic polymers, polylactide and polylactide-co-glycolide particles, poly-N-acetyl glucosamine-based polymer matrix, particles composed of polysaccharides or chemically modified polysaccharides, liposomes and lipid-based particles, particles composed of glycerol monoesters, etc. The saponins may also be formulated in the presence of cholesterol to form particulate structures such as liposomes or ISCOMs. Furthermore, the saponins may be formulated together with a polyoxyethylene ether or ester, in either a non-particulate solution or suspension, or in a particulate structure such as a paucilamelar liposome or ISCOM. The saponins may also be formulated with excipients such as Carbopol® to increase viscosity, or may be formulated in a dry powder form with a powder excipient such as lactose.

In one preferred embodiment, the adjuvant system includes the combination of a monophosphoryl lipid A and a saponin derivative, such as the combination of QS21 and 3D-MPL® adjuvant, as described in WO 94/00153, or a less reactogenic composition where the QS21 is quenched with cholesterol, as described in WO 96/33739. Other preferred formulations comprise an oil-in-water emulsion and tocopherol. Another particularly preferred adjuvant formulation employing QS21, 3D-MPL® adjuvant and tocopherol in an oil-in-water emulsion is described in WO 95/17210.

Another enhanced adjuvant system involves the combination of a CpG-containing oligonucleotide and a saponin derivative particularly the combination of CpG and QS21 as disclosed in WO 00/09159. Preferably the formulation additionally comprises an oil in water emulsion and tocopherol.

Other preferred adjuvants include Montanide ISA 720 (Seppic, France), SAF (Chiron, Calif., United States), ISCOMS (CSL), MF-59 (Chiron), the SBAS series of adjuvants (e.g., SBAS-2, AS2', AS2," SBAS-4, or SBAS6, available from SmithKline Beecham, Rixensart, Belgium), Detox (Corixa, Hamilton, Mont.), RC-529 (Corixa, Hamilton, Mont.) and other aminoalkyl glucosaminide 4-phosphates (AGPs), such as those described in pending U.S. patent application Ser. No. 08/853,826 (now U.S. Pat. No. 6,113,918) and Ser. No. 09/074,720 (now U.S. Pat. No. 6,355,257), the disclosures of which are incorporated herein by reference in their entireties, and polyoxyethylene ether adjuvants such as those described in WO 99/52549A1.

Other preferred adjuvants include adjuvant molecules of the general formula $$HO(CH_2CH_2O)_n\text{-}A\text{-}R, \qquad (I)$$

wherein, n is 1-50, A is a bond or —C(O)—, R is $C_{1\text{-}50}$ alkyl or Phenyl $C_{1\text{-}50}$ alkyl.

One embodiment of the present invention consists of a vaccine formulation comprising a polyoxyethylene ether of general formula (I), wherein n is between 1 and 50, preferably 4-24, most preferably 9; the R component is $C_{1\text{-}50}$, preferably $C_4$-$C_{20}$ alkyl and most preferably $C_{12}$ alkyl, and A is a bond. The concentration of the polyoxyethylene ethers should be in the range 0.1-20%, preferably from 0.1-10%, and most preferably in the range 0.1-1%. Preferred polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck index ($12^{th}$ edition: entry 7717). These adjuvant molecules are described in WO 99/52549.

The polyoxyethylene ether according to the general formula (I) above may, if desired, be combined with another adjuvant. For example, a preferred adjuvant combination is preferably with CpG as described in the pending UK patent application GB 9820956.2.

Any vaccine provided herein may be prepared using well known methods that result in a combination of antigen, immune response enhancer and a suitable carrier or excipient. The compositions described herein may be administered as part of a sustained release formulation (i.e., a formulation such as a capsule, sponge or gel (composed of polysaccharides, for example) that effects a slow release of compound following administration). Such formulations may generally be prepared using well known technology (see, e.g., Coombes et al, *Vaccine* 14:1429-1438 (1996)) and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane.

Carriers for use within such formulations are biocompatible, and may also be biodegradable; preferably the formulation provides a relatively constant level of active component release. Such carriers include microparticles of poly(lactide-co-glycolide), polyacrylate, latex, starch, cellulose, dextran and the like. Other delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see, e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau& Steinman, *Nature* 392:245-251 (1998)) and have been shown to be effective as a physiological adjuvant for eliciting prophylactic or therapeutic antitumor immunity (see Timmerman & Levy, *Ann. Rev. Med.* 50:507-529 (1999)). In general, dendritic cells may be identified based on their typical shape (stellate in situ, with marked cytoplasmic processes (dendrites) visible in vitro), their ability to take up, process and present antigens with high efficiency and their ability to activate naïve T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med.* 4:594-600 (1998)).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide encoding a protein (or portion or other variant thereof) such that the polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and Cell Biology* 75:456-460 (1997). Antigen loading of dendritic cells may be achieved by incubating dendritic cells or progenitor cells with the polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Vaccines and pharmaceutical compositions may be presented in unit-dose or multi-dose containers, such as sealed ampoules or vials. Such containers are preferably hermetically sealed to preserve sterility of the formulation until use. In general, formulations may be stored as suspensions, solutions or emulsions in oily or aqueous vehicles. Alternatively, a vaccine or pharmaceutical composition may be stored in a freeze-dried condition requiring only the addition of a sterile liquid carrier immediately prior to use.

XI. Diagnostic Kits

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a protein in a biological sample. Such kits generally comprise at least one oligonucleotide probe or primer, as described above, that hybridizes to a polynucleotide encoding a protein. Such an oligonucleotide may be used, for example, within a PCR or hybridization assay. Additional components that may be present within such kits include a second oligonucleotide and/or a diagnostic reagent or container to facilitate the detection of a polynucleotide encoding a protein of the invention.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

XII. Examples

The following examples are provided by way of illustration only and not by way of limitation. Those of skill in the art will readily recognize a variety of noncritical parameters that could be changed or modified to yield essentially similar results.

Example 1

Recombinant Fusion Proteins of M. tuberculosis Antigens Exhibit Increased Serological Sensitivity A. Materials and Methods
1. Construction of Vectors Encoding Fusion Proteins: TbF14

TbF14 is a fusion protein of the amino acid sequence encoding the Mtb81 antigen fused to the amino acid sequence encoding the Mo2 antigen. A sequence encoding Mo2 was PCR amplified with the following primers: PDM-294 ($T_m$ 64° C.) CGTAATCACGTGCAGAAGTACGGCGGATC (SEQ ID NO:14) and PDM-295 ($T_m$ 63° C.) CCGACTAGAATTCACTATTGACAGGCCCATC (SEQ ID NO:15).

DNA amplification was performed using 10 μl 10×Pfu buffer, 1 μl 10 mM dNTPs, 2 μl each of the PCR primers at 10 μM concentration, 83 μl water, 1.5 μl Pfu DNA polymerase (Stratagene, La Jolla, Calif.) and 50 ng DNA template. For Mo2 antigen, denaturation at 96° C. was performed for 2 min; followed by 40 cycles of 96° C. for 20 sec, 63° C. for 15 sec and 72° C. for 2.5 min; and finally by 72° C. for 5 min.

A sequence encoding Mtb81 was PCR amplified with the following primers: TABLE-U.S. Pat. No. 00002 PDM-268 ($T_m$ 66° C.) (SEQ ID NO: 16) CTAAGTAGTACTGATCGCGTGTCGGTGGGC and PDM-296 ($T_m$ 64° C.) (SEQ ID NO: 17) CATCGATAGGCCTGGCCGCATCGTCACC. The amplification reaction was performed using the same mix as above, as follows: denaturation at 96° C. for 2 min; followed by 40 cycles of 96° C. for 20 sec, 65° C. for 15 sec, 72° C. for 5 min; and finally by 72° C. for 5 min.

The Mo2 PCR product was digested with Eco72I (Stratagene, La Jolla Calif.) and EcoRI (NEB, Beverly, Mass.). The Mtb81 PCR product was digested with FseI and StuI (NEB, Beverly, Mass.). These two products were then cloned into an expression plasmid (a modified pET28 vector) with a hexa-histidine in frame, in a three way ligation that was digested with FseI and EcoRI. The sequences was confirmed, then the expression plasmid was transformed into the BL21pLysE *E. coli* strain (Novagen, Madison, Wis.) for expression of the recombinant protein.

2. Construction of Vectors Encoding Fusion Proteins: TbF15

TbF15 is a fusion of antigens Ra3, 38 kD (with an N-terminal cysteine), 38-1, and FL TbH4 from *Mycobacterium tuberculosis*, and was prepared as follows. TbF15 was made using the fusion constructs TbF6 and TbF10.

TbF6 was made as follows (see PCT/US99/03268 and PCT/US99/03265). First, the FL (full-length) TbH4 coding region was PCR amplified with the following primers: PDM-157 CTAGTTAGTACTCAGTCGCAGACCGTG (SEQ ID NO:18) ($T_m$ 61° C.) and PDM-160 GCAGTGACGAATTCACTTCGACTCC (SEQ ID NO:19) ($T_m$ 59° C.), using the following conditions: 10 μl 10×Pfu buffer, 1 μl 10 mM dNTPs, 2 μl 10 μM each oligo, 82 μl sterile water, 1.5 μl Accuzyme (ISC, Kaysville, Utah), 200 ng *Mycobacterium tuberculosis* genomic DNA. Denaturation at 96° C. was performed for 2 minutes; followed by 40 cycles of 96° C. for 20 seconds, 61° C. 15 seconds, and 72° C. 5 minutes; and finally by 72° C. 10 minutes.

The PCR product was digested with ScaI and EcoRI and cloned into pET28Ra3/38 kD/38-1A, described below, which was digested with DraI and EcoRI.

pET28Ra3/38 kD/38-1A was made by inserting a DraI site at the end of 38-1 before the stop codon using the following conditions. The 38-1 coding region was PCR amplified with the following primers: PDM-69 GGATCCAGCGCTGAGATGAAGACCGATGCCGCT (SEQ ID NO:19) ($T_m$ 68° C.) and PDM-83 GGATATCTGCAGAATTCAGGTTTAAAGCCCATTTGCGA (SEQ ID NO:20) ($T_m$ 64° C.), using the following conditions: 10 μl 10×Pfu buffer, 1 μl 10 mM dNTPs, 2 μl 10 μM each oligo, 82 μl sterile water, 1.5 μl Accuzyme (ISC, Kaysville, Utah), 50 ng plasmid DNA. Denaturation at 96° C. was performed for 2 minutes; followed by forty cycles of 96° C. for 20 seconds, 66° C. for 15 seconds and 72° C. for 1 minute 10 seconds; and finally 72° C. 4 minutes.

The 38-1 PCR product was digested with Eco471III and EcoRI and cloned into the pT7ΔL2Ra3/38 kD construct (described in WO/9816646 and WO/9816645) which was digested with EcoRI and Eco47III. The correct construct was confirmed through sequence analysis. The Ra3/38 kD/38-1A coding region was then subcloned into pET28 His (a modified pET28 vector) at the NdeI and EcoRI sites. The correct construct (called TbF6) was confirmed through sequence analysis.

Fusion construct TbF10, which replaces the N-terminal cysteine of 38 kD, was made as follows. To replace the cysteine residue at the N-terminus, the 38 kD-38-1 coding region from the TbF fusion (described in WO/9816646 and WO/9816645) was amplified using the following primers: PDM-192 TGTGGCTCGAAACCACCGAGCGGTTC (SEQ ID NO:21) ($T_m$ 64° C.) and PDM-60 GAGAGAAT-TCTCAGAAGCCCATTTGCGAGGACA (SEQ ID NO:22) ($T_m$ 64° C.), using the following conditions: 10 μl 10×Pfu buffer, 1 μl 10 mM dNTPs, 2 μl 10 μM each oligo, 83 μl sterile water, 1.5 μl Pfu DNA polymerase (Stratagene, La Jolla, Calif.), and 50 ng plasmid TbF DNA. The amplification reaction was performed as follows: 96° C. for 2 minutes; followed by 40 cycles of 96° C. for 20 seconds, 64° C. 15 seconds, and 72° C. 4 minutes; and finally 72° C. 4 minutes. Digest the PCR product with Eco RI and clone into pT7ΔL2Ra3 which has been digested with StuI and Eco RI. Digest the resulting construct with NdeI and EcoRI and clone into pET28 at those sites. The resulting clone (called TbF10) will be TBF+a cysteine at the 5' end of the 38 kD coding region. Transform into BL21 and HMS 174 with pLys S.

The pET28TbF6 (TbF6, described above) construct was digested with StuI (NEB, Beverly, Mass.) and EcoRI, which released a 1.76 kb insert containing the very back portion of the 38 kD/38-1/FL TbH4 fusion region. This insert was gel purified. The pET28TbF10 construct (TbF10, described above) was digested with the same enzymes and the vector backbone, consisting of 6.45 kb containing the his-tag, the Ra3 coding region and most of the Δ38 kD coding region. This insert was gel purified. The insert and vector were ligated and transformed. The correct construct, called TbF15, was confirmed through sequence analysis, then transformed into the BL21 pLysS *E. coli* strain (Novagen, Madison Wis.). This fusion protein contained the original Cys at the amino terminus of the 38 kD protein.

B. Expression of Fusion Proteins

1. Expression of Fusion Proteins

The recombinant proteins were expressed in *E. coli* with six histidine residues at the amino-terminal portion using the pET plasmid vector and a T7 RNA polymerase expression system (Novagen, Madison, Wis.). *E. coli* strain BL21 (DE3) pLysE (Novagen) was used for high level expression. The recombinant (His-Tag) fusion proteins were purified from the soluble supernatant or the insoluble inclusion body of 1 L of IPTG induced batch cultures by affinity chromatography using the one step QIAexpress Ni-NTA Agarose matrix (QIAGEN, Chatsworth, Calif.) in the presence of 8M urea.

Briefly, 20 ml of an overnight saturated culture of BL21 containing the pET construct was added into 1 L of 2×YT media containing 30 μg/ml kanamycin and 34 μg/ml chloramphenicol, grown at 37° C. with shaking. The bacterial cultures were induced with 1 mM IPTG at an OD 560 of 0.3 and grown for an additional 3 h (OD=1.3 to 1.9). Cells were harvested from 1 L batch cultures by centrifugation and resuspended in 20 ml of binding buffer (0.1 M sodium phosphate, pH 8.0; 10 mM Tris-HCl, pH 8.0) containing 2 mM PMSF and 20 μg/ml leupeptin plus one complete protease inhibitor tablet (Boehringer Mannheim) per 25 ml. *E. coli* was lysed by freeze-thaw followed by brief sonication, then spun at 12 k rpm for 30 min to pellet the inclusion bodies.

The inclusion bodies were washed three times in 1% CHAPS in 10 mM Tris-HCl (pH 8.0). This step greatly reduced the level of contaminating LPS. The inclusion body was finally solubilized in 20 ml of binding buffer containing 8 M urea or 8M urea was added directly into the soluble supernatant. Recombinant fusion proteins with His-Tag residues were batch bound to Ni-NTA agarose resin (5 ml resin per 1 L inductions) by rocking at room temperature for 1 h and the complex passed over a column. The flow through was passed twice over the same column and the column washed three times with 30 ml each of wash buffer (0.1 M sodium phosphate and 10 mM Tris-HCl, pH 6.3) also containing 8 M urea. Bound protein was eluted with 30 ml of 150 mM imidazole in wash buffer and 5 ml fractions collected. Fractions containing each recombinant fusion protein were pooled, dialyzed against 10 mM Tris-HCl (pH 8.0) bound one more time to the Ni-NTA matrix, eluted and dialyzed in 10 mM Tris-HCl (pH 7.8). The yield of recombinant protein varies from 25-150 mg per liter of induced bacterial culture with greater than 98% purity. Recombinant proteins were assayed for endotoxin contamination using the *Limulus* assay (BioWhittaker) and were shown to contain <100 E.U./mg.

2. Serological Assays

ELISA assays were performed with TbF15 using methods known to those of skill in the art, with 200 ng/well of antigen. ELISA assays are performed with TbF14 using methods known to those of skill in the art, with 200 ng/well of antigen.

3. Results

The TbF15 fusion protein containing TbRa3, 38 kD (with N terminal cysteine), Tb38-1, and full length (FL) TbH4 as described above was used as the solid phase antigen in ELISA. The ELISA protocol is as described above. The fusion recombinant was coated at 200 ng/well. A panel of sera were chosen from a group of TB patients that had previously been shown by ELISA to be positive or borderline positive with these antigens. Such a panel enabled the direct comparison of the fusions with and without the cysteine residue in the 38 kD component. The data are outlined in FIG. 5. A total of 23 TB sera were studied and of these 20/23 were detected by TbF6 versus 22/23 for TbF15. Improvements in reactivity were seen in the low reactive samples when TbF15 was used.

One of skill in the art will appreciate that the order of the individual antigens within each fusion protein may be changed and that comparable activity would be expected provided that each of the epitopes is still functionally available. In addition, truncated forms of the proteins containing active epitopes may be used in the construction of fusion proteins.

Example 2

Cloning, Construction, and Expression of HTCC#1 Full-Length, Overlapping Halves, and Deletions as Fusion Constructs HTCC#1 (aka Mtb40) was cloned by direct T cell expression screening using a T cell line derived from a healthy PPD positive donor to directly screen an *E. coli* based Mtb expression library.

A. Construction and Screening of the Plasmid Expression Library

Genomic DNA from *M. tuberculosis* Erdman strain was randomly sheared to an average size of 2 kb and blunt ended with Klenow polymerase, before EcoRI adaptors were added. The insert was subsequently ligated into the 1 screen phage vector and packaged in vitro using the PhageMaker extract (Novagen). The phage library (Erd 1 screen) was amplified and a portion was converted into a plasmid expression library. Conversion from phage to plasmid (phagemid) library was performed as follows: the Erd 1 Screen phage library was converted into a plasmid library by autosubcloning using the *E. coli* host strain BM25.8 as suggested by the manufacturer (Novagen). Plasmid DNA was purified from BM25.8 cultures containing the pSCREEN recombinants and used to transform competent cells of the expressing host strain BL21 (DE3) pLysS. Transformed cells were aliquoted into 96 well micro titer plates with each well containing a pool size of ~50 colonies. Replica plates of the 96 well plasmid library format were induced with IPTG to allow recombinant protein expression. Following induction, the plates were centrifuged to pellet the *E. coli* and the bacterial pellet was resuspended in 200 µl of 1×PBS.

Autologous dendritic cells were subsequently fed with the *E. coli*, washed and exposed to specific T cell lines in the presence of antibiotics to inhibit the bacterial growth. T cell recognition was detected by proliferation and/or production of IFN-γ. Wells that score positive were then broken down using the same protocol until a single clone could be detected. The gene was then sequenced, sub-cloned, expressed and the recombinant protein evaluated.

B. Expression in *E. coli* of the Full-Length and Overlapping Constructs of HTCC#1

One of the identified positive wells was further broken down until a single reactive clone (HTCC#1) was identified. Sequencing of the DNA insert followed by search of the Genebank database revealed a 100% identity to sequences within the *M. tuberculosis* locus MTCY7H$_7$B (gene identification MTCY07H$_7$B.06) located on region B of the cosmid clone SCY07H7. The entire open reading frame is 1,200 by long and codes for a 40 kDa (392 amino acids) protein (FIG. 1; HTCC#1 FL). Oligonucleotide PCR primers [5' (5'-CAA TTA CAT ATG CAT CAC CAT CAC CAT CAC ATG AGC AGA GCG TTC ATC ATC-3') (SEQ ID NO: 201) and 3' (5'-CAT GGA ATT CGC CGT TAG ACG ACG TTT CGT A-3') (SEQ ID NO: 202)] were designed to amplify the full-length sequence of HTCC#1 from genomic DNA of the virulent Erdman strain.

The 5' oligonucleotide contained an Nde I restriction site preceding the ATG initiation codon (underlined) followed by nucleotide sequences encoding six histidines (bold) and sequences derived from the gene (italic). The resultant PCR products was digested with NdeI and EcoRI and subcloned into the pET17b vector similarly digested with NdeI and EcoRI. Ligation products were initially transformed into *E. coli* XL1-Blue competent cells (Stratagene, La Jolla, Calif.) and were subsequently transformed into *E. coli* BL-21 (pLysiE) host cells (Novagen, Madison, Wis.) for expression.

C. Expression of the Full Length and Overlapping Constructs of HTCC#1

Several attempts to express the full-length sequence of HTCC#1 in *E. coli* failed either because no transformants could be obtained or because the *E. coli* host cells were lysed following IPTG induction. HTCC#1 is 392 amino acids long and has 3 trans-membrane (TM) domains which are presumably responsible for the lysing of the *E. coli* culture following IPTG induction.

Thus expression of HTCC#1 was initially attempted by constructing two overlapping fragments coding for the amino (residues 1-223; FIG. 2) and carboxy (residues 184-392; FIG. 2) halves.

The N-terminal (residues 1-223) fragment containing the first of the 3 putative transmembrane domains killed (lysed) the host cells, while the C-terminal (residues 184-392) half expressed at high levels in the same host cell. Thus the two trans-membrane domains located in the C-terminal half do not appear to be toxic.

The N-terminal fragment, comprising amino acid residues 1-128 (devoid of the transmembrane domain), was therefore engineered for expression in the same pET17b vector system (FIG. 2). This construct expressed quite well and there was no toxicity associated with the expressing *E. coli* host.

D. Expression in *E. coli* of the Full-Length HTCC#1 as an TbRa12 Fusion Construct Because of problems associated with the expression of full length HTCC#1, we evaluated the utility of an TbRa12 fusion construct for the generation of a fusion protein that would allow for the stable expression of recombinant HTCC#1.

pET17b vector (Novagen) was modified to include TbRa12, a 14 kDa C-terminal fragment of the serine protease antigen MTB32A of *Mycobacterium tuberculosis* (Skeiky et al.). For use as an expression vector, the 3' stop codon of the TbRa12 was substituted with an in frame EcoRI site and the N-terminal end was engineered so as to code for six His-tag residues immediately following the initiator Met. This would facilitate a simple one step purification protocol of TbRa12 recombinant proteins by affinity chromatography over Ni-NTA matrix.

Specifically, the C-terminal fragment of antigen MTB32A was amplified by standard PCR methods using the oligonucleotide primers 5'(dCAT CAC CAT CAC CAT CAC ACG GCC GCG TCC GATAAC TTC) (SEQ ID NO:203) and 3' (5'-CTA ATC GAA TTC GGC CGG GGG TCC CTC GGC CAA) (SEQ ID NO:204). The 450 by product was digested with NdeI and EcoRI and cloned into the pET17b expression vector similarly digested with the same enzymes.

Recombinant HTCC#1 was engineered for expression as a fusion protein with TbRa12 by designing oligonucleotide primers to specifically amplify the full length form. The 5' oligonucleotide contained a thrombin recognition site. The resulting PCR amplified product was digested with EcoRI and subcloned into the EcoRI site of the pET-TbRa12 vector. Following transformation into the *E. coli* host strain (XL 1-blue; Stratagene), clones containing the correct size insert were submitted for sequencing in order to identify those that are in frame with the TbRa12 fusion. Subsequently, the DNA of interest (FIG. 3) was transformed into the BL-21 (pLysE) bacterial host and the fusion protein was expressed following induction of the culture with IPTG.

E. Expression in *E. coli* of HTCC#1 With Deletions of the Trans-Membrane Domain(s)

Given the prediction that the 3 predicted trans-membrane (TM) domains are responsible for lysing the *E. coli* host following IPTG induction, recombinant constructs lacking the TM domains were engineered for expression in *E. coli.*

1. Recombinant HTCC#1 with deletion of the first TM ΔTM-1). A deletion construct lacking the first trans-membrane domain (amino acid residues 150-160) was engineered for expression *E. coli* (FIG. 4). This construct expressed reasonably well and enough (low mg quantities) was purified for in vitro studies. This recombinant antigen was comparable in in vitro assays to that of the full-length Ra-12-fusion construct.

T-cell epitope mapping of HTCC#1. Because of the generally low level of expression using the ΔTM-1 construct, the design of the final form of HTCC#1 for expression in *E. coli* was based on epitope mapping. The T-cell epitope was mapped using 30 overlapping peptides (FIG. 4) on PBMC read out (on four PPD+ donors). The data revealed that peptides 8 through 16 (amino acid residues 92-215) were not immunogenic (FIG. 4).

2. Recombinant HTCC#1 with deletion of all of the TM domains (ATM-2): A deletion construct of HTCC#1 lacking residues 101 to 203 with a predicted molecular weight of 30.4 kDa was engineered for expression in *E. coli*. The full length HTCC#1 is 40 kDa. There was no toxicity associated with this new deletion construct and the expression level was higher than that of the ΔTM-1 construct (FIG. 4).

F. Fusion Constructs of HTCC#1 and TbH9:

FIG. 5 shows a sequence of HTCC#1 (184-392)-TbH9-HTCC#1 (1-129)

FIG. 6 shows a sequence of HTCC#1 (1-149)-TbH9-HTCC#1 (161-392)

FIG. 7 shows a sequence of HTCC#1 (184-392)-TbH9-HTCC#1 (1-200)

One of skill in the art will appreciate that the order of the individual antigens within each fusion protein may be changed and that comparable activity would be expected provided that each of the epitopes is still functionally available. In addition, truncated forms of the proteins containing active epitopes may be used in the construction of fusion proteins.

From the foregoing, it will be appreciated that, although specific embodiments of the invention have been described herein for the purpose of illustration, various modifications may be made without deviating from the spirit and scope of the invention.

SEQUENCE LISTING

<160> NUMBER OF SEQ ID NOS: 178

<210> SEQ ID NO 1
<211> LENGTH: 2220
<212> TYPE: DNA
<213> ORGANISM: Mycobacterium tuberculosis

<400> SEQUENCE: 1

```
actgatcgcg tgtcggtggg caacttgcgc atcgctcggg tgctctacga cttcgtgaac      60
aatgaagccc tgcctggcac cgatatcgac ccggacagct tctgggcggg cgtcgacaar     120
gtcgtcgccg acctgacccc gcagaaccaa gctctgttga acgccgcga cgagctgcag     180 gcgcagatcg acaagtggca ccggcgtcgg gtgatcgagc ccatcgacat ggatgcctac     240
cgccagttcc tcaccgagat cggctacctg cttcccgaac ctgatgactt caccatcacc     300
acgtccggtg tcgacgctga gatcaccacg accgccggcc cccagctggt ggtgccggtg     360
ctcaacgcgc ggtttgctct gaacgcggcc aacgctcgct ggggctccct ctacgacgcc     420
ttgtatggca ccgatgtcat ccccgagacc gacgcgccg aaaaaggccc cacgtacaac     480
aaggttcgtg gcgacaaggt gatcgcgtat gcccgcaagt tcctcgacga cagtgttccg     540
ctgtcgtcgg gttcctttgg cgacgccacc ggtttcacag tgcaggatgg ccagctcgtg     600
gttgccttgc cggataagtc caccggcctg gccaaccccg gccagttcgc cggctacacc     660
ggcgcagccg agtcgccgac atcggtgctg ctaatcaatc acggtttgca catcgagatc     720
ctgatcgatc cggagtcgca ggtcggcacc accgaccggg ccggcgtcaa ggacgtgatc     780
ctggaatccg cgatcaccac gatcatggac ttcgaggact cggtggccgc cgtggacgcc     840
gccgacaagg tgctgggtta tcggaactgg ctcggcctga acaagggcga cctggcagca     900
gcggtagaca aggacggcac cgctttcctg cgggtgctca atagggaccg gaactacacc     960
gcacccggcg gtggccagtt cacgctgcct ggacgcagcc tcatgttcgt ccgcaacgtc    1020
ggtcacttga tgacgaatga cgccatcgtc gacactgacg gcagcgaggt gttcgaaggc    1080
atcatggatg ccctattcac cggcctgatc gccatccacg ggctaaaggc cagcgacgtc    1140
aacgggccgc tgatcaacag ccgcaccggc tccatctaca tcgtcaagcc gaagatgcac    1200
ggtccggccg aggtggcgtt tacctgcgaa ctgttcagcc gggttgaaga tgtgctgggg    1260
ttgccgcaaa acaccatgaa gatcggcatc atggacgagg aacgccggac cacggtcaac    1320
ctcaaggcgt gcatcaaagc tgccgcggac cgcgtggtgt tcatcaacac cgggttcctg    1380
gaccgcaccg gcgatgaaat ccacacctcg atggaggccg ccccgatggt gcgcaagggc    1440
accatgaaga gccagccgtg gatcttggcc tacgaggacc acaacgtcga tgccggcctg    1500
```

```
gccgccgggt tcagcggccg agcccaggtc ggcaagggca tgtggacaat gaccgagctg    1560
atggccgaca tggtcgagac aaaaatcgcc cagccgcgcg ccggggccag caccgcctgg    1620
gttccctctc ccactgcggc caccctgcat gcgctgcact accaccaggt cgacgtcgcc    1680
gcggtgcaac aaggactggc ggggaagcgt cgcgccacca tcgaacaatt gctgaccatt    1740
ccgctggcca aggaattggc ctgggctccc gacgagatcc gcgaagaggt cgacaacaac    1800
tgtcaatcca cctcggcta cgtggttcgc tgggttgatc aaggtgtcgg ctgctcgaag    1860
gtgcccgaca tccacgacgt cgcgctcatg gaggaccggg ccacgctgcg aatctccagc    1920
caattgttgg ccaactggct cgccacggt gtgatcacca gcgcggatgt gcgggccagc    1980
ttggagcgga tggcgccgtt ggtcgatcga caaaacgcgg gcgacgtggc ataccgaccg    2040
atggcaccca acttcgacga cagtatcgcc ttcctggccg cgcaggagct gatcttgtcc    2100
ggggcccagc agcccaacgg ctacaccgag ccgatcctgc accgacgtcg tcgggagttt    2160
aaggcccggg ccgctgagaa gccggcccca tcggacaggg ccggtgacga tgcggccagg    2220
```

<210> SEQ ID NO 2
<211> LENGTH: 740
<212> TYPE: PRT
<213> ORGANISM: Mycobacterium tuberculosis

<400> SEQUENCE: 2

```
Thr Asp Arg Val Ser Val Gly Asn Leu Arg Ile Ala Arg Val Leu Tyr
1               5                   10                  15

Asp Phe Val Asn Asn Glu Ala Leu Pro Gly Thr Asp Ile Asp Pro Asp
            20                  25                  30

Ser Phe Trp Ala Gly Val Asp Lys Val Val Ala Asp Leu Thr Pro Gln
        35                  40                  45

Asn Gln Ala Leu Leu Asn Ala Arg Asp Glu Leu Gln Ala Gln Ile Asp
    50                  55                  60

Lys Trp His Arg Arg Val Ile Glu Pro Ile Asp Met Asp Ala Tyr
65                  70                  75                  80

Arg Gln Phe Leu Thr Glu Ile Gly Tyr Leu Leu Pro Glu Pro Asp Asp
                85                  90                  95

Phe Thr Ile Thr Thr Ser Gly Val Asp Ala Glu Ile Thr Thr Thr Ala
            100                 105                 110

Gly Pro Gln Leu Val Pro Val Leu Asn Ala Arg Phe Ala Leu Asn
        115                 120                 125

Ala Ala Asn Ala Arg Trp Gly Ser Leu Tyr Asp Ala Leu Tyr Gly Thr
    130                 135                 140

Asp Val Ile Pro Glu Thr Asp Gly Ala Glu Lys Gly Pro Thr Tyr Asn
145                 150                 155                 160

Lys Val Arg Gly Asp Lys Val Ile Ala Tyr Ala Arg Lys Phe Leu Asp
                165                 170                 175

Asp Ser Val Pro Leu Ser Ser Gly Ser Phe Gly Asp Ala Thr Gly Phe
            180                 185                 190

Thr Val Gln Asp Gly Gln Leu Val Val Ala Leu Pro Asp Lys Ser Thr
        195                 200                 205

Gly Leu Ala Asn Pro Gly Gln Phe Ala Gly Tyr Thr Gly Ala Ala Glu
    210                 215                 220

Ser Pro Thr Ser Val Leu Leu Ile Asn His Gly Leu His Ile Glu Ile
225                 230                 235                 240

Leu Ile Asp Pro Glu Ser Gln Val Gly Thr Thr Asp Arg Ala Gly Val
                245                 250                 255
```

```
Lys Asp Val Ile Leu Glu Ser Ala Ile Thr Thr Ile Met Asp Phe Glu
            260                 265                 270

Asp Ser Val Ala Ala Val Asp Ala Asp Lys Val Leu Gly Tyr Arg
        275                 280                 285

Asn Trp Leu Gly Leu Asn Lys Gly Asp Leu Ala Ala Val Asp Lys
290                 295                 300

Asp Gly Thr Ala Phe Leu Arg Val Leu Asn Arg Asp Arg Asn Tyr Thr
305                 310                 315                 320

Ala Pro Gly Gly Gly Gln Phe Thr Leu Pro Gly Arg Ser Leu Met Phe
                325                 330                 335

Val Arg Asn Val Gly His Leu Met Thr Asn Asp Ala Ile Val Asp Thr
            340                 345                 350

Asp Gly Ser Glu Val Phe Glu Gly Ile Met Asp Ala Leu Phe Thr Gly
        355                 360                 365

Leu Ile Ala Ile His Gly Leu Lys Ala Ser Asp Val Asn Gly Pro Leu
370                 375                 380

Ile Asn Ser Arg Thr Gly Ser Ile Tyr Ile Val Lys Pro Lys Met His
385                 390                 395                 400

Gly Pro Ala Glu Val Ala Phe Thr Cys Glu Leu Phe Ser Arg Val Glu
                405                 410                 415

Asp Val Leu Gly Leu Pro Gln Asn Thr Met Lys Ile Gly Ile Met Asp
            420                 425                 430

Glu Glu Arg Arg Thr Thr Val Asn Leu Lys Ala Cys Ile Lys Ala Ala
        435                 440                 445

Ala Asp Arg Val Val Phe Ile Asn Thr Gly Phe Leu Asp Arg Thr Gly
450                 455                 460

Asp Glu Ile His Thr Ser Met Glu Ala Gly Pro Met Val Arg Lys Gly
465                 470                 475                 480

Thr Met Lys Ser Gln Pro Trp Ile Leu Ala Tyr Glu Asp His Asn Val
                485                 490                 495

Asp Ala Gly Leu Ala Ala Gly Phe Ser Gly Arg Ala Gln Val Gly Lys
            500                 505                 510

Gly Met Trp Thr Met Thr Glu Leu Met Ala Asp Met Val Glu Thr Lys
        515                 520                 525

Ile Ala Gln Pro Arg Ala Gly Ala Ser Thr Ala Trp Val Pro Ser Pro
530                 535                 540

Thr Ala Ala Thr Leu His Ala Leu His Tyr His Gln Val Asp Val Ala
545                 550                 555                 560

Ala Val Gln Gln Gly Leu Ala Gly Lys Arg Arg Ala Thr Ile Glu Gln
                565                 570                 575

Leu Leu Thr Ile Pro Leu Ala Lys Glu Leu Ala Trp Ala Pro Asp Glu
            580                 585                 590

Ile Arg Glu Glu Val Asp Asn Asn Cys Gln Ser Ile Leu Gly Tyr Val
        595                 600                 605

Val Arg Trp Val Asp Gln Gly Val Gly Cys Ser Lys Val Pro Asp Ile
610                 615                 620

His Asp Val Ala Leu Met Glu Asp Arg Ala Thr Leu Arg Ile Ser Ser
625                 630                 635                 640

Gln Leu Leu Ala Asn Trp Leu Arg His Gly Val Ile Thr Ser Ala Asp
                645                 650                 655

Val Arg Ala Ser Leu Glu Arg Met Ala Pro Leu Val Asp Arg Gln Asn
            660                 665                 670

Ala Gly Asp Val Ala Tyr Arg Pro Met Ala Pro Asn Phe Asp Asp Ser
        675                 680                 685
```

```
Ile Ala Phe Leu Ala Ala Gln Glu Leu Ile Leu Ser Gly Ala Gln Gln
        690                 695                 700

Pro Asn Gly Tyr Thr Glu Pro Ile Leu His Arg Arg Arg Arg Glu Phe
705                 710                 715                 720

Lys Ala Arg Ala Ala Glu Lys Pro Ala Pro Ser Asp Arg Ala Gly Asp
                725                 730                 735

Asp Ala Ala Arg
            740

<210> SEQ ID NO 3
<211> LENGTH: 1278
<212> TYPE: DNA
<213> ORGANISM: Mycobacterium tuberculosis

<400> SEQUENCE: 3
gtgcagaagt acggcggatc ctcggtggcc gacgccgaac ggattcgccg cgtcgccgaa    60
cgcatcgtcg ccaccaagaa gcaaggcaat gacgtcgtcg tcgtcgtctc tgccatgggg   120
gataccaccg acgacctgct ggatctggct cagcaggtgt gcccggcgcc gccgcctcgg   180
gagctggaca tgctgcttac cgccggtgaa cgcatctcga atgcgttggt ggccatggcc   240
atcgagtcgc tcggcgcgca tgcccggtcg ttcaccggtt cgcaggccgg ggtgatcacc   300
accggcaccc acgcaacgc caagatcatc gacgtcacgc cggggcggct gcaaaccgcc   360
cttgaggagg gcgggtcgt tttggtggcc ggattccaag gggtcagcca ggacaccaag   420
gatgtcacga cgttgggccg cggcggctcg acaccaccg ccgtcgccat ggccgccgcg   480
ctgggtgccg atgtctgtga gatctacacc gacgtggacg gcatcttcag cgccgacccg   540
cgcatcgtgc gcaacgcccg aaagctcgac accgtgacct tcgaggaaat gctcgagatg   600
gcggcctgcg gcgccaaggt gctgatgctg cgctgcgtgg aatacgctcg ccgccataat   660
attccggtgc acgtccggtc gtcgtactcg gacagaccgg gcaccgtcgt tgtcggatcg   720
atcaaggacg tacccatgga agaccccatc ctgaccggag tcgcgcacga ccgcagcgag   780
gccaaggtga ccatcgtcgg gctgcccgac atccccgggt atgcggccaa ggtgtttagg   840
gcggtggcca gacgccgacg tcaacatcga catggtgctg cagaacgtct ccaaggtcga   900
ggacggcaag accgacatca ccttcacctg ctcccgcaga cgtcgggccc gccgccgtgg   960
aaaaactgga ctcgctcaga aacgagatcg gcttctacac agctgctgta cgacgaccac  1020
atcggcaagg tatcgctgat cggtgccggc atgcgcagcc accccggggt caccgcgacg  1080
ttctgtgagg cgctggcggc ggtggggggtc aacatcgagc tgatctccac ctcggaagat  1140
cagagatctc ggtgttgtgc cgcgacaccg aactggacaa ggccgtggtc gcgctgcatg  1200
aagcgttcgg gctcggcggc gacgaggagg ccacggtgta cgcggggacg ggacggtaga  1260
tgggcctgtc aatagtga                                                1278

<210> SEQ ID NO 4
<211> LENGTH: 836
<212> TYPE: PRT
<213> ORGANISM: Mycobacterium tuberculosis

<400> SEQUENCE: 4

Val Gln Lys Tyr Gly Gly Ser Ser Val Ala Asp Ala Glu Arg Ile Arg
1               5                   10                  15

Arg Val Ala Glu Arg Ile Val Ala Thr Lys Lys Gln Gly Asn Asp Val
            20                  25                  30

Val Val Val Val Ser Ala Met Gly Asp Thr Thr Asp Asp Leu Leu Asp
```

```
                35                  40                  45
Leu Ala Gln Gln Val Cys Pro Ala Pro Pro Arg Glu Leu Asp Met
 50                  55                  60
Leu Leu Thr Ala Gly Glu Arg Ile Ser Asn Ala Leu Val Ala Met Ala
 65                      70                  75                  80
Ile Glu Ser Leu Gly Ala His Ala Arg Ser Phe Thr Gly Ser Gln Ala
                     85                  90                  95
Gly Val Ile Thr Thr Gly Thr His Gly Asn Ala Lys Ile Ile Asp Val
                100                     105                 110
Thr Pro Gly Arg Leu Gln Thr Ala Leu Glu Glu Gly Arg Val Val Leu
                115                     120                 125
Val Ala Gly Phe Gln Gly Val Ser Gln Asp Thr Lys Asp Val Thr Thr
            130                     135                 140
Leu Gly Arg Gly Gly Ser Asp Thr Thr Ala Val Ala Met Ala Ala Ala
145                     150                 155                 160
Leu Gly Ala Asp Val Cys Glu Ile Tyr Thr Asp Val Asp Gly Ile Phe
                    165                 170                 175
Ser Ala Asp Pro Arg Ile Val Arg Asn Ala Arg Lys Leu Asp Thr Val
                180                     185                 190
Thr Phe Glu Glu Met Leu Glu Met Ala Ala Cys Gly Ala Lys Val Leu
                195                     200                 205
Met Leu Arg Cys Val Glu Tyr Ala Arg Arg His Asn Ile Pro Val His
        210                     215                 220
Val Arg Ser Ser Tyr Ser Asp Arg Pro Gly Thr Val Val Gly Ser
225                     230                     235                 240
Ile Lys Asp Val Pro Met Glu Asp Pro Ile Leu Thr Gly Val Ala His
                    245                 250                     255
Asp Arg Ser Glu Ala Lys Val Thr Ile Val Gly Leu Pro Asp Ile Pro
                260                     265                 270
Gly Tyr Ala Ala Lys Val Phe Arg Ala Val Ala Arg Arg Arg Gln
        275                     280                 285
His Arg His Gly Ala Ala Glu Arg Leu Gln Gly Arg Gly Arg Gln Asp
    290                     295                 300
Arg His His Leu His Leu Leu Pro Gln Thr Ser Gly Pro Pro Trp
305                     310                 315                     320
Lys Asn Trp Thr Arg Ser Glu Thr Arg Ser Ala Ser Thr Gln Leu Leu
                325                     330                 335
Tyr Asp Asp His Ile Gly Lys Val Ser Leu Ile Gly Ala Gly Met Arg
                340                     345                 350
Ser His Pro Gly Val Thr Ala Thr Phe Cys Glu Ala Leu Ala Ala Val
                355                     360                 365
Gly Val Asn Ile Glu Leu Ile Ser Thr Ser Glu Asp Gln Arg Ser Arg
                370                     375                 380
Cys Cys Ala Ala Thr Pro Asn Trp Thr Arg Pro Trp Ser Arg Cys Met
385                     390                 395                     400
Lys Arg Ser Gly Ser Ala Ala Thr Arg Arg Pro Arg Val Gln Lys Tyr
                405                     410                 415
Gly Gly Ser Ser Val Ala Asp Ala Glu Arg Ile Arg Arg Val Ala Glu
                420                     425                 430
Arg Ile Val Ala Thr Lys Lys Gln Gly Asn Asp Val Val Val Val
                435                     440                 445
Ser Ala Met Gly Asp Thr Thr Asp Asp Leu Leu Asp Leu Ala Gln Gln
450                     455                 460
```

Val Cys Pro Ala Pro Pro Arg Glu Leu Asp Met Leu Leu Thr Ala
465                 470                 475                 480

Gly Glu Arg Ile Ser Asn Ala Leu Val Ala Met Ala Ile Glu Ser Leu
            485                 490                 495

Gly Ala His Ala Arg Ser Phe Thr Gly Ser Gln Ala Gly Val Ile Thr
                500                 505                 510

Thr Gly Thr His Gly Asn Ala Lys Ile Ile Asp Val Thr Pro Gly Arg
            515                 520                 525

Leu Gln Thr Ala Leu Glu Glu Gly Arg Val Val Leu Val Ala Gly Phe
530                 535                 540

Gln Gly Val Ser Gln Asp Thr Lys Asp Val Thr Thr Leu Gly Arg Gly
545                 550                 555                 560

Gly Ser Asp Thr Thr Ala Val Ala Met Ala Ala Ala Leu Gly Ala Asp
                565                 570                 575

Val Cys Glu Ile Tyr Thr Asp Val Asp Gly Ile Phe Ser Ala Asp Pro
                580                 585                 590

Arg Ile Val Arg Asn Ala Arg Lys Leu Asp Thr Val Thr Phe Glu Glu
            595                 600                 605

Met Leu Glu Met Ala Ala Cys Gly Ala Lys Val Leu Met Leu Arg Cys
610                 615                 620

Val Glu Tyr Ala Arg Arg His Asn Ile Pro Val His Val Arg Ser Ser
625                 630                 635                 640

Tyr Ser Asp Arg Pro Gly Thr Val Val Gly Ser Ile Lys Asp Val
                645                 650                 655

Pro Met Glu Asp Pro Ile Leu Thr Gly Val Ala His Asp Arg Ser Glu
                660                 665                 670

Ala Lys Val Thr Ile Val Gly Leu Pro Asp Ile Pro Gly Tyr Ala Ala
            675                 680                 685

Lys Val Phe Arg Ala Val Ala Arg Arg Arg Gln His Arg His Gly
690                 695                 700

Ala Ala Glu Arg Leu Gln Gly Arg Gly Arg Gln Asp Arg His His Leu
705                 710                 715                 720

His Leu Leu Pro Gln Thr Ser Gly Pro Pro Trp Lys Asn Trp Thr
                725                 730                 735

Arg Ser Glu Thr Arg Ser Ala Ser Thr Gln Leu Leu Tyr Asp Asp His
            740                 745                 750

Ile Gly Lys Val Ser Leu Ile Gly Ala Gly Met Arg Ser His Pro Gly
            755                 760                 765

Val Thr Ala Thr Phe Cys Glu Ala Leu Ala Ala Val Gly Val Asn Ile
770                 775                 780

Glu Leu Ile Ser Thr Ser Glu Asp Gln Arg Ser Arg Cys Cys Ala Ala
785                 790                 795                 800

Thr Pro Asn Trp Thr Arg Pro Trp Ser Arg Cys Met Lys Arg Ser Gly
                805                 810                 815

Ser Ala Ala Thr Arg Arg Pro Arg Cys Thr Arg Gly Arg Asp Gly Arg
            820                 825                 830

Trp Ala Cys Gln
        835

<210> SEQ ID NO 5
<211> LENGTH: 542
<212> TYPE: DNA
<213> ORGANISM: Mycobacterium tuberculosis
<220> FEATURE:
<221> NAME/KEY: misc_feature
<222> LOCATION: (406)..(406)

<223> OTHER INFORMATION: n is a, c, g, or t

<400> SEQUENCE: 5

```
gaattcggca cgagaggtga tcgacatcat cgggaccagc cccacatcct gggaacaggc      60
ggcggcggag gcggtccagc gggcgcggga tagcgtcgat gacatccgcg tcgctcgggt     120
cattgagcag gacatggccg tggacagcgc cggcaagatc acctaccgca tcaagctcga     180
agtgtcgttc aagatgaggc cggcgcaacc gcgctagcac gggccggcga gcaagacgca     240
aaatcgcacg gtttgcggtt gattcgtgcg attttgtgtc tgctcgccga ggcctaccag     300
gcgcggccca ggtccgcgtg ctgccgtatc caggcgtgca tcgcgattcc ggcggccacg     360
ccggagttaa tgcttcgcgt cgacccgaac tgggcgatcc gccggngagc tgatcgatga     420
ccgtggccag cccgtcgatg cccgagttgc ccgaggaaac gtgctgccag gccggtagga     480
agcgtccgta ggcggcggtg ctgaccggct ctgcctgcgc cctcagtgcg ccagcgagc      540
gg                                                                    542
```

<210> SEQ ID NO 6
<211> LENGTH: 64
<212> TYPE: PRT
<213> ORGANISM: Mycobacterium tuberculosis

<400> SEQUENCE: 6

```
Val Ile Asp Ile Ile Gly Thr Ser Pro Thr Ser Trp Glu Gln Ala Ala
 1               5                  10                  15

Ala Glu Ala Val Gln Arg Ala Arg Asp Ser Val Asp Asp Ile Arg Val
                20                  25                  30

Ala Arg Val Ile Glu Gln Asp Met Ala Val Asp Ser Ala Gly Lys Ile
                35                  40                  45

Thr Tyr Arg Ile Lys Leu Glu Val Ser Phe Lys Met Arg Pro Ala Gln
            50                  55                  60
```

<210> SEQ ID NO 7
<211> LENGTH: 1993
<212> TYPE: DNA
<213> ORGANISM: Mycobacterium tuberculosis

<400> SEQUENCE: 7

```
tgttcttcga cggcaggctg gtggaggaag ggcccaccga acagctgttc tcctcgccga      60
agcatgcgga aaccgcccga tacgtcgccg gactgtcggg ggacgtcaag gacgccaagc     120
gcggaaattg aagagcacag aaaggtatgg cgtgaaaatt cgtttgcata cgctgttggc     180
cgtgttgacc gctgcgccgc tgctgctagc agcggcgggc tgtggctcga aaccaccgag     240
cggttcgcct gaaacgggcg ccggcgccgg tactgtcgcg actaccccg cgtcgtcgcc     300
ggtgacgttg gcggagaccg gtagcacgct gctctacccg ctgttcaacc tgtggggtcc     360
ggcctttcac gagaggtatc cgaacgtcac gatcaccgct cagggcaccg gttctggtgc     420
cgggatcgcg caggccgccg ccgggacggt caacattggg gcctccgacg cctatctgtc     480
ggaaggtgat atggccgcgc acaagggct gatgaacatc gcgctagcca tctccgctca     540
gcaggtcaac tacaacctgc ccggagtgag cgagcacctc aagctgaacg gaaaagtcct     600
ggcggccatg taccagggca ccatcaaaac ctgggacgac ccgcagatcg ctgcgctcaa     660
ccccggcgtg aacctgcccg gcaccgcggt agttccgctg caccgctccg acgggtccgg     720
tgacaccttc ttgttcaccc agtacctgtc caagcaagat cccgagggct ggggcaagtc     780
gcccggcttc ggcaccaccg tcgacttccc ggcggtgccg ggtgcgctgg gtgagaacgg     840
```

-continued

```
caacggcggc atggtgaccg gttgcgccga caccgggc tgcgtggcct atatcggcat    900
cagcttcctc gaccaggcca gtcaacgggg actcggcgag gcccaactag caatagctc    960
tggcaatttc ttgttgcccg acgcgcaaag cattcaggcc gcggcggctg cttcgcatc   1020
gaaaaccccg gcgaaccagg cgatttcgat gatcgacggg cccgcccgg acggctaccc   1080
gatcatcaac tacgagtacg ccatcgtcaa caaccggcaa aaggacgccg ccaccgcgca   1140
gaccttgcag gcatttctgc actgggcgat caccgacggc aacaaggcct cgttcctcga   1200
ccaggttcat ttccagccgc tgccgcccgc ggtggtgaag ttgtctgacg cgttgatcgc   1260
gacgatttcc agctagcctc gttgaccacc acgcgacaga acctccgtc gggccatcgg   1320
gctgctttgc ggagcatgct ggcccgtgcc ggtgaagtcg gccgcgctgg cccggccatc   1380
cggtggttgg gtgggatagg tgcggtgatc ccgctgcttg cgctggtctt ggtgctggtg   1440
gtgctggtca tcgaggcgat gggtgcgatc aggctcaacg ggttgcattt cttcaccgcc   1500
accgaatgga atccaggcaa cacctacggc gaaaccgttg tcaccgacgc gtcgcccatc   1560
cggtcggcgc tactacgggg cgttgccgc tgatcgtcgg gacgctggcg acctcggcaa   1620
tcgccctgat catcgcggtg ccggtctctg taggagcggc gctggtgatc gtggaacggc   1680
tgccgaaacg gttggccgag gctgtgggaa tagtcctgga attgctcgcc ggaatcccca   1740
gcgtggtcgt cggtttgtgg ggggcaatga cgttcgggcc gttcatcgct catcacatcg   1800
ctccggtgat cgctcacaac gctcccgatg tgccggtgct gaactacttg cgcggcgacc   1860
cgggcaacgg ggagggcatg ttggtgtccg gtctggtgtt ggcggtgatg gtcgttccca   1920
ttatcgccac caccactcat gacctgttcc ggcaggtgcc ggtgttgccc cgggagggcg   1980
cgatcgggaa ttc                                                     1993
```

<210> SEQ ID NO 8
<211> LENGTH: 375
<212> TYPE: PRT
<213> ORGANISM: Mycobacterium tuberculosis

<400> SEQUENCE: 8

Thr Met Lys Ile Arg Leu His Thr Leu Leu Ala Val Leu Thr Ala Ala
1               5                   10                  15

Pro Leu Leu Ala Ala Ala Gly Cys Gly Ser Lys Pro Pro Ser Gly
            20                  25                  30

Ser Pro Glu Thr Gly Ala Gly Ala Gly Thr Val Ala Thr Thr Pro Ala
        35                  40                  45

Ser Ser Pro Val Thr Leu Ala Glu Thr Gly Ser Thr Leu Leu Tyr Pro
    50                  55                  60

Leu Phe Asn Leu Trp Gly Pro Ala Phe His Glu Arg Tyr Pro Asn Val
65                  70                  75                  80

Thr Ile Thr Ala Gln Gly Thr Gly Ser Gly Ala Gly Ile Ala Gln Ala
                85                  90                  95

Ala Ala Gly Thr Val Asn Ile Gly Ala Ser Asp Ala Tyr Leu Ser Glu
            100                 105                 110

Gly Asp Met Ala Ala His Lys Gly Leu Met Asn Ile Ala Leu Ala Ile
        115                 120                 125

Ser Ala Gln Gln Val Asn Tyr Asn Leu Pro Gly Val Ser Glu His Leu
    130                 135                 140

Lys Leu Asn Gly Lys Val Leu Ala Ala Met Tyr Gln Gly Thr Ile Lys
145                 150                 155                 160

Thr Trp Asp Asp Pro Gln Ile Ala Ala Leu Asn Pro Gly Val Asn Leu
                165                 170                 175

Pro Gly Thr Ala Val Pro Leu His Arg Ser Asp Gly Ser Gly Asp
            180                 185                 190

Thr Phe Leu Phe Thr Gln Tyr Leu Ser Lys Gln Asp Pro Glu Gly Trp
            195                 200                 205

Gly Lys Ser Pro Gly Phe Gly Thr Thr Val Asp Phe Pro Ala Val Pro
        210                 215                 220

Gly Ala Leu Gly Glu Asn Gly Asn Gly Gly Met Val Thr Gly Cys Ala
225                 230                 235                 240

Glu Thr Pro Gly Cys Val Ala Tyr Ile Gly Ile Ser Phe Leu Asp Gln
                245                 250                 255

Ala Ser Gln Arg Gly Leu Gly Glu Ala Gln Leu Gly Asn Ser Ser Gly
            260                 265                 270

Asn Phe Leu Leu Pro Asp Ala Gln Ser Ile Gln Ala Ala Ala Gly
            275                 280                 285

Phe Ala Ser Lys Thr Pro Ala Asn Gln Ala Ile Ser Met Ile Asp Gly
        290                 295                 300

Pro Ala Pro Asp Gly Tyr Pro Ile Ile Asn Tyr Glu Tyr Ala Ile Val
305                 310                 315                 320

Asn Asn Arg Gln Lys Asp Ala Ala Thr Ala Gln Thr Leu Gln Ala Phe
                325                 330                 335

Leu His Trp Ala Ile Thr Asp Gly Asn Lys Ala Ser Phe Leu Asp Gln
            340                 345                 350

Val His Phe Gln Pro Leu Pro Pro Ala Val Val Lys Leu Ser Asp Ala
            355                 360                 365

Leu Ile Ala Thr Ile Ser Ser
            370                 375

<210> SEQ ID NO 9
<211> LENGTH: 327
<212> TYPE: DNA
<213> ORGANISM: Mycobacterium tuberculosis

<400> SEQUENCE: 9
cggcacgaga gaccgatgcc gctaccctcg cgcaggaggc aggtaatttc gagcggatct     60
ccggcgacct gaaaacccag atcgaccagg tggagtcgac ggcaggttcg ttgcagggcc    120
agtggcgcgg cgcggcgggg acggccgccc aggccgcgt ggtgcgcttc caagaagcag    180
ccaataagca gaagcaggaa ctcgacgaga tctcgacgaa tattcgtcag gccggcgtcc    240
aatactcgag ggccgacgag gagcagcagc aggcgctgtc ctcgcaaatg ggcttctgac    300
ccgctaatac gaaaagaaac ggagcaa                                       327

<210> SEQ ID NO 10
<211> LENGTH: 95
<212> TYPE: PRT
<213> ORGANISM: Mycobacterium tuberculosis

<400> SEQUENCE: 10

Thr Asp Ala Ala Thr Leu Ala Gln Glu Ala Gly Asn Phe Glu Arg Ile
1               5                   10                  15

Ser Gly Asp Leu Lys Thr Gln Ile Asp Gln Val Glu Ser Thr Ala Gly
            20                  25                  30

Ser Leu Gln Gly Gln Trp Arg Gly Ala Ala Gly Thr Ala Ala Gln Ala
        35                  40                  45

Ala Val Val Arg Phe Gln Glu Ala Ala Asn Lys Gln Lys Gln Glu Leu
    50                  55                  60

Asp Glu Ile Ser Thr Asn Ile Arg Gln Ala Gly Val Gln Tyr Ser Arg
65                  70                  75                  80

Ala Asp Glu Glu Gln Gln Gln Ala Leu Ser Ser Gln Met Gly Phe
            85                  90                  95

<210> SEQ ID NO 11
<211> LENGTH: 702
<212> TYPE: DNA
<213> ORGANISM: Mycobacterium tuberculosis
<220> FEATURE:
<221> NAME/KEY: misc_feature
<222> LOCATION: (325)..(325)
<223> OTHER INFORMATION: n is a, c, g, or t
<220> FEATURE:
<221> NAME/KEY: misc_feature
<222> LOCATION: (328)..(328)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (353)..(353)
<223> OTHER INFORMATION: n is a, c, g, or t
<220> FEATURE:
<221> NAME/KEY: misc_feature
<222> LOCATION: (442)..(442)
<223> OTHER INFORMATION: n is a, c, g, or t
<220> FEATURE:
<221> NAME/KEY: misc_feature
<222> LOCATION: (659)..(659)
<223> OTHER INFORMATION: n is a, c, g, or t
<220> FEATURE:
<221> NAME/KEY: misc_feature
<222> LOCATION: (679)..(679)
<223> OTHER INFORMATION: n is a, c, g, or t

<400> SEQUENCE: 11
cggcacgagg atcggtaccc cgcggcatcg gcagctgccg attcgccggg tttccccacc      60
cgaggaaagc cgctaccaga tggcgctgcc gaagtagggc gatccgttcg cgatgccggc     120
atgaacgggc ggcatcaaat tagtgcagga acctttcagt ttagcgacga taatggctat     180
agcactaagg aggatgatcc gatatgacgc agtcgcagac cgtgacggtg atcagcaag      240 agattttgaa cagggccaac gaggtggagg ccccgatggc ggaccaccg actgatgtcc      300 ccatcacacc gtgcgaactc acggnggnta aaaacgccgc caacagntg gtnttgtccg      360 ccgacaacat gcgggaatac ctggcggccg gtgccaaaga gcggcagcgt ctggcgacct     420
cgctgcgcaa cgcggccaag gngtatgcg aggttgatga ggaggctgcg accgcgctgg     480
acaacgacgg cgaaggaact gtgcaggcag atcggccgg ggccgtcgga ggggacagtt     540
cggccgaact aaccgatacg ccgagggtgg ccacggccgg tgaacccaac ttcatggatc     600
tcaaagaagc ggcaaggaag ctcgaaacgg gcgaccaagg cgcatcgctc gcgcactgng     660
gggatgggtg gaacacttnc accctgacgc tgcaaggcga cg                       702

<210> SEQ ID NO 12
<211> LENGTH: 392
<212> TYPE: PRT
<213> ORGANISM: Mycobacterium tuberculosis

<400> SEQUENCE: 12

Met Ser Arg Ala Phe Ile Ile Asp Pro Thr Ile Ser Ala Ile Asp Gly
1               5                   10                  15

Leu Tyr Asp Leu Leu Gly Ile Gly Ile Pro Asn Gln Gly Gly Ile Leu
            20                  25                  30

Tyr Ser Ser Leu Glu Tyr Phe Glu Lys Ala Leu Glu Glu Leu Ala Ala
           35                  40                  45

Ala Phe Pro Gly Asp Gly Trp Leu Gly Ser Ala Ala Asp Lys Tyr Ala
 50                  55                  60

Gly Lys Asn Arg Asn His Val Asn Phe Phe Gln Glu Leu Ala Asp Leu
 65                  70                  75                  80

Asp Arg Gln Leu Ile Ser Leu Ile His Asp Gln Ala Asn Ala Val Gln
                 85                  90                  95

Thr Thr Arg Asp Ile Leu Glu Gly Ala Lys Lys Gly Leu Glu Phe Val
            100                 105                 110

Arg Pro Val Ala Val Asp Leu Thr Tyr Ile Pro Val Val Gly His Ala
            115                 120                 125

Leu Ser Ala Ala Phe Gln Ala Pro Phe Cys Ala Gly Ala Met Ala Val
130                 135                 140

Val Gly Gly Ala Leu Ala Tyr Leu Val Val Lys Thr Leu Ile Asn Ala
145                 150                 155                 160

Thr Gln Leu Leu Lys Leu Leu Ala Lys Leu Ala Glu Leu Val Ala Ala
                165                 170                 175

Ala Ile Ala Asp Ile Ile Ser Asp Val Ala Asp Ile Ile Lys Gly Thr
            180                 185                 190

Leu Gly Glu Val Trp Glu Phe Ile Thr Asn Ala Leu Asn Gly Leu Lys
            195                 200                 205

Glu Leu Trp Asp Lys Leu Thr Gly Trp Val Thr Gly Leu Phe Ser Arg
210                 215                 220

Gly Trp Ser Asn Leu Glu Ser Phe Phe Ala Gly Val Pro Gly Leu Thr
225                 230                 235                 240

Gly Ala Thr Ser Gly Leu Ser Gln Val Thr Gly Leu Phe Gly Ala Ala
                245                 250                 255

Gly Leu Ser Ala Ser Ser Gly Leu Ala His Ala Asp Ser Leu Ala Ser
            260                 265                 270

Ser Ala Ser Leu Pro Ala Leu Ala Gly Ile Gly Gly Ser Gly Phe
            275                 280                 285

Gly Gly Leu Pro Ser Leu Ala Gln Val His Ala Ala Ser Thr Arg Gln
290                 295                 300

Ala Leu Arg Pro Arg Ala Asp Gly Pro Val Gly Ala Ala Ala Glu Gln
305                 310                 315                 320

Val Gly Gly Gln Ser Gln Leu Val Ser Ala Gln Gly Ser Gln Gly Met
                325                 330                 335

Gly Gly Pro Val Gly Met Gly Met His Pro Ser Ser Gly Ala Ser
            340                 345                 350

Lys Gly Thr Thr Thr Lys Lys Tyr Ser Glu Gly Ala Ala Ala Gly Thr
            355                 360                 365

Glu Asp Ala Glu Arg Ala Pro Val Glu Ala Asp Ala Gly Gly Gly Gln
370                 375                 380

Lys Val Leu Val Arg Asn Val Val
385                 390

<210> SEQ ID NO 13
<211> LENGTH: 1200
<212> TYPE: DNA
<213> ORGANISM: Mycobacterium tuberculosis

<400> SEQUENCE: 13
caggcatgag cagagcgttc atcatcgatc caacgatcag tgccattgac ggcttgtacg    60
accttctggg gattggaata cccaaccaag ggggtatcct ttactcctca ctagagtact   120

-continued

```
tcgaaaaagc cctggaggag ctggcagcag cgtttccggg tgatggctgg ttaggttcgg      180
ccgcggacaa atacgccggc aaaaaccgca accacgtgaa ttttttccag gaactggcag      240
acctcgatcg tcagctcatc agcctgatcc acgaccaggc caacgcggtc cagacgaccc      300
gcgacatcct ggagggcgcc aagaaaggtc tcgagttcgt gcgcccggtg gctgtggacc      360
tgacctacat cccggtcgtc gggcacgccc tatcggccgc cttccaggcg ccgttttgcg      420
cgggcgcgat ggccgtagtg ggcggcgcgc ttgcctactt ggtcgtgaaa acgctgatca      480
acgcgactca actcctcaaa ttgcttgcca aattggcgga gttggtcgcg ccgccattg      540 cggacatcat ttcggatgtg gcggacatca tcaagggcac cctcggagaa gtgtgggagt      600
tcatcacaaa cgcgctcaac ggcctgaaag agctttggga caagctcacg gggtgggtga      660
ccggactgtt ctctcgaggg tggtcgaacc tggagtcctt ctttgcgggc gtccccggct      720
tgaccggcgc gaccagcggc ttgtcgcaag tgactggctt gttcggtgcg gccggtctgt      780
ccgcatcgtc gggcttggct cacgcggata gcctggcgag ctcagccagc ttgcccgccc      840
tggccggcat tgggggcggg tccggttttg ggggcttgcc gagcctggct caggtccatg      900
ccgcctcaac tcgcaggcg ctacggcccc gagctgatgg cccggtcggc gccgctgccg      960
agcaggtcgg cgggcagtcg cagctggtct ccgcgcaggg ttcccaaggt atgggcggac    1020
ccgtaggcat gggcggcatg caccctctt cgggggcgtc gaaagggacg acgacgaaga    1080
agtactcgga aggcgcggcg gcgggcactg aagacgccga gcgcgcgcca gtcgaagctg    1140
acgcgggcgg tgggcaaaag gtgctggtac gaaacgtcgt ctaacggcat ggcgagccaa    1200
```

<210> SEQ ID NO 14
<211> LENGTH: 394
<212> TYPE: PRT
<213> ORGANISM: Mycobacterium tuberculosis

<400> SEQUENCE: 14

```
Thr Met Ser Arg Ala Phe Ile Ile Asp Pro Thr Ile Ser Ala Ile Asp
1               5                   10                  15

Gly Leu Tyr Asp Leu Leu Gly Ile Gly Ile Pro Asn Gln Gly Gly Ile
            20                  25                  30

Leu Tyr Ser Ser Leu Glu Tyr Phe Glu Lys Ala Leu Glu Glu Leu Ala
        35                  40                  45

Ala Ala Phe Pro Gly Asp Gly Trp Leu Gly Ser Ala Ala Asp Lys Tyr
    50                  55                  60

Ala Gly Lys Asn Arg Asn His Val Asn Phe Gln Glu Leu Ala Asp
65                  70                  75                  80

Leu Asp Arg Gln Leu Ile Ser Leu Ile His Asp Gln Ala Asn Ala Val
                85                  90                  95

Gln Thr Thr Arg Asp Ile Leu Glu Gly Ala Lys Lys Gly Leu Glu Phe
            100                 105                 110

Val Arg Pro Val Ala Val Asp Leu Thr Tyr Ile Pro Val Val Gly His
        115                 120                 125

Ala Leu Ser Ala Ala Phe Gln Ala Pro Phe Cys Ala Gly Ala Met Ala
    130                 135                 140

Val Val Gly Gly Ala Leu Ala Tyr Leu Val Val Lys Thr Leu Ile Asn
145                 150                 155                 160

Ala Thr Gln Leu Leu Lys Leu Leu Ala Lys Leu Ala Glu Leu Val Ala
                165                 170                 175

Ala Ala Ile Ala Asp Ile Ile Ser Asp Val Ala Asp Ile Ile Lys Gly
            180                 185                 190
```

```
Thr Leu Gly Glu Val Trp Glu Phe Ile Thr Asn Ala Leu Asn Gly Leu
            195                 200                 205

Lys Glu Leu Trp Asp Lys Leu Thr Gly Trp Val Thr Gly Leu Phe Ser
        210                 215                 220

Arg Gly Trp Ser Asn Leu Glu Ser Phe Phe Ala Gly Val Pro Gly Leu
225                 230                 235                 240

Thr Gly Ala Thr Ser Gly Leu Ser Gln Val Thr Gly Leu Phe Gly Ala
                245                 250                 255

Ala Gly Leu Ser Ala Ser Ser Gly Leu Ala His Ala Asp Ser Leu Ala
            260                 265                 270

Ser Ser Ala Ser Leu Pro Ala Leu Ala Gly Ile Gly Gly Ser Gly
        275                 280                 285

Phe Gly Gly Leu Pro Ser Leu Ala Gln Val His Ala Ala Ser Thr Arg
        290                 295                 300

Gln Ala Leu Arg Pro Arg Ala Asp Gly Pro Val Gly Ala Ala Ala Glu
305                 310                 315                 320

Gln Val Gly Gly Gln Ser Gln Leu Val Ser Ala Gly Ser Gln Gly
            325                 330                 335

Met Gly Gly Pro Val Gly Met Gly Gly Met His Pro Ser Ser Gly Ala
        340                 345                 350

Ser Lys Gly Thr Thr Thr Lys Lys Tyr Ser Glu Gly Ala Ala Ala Gly
            355                 360                 365

Thr Glu Asp Ala Glu Arg Ala Pro Val Glu Ala Asp Ala Gly Gly Gly
        370                 375                 380

Gln Lys Val Leu Val Arg Asn Val Val Pro
385                 390
```

```
<210> SEQ ID NO 15
<211> LENGTH: 726
<212> TYPE: DNA
<213> ORGANISM: Mycobacterium tuberculosis

<400> SEQUENCE: 15
atgcatcacc atcaccatca catgagcaga gcgttcatca tcgatccaac gatcagtgcc      60
attgacggct tgtacgacct tctggggatt ggaataccca accaagggg tatcctttac      120
tcctcactag agtacttcga aaaagccctg gaggagctgg cagcagcgtt ccgggtgat    180
ggctggttag gttcggccgc ggacaaatac gccggcaaaa accgcaacca cgtgaatttt    240
ttccaggaac tggcagacct cgatcgtcag ctcatcagcc tgatccacga ccaggccaac    300
gcggtccaga cgacccgcga catcctggag ggcgccaaga aggtctcga gttcgtgcgc    360
ccggtggctg tggacctgac ctacatcccg gtcgtcgggc acgccctatc ggccgccttc    420
caggcgccgt tttgcgcggg cgcgatggcc gtagtgggcg gcgcgcttgc ctacttggtc    480
gtgaaaacgc tgatcaacgc gactcaactc ctcaaattgc ttgccaaatt ggcggagttg    540
gtcgcggccg ccattgcgga catcatttcg gatgtggcgg acatcatcaa gggcatcctc    600
ggagaagtgt gggagttcat cacaaacgcg ctcaacggcc tgaaagagct ttgggacaag    660
ctcacggggt gggtgaccgg actgttctct cgagggtggt cgaacctgga gtccttctaa    720
gaattc                                                                 726
```

```
<210> SEQ ID NO 16
<211> LENGTH: 239
<212> TYPE: PRT
<213> ORGANISM: Mycobacterium tuberculosis
```

<400> SEQUENCE: 16

```
Met His His His His His Met Ser Arg Ala Phe Ile Ile Asp Pro
1               5                   10                  15

Thr Ile Ser Ala Ile Asp Gly Leu Tyr Asp Leu Gly Ile Gly Ile
            20                  25                  30

Pro Asn Gln Gly Gly Ile Leu Tyr Ser Ser Leu Glu Tyr Phe Glu Lys
        35                  40                  45

Ala Leu Glu Glu Leu Ala Ala Ala Phe Pro Gly Asp Gly Trp Leu Gly
50                  55                  60

Ser Ala Ala Asp Lys Tyr Ala Gly Lys Asn Arg Asn His Val Asn Phe
65                  70                  75                  80

Phe Gln Glu Leu Ala Asp Leu Asp Arg Gln Leu Ile Ser Leu Ile His
                85                  90                  95

Asp Gln Ala Asn Ala Val Gln Thr Thr Arg Asp Ile Leu Glu Gly Ala
            100                 105                 110

Lys Lys Gly Leu Glu Phe Val Arg Pro Val Ala Val Asp Leu Thr Tyr
        115                 120                 125

Ile Pro Val Val Gly His Ala Leu Ser Ala Ala Phe Gln Ala Pro Phe
130                 135                 140

Cys Ala Gly Ala Met Ala Val Val Gly Gly Ala Leu Ala Tyr Leu Val
145                 150                 155                 160

Val Lys Thr Leu Ile Asn Ala Thr Gln Leu Leu Lys Leu Leu Ala Lys
                165                 170                 175

Leu Ala Glu Leu Val Ala Ala Ala Ile Ala Asp Ile Ile Ser Asp Val
            180                 185                 190

Ala Asp Ile Ile Lys Gly Ile Leu Gly Glu Val Trp Glu Phe Ile Thr
        195                 200                 205

Asn Ala Leu Asn Gly Leu Lys Glu Leu Trp Asp Lys Leu Thr Gly Trp
210                 215                 220

Val Thr Gly Leu Phe Ser Arg Gly Trp Ser Asn Leu Glu Ser Phe
225                 230                 235
```

<210> SEQ ID NO 17
<211> LENGTH: 209
<212> TYPE: DNA
<213> ORGANISM: Mycobacterium tuberculosis

<400> SEQUENCE: 17

```
cggacaaata cgccggcaaa aaccgcaacc acgtgaattt tttccaggaa ctggcagacc    60
tcgatcgtca gctcatcagc ctgatccacg accaggccaa cgcggtccag acgacccgcg   120
acatcctgga gggcgccaag aaaggtctcg agttcgtgcg cccggtggct gtggacctga   180
cctacatccc ggtcgtcggg cacgcccta                                     209
```

<210> SEQ ID NO 18
<211> LENGTH: 23
<212> TYPE: PRT
<213> ORGANISM: Mycobacterium tuberculosis

<400> SEQUENCE: 18

```
Leu Gly Ile Gly Ile Pro Asn Gln Gly Gly Ile Leu Tyr Ser Ser Leu
1               5                   10                  15

Glu Tyr Phe Glu Lys Ala Leu
            20
```

<210> SEQ ID NO 19
<211> LENGTH: 411

```
<212> TYPE: DNA
<213> ORGANISM: Mycobacterium tuberculosis

<400> SEQUENCE: 19
atgcatcacc atcaccatca catgagcaga gcgttcatca tcgatccaac gatcagtgcc    60
attgacggct tgtacgacct t

```
aaattggcgg agttggtcgc ggccgccatt gcggacatca tttcggatgt ggcggacatc    600
atcaagggca tcctcggaga atgggagttc atcacaaacg cgctcaacgg cctgaaagag    660
ctttgggacg tgaagctcac ggggtggctg accggactgt tctctcgagg gtggtcgaac    720
ctggagtcct tctttgcggg cgtccccggc ttgaccggcg cgaccagcgg cttgtcgcaa    780
gtgactggct tgttcggtgc ggccggtctg tccgcatcgt cgggcttggc tcacgcggat    840
agcctggcga gctcagccag cttgcccgcc ctggccggca ttgggggcgg gtccggtttt    900
gggggcttgc cgagcctggc tcaggtccat gccgcctcaa ctcggcaggc gctacggccc    960
cgagctgatg gcccggtcgg cgccgctgcc gagcaggtcg gcgggcagtc gcagctggtc   1020
tccgcgcagg gttcccaagg tatgggcgga cccgtaggca tgggcggcat gcacccctct   1080
tcggggcgt cgaaagggac gacgacgaag aagtactcgg aaggcgcggc ggcgggcact   1140
gaagacgccg agcgcgcgcc agtcgaagct gacgcgggcg gtgggcaaaa ggtgctggta   1200
cgaaacgtcg tctaacggcg aattc                                        1225
```

<210> SEQ ID NO 22
<211> LENGTH: 403
<212> TYPE: PRT
<213> ORGANISM: Mycobacterium tuberculosis

<400> SEQUENCE: 22

```
Met His His His His His Met Ser Arg Ala Phe Ile Ile Asp Pro
1               5                   10                  15

Thr Ile Ser Ala Ile Asp Gly Leu Tyr Asp Leu Leu Gly Ile Gly
            20                  25                  30

Pro Asn Gln Gly Gly Ile Leu Tyr Ser Ser Leu Glu Tyr Phe Glu Lys
        35                  40                  45

Ala Leu Glu Glu Leu Ala Ala Ala Phe Pro Gly Asp Gly Trp Leu Gly
    50                  55                  60

Ser Ala Ala Asp Lys Tyr Ala Gly Lys Asn Arg Asn His Val Asn Phe
65                  70                  75                  80

Phe Gln Glu Leu Ala Asp Leu Asp Arg Gln Leu Ile Ser Leu Ile His
                85                  90                  95

Asp Gln Ala Asn Ala Val Gln Thr Thr Arg Asp Ile Leu Glu Gly Ala
            100                 105                 110

Lys Lys Gly Leu Glu Phe Val Arg Pro Val Ala Val Asp Leu Thr Tyr
        115                 120                 125

Ile Pro Val Val Gly His Ala Leu Ser Ala Ala Phe Gln Ala Pro Phe
    130                 135                 140

Cys Ala Gly Ala Met Ala Val Val Gly Gly Ala Leu Lys Leu Ala Tyr
145                 150                 155                 160

Leu Val Val Lys Thr Leu Ile Asn Ala Lys Leu Thr Gln Leu Leu Lys
                165                 170                 175

Leu Leu Ala Lys Leu Ala Glu Leu Val Ala Ala Ile Ala Asp Ile
            180                 185                 190

Ile Ser Asp Val Ala Asp Ile Ile Lys Gly Ile Leu Gly Glu Val Trp
        195                 200                 205

Glu Phe Ile Thr Asn Ala Leu Asn Gly Leu Lys Glu Leu Trp Asp Lys
    210                 215                 220

Leu Thr Gly Trp Val Thr Gly Leu Phe Ser Arg Gly Trp Ser Asn Leu
225                 230                 235                 240

Glu Ser Phe Phe Ala Gly Val Pro Gly Leu Thr Gly Ala Thr Ser Gly
                245                 250                 255
```

```
Leu Ser Gln Val Thr Gly Leu Phe Gly Ala Ala Gly Leu Ser Ala Ser
            260                 265                 270

Ser Gly Leu Ala His Ala Asp Ser Leu Ala Ser Ser Ala Ser Leu Pro
                275                 280                 285

Ala Leu Ala Gly Ile Gly Gly Ser Gly Phe Gly Gly Leu Pro Ser
            290                 295                 300

Leu Ala Gln Val His Ala Ala Ser Thr Arg Gln Ala Leu Arg Pro Arg
305                 310                 315                 320

Ala Asp Gly Pro Val Gly Ala Ala Glu Gln Val Gly Gly Gln Ser
                325                 330                 335

Gln Leu Val Ser Ala Gln Ser Gln Gly Met Gly Pro Val Gly
            340                 345                 350

Met Gly Gly Met His Pro Ser Ser Gly Ala Ser Lys Gly Thr Thr Thr
            355                 360                 365

Lys Lys Tyr Ser Glu Gly Ala Ala Gly Thr Glu Asp Ala Glu Arg
            370                 375                 380

Ala Pro Val Glu Ala Asp Ala Gly Gly Gly Gln Lys Val Leu Val Arg
385                 390                 395                 400

Asn Val Val

<210> SEQ ID NO 23
<211> LENGTH: 1225
<212> TYPE: DNA
<213> ORGANISM: Mycobacterium tuberculosis

<400> SEQUENCE: 23
catatgcatc accatcacca tcacatgagc agagcgttca tcatcgatcc aacgatcagt      60
gccattgacg gcttgtacga ccttctgggg attggaatac ccaaccaagg gggtatcctt     120
tactcctcac tagagtactt cgaaaaagcc ctggaggagc tggcagcagc gtttccgggt     180
gatggctggt taggttcggc cgcggacaaa tacgccggca aaaaccgcaa ccacgtgaat     240 ttttccagg aactggcaga cctcgatcgt cagctcatca gcctgatcca cgaccaggcc     300
aacgcggtcc agacgacccg cgacaagctt atcctggagg cgccaagaa aggtctcgag     360 ttcgtgcgcc cggtggctgt ggacctgacc tacatcccgg tcgtcgggca cgccctatcg     420
gccgccttcc aggcgccgtt tgcgcgggc gcgatggccg tagtgggcgg cgcgcttgcc     480
tacttggtcg tgaaaacgct gatcaacgcg actcaactcc tcaaattgct tgccaaattg     540
gcggagttgg tcgcggccgc cattgcggac atcatttcgg atgtgggcgga catcatcaag     600 ggcatcctcg agaagtgtg ggagttcatc acaaacgcga agcttctcaa cggcctgaaa     660
gagctttggg acaagctcac ggggtgggtg accggactgt tctctcgagg gtggtcgaac     720
ctggagtcct tctttgcggg cgtcccggc ttgaccggcg cgaccagcgg cttgtcgcaa     780
gtgactggct tgttcggtgc ggccggtctg tccgcatcgt cgggcttggc tcacgcggat     840
agcctggcga gctcagccag cttgcccgcc ctggccggca ttggggggcgg gtccggttt     900 gggggcttgc cgagcctggc tcaggtccat gccgcctcaa ctcggcaggc gctacggccc     960
cgagctgatg gcccggtcgg cgccgctgcc gagcaggtcg gcgggcagtc gcagctggtc    1020
tccgcgcagg gttcccaagg tatgggcgga cccgtaggca tgggcggcat gcacccctct    1080
tcgggggcgt cgaaagggac gacgacgaag aagtactcgg aaggcgcggc ggcgggcact    1140
gaagacgccg agcgcgcgcc agtcgaagct gacgcgggcg gtgggcaaaa ggtgctggta    1200
cgaaacgtcg tctaacggcg aattc                                         1225
```

```
<210> SEQ ID NO 24
<211> LENGTH: 403
<212> TYPE: PRT
<213> ORGANISM: Mycobacterium tuberculosis

<400> SEQUENCE: 24

Met His His His His His Met Ser Arg Ala Phe Ile Ile Asp Pro
1               5                   10                  15

Thr Ile Ser Ala Ile Asp Gly Leu Tyr Asp Leu Leu Gly Ile Gly
            20                  25                  30

Pro Asn Gln Gly Gly Ile Leu Tyr Ser Ser Leu Glu Tyr Phe Glu Lys
                35                  40                  45

Ala Leu Glu Glu Leu Ala Ala Ala Phe Pro Gly Asp Gly Trp Leu Gly
        50                  55                  60

Ser Ala Ala Asp Lys Tyr Ala Gly Lys Asn Arg Asn His Val Asn Phe
65                  70                  75                  80

Phe Gln Glu Leu Ala Asp Leu Asp Arg Gln Leu Ile Ser Leu Ile His
                85                  90                  95

Asp Gln Ala Asn Ala Val Gln Thr Thr Arg Asp Lys Leu Ile Leu Glu
            100                 105                 110

Gly Ala Lys Lys Gly Leu Glu Phe Val Arg Pro Val Ala Val Asp Leu
        115                 120                 125

Thr Tyr Ile Pro Val Val Gly His Ala Leu Ser Ala Ala Phe Gln Ala
130                 135                 140

Pro Phe Cys Ala Gly Ala Met Ala Val Val Gly Gly Ala Leu Ala Tyr
145                 150                 155                 160

Leu Val Val Lys Thr Leu Ile Asn Ala Thr Gln Leu Leu Lys Leu Leu
                165                 170                 175

Ala Lys Leu Ala Glu Leu Val Ala Ala Ile Ala Asp Ile Ile Ser
            180                 185                 190

Asp Val Ala Asp Ile Ile Lys Gly Ile Leu Gly Glu Val Trp Glu Phe
        195                 200                 205

Ile Thr Asn Ala Lys Leu Leu Asn Gly Leu Lys Glu Leu Trp Asp Lys
210                 215                 220

Leu Thr Gly Trp Val Thr Gly Leu Phe Ser Arg Gly Trp Ser Asn Leu
225                 230                 235                 240

Glu Ser Phe Phe Ala Gly Val Pro Gly Leu Thr Gly Ala Thr Ser Gly
                245                 250                 255

Leu Ser Gln Val Thr Gly Leu Phe Gly Ala Ala Gly Leu Ser Ala Ser
            260                 265                 270

Ser Gly Leu Ala His Ala Asp Ser Leu Ala Ser Ser Ala Ser Leu Pro
        275                 280                 285

Ala Leu Ala Gly Ile Gly Gly Ser Gly Phe Gly Gly Leu Pro Ser
290                 295                 300

Leu Ala Gln Val His Ala Ser Thr Arg Gln Ala Leu Arg Pro Arg
305                 310                 315                 320

Ala Asp Gly Pro Val Gly Ala Ala Glu Gln Val Gly Gly Gln Ser
                325                 330                 335

Gln Leu Val Ser Ala Gln Gly Ser Gln Gly Met Gly Gly Pro Val Gly
            340                 345                 350

Met Gly Gly Met His Pro Ser Ser Gly Ala Ser Lys Gly Thr Thr Thr
        355                 360                 365

Lys Lys Tyr Ser Glu Gly Ala Ala Ala Gly Thr Glu Asp Ala Glu Arg
370                 375                 380

Ala Pro Val Glu Ala Asp Ala Gly Gly Gly Gln Lys Val Leu Val Arg
```

385         390         395         400

Asn Val Val

<210> SEQ ID NO 25
<211> LENGTH: 3058
<212> TYPE: DNA
<213> ORGANISM: Mycobacterium tuberculosis

<400> SEQUENCE: 25

| | | | | | |
|---|---|---|---|---|---|
| gatcgtaccc | gtgcgagtgc | tcgggccgtt | tgaggatgga | gtgcacgtgt | ctttcgtgat | 60 |
| ggcataccca | gagatgttgg | cggcggcggc | tgacaccctg | cagagcatcg | gtgctaccac | 120 |
| tgtggctagc | aatgccgctg | cggcggcccc | gacgactggg | gtggtgcccc | ccgctgccga | 180 |
| tgaggtgtcg | gcgctgactg | cggcgcactt | cgccgcacat | gcggcgatgt | atcagtccgt | 240 |
| gagcgctcgg | gctgctgcga | ttcatgacca | gttcgtggcc | acccttgcca | gcagcgccag | 300 |
| ctcgtatgcg | gccactgaag | tcgccaatgc | ggcggcggcc | agctaagcca | ggaacagtcg | 360 |
| gcacgagaaa | ccacgagaaa | tagggacacg | taatggtgga | tttcggggcg | ttaccaccgg | 420 |
| agatcaactc | cgcgaggatg | tacgccggcc | cgggttcggc | ctcgctggtg | gccgcggctc | 480 |
| agatgtggga | cagcgtggcg | agtgacctgt | tttcggccgc | gtcggcgttt | cagtcggtgg | 540 |
| tctggggtct | gacggtgggg | tcgtggatag | gttcgtcggc | gggtctgatg | gtggcggcgg | 600 |
| cctcgccgta | tgtggcgtgg | atgagcgtca | ccgcggggca | ggccgagctg | accgccgccc | 660 |
| aggtccgggt | tgctgcggcg | gcctacgaga | cggcgtatgg | gctgacggtg | cccccgccgg | 720 |
| tgatcgccga | gaaccgtgct | gaactgatga | ttctgatagc | gaccaacctc | ttggggcaaa | 780 |
| acaccccggc | gatcgcggtc | aacgaggccg | aatacggcga | gatgtgggcc | caagacgccg | 840 |
| ccgcgatgtt | tggctacgcc | gcggcgacgg | cgacggcgac | ggcgacgttg | ctgccgttcg | 900 |
| aggaggcgcc | ggagatgacc | agcgcgggtg | ggctcctcga | gcaggccgcc | gcggtcgagg | 960 |
| aggcctccga | caccgccgcg | gcgaaccagt | tgatgaacaa | tgtgccccag | gcgctgcaac | 1020 |
| agctggccca | gccacgcag | ggcaccacgc | cttcttccaa | gctgggtggc | ctgtggaaga | 1080 |
| cggtctcgcc | gcatcggtcg | ccgatcagca | acatggtgtc | gatggccaac | aaccacatgt | 1140 |
| cgatgaccaa | ctcgggtgtg | tcgatgacca | cacccttgag | ctcgatgttg | aagggctttg | 1200 |
| ctccggcggc | ggccgcccag | gccgtgcaaa | ccgcggcgca | aaacggggtc | cgggcgatga | 1260 |
| gctcgctggg | cagctcgctg | ggttcttcgg | gtctgggcgg | tggggtggcc | gccaacttgg | 1320 |
| gtcgggcggc | ctcggtcggt | tcgttgtcgg | tgccgcaggc | ctgggccgcg | gccaaccagg | 1380 |
| cagtcacccc | ggcggcgcgg | gcgctgccgc | tgaccagcct | gaccagcgcc | gcggaaagag | 1440 |
| ggcccgggca | gatgctgggc | gggctgccgg | tgggcagat | gggcgccagg | gccggtggtg | 1500 |
| ggctcagtgg | tgtgctgcgt | gttccgccgc | gaccctatgt | gatgccgcat | tctccggcgg | 1560 |
| ccggctagga | gaggggcgc | agactgtcgt | tatttgacca | gtgatcggcg | gtctcggtgt | 1620 |
| ttccgcggcc | ggctatgaca | acagtcaatg | tgcatgacaa | gttacaggta | ttaggtccag | 1680 |
| gttcaacaag | gagacaggca | acatggcctc | acgttttatg | acggatccgc | acgcgatgcg | 1740 |
| ggacatggcg | ggccgttttg | aggtgcacgc | ccagacggtg | gaggacgagg | ctcgccggat | 1800 |
| gtgggcgtcc | gcgcaaaaca | tttcggtgc | gggctggagt | ggcatggccg | aggcgacctc | 1860 |
| gctagacacc | atggcccaga | tgaatcaggc | gtttcgcaac | atcgtgaaca | tgctgcacgg | 1920 |
| ggtgcgtgac | gggctggttc | gcgacgccaa | caactacgag | cagcaagagc | aggcctccca | 1980 |
| gcagatcctc | agcagctaac | gtcagccgct | gcagcacaat | acttttacaa | gcgaaggaga | 2040 |

-continued

```
acaggttcga tgaccatcaa ctatcaattc ggggatgtcg acgctcacgg cgccatgatc    2100
cgcgctcagg ccgggttgct ggaggccgag catcaggcca tcattcgtga tgtgttgacc    2160
gcgagtgact tttggggcgg cgccggttcg gcggcctgcc aggggttcat tacccagttg    2220
ggccgtaact tccaggtgat ctacgagcag gccaacgccc acgggcagaa ggtgcaggct    2280
gccggcaaca acatggcgca aaccgacagc gccgtcggct ccagctgggc ctgacaccag    2340
gccaaggcca gggacgtggt gtacgagtga agttcctcgc gtgatccttc gggtggcagt    2400
ctaagtggtc agtgctgggg tgttggtggt ttgctgcttg gcgggttctt cggtgctggt    2460
cagtgctgct cgggctcggg tgaggacctc gaggcccagg tagcgccgtc cttcgatcca    2520
ttcgtcgtgt tgttcggcga ggacggctcc gacgaggcgg atgatcgagg gcggtcggg    2580 gaagatgccc acgacgtcgg ttcggcgtcg tacctctcgg ttgaggcgtt cctgggggtt    2640
gttggaccag atttggcgcc agatctgctt ggggaaggcg gtgaacgcca gcaggtcggt    2700
gcgggcggtg tcgaggtgct cggccaccgc ggggagtttg tcggtcagag cgtcgagtac    2760
ccgatcatat tgggcaacaa ctgattcggc gtcgggctgg tcgtagatgg agtgcagcag    2820
ggtgcgcacc cacggccagg agggcttcgg ggtggctgcc atcagattgg ctgcgtagtg    2880
ggttctgcag cgctgccagg ccgctgcggg cagggtggcg ccgatcgcgg ccaccaggcc    2940
ggcgtgggcg tcgctggtga ccagcgcgac cccggacagg ccgcgggcga ccaggtcgcg    3000
gaagaacgcc agccagccgg ccccgtcctc ggcggaggtg acctggatgc ccaggatc     3058
```

<210> SEQ ID NO 26
<211> LENGTH: 391
<212> TYPE: PRT
<213> ORGANISM: Mycobacterium tuberculosis

<400> SEQUENCE: 26

```
Met Val Asp Phe Gly Ala Leu Pro Pro Glu Ile Asn Ser Ala Arg Met
1               5                   10                  15

Tyr Ala Gly Pro Gly Ser Ala Ser Leu Val Ala Ala Gln Met Trp
                20                  25                  30

Asp Ser Val Ala Ser Asp Leu Phe Ser Ala Ala Ser Ala Phe Gln Ser
        35                  40                  45

Val Val Trp Gly Leu Thr Val Gly Ser Trp Ile Gly Ser Ser Ala Gly
    50                  55                  60

Leu Met Val Ala Ala Ser Pro Tyr Val Ala Trp Met Ser Val Thr
65                  70                  75                  80

Ala Gly Gln Ala Glu Leu Thr Ala Ala Gln Val Arg Val Ala Ala Ala
                85                  90                  95

Ala Tyr Glu Thr Ala Tyr Gly Leu Thr Val Pro Pro Val Ile Ala
                100                 105                 110

Glu Asn Arg Ala Glu Leu Met Ile Leu Ile Ala Thr Asn Leu Leu Gly
                115                 120                 125

Gln Asn Thr Pro Ala Ile Ala Val Asn Glu Ala Glu Tyr Gly Glu Met
        130                 135                 140

Trp Ala Gln Asp Ala Ala Ala Met Phe Gly Tyr Ala Ala Ala Thr Ala
145                 150                 155                 160

Thr Ala Thr Ala Thr Leu Leu Pro Phe Glu Glu Ala Pro Glu Met Thr
                165                 170                 175

Ser Ala Gly Gly Leu Leu Glu Gln Ala Ala Val Glu Glu Ala Ser
                180                 185                 190

Asp Thr Ala Ala Ala Asn Gln Leu Met Asn Asn Val Pro Gln Ala Leu
        195                 200                 205
```

Gln Gln Leu Ala Gln Pro Thr Gln Gly Thr Thr Pro Ser Ser Lys Leu
    210                 215                 220

Gly Gly Leu Trp Lys Thr Val Ser Pro His Arg Ser Pro Ile Ser Asn
225                 230                 235                 240

Met Val Ser Met Ala Asn Asn His Met Ser Met Thr Asn Ser Gly Val
                245                 250                 255

Ser Met Thr Asn Thr Leu Ser Ser Met Leu Lys Gly Phe Ala Pro Ala
            260                 265                 270

Ala Ala Ala Gln Ala Val Gln Thr Ala Ala Gln Asn Gly Val Arg Ala
        275                 280                 285

Met Ser Ser Leu Gly Ser Ser Leu Gly Ser Ser Gly Leu Gly Gly Gly
    290                 295                 300

Val Ala Ala Asn Leu Gly Arg Ala Ala Ser Val Gly Ser Leu Ser Val
305                 310                 315                 320

Pro Gln Ala Trp Ala Ala Ala Asn Gln Ala Val Thr Pro Ala Ala Arg
                325                 330                 335

Ala Leu Pro Leu Thr Ser Leu Thr Ser Ala Ala Glu Arg Gly Pro Gly
            340                 345                 350

Gln Met Leu Gly Gly Leu Pro Val Gly Gln Met Gly Ala Arg Ala Gly
        355                 360                 365

Gly Gly Leu Ser Gly Val Leu Arg Val Pro Pro Arg Pro Tyr Val Met
    370                 375                 380

Pro His Ser Pro Ala Ala Gly
385                 390

<210> SEQ ID NO 27
<211> LENGTH: 447
<212> TYPE: DNA
<213> ORGANISM: Mycobacterium tuberculosis

<400> SEQUENCE: 27
cggtatgaac acggccgcgt ccgataactt ccagctgtcc cagggtgggc agggattcgc     60
cattccgatc gggcaggcga tggcgatcgc gggccagatc cgatcgggtg ggggtcacc    120 caccgttcat atcgggccta ccgccttcct cggcttgggt gttgtcgaca caacggcaa    180 cggcgcacga gtccaacgcg tggtcgggag cgctccggcg gcaagtctcg gcatctccac    240
cggcgacgtg atcaccgcgg tcgacggcgc tccgatcaac tcggccaccg cgatggcgga    300
cgcgcttaac gggcatcatc ccggtgacgt catctcggtg aactggcaaa ccaagtcggg    360
cggcacgcgt acagggaacg tgacattggc cgagggaccc ccggcctgat ttcgtcgygg    420
ataccacccg ccggccggcc aattgga                                       447

<210> SEQ ID NO 28
<211> LENGTH: 132
<212> TYPE: PRT
<213> ORGANISM: Mycobacterium tuberculosis

<400> SEQUENCE: 28

Thr Ala Ala Ser Asp Asn Phe Gln Leu Ser Gln Gly Gly Gln Gly Phe
1               5                   10                  15

Ala Ile Pro Ile Gly Gln Ala Met Ala Ile Ala Gly Gln Ile Arg Ser
            20                  25                  30

Gly Gly Gly Ser Pro Thr Val His Ile Gly Pro Thr Ala Phe Leu Gly
        35                  40                  45

Leu Gly Val Val Asp Asn Asn Gly Asn Gly Ala Arg Val Gln Arg Val
    50                  55                  60

```
Val Gly Ser Ala Pro Ala Ala Ser Leu Gly Ile Ser Thr Gly Asp Val
 65                  70                  75                  80

Ile Thr Ala Val Asp Gly Ala Pro Ile Asn Ser Ala Thr Ala Met Ala
                 85                  90                  95

Asp Ala Leu Asn Gly His His Pro Gly Asp Val Ile Ser Val Asn Trp
            100                 105                 110

Gln Thr Lys Ser Gly Gly Thr Arg Thr Gly Asn Val Thr Leu Ala Glu
        115                 120                 125

Gly Pro Pro Ala
    130
```

<210> SEQ ID NO 29
<211> LENGTH: 1872
<212> TYPE: DNA
<213> ORGANISM: Mycobacterium tuberculosis
<220> FEATURE:
<221> NAME/KEY: misc_feature
<222> LOCATION: (1460)..(1460)
<223> OTHER INFORMATION: n is a, c, g, or t
<220> FEATURE:
<221> NAME/KEY: misc_feature
<222> LOCATION: (1854)..(1854)
<223> OTHER INFORMATION: n is a, c, g, or t

<400> SEQUENCE: 29

| | | | | | |
|---|---|---|---|---|---|
| gactacgttg | gtgtagaaaa | atcctgccgc | ccggacccct | aaggctggga | caatttctga | 60 |
| tagctacccc | gacacaggag | gttacgggat | gagcaattcg | cgccgccgct | cactcaggtg | 120 |
| gtcatggttg | ctgagcgtgc | tggctgccgt | cgggctgggc | ctggccacgg | cgccggccca | 180 |
| ggcggccccg | ccggccttgt | cgcaggaccg | gttcgccgac | ttccccgcgc | tgccctcga | 240 |
| cccgtccgcg | atggtcgccc | aagtggcgcc | acaggtggtc | aacatcaaca | ccaaactggg | 300 |
| ctacaacaac | gccgtgggcg | ccgggaccgg | catcgtcatc | gatcccaacg | gtgtcgtgct | 360 |
| gaccaacaac | cacgtgatcg | cgggcgccac | cgacatcaat | gcgttcagcg | tcggctccgg | 420 |
| ccaaacctac | ggcgtcgatg | tggtcgggta | tgaccgcacc | caggatgtcg | cggtgctgca | 480 |
| gctgcgcggt | gccggtggcc | tgccgtcggc | ggcgatcggt | ggcggcgtcg | cggttggtga | 540 |
| gcccgtcgtc | gcgatgggca | acagcggtgg | gcagggcgga | acgccccgtg | cggtgcctgg | 600 |
| cagggtggtc | gcgctcggcc | aaaccgtgca | ggcgtcggat | tcgctgaccg | gtgccgaaga | 660 |
| gacattgaac | gggttgatcc | agttcgatgc | cgcaatccag | cccggtgatt | cgggcgggcc | 720 |
| cgtcgtcaac | ggcctaggac | aggtggtcgg | tatgaacacg | gccgcgtccg | ataacttcca | 780 |
| gctgtcccag | ggtgggcagg | gattcgccat | tccgatcggg | caggcgatgg | cgatcgcggg | 840 |
| ccaaatccga | tcgggtgggg | ggtcacccac | cgttcatatc | gggcctaccg | ccttcctcgg | 900 |
| cttgggtgtt | gtcgacaaca | acggcaacgg | cgcacgagtc | caacgcgtgg | tcggaagcgc | 960 |
| tccggcggca | agtctcggca | tctccaccgg | cgacgtgatc | accgcggtcg | acggcgctcc | 1020 |
| gatcaactcg | gccaccgcga | tggcggacgc | gcttaacggg | catcatcccg | gtgacgtcat | 1080 |
| ctcggtgaac | tggcaaaacca | agtcgggcgg | cacgcgtaca | gggaacgtga | cattggccga | 1140 |
| gggaccccccg | gcctgatttg | tcgcggatac | cacccgccgg | ccggccaatt | ggattggcgc | 1200 |
| cagccgtgat | tgccgcgtga | gccccgagt | tccgtctccc | gtgcgcgtgg | cattgtggaa | 1260 |
| gcaatgaacg | aggcagaaca | cagcgttgag | caccctcccg | tgcagggcag | ttacgtcgaa | 1320 |
| ggcggtgtgg | tcgagcatcc | ggatgccaag | gacttcggca | gcgccgccgc | cctgcccgcc | 1380 |
| gatccgacct | ggtttaagca | cgccgtcttc | tacgaggtgc | tggtccgggc | gttcttcgac | 1440 |

```
gccagcgcgg acggttccgn cgatctgcgt ggactcatcg atcgcctcga ctacctgcag   1500
tggcttggca tcgactgcat ctgttgccgc cgttcctacg actcaccgct gcgcgacggc   1560
ggttacgaca ttcgcgactt ctacaaggtg ctgcccgaat tcggcaccgt cgacgatttc   1620
gtcgccctgg tcgacaccgc tcaccggcga ggtatccgca tcatcaccga cctggtgatg   1680
aatcacacct cggagtcgca ccctggtttt caggagtccc gccgcgaccc agacggaccg   1740
tacggtgact attacgtgtg gagcgacacc agcgagcgct acaccgacgc ccggatcatc   1800
ttcgtcgaca ccgaagagtc gaactggtca ttcgatcctg tccgccgaca gttnctactg   1860
gcaccgattc tt                                                        1872

<210> SEQ ID NO 30
<211> LENGTH: 355
<212> TYPE: PRT
<213> ORGANISM: Mycobacterium tuberculosis

<400> SEQUENCE: 30

Met Ser Asn Ser Arg Arg Ser Leu Arg Trp Ser Trp Leu Leu Ser
1               5                   10                  15

Val Leu Ala Ala Val Gly Leu Gly Leu Ala Thr Ala Pro Ala Gln Ala
                20                  25                  30

Ala Pro Pro Ala Leu Ser Gln Asp Arg Phe Ala Asp Phe Pro Ala Leu
            35                  40                  45

Pro Leu Asp Pro Ser Ala Met Val Ala Gln Val Ala Pro Gln Val Val
        50                  55                  60

Asn Ile Asn Thr Lys Leu Gly Tyr Asn Asn Ala Val Gly Ala Gly Thr
65                  70                  75                  80

Gly Ile Val Ile Asp Pro Asn Gly Val Val Leu Thr Asn Asn His Val
                85                  90                  95

Ile Ala Gly Ala Thr Asp Ile Asn Ala Phe Ser Val Gly Ser Gly Gln
            100                 105                 110

Thr Tyr Gly Val Asp Val Val Gly Tyr Asp Arg Thr Gln Asp Val Ala
        115                 120                 125

Val Leu Gln Leu Arg Gly Ala Gly Gly Leu Pro Ser Ala Ala Ile Gly
    130                 135                 140

Gly Gly Val Ala Val Gly Glu Pro Val Val Ala Met Gly Asn Ser Gly
145                 150                 155                 160

Gly Gln Gly Gly Thr Pro Arg Ala Val Pro Gly Arg Val Val Ala Leu
                165                 170                 175

Gly Gln Thr Val Gln Ala Ser Asp Ser Leu Thr Gly Ala Glu Glu Thr
            180                 185                 190

Leu Asn Gly Leu Ile Gln Phe Asp Ala Ala Ile Gln Pro Gly Asp Ser
        195                 200                 205

Gly Gly Pro Val Val Asn Gly Leu Gly Gln Val Val Gly Met Asn Thr
    210                 215                 220

Ala Ala Ser Asp Asn Phe Gln Leu Ser Gln Gly Gly Gln Gly Phe Ala
225                 230                 235                 240

Ile Pro Ile Gly Gln Ala Met Ala Ile Ala Gly Gln Ile Arg Ser Gly
                245                 250                 255

Gly Gly Ser Pro Thr Val His Ile Gly Pro Thr Ala Phe Leu Gly Leu
            260                 265                 270

Gly Val Val Asp Asn Asn Gly Asn Gly Ala Arg Val Gln Arg Val Val
        275                 280                 285

Gly Ser Ala Pro Ala Ala Ser Leu Gly Ile Ser Thr Gly Asp Val Ile
    290                 295                 300
```

```
Thr Ala Val Asp Gly Ala Pro Ile Asn Ser Ala Thr Ala Met Ala Asp
305                 310                 315                 320

Ala Leu Asn Gly His His Pro Gly Asp Val Ile Ser Val Asn Trp Gln
                325                 330                 335

Thr Lys Ser Gly Gly Thr Arg Thr Gly Asn Val Thr Leu Ala Glu Gly
            340                 345                 350

Pro Pro Ala
        355

<210> SEQ ID NO 31
<211> LENGTH: 1441
<212> TYPE: DNA
<213> ORGANISM: Mycobacterium tuberculosis

<400> SEQUENCE: 31
```

| | | | | | |
|---|---|---|---|---|---|
| gaggttgctg | gcaatggatt | tcgggctttt | acctccggaa | gtgaattcaa | gccgaatgta | 60 |
| ttccggtccg | gggccggagt | cgatgctagc | cgccgcggcc | gcctgggacg | gtgtggccgc | 120 |
| ggagttgact | tccgccgcgg | tctcgtatgg | atcggtggtg | tcgacgctga | tcgttgagcc | 180 |
| gtggatgggg | ccggcggcgg | ccgcgatggc | ggccgcggca | acgccgtatg | tggggtggct | 240 |
| ggccgccacg | gcggcgctgg | cgaaggagac | ggccacacag | gcgagggcag | cggcggaagc | 300 |
| gtttgggacg | gcgttcgcga | tgacggtgcc | accatccctc | gtcgcggcca | accgcagccg | 360 |
| gttgatgtcg | ctggtcgcgg | cgaacattct | ggggcaaaac | agtgcggcga | tcgcggctac | 420 |
| ccaggccgag | tatgccgaaa | tgtgggccca | agacgctgcc | gtgatgtaca | gctatgaggg | 480 |
| ggcatctgcg | gccgcgtcgg | cgttgccgcc | gttcactcca | cccgtgcaag | gcaccggccc | 540 |
| ggccgggccc | gcggccgcag | ccgcggcgac | ccaagccgcc | ggtgcgggcg | ccgttgcgga | 600 |
| tgcacaggcg | acactggccc | agctgccccc | ggggatcctg | agcgacattc | tgtccgcatt | 660 |
| ggccgccaac | gctgatccgc | tgacatcggg | actgttgggg | atcgcgtcga | ccctcaaccc | 720 |
| gcaagtcgga | tccgctcagc | cgatagtgat | ccccacccg | ataggggaat | tggacgtgat | 780 |
| cgcgctctac | attgcatcca | tcgcgaccgg | cagcattgcg | ctcgcgatca | cgaacacggc | 840 |
| cagaccctgg | cacatcggcc | tatacgggaa | cgccggcggg | ctgggaccga | cgcagggcca | 900 |
| tccactgagt | tcgcgaccg | acgagccgga | gccgcactgg | ggccccttcg | ggggcgcggc | 960 |
| gccggtgtcc | gcgggcgtcg | gccacgcagc | attagtcgga | gcgttgtcgg | tgccgcacag | 1020 |
| ctggaccacg | gccgcccgg | agatccagct | cgccgttcag | gcaacaccca | ccttcagctc | 1080 |
| cagcgccggc | gccgacccga | cggccctaaa | cgggatgccg | gcaggcctgc | tcagcgggat | 1140 |
| ggctttggcg | agcctggccg | cacgcggcac | gacgggcggt | ggcggcaccc | gtagcggcac | 1200 |
| cagcactgac | ggccaagagg | acggccgcaa | accccggta | gttgtgatta | gagagcagcc | 1260 |
| gccgcccgga | aaccccccgc | ggtaaaagtc | cggcaaccgt | tcgtcgccgc | gcggaaaatg | 1320 |
| cctggtgagc | gtggctatcc | gacgggccgt | tcacaccgct | tgtagtagcg | tacggctatg | 1380 |
| gacgacggtg | tctggattct | cggcggctat | cagagcgatt | ttgctcgcaa | cctcagcaaa | 1440 |
| g | | | | | | 1441 |

```
<210> SEQ ID NO 32
<211> LENGTH: 423
<212> TYPE: PRT
<213> ORGANISM: Mycobacterium tuberculosis

<400> SEQUENCE: 32

Met Asp Phe Gly Leu Leu Pro Pro Glu Val Asn Ser Ser Arg Met Tyr
```

-continued

```
1               5                   10                  15
Ser Gly Pro Gly Pro Glu Ser Met Leu Ala Ala Ala Ala Trp Asp
                20                  25                  30

Gly Val Ala Ala Glu Leu Thr Ser Ala Ala Val Ser Tyr Gly Ser Val
                35                  40                  45

Val Ser Thr Leu Ile Val Glu Pro Trp Met Gly Pro Ala Ala Ala
    50                  55                  60

Met Ala Ala Ala Thr Pro Tyr Val Gly Trp Leu Ala Thr Ala
65                  70                  75                  80

Ala Leu Ala Lys Glu Thr Ala Thr Gln Ala Arg Ala Ala Glu Ala
                85                  90                  95

Phe Gly Thr Ala Phe Ala Met Thr Val Pro Pro Ser Leu Val Ala Ala
                100                 105                 110

Asn Arg Ser Arg Leu Met Ser Leu Val Ala Ala Asn Ile Leu Gly Gln
                115                 120                 125

Asn Ser Ala Ala Ile Ala Ala Thr Gln Ala Glu Tyr Ala Glu Met Trp
130                 135                 140

Ala Gln Asp Ala Ala Val Met Tyr Ser Tyr Glu Gly Ala Ser Ala Ala
145                 150                 155                 160

Ala Ser Ala Leu Pro Pro Phe Thr Pro Pro Val Gln Gly Thr Gly Pro
                165                 170                 175

Ala Gly Pro Ala Ala Ala Ala Ala Thr Gln Ala Ala Gly Ala Gly
                180                 185                 190

Ala Val Ala Asp Ala Gln Ala Thr Leu Ala Gln Leu Pro Pro Gly Ile
                195                 200                 205

Leu Ser Asp Ile Leu Ser Ala Leu Ala Ala Asn Ala Asp Pro Leu Thr
                210                 215                 220

Ser Gly Leu Leu Gly Ile Ala Ser Thr Leu Asn Pro Gln Val Gly Ser
225                 230                 235                 240

Ala Gln Pro Ile Val Ile Pro Thr Pro Ile Gly Glu Leu Asp Val Ile
                245                 250                 255

Ala Leu Tyr Ile Ala Ser Ile Ala Thr Gly Ser Ile Ala Leu Ala Ile
                260                 265                 270

Thr Asn Thr Ala Arg Pro Trp His Ile Gly Leu Tyr Gly Asn Ala Gly
                275                 280                 285

Gly Leu Gly Pro Thr Gln Gly His Pro Leu Ser Ser Ala Thr Asp Glu
                290                 295                 300

Pro Glu Pro His Trp Gly Pro Phe Gly Gly Ala Ala Pro Val Ser Ala
305                 310                 315                 320

Gly Val Gly His Ala Ala Leu Val Gly Ala Leu Ser Val Pro His Ser
                325                 330                 335

Trp Thr Thr Ala Ala Pro Glu Ile Gln Leu Ala Val Gln Ala Thr Pro
                340                 345                 350

Thr Phe Ser Ser Ser Ala Gly Ala Asp Pro Thr Ala Leu Asn Gly Met
                355                 360                 365

Pro Ala Gly Leu Leu Ser Gly Met Ala Leu Ala Ser Leu Ala Ala Arg
                370                 375                 380

Gly Thr Thr Gly Gly Gly Thr Arg Ser Gly Thr Ser Thr Asp Gly
385                 390                 395                 400

Gln Glu Asp Gly Arg Lys Pro Pro Val Val Ile Arg Glu Gln Pro
                405                 410                 415

Pro Pro Gly Asn Pro Pro Arg
                420
```

```
<210> SEQ ID NO 33
<211> LENGTH: 1742
<212> TYPE: DNA
<213> ORGANISM: Mycobacterium tuberculosis
<220> FEATURE:
<221> NAME/KEY: misc_feature
<222> LOCATION: (497)..(497)
<223> OTHER INFORMATION: n is a, c, g, or t
<220> FEATURE:
<221> NAME/KEY: misc_feature
<222> LOCATION: (500)..(500)
<223> OTHER INFORMATION: n is a, c, g, or t
<220> FEATURE:
<221> NAME/KEY: misc_feature
<222> LOCATION: (1136)..(1136)
<223> OTHER INFORMATION: n is a, c, g, or t
<220> FEATURE:
<221> NAME/KEY: misc_feature
<222> LOCATION: (1445)..(1445)
<223> OTHER INFORMATION: n is a, c, g, or t
<220> FEATURE:
<221> NAME/KEY: misc_feature
<222> LOCATION: (1487)..(1487)
<223> OTHER INFORMATION: n is a, c, g, or t
<220> FEATURE:
<221> NAME/KEY: misc_feature
<222> LOCATION: (1509)..(1509)
<223> OTHER INFORMATION: n is a, c, g, or t
<220> FEATURE:
<221> NAME/KEY: misc_feature
<222> LOCATION: (1515)..(1515)
<223> OTHER INFORMATION: n is a, c, g, or t

<400> SEQUENCE: 33
ccgctctctt tcaacgtcat aagttcggtg ggccagtcgg ccgcgcgtgc atatggcacc      60
aataacgcgt gtcccatgga tacccggacc gcacgacggt agagcggatc agcgcagccg     120
gtgccgaaca ctaccgcgtc cacgctcagc cctgccgcgt tgcggaagat cgagcccagg     180
ttctcatggt cgttaacgcc ttccaacact gcgacggtgc gcgccccggc gaccacctga     240
gcaacgctcg gctccggcac ccggcgcgcg gctgccaaca ccccacgatt gagatggaag     300
ccgatcaccc gtgccatgac atcagccgac gctcgatagt acggcgcgcc gacaccggcc     360
agatcatcct tgagctcggc cagccggcgg tcggtgccga acagcgccag cggcgtgaac     420
cgtgaggcca gcatgcgctg caccaccagc acaccctcgg cgatcaccaa cgccttgccg     480
gtcggcagat cgggacnacn gtcgatgctg ttcaggtcac ggaaatcgtc gagccgtggg     540
tcgtcgggat cgcagacgtc ctgaacatcg aggccgtcgg ggtgctgggc acaacggcct     600
tcggtcacgg gctttcgtcg accagagcca gcatcagatc ggcggcgctg cgcaggatgt     660
cacgctcgct gcggttcagc gtcgcgagcc gctcagccag ccactcttgc agagagccgt     720
tgctgggatt aattgggaga ggaagacagc atgtcgttcg tgaccacaca gccggaagcc     780
ctggcagctg cggcggcgaa cctacagggt attggcacga caatgaacgc ccagaacgcg     840
gccgcggctg ctccaaccac cggagtagtg cccgcagccg ccgatgaagt atcagcgctg     900
accgcggctc agtttgctgc gcacgcgcag atgtaccaaa cggtcagcgc ccaggccgcg     960
gccattcacg aaatgttcgt gaacacgctg gtggccagtt ctggctcata cgcggccacc    1020
gaggcggcca acgcagccgc tgccggctga acggctcgc acgaacctgc tgaaggagag    1080
ggggaacatc cggagttctc gggtcagggg ttgcgccagc gcccagccga ttcagntatc    1140
ggcgtccata acagcagacg atctaggcat tcagtactaa ggagacaggc aacatggcct    1200
cacgttttat gacggatccg catgcgatgc gggacatggc gggccgtttt gaggtgcacg    1260
cccagacggt ggaggacgag gctcgccgga tgtgggcgtc cgcgcaaaac atttccggtg    1320
```

```
cgggctggag tggcatggcc gaggcgacct cgctagacac catgacctag atgaatcagg    1380
cgtttcgcaa catcgtgaac atgctgcacg gggtgcgtga cgggctggtt cgcgacgcca    1440
acaantacga acagcaagag caggcctccc agcagatcct gagcagntag cgccgaaagc    1500
cacagctgng tacgntttct cacattagga gaacaccaat atgacgatta attaccagtt    1560
cggggacgtc gacgctcatg gcgccatgat ccgcgctcag gcggcgtcgc ttgaggcgga    1620
gcatcaggcc atcgttcgtg atgtgttggc cgcgggtgac ttttgggcg gcgccggttc     1680 ggtggcttgc caggagttca ttacccagtt gggccgtaac ttccaggtga tctacgagca    1740
gg                                                                   1742
```

<210> SEQ ID NO 34
<211> LENGTH: 94
<212> TYPE: PRT
<213> ORGANISM: Mycobacterium tuberculosis

<400> SEQUENCE: 34

```
Met Thr Ile Asn Tyr Gln Phe Gly Asp Val Asp Ala His Gly Ala Met
1               5                   10                  15

Ile Arg Ala Leu Ala Gly Leu Leu Glu Ala Glu His Gln Ala Ile Ile
            20                  25                  30

Ser Asp Val Leu Thr Ala Ser Asp Phe Trp Gly Gly Ala Gly Ser Ala
        35                  40                  45

Ala Cys Gln Gly Phe Ile Thr Gln Leu Gly Arg Asn Phe Gln Val Ile
    50                  55                  60

Tyr Glu Gln Ala Asn Ala His Gly Gln Lys Val Gln Ala Ala Gly Asn
65                  70                  75                  80

Asn Met Ala Gln Thr Asp Ser Ala Val Gly Ser Ser Trp Ala
                85                  90
```

<210> SEQ ID NO 35
<211> LENGTH: 585
<212> TYPE: DNA
<213> ORGANISM: Mycobacterium tuberculosis

<400> SEQUENCE: 35

```
tggattccga tagcggtttc ggcccctcga cgggcgacca cggcgcgcag gcctccgaac     60
ggggggccgg gacgctggga ttcgccggga ccgcaaccaa agaacgccgg gtccgggcgg    120
tcgggctgac cgcactggcc ggtgatgagt tcggcaacgg ccccggatg ccgatggtgc     180 cggggacctg ggagcagggc agcaacgagc ccgaggcgcc cgacggatcg gggagagggg    240
gaggcgacgg cttaccgcac gacagcaagt aaccgaattc gaatcacgt ggacccgtac     300 gggtcgaaag gagagatgtt atgagccttt ggatgctca tatcccacag ttggtggcct    360
cccagtcggc gtttgccgcc aaggcgggggc tgatgcggca cacgatcggt caggccgagc   420
aggcggcgat gtcggctcag gcgtttcacc agggggagtc gtcggcggcg tttcaggccg    480
cccatgcccg gtttgtggcg gcggccgcca aagtcaacac cttgttggat gtcgcgcagg    540
cgaatctggg tgaggccgcc ggtacctatg tggccgccga tgctg                    585
```

<210> SEQ ID NO 36
<211> LENGTH: 97
<212> TYPE: PRT
<213> ORGANISM: Mycobacterium tuberculosis

<400> SEQUENCE: 36

```
Met Ser Leu Leu Asp Ala His Ile Pro Gln Leu Val Ala Ser Gln Ser
1               5                   10                  15
```

```
Ala Phe Ala Ala Lys Ala Gly Leu Met Arg His Thr Ile Gly Gln Ala
            20                  25                  30

Glu Gln Ala Ala Met Ser Ala Gln Ala Phe His Gln Gly Glu Ser Ser
        35                  40                  45

Ala Ala Phe Gln Ala Ala His Ala Arg Phe Val Ala Ala Ala Ala Lys
    50                  55                  60

Val Asn Thr Leu Leu Asp Val Ala Gln Ala Asn Leu Gly Glu Ala Ala
65                  70                  75                  80

Gly Thr Tyr Val Ala Ala Asp Ala Ala Ala Ser Thr Tyr Thr Gly
                85                  90                  95

Phe

<210> SEQ ID NO 37
<211> LENGTH: 500
<212> TYPE: DNA
<213> ORGANISM: Mycobacterium tuberculosis

<400> SEQUENCE: 37
cgtggcaatg tcgttgaccg tcggggccgg ggtcgcctcc gcagatcccg tggacgcggt      60
cattaacacc acctgcaatt acgggcaggt agtagctgcg ctcaacgcga cggatccggg     120
ggctgccgca cagttcaacg cctcaccggt ggcgcagtcc tatttgcgca atttcctcgc     180
cgcaccgcca cctcagcgcg ctgccatggc cgcgcaattg caagctgtgc cggggggcgg     240
acagtacatc ggccttgtcg agtcggttgc cggctcctgc aacaactatt aagcccatgc     300 gggcccccatc ccgcgacccg gcatcgtcgc cggggctagg ccagattgcc ccgctcctca     360
acgggccgca tcccgcgacc cggcatcgtc gccggggcta ggccagattg ccccgctcct     420
caacgggccg catctcgtgc cgaattcctg cagcccgggg gatccactag ttctagagcg     480
gccgccaccg cggtggagct                                                500

<210> SEQ ID NO 38
<211> LENGTH: 96
<212> TYPE: PRT
<213> ORGANISM: Mycobacterium tuberculosis

<400> SEQUENCE: 38

Val Ala Met Ser Leu Thr Val Gly Ala Gly Val Ala Ser Ala Asp Pro
1               5                   10                  15

Val Asp Ala Val Ile Asn Thr Thr Cys Asn Tyr Gly Gln Val Val Ala
            20                  25                  30

Ala Leu Asn Ala Thr Asp Pro Gly Ala Ala Ala Gln Phe Asn Ala Ser
        35                  40                  45

Pro Val Ala Gln Ser Tyr Leu Arg Asn Phe Leu Ala Ala Pro Pro Pro
    50                  55                  60

Gln Arg Ala Ala Met Ala Ala Gln Leu Gln Ala Val Pro Gly Ala Ala
65                  70                  75                  80

Gln Tyr Ile Gly Leu Val Glu Ser Val Ala Gly Ser Cys Asn Asn Tyr
                85                  90                  95

<210> SEQ ID NO 39
<211> LENGTH: 999
<212> TYPE: DNA
<213> ORGANISM: Mycobacterium tuberculosis

<400> SEQUENCE: 39
atgcatcacc atcaccatca catgcatcag gtggacccca acttgacacg tcgcaaggga      60
```

```
cgattggcgg cactggctat cgcggcgatg gccagcgcca gcctggtgac cgttgcggtg    120
cccgcgaccg ccaacgccga tccggagcca gcgcccccgg tacccacaac ggccgcctcg    180
ccgccgtcga ccgctgcagc gccacccgca ccggcgacac ctgttgcccc cccaccaccg    240
gccgccgcca acacgccgaa tgcccagccg ggcgatccca acgcagcacc tccgccggcc    300
gacccgaacg caccgccgcc acctgtcatt gccccaaacg caccccaacc tgtccggatc    360
gacaacccgg ttggaggatt cagcttcgcg ctgcctgctg gctgggtgga gtctgacgcc    420
gcccacttcg actacggttc agcactcctc agcaaaacca ccggggaccc gccatttccc    480
ggacagccgc cgccggtggc caatgacacc cgtatcgtgc tcggccggct agaccaaaag    540
ctttacgcca gcgccgaagc caccgactcc aaggccgcgg cccggttggg ctcggacatg    600
ggtgagttct atatgcccta cccgggcacc cggatcaacc aggaaaccgt ctcgctcgac    660
gccaacgggg tgtctggaag cgcgtcgtat tacgaagtca agttcagcga tccgagtaag    720
ccgaacggcc agatctggac gggcgtaatc ggctcgcccg cggcgaacgc accggacgcc    780
gggccccctc agcgctggtt tgtggtatgg ctcgggaccg ccaacaaccc ggtggacaag    840
ggcgcggcca aggcgctggc cgaatcgatc cggcctttgg tcgccccgcc gccggcgccg    900
gcaccggctc ctgcagagcc cgctccggcg ccggcgccgg ccggggaagt cgctcctacc    960
ccgacgacac cgacaccgca gcggacctta ccggcctga                           999
```

<210> SEQ ID NO 40
<211> LENGTH: 332
<212> TYPE: PRT
<213> ORGANISM: Mycobacterium tuberculosis

<400> SEQUENCE: 40

```
Met His His His His His Met His Gln Val Asp Pro Asn Leu Thr
1               5                   10                  15

Arg Arg Lys Gly Arg Leu Ala Ala Leu Ala Ile Ala Ala Met Ala Ser
            20                  25                  30

Ala Ser Leu Val Thr Val Ala Val Pro Ala Thr Ala Asn Ala Asp Pro
        35                  40                  45

Glu Pro Ala Pro Pro Val Pro Thr Thr Ala Ala Ser Pro Pro Ser Thr
    50                  55                  60

Ala Ala Ala Pro Pro Ala Pro Thr Pro Val Ala Pro Pro Pro
65                  70                  75                  80

Ala Ala Ala Asn Thr Pro Asn Ala Gln Pro Gly Asp Pro Asn Ala Ala
                85                  90                  95

Pro Pro Pro Ala Asp Pro Asn Ala Pro Pro Pro Val Ile Ala Pro
            100                 105                 110

Asn Ala Pro Gln Pro Val Arg Ile Asp Asn Pro Val Gly Gly Phe Ser
        115                 120                 125

Phe Ala Leu Pro Ala Gly Trp Val Glu Ser Asp Ala Ala His Phe Asp
    130                 135                 140

Tyr Gly Ser Ala Leu Leu Ser Lys Thr Thr Gly Asp Pro Pro Phe Pro
145                 150                 155                 160

Gly Gln Pro Pro Val Ala Asn Asp Thr Arg Ile Val Leu Gly Arg
                165                 170                 175

Leu Asp Gln Lys Leu Tyr Ala Ser Ala Glu Ala Thr Asp Ser Lys Ala
            180                 185                 190

Ala Ala Arg Leu Gly Ser Asp Met Gly Glu Phe Tyr Met Pro Tyr Pro
        195                 200                 205

Gly Thr Arg Ile Asn Gln Glu Thr Val Ser Leu Asp Ala Asn Gly Val
```

```
                210                 215                 220
Ser Gly Ser Ala Ser Tyr Tyr Glu Val Lys Phe Ser Asp Pro Ser Lys
225                 230                 235                 240

Pro Asn Gly Gln Ile Trp Thr Gly Val Ile Gly Ser Pro Ala Ala Asn
                245                 250                 255

Ala Pro Asp Ala Gly Pro Pro Gln Arg Trp Phe Val Val Trp Leu Gly
                260                 265                 270

Thr Ala Asn Asn Pro Val Asp Lys Gly Ala Ala Lys Ala Leu Ala Glu
                275                 280                 285

Ser Ile Arg Pro Leu Val Ala Pro Pro Ala Pro Ala Pro Ala Pro
                290                 295                 300

Ala Glu Pro Ala Pro Ala Pro Ala Gly Glu Val Ala Pro Thr
305                 310                 315                 320

Pro Thr Thr Pro Thr Pro Gln Arg Thr Leu Pro Ala
                325                 330

<210> SEQ ID NO 41
<211> LENGTH: 339
<212> TYPE: DNA
<213> ORGANISM: Mycobacterium tuberculosis

<400> SEQUENCE: 41
atgaagttga agtttgctcg cctgagtact gcgatactgg gttgtgcagc ggcgcttgtg     60
tttcctgcct cggttgccag cgcagatcca cctgacccgc atcagccgga catgacgaaa    120
ggctattgcc cgggtggccg atggggtttt ggcgacttgg ccgtgtgcga cggcgagaag    180
taccccgacg gctcgttttg gcaccagtgg atgcaaacgt ggtttaccgg cccacagttt    240
tacttcgatt gtgtcagcgg cggtgagccc ctccccggcc cgccgccacc gggtggttgc    300
ggtggggcaa ttccgtccga gcagcccaac gctccctga                          339

<210> SEQ ID NO 42
<211> LENGTH: 112
<212> TYPE: PRT
<213> ORGANISM: Mycobacterium tuberculosis

<400> SEQUENCE: 42

Met Lys Leu Lys Phe Ala Arg Leu Ser Thr Ala Ile Leu Gly Cys Ala
1               5                  10                  15

Ala Ala Leu Val Phe Pro Ala Ser Val Ala Ser Ala Asp Pro Pro Asp
                20                  25                  30

Pro His Gln Pro Asp Met Thr Lys Gly Tyr Cys Pro Gly Gly Arg Trp
                35                  40                  45

Gly Phe Gly Asp Leu Ala Val Cys Asp Gly Glu Lys Tyr Pro Asp Gly
                50                  55                  60

Ser Phe Trp His Gln Trp Met Gln Thr Trp Phe Thr Gly Pro Gln Phe
65                  70                  75                  80

Tyr Phe Asp Cys Val Ser Gly Gly Glu Pro Leu Pro Gly Pro Pro Pro
                85                  90                  95

Pro Gly Gly Cys Gly Gly Ala Ile Pro Ser Glu Gln Pro Asn Ala Pro
                100                 105                 110

<210> SEQ ID NO 43
<211> LENGTH: 154
<212> TYPE: DNA
<213> ORGANISM: Mycobacterium tuberculosis

<400> SEQUENCE: 43
```

```
atgacagagc agcagtggaa tttcgcgggt atcgaggccg cggcaagcgc aatccaggga      60
aatgtcacgt ccattcattc cctccttgac gagggaagc agtccctgac caagctcgca     120
gcggcctggg gcggtagcgg ttcggaagcg tacc                                 154
```

<210> SEQ ID NO 44
<211> LENGTH: 51
<212> TYPE: PRT
<213> ORGANISM: Mycobacterium tuberculosis

<400> SEQUENCE: 44

```
Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr
    50
```

<210> SEQ ID NO 45
<211> LENGTH: 154
<212> TYPE: DNA
<213> ORGANISM: Mycobacterium tuberculosis

<400> SEQUENCE: 45

```
atgacagagc agcagtggaa tttcgcgggt atcgaggccg cggcaagcgc aatccaggga      60
aatgtcacgt ccattcattc cctccttgac gagggaagc agtccctgac caagctcgca     120
gcggcctggg gcggtagcgg ttcggaagcg tacc                                 154
```

<210> SEQ ID NO 46
<211> LENGTH: 51
<212> TYPE: PRT
<213> ORGANISM: Mycobacterium tuberculosis

<400> SEQUENCE: 46

```
Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr
    50
```

<210> SEQ ID NO 47
<211> LENGTH: 2310
<212> TYPE: DNA
<213> ORGANISM: Mycobacterium tuberculosis

<400> SEQUENCE: 47

```
ccagcccccg ccccgcccac gccgaggtat gtggactgat ggccaaagcg tcagagaccg      60
aacgttcggg cccggcacc caaccggcgg acgcccagac cgcgacgtcc gcgacggttc     120 gaccctgag cacccaggcg gtgttccgcc ccgatttcgg cgatgaggac aacttccccc     180
atccgacgct cggcccggac accgagccgc aagaccggat ggccaccacc agccgggtgc     240
gcccgccggt cagacggctg gcggcggcc tggtggaaat cccgcgggcg cccgatatcg     300
atccgcttga ggccctgatg accaaccccgg tggtgccgga gtccaagcgg ttctgctgga     360
```

```
actgtggacg tcccgtcggc cggtccgact cggagaccaa gggagcttca gagggctggt    420
gtccctattg cggcagcccg tattcgttcc tgccgcagct aaatcccggg gacatcgtcg    480
ccggccagta cgaggtcaaa ggctgcatcg cgcacggcgg actgggctgg atctacctcg    540
ctctcgaccg caatgtcaac ggccgtccgg tggtgctcaa gggcctggtg cattccggtg    600
atgccgaagc gcaggcaatg gcgatggccg aacgccagtt cctggccgag gtggtgcacc    660
cgtcgatcgt gcagatcttc aactttgtcg agcacaccga caggcacggg gatccggtcg    720
gctacatcgt gatggaatac gtcggcgggc aatcgctcaa acgcagcaag ggtcagaaac    780
tgcccgtcgc ggaggccatc gcctacctgc tggagatcct gccggcgctg agctacctgc    840
attccatcgg cttggtctac aacgacctga agccggaaaa catcatgctg accgaggaac    900
agctcaagct gatcgacctg ggcgcggtat cgcggatcaa ctcgttcggc tacctctacg    960
ggaccccagg cttccaggcg cccgagatcg tgcggaccgg tccgacggtg ccaccgaca   1020
tctacaccgt gggacgcacg ctcgcggcgc tcacgctgga cctgcccacc cgcaatggcc   1080
gttatgtgga tgggctaccc gaagacgacc cggtgctgaa aacctacgac tcttacggcc   1140
ggttgctgcg cagggccatc gaccccgatc gcgcggcaacg gttcaccacc gccgaagaga   1200
tgtccgcgca attgacgggc gtgttgcggg aggtggtcgc ccaggacacc ggggtgccgc   1260
ggccagggct atcaacgatc ttcagtccca gtcggtcgac atttggagtg gacctgctgg   1320
tggcgcacac cgacgtgtat ctggacgggc aggtgcacgc ggagaagctg accgccaacg   1380
agatcgtgac cgcgctgtcg gtgccgctgg tcgatccgac cgacgtcgca gcttcggtcc   1440
tgcaggccac ggtgctctcc cagccggtgc agaccctaga ctcgctgcgc gcggcccgcc   1500
acggtgcgct ggacgccgac ggcgtcgact tctccgagtc agtggagctg ccgctaatgg   1560
aagtccgcgc gctgctggat ctcggcgatg tggccaaggc cacccgaaaa ctcgacgatc   1620
tggccgaacg cgttggctgg cgatggcgat tggtctggta ccgggccgtc gccgagctgc   1680
tcaccggcga ctatgactcg gccaccaaac atttcaccga ggtgctggat acctttcccg   1740
gcgagctggc gcccaagctc gccctggccg ccaccgccga actagccggc aacaccgacg   1800
aacacaagtt ctatcagacg gtgtggagca ccaacgacgg cgtgatctcg gcggctttcg   1860
gactggccag agcccggtcg gccgaaggtg atcgggtcgg cgccgtgcgc acgctcgacg   1920
aggtaccgcc cacttctcgg catttcacca cggcacggct gaccagcgcg gtgactctgt   1980
tgtccggccg gtcaacgagt gaagtcaccg aggaacagat ccgcgacgcc gcccgaagag   2040
tggaggcgct gccccgacc gaaccacgcg tgctgcagat ccgcgccctg gtgctgggtg   2100
gcgcgctgga ctggctgaag gacaacaagg ccagcaccaa ccacatcctc ggtttcccgt   2160
tcaccagtca cgggctgcgg ctgggtgtcg aggcgtcact gcgcagcctg gcccgggtag   2220
ctcccactca acggcatcgc tacacgctgg tggacatggc caacaaggtc cggcccacca   2280
gcacgttcta agccgcccga gtgtgaatcg                                    2310
```

<210> SEQ ID NO 48
<211> LENGTH: 750
<212> TYPE: PRT
<213> ORGANISM: Mycobacterium tuberculosis

<400> SEQUENCE: 48

```
Met Ala Lys Ala Ser Glu Thr Glu Arg Ser Gly Pro Gly Thr Gln Pro
1               5                   10                  15

Ala Asp Ala Gln Thr Ala Thr Ser Ala Thr Val Arg Pro Leu Ser Thr
            20                  25                  30
```

-continued

```
Gln Ala Val Phe Arg Pro Asp Phe Gly Asp Glu Asp Asn Phe Pro His
             35                  40                  45
Pro Thr Leu Gly Pro Asp Thr Glu Pro Gln Asp Arg Met Ala Thr Thr
 50                  55                  60
Ser Arg Val Arg Pro Pro Val Arg Arg Leu Gly Gly Gly Leu Val Glu
 65                  70                  75                  80
Ile Pro Arg Ala Pro Asp Ile Asp Pro Leu Glu Ala Leu Met Thr Asn
                 85                  90                  95
Pro Val Val Pro Glu Ser Lys Arg Phe Cys Trp Asn Cys Gly Arg Pro
            100                 105                 110
Val Gly Arg Ser Asp Ser Glu Thr Lys Gly Ala Ser Glu Gly Trp Cys
            115                 120                 125
Pro Tyr Cys Gly Ser Pro Tyr Ser Phe Leu Pro Gln Leu Asn Pro Gly
        130                 135                 140
Asp Ile Val Ala Gly Gln Tyr Glu Val Lys Gly Cys Ile Ala His Gly
145                 150                 155                 160
Gly Leu Gly Trp Ile Tyr Leu Ala Leu Asp Arg Asn Val Asn Gly Arg
                165                 170                 175
Pro Val Val Leu Lys Gly Leu Val His Ser Gly Asp Ala Glu Ala Gln
            180                 185                 190
Ala Met Ala Met Ala Glu Arg Gln Phe Leu Ala Glu Val Val His Pro
        195                 200                 205
Ser Ile Val Gln Ile Phe Asn Phe Val Glu His Thr Asp Arg His Gly
210                 215                 220
Asp Pro Val Gly Tyr Ile Val Met Glu Tyr Val Gly Gly Gln Ser Leu
225                 230                 235                 240
Lys Arg Ser Lys Gly Gln Lys Leu Pro Val Ala Glu Ala Ile Ala Tyr
                245                 250                 255
Leu Leu Glu Ile Leu Pro Ala Leu Ser Tyr Leu His Ser Ile Gly Leu
            260                 265                 270
Val Tyr Asn Asp Leu Lys Pro Glu Asn Ile Met Leu Thr Glu Glu Gln
        275                 280                 285
Leu Lys Leu Ile Asp Leu Gly Ala Val Ser Arg Ile Asn Ser Phe Gly
290                 295                 300
Tyr Leu Tyr Gly Thr Pro Gly Phe Gln Ala Pro Glu Ile Val Arg Thr
305                 310                 315                 320
Gly Pro Thr Val Ala Thr Asp Ile Tyr Thr Val Gly Arg Thr Leu Ala
                325                 330                 335
Ala Leu Thr Leu Asp Leu Pro Thr Arg Asn Gly Arg Tyr Val Asp Gly
            340                 345                 350
Leu Pro Glu Asp Pro Val Leu Lys Thr Tyr Asp Ser Tyr Gly Arg
        355                 360                 365
Leu Leu Arg Arg Ala Ile Asp Pro Asp Pro Gln Arg Phe Thr Thr
370                 375                 380
Ala Glu Glu Met Ser Ala Gln Leu Thr Gly Val Leu Arg Glu Val Val
385                 390                 395                 400
Ala Gln Asp Thr Gly Val Pro Arg Pro Gly Leu Ser Thr Ile Phe Ser
                405                 410                 415
Pro Ser Arg Ser Thr Phe Gly Val Asp Leu Leu Val Ala His Thr Asp
            420                 425                 430
Val Tyr Leu Asp Gly Gln Val His Ala Glu Lys Leu Thr Ala Asn Glu
        435                 440                 445
Ile Val Thr Ala Leu Ser Val Pro Leu Val Asp Pro Thr Asp Val Ala
450                 455                 460
```

Ala Ser Val Leu Gln Ala Thr Val Leu Ser Gln Pro Val Gln Thr Leu
465                 470                 475                 480

Asp Ser Leu Arg Ala Arg His Gly Ala Leu Asp Ala Asp Gly Val
        485                 490                 495

Asp Phe Ser Glu Ser Val Glu Leu Pro Leu Met Glu Val Arg Ala Leu
                500                 505                 510

Leu Asp Leu Gly Asp Val Ala Lys Ala Thr Arg Lys Leu Asp Asp Leu
            515                 520                 525

Ala Glu Arg Val Gly Trp Arg Trp Arg Leu Val Trp Tyr Arg Ala Val
530                 535                 540

Ala Glu Leu Leu Thr Gly Asp Tyr Asp Ser Ala Thr Lys His Phe Thr
545                 550                 555                 560

Glu Val Leu Asp Thr Phe Pro Gly Glu Leu Ala Pro Lys Leu Ala Leu
                565                 570                 575

Ala Ala Thr Ala Glu Leu Ala Gly Asn Thr Asp Glu His Lys Phe Tyr
            580                 585                 590

Gln Thr Val Trp Ser Thr Asn Asp Gly Val Ile Ser Ala Ala Phe Gly
        595                 600                 605

Leu Ala Arg Ala Arg Ser Ala Glu Gly Asp Arg Val Gly Ala Val Arg
610                 615                 620

Thr Leu Asp Glu Val Pro Pro Thr Ser Arg His Phe Thr Thr Ala Arg
625                 630                 635                 640

Leu Thr Ser Ala Val Thr Leu Leu Ser Gly Arg Ser Thr Ser Glu Val
                645                 650                 655

Thr Glu Glu Gln Ile Arg Asp Ala Ala Arg Val Glu Ala Leu Pro
            660                 665                 670

Pro Thr Glu Pro Arg Val Leu Gln Ile Arg Ala Leu Val Leu Gly Gly
        675                 680                 685

Ala Leu Asp Trp Leu Lys Asp Asn Lys Ala Ser Thr Asn His Ile Leu
690                 695                 700

Gly Phe Pro Phe Thr Ser His Gly Leu Arg Leu Gly Val Glu Ala Ser
705                 710                 715                 720

Leu Arg Ser Leu Ala Arg Val Ala Pro Thr Gln Arg His Arg Tyr Thr
                725                 730                 735

Leu Val Asp Met Ala Asn Lys Val Arg Pro Thr Ser Thr Phe
            740                 745                 750

<210> SEQ ID NO 49
<211> LENGTH: 1920
<212> TYPE: DNA
<213> ORGANISM: Mycobacterium tuberculosis

<400> SEQUENCE: 49
cacgactgcc cgactgaacc cgaactagtc agcacaaacc gaagtaggaa gacgaaaagc    60
tatggctgag ttgacaatcc cgctgatga catccagagc gcaatcgaag agtacgtaag    120
ctctttcacc gccgacacca gtagagagga agtcggtacc gtcgtcgatg ccggggacgg    180
catcgcacac gtcgagggtt tgccatcggt gatgacccaa gagctgctcg aattcccggg    240
cggaatcctc ggcgtcgccc tcaacctcga cgagcacagc gtcggcgcgg tgatcctcgg    300
tgacttcgag aacatcgaag aaggtcagca ggtcaagcgc accggcgaag tcttatcggt    360
tccggttggc gacgggtttt tggggcgggt ggttaacccg ctcggccagc cgatcgacgg    420
gcgcggagac gtcgactccg atactcggcg cgcgctggag ctccaggcgc ctcggtggt    480 gcaccggcaa ggcgtgaagg agccgttgca gaccgggatc aaggcgattg acgcgatgac    540

```
cccgatcggc cgcggccagc gccagctgat catcggcgac cgcaagaccg gcaaaaccgc      600
cgtctgcgtc gacaccatcc tcaaccagcg gcagaactgg gagtccggtg atcccaagaa      660
gcaggtgcgc tgtgtatacg tggccatcgg gcagaaggga actaccatcg ccgcggtacg      720
ccgcacactg gaagagggcg gtgcgatgga ctacaccacc atcgtcgcgg ccgcggcgtc      780
ggagtccgcc ggtttcaaat ggcttgcgcc gtacaccggt tcggcgatcg cccagcactg      840
gatgtacgag ggcaagcatg tgctgatcat cttcgacgac ctgactaagc aggccgaggc      900
ataccgggcg atctcgctgc tgctgcgccg tccgccccgg cgtgaggcct accccggcga      960
tgtgttctat ctgcattcgc ggcttttgga gcgctgcgcc aaactgtccg acgatctcgg      1020
tggcggctcg ctaacgggtc tgccgatcat cgagaccaag gccaacgaca tctcggccta      1080
catcccgacc aacgtcatct cgatcaccga cgggcaatgt ttcctggaaa ccgacctgtt      1140
caaccagggc gtccggccgg ccatcaacgt cggtgtgtcg gtgtcccgag tcggcggcgc      1200
ggcgcagatc aaggctatga agaggtcgc cggaagcctc cgcttggacc tttcgcaata      1260
ccgcgagcta aagctttcg ccgctttcgc ttctgatttg gacgccgcat cgaaggcgca      1320
gttggagcgc ggcgcccggc tggtcgagct gctcaagcag ccgcaatccc agcccatgcc      1380
cgttgaggag caagtggttt cgatcttcct gggcaccggc ggtcacctgg actcggtgcc      1440
cgtcgaggac gtccggcggt tcgaaaccga attactggac acatgcgggg cctccgaaga      1500
agagatttg actgagatcc gggacagcca aaagctcacc gaggaggccg ccgacaagct      1560
caccgaggtc atcaagaact tcaagaaggg cttcgcggcc accggtggcg gctctgtggt      1620
gcccgacgaa catgtcgagg ccctcgacga ggataagctc gccaaggaag ccgtgaaggt      1680
caaaaagccg gcgccgaaga agaagaaata gctaaccatg gctgccacac ttcgcgaact      1740
acgcgggcgg atccgctcgg cagggtcgat caaaaagatc accaaggccc aggagctgat      1800
tgcgacatcg cgcatcgcca gggcgcaggc tcggctcgag tccgctcggc cctacgcttt      1860
tgagatcacc cggatgctta ccaccctggc cgctgaagcc gcactggacc atccgttgct      1920
```

<210> SEQ ID NO 50
<211> LENGTH: 549
<212> TYPE: PRT
<213> ORGANISM: Mycobacterium tuberculosis

<400> SEQUENCE: 50

```
Met Ala Glu Leu Thr Ile Pro Ala Asp Asp Ile Gln Ser Ala Ile Glu
 1               5                  10                  15

Glu Tyr Val Ser Ser Phe Thr Ala Asp Thr Ser Arg Glu Glu Val Gly
             20                  25                  30

Thr Val Val Asp Ala Gly Asp Gly Ile Ala His Val Glu Gly Leu Pro
         35                  40                  45

Ser Val Met Thr Gln Glu Leu Leu Glu Phe Pro Gly Gly Ile Leu Gly
     50                  55                  60

Val Ala Leu Asn Leu Asp Glu His Ser Val Gly Ala Val Ile Leu Gly
 65                  70                  75                  80

Asp Phe Glu Asn Ile Glu Glu Gly Gln Gln Val Lys Arg Thr Gly Glu
                 85                  90                  95

Val Leu Ser Val Pro Val Gly Asp Gly Phe Leu Gly Arg Val Val Asn
            100                 105                 110

Pro Leu Gly Gln Pro Ile Asp Gly Arg Gly Asp Val Asp Ser Asp Thr
        115                 120                 125

Arg Arg Ala Leu Glu Leu Gln Ala Pro Ser Val Val His Arg Gln Gly
```

```
            130                 135                 140
Val Lys Glu Pro Leu Gln Thr Gly Ile Lys Ala Ile Asp Ala Met Thr
145                 150                 155                 160

Pro Ile Gly Arg Gly Gln Arg Gln Leu Ile Ile Gly Asp Arg Lys Thr
            165                 170                 175

Gly Lys Thr Ala Val Cys Val Asp Thr Ile Leu Asn Gln Arg Gln Asn
        180                 185                 190

Trp Glu Ser Gly Asp Pro Lys Lys Gln Val Arg Cys Val Tyr Val Ala
        195                 200                 205

Ile Gly Gln Lys Gly Thr Thr Ile Ala Ala Val Arg Arg Thr Leu Glu
    210                 215                 220

Glu Gly Gly Ala Met Asp Tyr Thr Thr Ile Val Ala Ala Ala Ala Ser
225                 230                 235                 240

Glu Ser Ala Gly Phe Lys Trp Leu Ala Pro Tyr Thr Gly Ser Ala Ile
            245                 250                 255

Ala Gln His Trp Met Tyr Glu Gly Lys His Val Leu Ile Ile Phe Asp
        260                 265                 270

Asp Leu Thr Lys Gln Ala Glu Ala Tyr Arg Ala Ile Ser Leu Leu Leu
        275                 280                 285

Arg Arg Pro Gly Arg Glu Ala Tyr Pro Gly Asp Val Phe Tyr Leu
290                 295                 300

His Ser Arg Leu Leu Glu Arg Cys Ala Lys Leu Ser Asp Asp Leu Gly
305                 310                 315                 320

Gly Gly Ser Leu Thr Gly Leu Pro Ile Ile Glu Thr Lys Ala Asn Asp
            325                 330                 335

Ile Ser Ala Tyr Ile Pro Thr Asn Val Ile Ser Ile Thr Asp Gly Gln
        340                 345                 350

Cys Phe Leu Glu Thr Asp Leu Phe Asn Gln Gly Val Arg Pro Ala Ile
        355                 360                 365

Asn Val Gly Val Ser Val Ser Arg Val Gly Gly Ala Ala Gln Ile Lys
    370                 375                 380

Ala Met Lys Glu Val Ala Gly Ser Leu Arg Leu Asp Leu Ser Gln Tyr
385                 390                 395                 400

Arg Glu Leu Glu Ala Phe Ala Ala Phe Ala Ser Asp Leu Asp Ala Ala
            405                 410                 415

Ser Lys Ala Gln Leu Glu Arg Gly Ala Arg Leu Val Glu Leu Leu Lys
        420                 425                 430

Gln Pro Gln Ser Gln Pro Met Pro Val Glu Glu Gln Val Val Ser Ile
        435                 440                 445

Phe Leu Gly Thr Gly Gly His Leu Asp Ser Val Pro Val Glu Asp Val
450                 455                 460

Arg Arg Phe Glu Thr Glu Leu Leu Asp His Met Arg Ala Ser Glu Glu
465                 470                 475                 480

Glu Ile Leu Thr Glu Ile Arg Asp Ser Gln Lys Leu Thr Glu Glu Ala
            485                 490                 495

Ala Asp Lys Leu Thr Glu Val Ile Lys Asn Phe Lys Lys Gly Phe Ala
        500                 505                 510

Ala Thr Gly Gly Gly Ser Val Val Pro Asp Glu His Val Glu Ala Leu
        515                 520                 525

Asp Glu Asp Lys Leu Ala Lys Glu Ala Val Lys Val Lys Lys Pro Ala
530                 535                 540

Pro Lys Lys Lys Lys
545
```

<210> SEQ ID NO 51
<211> LENGTH: 3523
<212> TYPE: DNA
<213> ORGANISM: Mycobacterium tuberculosis

<400> SEQUENCE: 51

| | | |
|---|---|---|
| atgcagcatc accaccatca ccacactgat cgcgtgtcgg tgggcaactt gcgcatcgct | 60 |
| cgggtgctct acgacttcgt gaacaatgaa gccctgcctg caccgatat cgacccggac | 120 |
| agcttctggg cgggcgtcga caaggtcgtc gccgacctga ccccgcagaa ccaagctctg | 180 |
| ttgaacgccc gcgacgagct gcaggcgcag atcgacaagt ggcaccggcg tcgggtgatc | 240 |
| gagcccatcg acatggatgc ctaccgccag ttcctcaccg agatcggcta cctgcttccc | 300 |
| gaacctgatg acttcaccat caccacgtcc ggtgtcgacg ctgagatcac cacgaccgcc | 360 |
| ggccccagc tggtggtgcc ggtgctcaac gcgcggtttg ctctgaacgc ggccaacgct | 420 |
| cgctggggct ccctctacga cgccttgtat ggcaccgatg tcatcccga gaccgacggc | 480 |
| gccgaaaaag gccccacgta caacaaggtt cgtggcgaca aggtgatcgc gtatgcccgc | 540 |
| aagttcctcg acgacagtgt tccgctgtcg tcgggttcct ttggcgacgc caccggtttc | 600 |
| acagtgcagg atggccagct cgtggttgcc ttgccggata agtccaccgg cctggccaac | 660 |
| cccggccagt cgccggcta caccggcgca gccgagtcgc cgacatcggt gctgctaatc | 720 |
| aatcacggtt tgcacatcga gatcctgatc gatccggagt cgcaggtcgg caccaccgac | 780 |
| cgggccggcg tcaaggacgt gatcctggaa tccgcgatca ccacgatcat ggacttcgag | 840 |
| gactcggtgg ccgccgtgga cgccgccgac aaggtgctgg gttatcggaa ctggctcggc | 900 |
| ctgaacaagg gcgacctggc agcagcggta gacaaggacg gcaccgcttt cctgcggggtg | 960 |
| ctcaataggg accggaacta caccgcaccc ggcggtggcc agttcacgct gcctggacgc | 1020 |
| agcctcatgt tcgtccgcaa cgtcggtcac ttgatgacga atgacgccat cgtcgacact | 1080 |
| gacggcagcg aggtgttcga aggcatcatg gatgccctat tcaccggcct gatcgccatc | 1140 |
| cacgggctaa aggccagcga cgtcaacggg ccgctgatca cagccgcac cggctccatc | 1200 |
| tacatcgtca gccgaagat gcacggtccg gcgaggtgc gtttacctg cgaactgttc | 1260 |
| agccgggttg aagatgtgct ggggttgccg caaaacacca tgaagatcgg catcatggac | 1320 |
| gaggaacgcc ggaccacggt caacctcaag gcgtgcatca agctgccgc ggaccgcgtg | 1380 |
| gtgttcatca caccgggtt cctggaccgc accggcgatg aaatccacac ctcgatggag | 1440 |
| gccgcccga tggtgcgcaa gggcaccatg aagagccagc cgtggatctt ggcctacgag | 1500 |
| gaccacaacg tcgatgccgg cctggccgcc gggttcagcg ccgagccca gtcggcaag | 1560 |
| ggcatgtgga caatgaccga gctgatggcc gacatggtcg agacaaaaat cgcccagccg | 1620 |
| cgcgccgggg ccagcaccgc ctgggttccc tctcccactg cggccaccct gcatgcgctg | 1680 |
| cactaccacc aggtcgacgt cgccgcggtg caacaaggac tggcggggaa cgtcgcgcc | 1740 |
| accatcgaac aattgctgac cattccgctg gccaaggaat tggcctgggc tcccgacgag | 1800 |
| atccgcgaag aggtcgacaa caactgtcaa tccatcctcg ctacgtggt tcgctgggtt | 1860 |
| gatcaaggtg tcggctgctc gaaggtgccc gacatccacg acgtcgcgct catggaggac | 1920 |
| cgggccacgt tgcgaatctc cagccaattg ttggccaact ggctgcgcca ggtgtgatc | 1980 |
| accagcgcgg atgtgcgggc cagcttggag cggatggcgc cgttggtcga tcgacaaaac | 2040 |
| gcgggcgacg tggcataccg accgatggca cccaacttcg acgacagtat cgccttcctg | 2100 |
| gccgcgcagg agctgatctt gtccggggcc cagcagccca acggctacac cgagccgatc | 2160 |

```
ctgcaccgac gtcgtcggga gtttaaggcc cgggccgctg agaagccggc cccatcggac    2220
agggccggtg acgatgcggc cagggtgcag aagtacggcg atcctcggt ggccgacgcc     2280 gaacggattc gccgcgtcgc cgaacgcatc gtcgccacca agaagcaagg caatgacgtc    2340
gtcgtcgtcg tctctgccat gggggatacc accgacgacc tgctggatct ggctcagcag    2400
gtgtgcccgg cgccgccgcc tcgggagctg gacatgctgc ttaccgccgg tgaacgcatc    2460
tcgaatgcgt tggtgccat ggccatcgag tcgctcggcg cgcatgcccg gtcgttcacc      2520
ggttcgcagg ccggggtgat caccaccggc acccacggca acgccaagat catcgacgtc    2580
acgccggggc ggctgcaaac cgcccttgag gaggggcggg tcgttttggt ggccggattc    2640 caagggtca gccaggacac caaggatgtc acgacgttgg gccgcggcgg ctcggacacc      2700
accgccgtcg ccatggccgc cgcgctgggt gccgatgtct gtgagatcta caccgacgtg    2760
gacggcatct tcagcgccga cccgcgcatc gtgcgcaacg cccgaaagct cgacaccgtg    2820
accttcgagg aaatgctcga gatggcggcc tgccggccca aggtgctgat gctgcgctgc    2880
gtggaatacg ctcgccgcca taatattccg gtgcacgtcc ggtcgtcgta ctcggacaga    2940
ccgggcaccg tcgttgtcgg atcgatcaag gacgtaccca tggaagaccc catcctgacc    3000
ggagtcgcgc acgaccgcag cgaggccaag gtgaccatcg tcgggctgcc cgacatcccc    3060
gggtatgcgg ccaaggtgtt tagggcggtg ccagacgcc gacgtcaaca tcgacatggt     3120
gctgcagaac gtctccaagg tcgaggacgg caagaccgac atcaccttca cctgctcccg    3180
cagacgtcgg gcccgccgcc gtggaaaaac tggactcgct cagaaacgag atcggcttct    3240
acacagctgc tgtacgacga ccacatcggc aaggtatcgc tgatcggtgc cggcatgcgc    3300
agccaccccg gggtcaccgc gacgttctgt gaggcgctgg cggcggtggg ggtcaacatc    3360
gagctgatct ccacctcgga agatcagaga tctcggtgtt gtgccgcgac accgaactgg    3420
acaaggccgt ggtcgcgctg catgaagcgt tcgggctcgg cggcgacgag gaggccacgg    3480
tgtacgcggg gacgggacgg tagatgggcc tgtcaatagt gaa                      3523
```

<210> SEQ ID NO 52
<211> LENGTH: 1172
<212> TYPE: PRT
<213> ORGANISM: Mycobacterium tuberculosis

<400> SEQUENCE: 52

```
Met Gln His His His His His His Thr Asp Arg Val Ser Val Gly Asn
1               5                   10                  15

Leu Arg Ile Ala Arg Val Leu Tyr Asp Phe Val Asn Asn Glu Ala Leu
            20                  25                  30

Pro Gly Thr Asp Ile Asp Pro Asp Ser Phe Trp Ala Gly Val Asp Lys
        35                  40                  45

Val Val Ala Asp Leu Thr Pro Gln Asn Gln Ala Leu Leu Asn Ala Arg
    50                  55                  60

Asp Glu Leu Gln Ala Gln Ile Asp Lys Trp His Arg Arg Val Ile
65                  70                  75                  80

Glu Pro Ile Asp Met Asp Ala Tyr Arg Gln Phe Leu Thr Glu Ile Gly
                85                  90                  95

Tyr Leu Leu Pro Glu Pro Asp Asp Phe Thr Ile Thr Thr Ser Gly Val
            100                 105                 110

Asp Ala Glu Ile Thr Thr Thr Ala Gly Pro Gln Leu Val Pro Val
        115                 120                 125

Leu Asn Ala Arg Phe Ala Leu Asn Ala Ala Asn Ala Arg Trp Gly Ser
    130                 135                 140
```

```
Leu Tyr Asp Ala Leu Tyr Gly Thr Asp Val Ile Pro Glu Thr Asp Gly
145                 150                 155                 160

Ala Glu Lys Gly Pro Thr Tyr Asn Lys Val Arg Gly Asp Lys Val Ile
            165                 170                 175

Ala Tyr Ala Arg Lys Phe Leu Asp Ser Val Pro Leu Ser Ser Gly
        180                 185                 190

Ser Phe Gly Asp Ala Thr Gly Phe Thr Val Gln Asp Gly Gln Leu Val
        195                 200                 205

Val Ala Leu Pro Asp Lys Ser Thr Gly Leu Ala Asn Pro Gly Gln Phe
        210                 215                 220

Ala Gly Tyr Thr Gly Ala Ala Glu Ser Pro Thr Ser Val Leu Leu Ile
225                 230                 235                 240

Asn His Gly Leu His Ile Glu Ile Leu Ile Asp Pro Glu Ser Gln Val
                245                 250                 255

Gly Thr Thr Asp Arg Ala Gly Val Lys Asp Val Ile Leu Glu Ser Ala
                260                 265                 270

Ile Thr Thr Ile Met Asp Phe Glu Asp Ser Val Ala Ala Val Asp Ala
            275                 280                 285

Ala Asp Lys Val Leu Gly Tyr Arg Asn Trp Leu Gly Leu Asn Lys Gly
290                 295                 300

Asp Leu Ala Ala Ala Val Asp Lys Asp Gly Thr Ala Phe Leu Arg Val
305                 310                 315                 320

Leu Asn Arg Asp Arg Asn Tyr Thr Ala Pro Gly Gly Gln Phe Thr
                325                 330                 335

Leu Pro Gly Arg Ser Leu Met Phe Val Arg Asn Val Gly His Leu Met
            340                 345                 350

Thr Asn Asp Ala Ile Val Asp Thr Asp Gly Ser Glu Val Phe Glu Gly
            355                 360                 365

Ile Met Asp Ala Leu Phe Thr Gly Leu Ile Ala Ile His Gly Leu Lys
370                 375                 380

Ala Ser Asp Val Asn Gly Pro Leu Ile Asn Ser Arg Thr Gly Ser Ile
385                 390                 395                 400

Tyr Ile Val Lys Pro Lys Met His Gly Pro Ala Glu Val Ala Phe Thr
                405                 410                 415

Cys Glu Leu Phe Ser Arg Val Glu Asp Val Leu Gly Leu Pro Gln Asn
            420                 425                 430

Thr Met Lys Ile Gly Ile Met Asp Glu Glu Arg Arg Thr Thr Val Asn
            435                 440                 445

Leu Lys Ala Cys Ile Lys Ala Ala Ala Asp Arg Val Val Phe Ile Asn
450                 455                 460

Thr Gly Phe Leu Asp Arg Thr Gly Asp Glu Ile His Thr Ser Met Glu
465                 470                 475                 480

Ala Gly Pro Met Val Arg Lys Gly Thr Met Lys Ser Gln Pro Trp Ile
                485                 490                 495

Leu Ala Tyr Glu Asp His Asn Val Asp Ala Gly Leu Ala Ala Gly Phe
            500                 505                 510

Ser Gly Arg Ala Gln Val Gly Lys Gly Met Trp Thr Met Thr Glu Leu
            515                 520                 525

Met Ala Asp Met Val Glu Thr Lys Ile Ala Gln Pro Arg Ala Gly Ala
            530                 535                 540

Ser Thr Ala Trp Val Pro Ser Pro Thr Ala Ala Thr Leu His Ala Leu
545                 550                 555                 560

His Tyr His Gln Val Asp Val Ala Ala Val Gln Gln Gly Leu Ala Gly
```

-continued

```
                565                 570                 575
Lys Arg Arg Ala Thr Ile Glu Gln Leu Leu Thr Ile Pro Leu Ala Lys
            580                 585                 590

Glu Leu Ala Trp Ala Pro Asp Glu Ile Arg Glu Val Asp Asn Asn
            595                 600             605

Cys Gln Ser Ile Leu Gly Tyr Val Arg Trp Val Asp Gln Gly Val
610                 615                 620

Gly Cys Ser Lys Val Pro Asp Ile His Asp Val Ala Leu Met Glu Asp
625                 630                 635                 640

Arg Ala Thr Leu Arg Ile Ser Ser Gln Leu Leu Ala Asn Trp Leu Arg
                645                 650                 655

His Gly Val Ile Thr Ser Ala Asp Val Arg Ala Ser Leu Glu Arg Met
            660                 665                 670

Ala Pro Leu Val Asp Arg Gln Asn Ala Gly Asp Val Ala Tyr Arg Pro
            675                 680                 685

Met Ala Pro Asn Phe Asp Asp Ser Ile Ala Phe Leu Ala Ala Gln Glu
            690                 695                 700

Leu Ile Leu Ser Gly Ala Gln Gln Pro Asn Gly Tyr Thr Glu Pro Ile
705                 710                 715                 720

Leu His Arg Arg Arg Glu Phe Lys Ala Arg Ala Ala Glu Lys Pro
                725                 730                 735

Ala Pro Ser Asp Arg Ala Gly Asp Ala Ala Arg Val Gln Lys Tyr
            740                 745                 750

Gly Gly Ser Ser Val Ala Asp Ala Glu Arg Ile Arg Arg Val Ala Glu
            755                 760                 765

Arg Ile Val Ala Thr Lys Lys Gln Gly Asn Asp Val Val Val Val
            770                 775                 780

Ser Ala Met Gly Asp Thr Thr Asp Asp Leu Leu Asp Leu Ala Gln Gln
785                 790                 795                 800

Val Cys Pro Ala Pro Pro Arg Glu Leu Asp Met Leu Leu Thr Ala
            805                 810                 815

Gly Glu Arg Ile Ser Asn Ala Leu Val Ala Met Ala Ile Glu Ser Leu
            820                 825                 830

Gly Ala His Ala Arg Ser Phe Thr Gly Ser Gln Ala Gly Val Ile Thr
            835                 840                 845

Thr Gly Thr His Gly Asn Ala Lys Ile Ile Asp Val Thr Pro Gly Arg
            850                 855                 860

Leu Gln Thr Ala Leu Glu Glu Gly Arg Val Val Leu Val Ala Gly Phe
865                 870                 875                 880

Gln Gly Val Ser Gln Asp Thr Lys Asp Val Thr Thr Leu Gly Arg Gly
                885                 890                 895

Gly Ser Asp Thr Thr Ala Val Ala Met Ala Ala Ala Leu Gly Ala Asp
            900                 905                 910

Val Cys Glu Ile Tyr Thr Asp Val Asp Gly Ile Phe Ser Ala Asp Pro
            915                 920                 925

Arg Ile Val Arg Asn Ala Arg Lys Leu Asp Thr Val Thr Phe Glu Glu
            930                 935                 940

Met Leu Glu Met Ala Ala Cys Gly Ala Lys Val Leu Met Leu Arg Cys
945                 950                 955                 960

Val Glu Tyr Ala Arg Arg His Asn Ile Pro Val His Val Arg Ser Ser
                965                 970                 975

Tyr Ser Asp Arg Pro Gly Thr Val Val Gly Ser Ile Lys Asp Val
            980                 985                 990
```

-continued

```
Pro Met Glu Asp Pro Ile Leu Thr  Gly Val Ala His Asp  Arg Ser Glu
        995                  1000                 1005

Ala Lys  Val Thr Ile Val Gly  Leu Pro Asp Ile Pro  Gly Tyr Ala
    1010                 1015                 1020

Ala Lys  Val Phe Arg Ala Val  Ala Arg Arg Arg Arg  Gln His Arg
    1025                 1030                 1035

His Gly  Ala Ala Glu Arg Leu  Gln Gly Arg Gly Arg  Gln Asp Arg
    1040                 1045                 1050

His His  Leu His Leu Leu Pro  Gln Thr Ser Gly Pro  Pro Pro Trp
    1055                 1060                 1065

Lys Asn  Trp Thr Arg Ser Glu  Thr Arg Ser Ala Ser  Thr Gln Leu
    1070                 1075                 1080

Leu Tyr  Asp Asp His Ile Gly  Lys Val Ser Leu Ile  Gly Ala Gly
    1085                 1090                 1095

Met Arg  Ser His Pro Gly Val  Thr Ala Thr Phe Cys  Glu Ala Leu
    1100                 1105                 1110

Ala Ala  Val Gly Val Asn Ile  Glu Leu Ile Ser Thr  Ser Glu Asp
    1115                 1120                 1125

Gln Arg  Ser Arg Cys Cys Ala  Ala Thr Pro Asn Trp  Thr Arg Pro
    1130                 1135                 1140

Trp Ser  Arg Cys Met Lys Arg  Ser Gly Ser Ala Ala  Thr Arg Arg
    1145                 1150                 1155

Pro Arg  Cys Thr Arg Gly Arg  Asp Gly Arg Trp Ala  Cys Gln
    1160                 1165                 1170

<210> SEQ ID NO 53
<211> LENGTH: 2952
<212> TYPE: DNA
<213> ORGANISM: Mycobacterium tuberculosis

<400> SEQUENCE: 53
atgggccatc atcatcatca tcacgtgatc gacatcatcg ggaccagccc cacatcctgg      60
gaacaggcgg cggcggaggc ggtccagcgg gcgcgggata gcgtcgatga catccgcgtc     120
gctcgggtca ttgagcagga catggccgtg gacagcgccg gcaagatcac ctaccgcatc     180
aagctcgaag tgtcgttcaa gatgaggccg gcgcaaccga ggtgtggctc gaaaccaccg     240
agcggttcgc ctgaaacggg cgccggcgcc ggtactgtcg cgactacccc cgcgtcgtcg     300
ccggtgacgt tggcggagac cggtagcacg ctgctctacc cgctgttcaa cctgtggggt     360
ccggcctttc acgagaggta tccgaacgtc acgatcaccg ctcagggcac cggttctggt     420
gccgggatcg cgcaggccgc cgccgggacg gtcaacattg ggcctccga cgcctatctg      480 tcggaaggtg atatggccgc gcacaagggg ctgatgaaca tcgcgctagc catctccgct     540
cagcaggtca actacaacct gcccggagtg agcgagcacc tcaagctgaa cggaaaagtc     600
ctggcggcca tgtaccaggg caccatcaaa acctgggacg acccgcagat cgctgcgctc     660
aaccccggcg tgaacctgcc cggcaccgcg gtagttccgc tgcaccgctc cgacgggtcc     720
ggtgacacct tcttgttcac ccagtacctg tccaagcaag atcccgaggg ctggggcaag     780
tcgcccggct tcggcaccac cgtcgacttc ccggcggtgc cgggtgcgct gggtgagaac     840
ggcaacggcg gcatggtgac cggttgcgcc gagacaccgg gctgcgtggc ctatatcggc     900
atcagcttcc tcgaccaggc cagtcaacgg ggactcggcg aggcccaact aggcaatagc     960
tctggcaatt tcttgttgcc cgacgcgcaa agcattcagg ccgcggcggc tggcttcgca    1020
tcgaaaaccc cggcgaacca ggcgatttcg atgatcgacg ggcccgcccc ggacggctac    1080
```

-continued

```
ccgatcatca actacgagta cgccatcgtc aacaaccggc aaaaggacgc cgccaccgcg    1140 caggaccttgc aggcatttct gcactgggcg atcaccgacg caacaaggc ctcgttcctc    1200 gaccaggttc atttccagcc gctgccgccc gcggtggtga agttgtctga cgcgttgatc    1260
gcgacgattt ccagcgctga gatgaagacc gatgccgcta ccctcgcgca ggaggcaggt    1320
aatttcgagc ggatctccgg cgacctgaaa acccagatcg accaggtgga gtcgacggca    1380
ggttcgttgc agggccagtg gcgcggcgcg cggggacgg ccgcccaggc cgcggtggtg    1440
cgcttccaag aagcagccaa taagcagaag caggaactcg acgagatctc gacgaatatt    1500
cgtcaggccg cgtccaata ctcgaggggcc gacgaggagc agcagcaggc gctgtcctcg    1560
caaatgggct ttactcagtc gcagaccgtg acggtggatc agcaagagat tttgaacagg    1620
gccaacgagt ggaggcccc gatggcggac ccaccgactg atgtccccat cacaccgtgc    1680
gaactcacgg cggctaaaaa cgccgcccaa cagctggtat tgtccgccga acatgcgg    1740 gaatacctgg cggccggtgc caaagagcgg cagcgtctgg cgacctcgct gcgcaacgcg    1800
gccaaggcgt atggcgaggt tgatgaggag gctgcgaccg cgctggacaa cgacggcgaa    1860
ggaactgtgc aggcagaatc ggccggggcc gtcggagggg acagttcggc cgaactaacc    1920
gatacgccga gggtggccac ggccggtgaa cccaacttca tggatctcaa agaagcggca    1980
aggaagctcg aaacgggcga ccaaggcgca tcgctcgcgc actttgcgga tgggtggaac    2040
actttcaacc tgacgctgca aggcgacgtc aagcggttcc gggggtttga caactgggaa    2100
ggcgatgcgg ctaccgcttg cgaggcttcg ctcgatcaac aacggcaatg gatactccac    2160
atggccaaat tgagcgctgc gatggccaag caggctcaat atgtcgcgca gctgcacgtg    2220
tgggctaggc gggaacatcc gacttatgaa gacatagtcg ggctcgaacg gctttacgcg    2280
gaaaaccctt cggcccgcga ccaaattctc ccggtgtacg cggagtatca gcagaggtcg    2340
gagaaggtgc tgaccgaata caacaacaag gcagccctgg aaccggtaaa cccgccgaag    2400 cctcccccg ccatcaagat cgacccgccc ccgcctccgc aagagcaggg attgatccct    2460
ggcttcctga tgccgccgtc tgacggctcc ggtgtgactc ccggtaccgg gatgccagcc    2520
gcaccgatgg ttccgcctac cggatcgccg ggtggtggcc tcccggctga cacggcggcg    2580
cagctgacgt cggctgggcg ggaagccgca gcgctgtcgg gcgacgtggc ggtcaaagcg    2640
gcatcgctcg gtggcggtgg aggcggcggg gtgccgtcgg cgccgttggg atccgcgatc    2700
gggggcgccg aatcggtgcg gcccgctggc gctggtgaca ttgccggctt aggccaggga    2760
agggccggcg gcgcgccgc gctgggcggc ggtggcatgg aatgccgat gggtgccgcg    2820 catcagggac aaggggcgc caagtccaag ggttctcagc aggaagacga ggcgctctac    2880
accgaggatc gggcatggac cgaggccgtc attggtaacc gtcggcgcca ggacagtaag    2940
gagtcgaagt ga                                                       2952
```

<210> SEQ ID NO 54
<211> LENGTH: 983
<212> TYPE: PRT
<213> ORGANISM: Mycobacterium tuberculosis

<400> SEQUENCE: 54

```
Met Gly His His His His His His Val Ile Asp Ile Ile Gly Thr Ser
1               5                   10                  15

Pro Thr Ser Trp Glu Gln Ala Ala Glu Ala Val Gln Arg Ala Arg
            20                  25                  30

Asp Ser Val Asp Asp Ile Arg Val Ala Arg Val Ile Glu Gln Asp Met
        35                  40                  45
```

```
Ala Val Asp Ser Ala Gly Lys Ile Thr Tyr Arg Ile Lys Leu Glu Val
         50                  55                  60

Ser Phe Lys Met Arg Pro Ala Gln Pro Arg Cys Gly Ser Lys Pro Pro
 65                  70                  75                  80

Ser Gly Ser Pro Glu Thr Gly Ala Gly Ala Gly Thr Val Ala Thr Thr
                 85                  90                  95

Pro Ala Ser Ser Pro Val Thr Leu Ala Glu Thr Gly Ser Thr Leu Leu
                100                 105                 110

Tyr Pro Leu Phe Asn Leu Trp Gly Pro Ala Phe His Glu Arg Tyr Pro
            115                 120                 125

Asn Val Thr Ile Thr Ala Gln Gly Thr Gly Ser Gly Ala Gly Ile Ala
130                 135                 140

Gln Ala Ala Gly Thr Val Asn Ile Gly Ala Ser Asp Ala Tyr Leu
145                 150                 155                 160

Ser Glu Gly Asp Met Ala Ala His Lys Gly Leu Met Asn Ile Ala Leu
                165                 170                 175

Ala Ile Ser Ala Gln Gln Val Asn Tyr Asn Leu Pro Gly Val Ser Glu
            180                 185                 190

His Leu Lys Leu Asn Gly Lys Val Leu Ala Ala Met Tyr Gln Gly Thr
        195                 200                 205

Ile Lys Thr Trp Asp Asp Pro Gln Ile Ala Ala Leu Asn Pro Gly Val
    210                 215                 220

Asn Leu Pro Gly Thr Ala Val Val Pro Leu His Arg Ser Asp Gly Ser
225                 230                 235                 240

Gly Asp Thr Phe Leu Phe Thr Gln Tyr Leu Ser Lys Gln Asp Pro Glu
                245                 250                 255

Gly Trp Gly Lys Ser Pro Gly Phe Gly Thr Thr Val Asp Phe Pro Ala
            260                 265                 270

Val Pro Gly Ala Leu Gly Glu Asn Gly Asn Gly Gly Met Val Thr Gly
        275                 280                 285

Cys Ala Glu Thr Pro Gly Cys Val Ala Tyr Ile Gly Ile Ser Phe Leu
290                 295                 300

Asp Gln Ala Ser Gln Arg Gly Leu Gly Glu Ala Gln Leu Gly Asn Ser
305                 310                 315                 320

Ser Gly Asn Phe Leu Leu Pro Asp Ala Gln Ser Ile Gln Ala Ala Ala
                325                 330                 335

Ala Gly Phe Ala Ser Lys Thr Pro Ala Asn Gln Ala Ile Ser Met Ile
            340                 345                 350

Asp Gly Pro Ala Pro Asp Gly Tyr Pro Ile Ile Asn Tyr Glu Tyr Ala
        355                 360                 365

Ile Val Asn Asn Arg Gln Lys Asp Ala Ala Thr Ala Gln Thr Leu Gln
    370                 375                 380

Ala Phe Leu His Trp Ala Ile Thr Asp Gly Asn Lys Ala Ser Phe Leu
385                 390                 395                 400

Asp Gln Val His Phe Gln Pro Leu Pro Pro Ala Val Val Lys Leu Ser
                405                 410                 415

Asp Ala Leu Ile Ala Thr Ile Ser Ser Ala Glu Met Lys Thr Asp Ala
            420                 425                 430

Ala Thr Leu Ala Gln Glu Ala Gly Asn Phe Glu Arg Ile Ser Gly Asp
        435                 440                 445

Leu Lys Thr Gln Ile Asp Gln Val Glu Ser Thr Ala Gly Ser Leu Gln
    450                 455                 460

Gly Gln Trp Arg Gly Ala Ala Gly Thr Ala Ala Gln Ala Ala Val Val
```

```
                465                 470                 475                 480
Arg Phe Gln Glu Ala Ala Asn Lys Gln Lys Gln Glu Leu Asp Glu Ile
                    485                 490                 495

Ser Thr Asn Ile Arg Gln Ala Gly Val Gln Tyr Ser Arg Ala Asp Glu
                500                 505                 510

Glu Gln Gln Gln Ala Leu Ser Ser Gln Met Gly Phe Thr Gln Ser Gln
                515                 520                 525

Thr Val Thr Val Asp Gln Gln Glu Ile Leu Asn Arg Ala Asn Glu Val
                530                 535                 540

Glu Ala Pro Met Ala Asp Pro Pro Thr Asp Val Pro Ile Thr Pro Cys
545                 550                 555                 560

Glu Leu Thr Ala Ala Lys Asn Ala Ala Gln Gln Leu Val Leu Ser Ala
                565                 570                 575

Asp Asn Met Arg Glu Tyr Leu Ala Ala Gly Ala Lys Glu Arg Gln Arg
                580                 585                 590

Leu Ala Thr Ser Leu Arg Asn Ala Ala Lys Ala Tyr Gly Glu Val Asp
                595                 600                 605

Glu Glu Ala Ala Thr Ala Leu Asp Asn Asp Gly Glu Gly Thr Val Gln
                610                 615                 620

Ala Glu Ser Ala Gly Ala Val Gly Gly Asp Ser Ser Ala Glu Leu Thr
625                 630                 635                 640

Asp Thr Pro Arg Val Ala Thr Ala Gly Glu Pro Asn Phe Met Asp Leu
                645                 650                 655

Lys Glu Ala Ala Arg Lys Leu Glu Thr Gly Asp Gln Gly Ala Ser Leu
                660                 665                 670

Ala His Phe Ala Asp Gly Trp Asn Thr Phe Asn Leu Thr Leu Gln Gly
                675                 680                 685

Asp Val Lys Arg Phe Arg Gly Phe Asp Asn Trp Glu Gly Asp Ala Ala
                690                 695                 700

Thr Ala Cys Glu Ala Ser Leu Asp Gln Gln Arg Gln Trp Ile Leu His
705                 710                 715                 720

Met Ala Lys Leu Ser Ala Ala Met Ala Lys Gln Ala Gln Tyr Val Ala
                725                 730                 735

Gln Leu His Val Trp Ala Arg Arg Glu His Pro Thr Tyr Glu Asp Ile
                740                 745                 750

Val Gly Leu Glu Arg Leu Tyr Ala Glu Asn Pro Ser Ala Arg Asp Gln
                755                 760                 765

Ile Leu Pro Val Tyr Ala Glu Tyr Gln Gln Arg Ser Glu Lys Val Leu
                770                 775                 780

Thr Glu Tyr Asn Asn Lys Ala Ala Leu Glu Pro Val Asn Pro Pro Lys
785                 790                 795                 800

Pro Pro Pro Ala Ile Lys Ile Asp Pro Pro Pro Gln Glu Gln
                805                 810                 815

Gly Leu Ile Pro Gly Phe Leu Met Pro Pro Ser Asp Gly Ser Gly Val
                820                 825                 830

Thr Pro Gly Thr Gly Met Pro Ala Ala Pro Met Val Pro Pro Thr Gly
                835                 840                 845

Ser Pro Gly Gly Gly Leu Pro Ala Asp Thr Ala Ala Gln Leu Thr Ser
                850                 855                 860

Ala Gly Arg Glu Ala Ala Ala Leu Ser Gly Asp Val Ala Val Lys Ala
865                 870                 875                 880

Ala Ser Leu Gly Gly Gly Gly Gly Gly Val Pro Ser Ala Pro Leu
                885                 890                 895
```

```
Gly Ser Ala Ile Gly Gly Ala Glu Ser Val Arg Pro Ala Gly Ala Gly
                900                 905                 910

Asp Ile Ala Gly Leu Gly Gln Gly Arg Ala Gly Gly Ala Ala Leu
        915                 920                 925

Gly Gly Gly Gly Met Gly Met Pro Met Gly Ala Ala His Gln Gly Gln
930                 935                 940

Gly Gly Ala Lys Ser Lys Gly Ser Gln Gln Glu Asp Glu Ala Leu Tyr
945                 950                 955                 960

Thr Glu Asp Arg Ala Trp Thr Glu Ala Val Ile Gly Asn Arg Arg Arg
                965                 970                 975

Gln Asp Ser Lys Glu Ser Lys
            980

<210> SEQ ID NO 55
<211> LENGTH: 1179
<212> TYPE: DNA
<213> ORGANISM: Mycobacterium tuberculosis

<400> SEQUENCE: 55
atgagcagag cgttcatcat cgatccaacg atcagtgcca ttgacggctt gtacgacctt      60
ctggggattg gaatacccaa ccaagggggt atcctttact cctcactaga gtacttcgaa     120
aaagccctgg aggagctggc agcagcgttt ccggtgatg gctggttagg ttcggccgcg      180
gacaaatacg ccggcaaaaa ccgcaaccac gtgaattttt tccaggaact ggcagacctc     240
gatcgtcagc tcatcagcct gatccacgac caggccaacg cggtccagac gacccgcgac     300
atcctggagg gcgccaagaa aggtctcgag ttcgtgcgcc cggtggctgt ggacctgacc     360
tacatcccgg tcgtcgggca cgccctatcg gccgccttcc aggcgccgtt ttgcgcgggc     420
gcgatggccg tagtgggcgg cgcgcttgcc tacttggtcg tgaaaacgct gatcaacgcg     480
actcaactcc tcaaattgct tgccaaattg gcggagttgg tcgcggccgc cattgcggac     540
atcatttcgg atgtggcgga catcatcaag ggcatcctcg agaagtgtg ggagttcatc      600 acaaacgcgc tcaacggcct gaaagagctt tgggacaagc tcacggggtg ggtgaccgga     660
ctgttctctc gagggtggtc gaacctggag tccttctttg cgggcgtccc cggcttgacc     720
ggcgcgacca gcggcttgtc gcaagtgact ggcttgttcg gtgcggccgg tctgtccgca     780
tcgtcgggct tggctcacgc ggatagcctg gcgagctcag ccagcttgcc cgccctggcc     840
ggcattgggg gcgggtccgg ttttggggc ttgccgagcc tggctcaggt ccatgccgcc      900
tcaactcggc aggcgctacg gccccgagct gatggcccgg tcgcgccgc tgccgagcag      960 gtcggcgggc agtcgcagct ggtctccgcg cagggttccc aaggtatggg cggacccgta    1020
ggcatgggcg gcatgcaccc ctcttcgggg gcgtcgaaag gacgacgac gaagaagtac     1080 tcggaaggcg cggcggcggg cactgaagac gccgagcgcg cgccagtcga agctgacgcg    1140
ggcggtgggc aaaaggtgct ggtacgaaac gtcgtctaa                            1179

<210> SEQ ID NO 56
<211> LENGTH: 392
<212> TYPE: PRT
<213> ORGANISM: Mycobacterium tuberculosis

<400> SEQUENCE: 56

Met Ser Arg Ala Phe Ile Ile Asp Pro Thr Ile Ser Ala Ile Asp Gly
1               5                   10                  15

Leu Tyr Asp Leu Leu Gly Ile Gly Ile Pro Asn Gln Gly Gly Ile Leu
            20                  25                  30
```

Tyr Ser Ser Leu Glu Tyr Phe Glu Lys Ala Leu Glu Leu Ala Ala
         35                  40                  45

Ala Phe Pro Gly Asp Gly Trp Leu Gly Ser Ala Ala Asp Lys Tyr Ala
 50                  55                  60

Gly Lys Asn Arg Asn His Val Asn Phe Phe Gln Glu Leu Ala Asp Leu
 65                  70                  75                  80

Asp Arg Gln Leu Ile Ser Leu Ile His Asp Gln Ala Asn Ala Val Gln
                 85                  90                  95

Thr Thr Arg Asp Ile Leu Glu Gly Ala Lys Lys Gly Leu Glu Phe Val
            100                 105                 110

Arg Pro Val Ala Val Asp Leu Thr Tyr Ile Pro Val Val Gly His Ala
            115                 120                 125

Leu Ser Ala Ala Phe Gln Ala Pro Phe Cys Ala Gly Ala Met Ala Val
130                 135                 140

Val Gly Gly Ala Leu Ala Tyr Leu Val Val Lys Thr Leu Ile Asn Ala
145                 150                 155                 160

Thr Gln Leu Leu Lys Leu Leu Ala Lys Leu Ala Glu Leu Val Ala Ala
                165                 170                 175

Ala Ile Ala Asp Ile Ile Ser Asp Val Ala Asp Ile Ile Lys Gly Ile
            180                 185                 190

Leu Gly Glu Val Trp Glu Phe Ile Thr Asn Ala Leu Asn Gly Leu Lys
            195                 200                 205

Glu Leu Trp Asp Lys Leu Thr Gly Trp Val Thr Gly Leu Phe Ser Arg
210                 215                 220

Gly Trp Ser Asn Leu Glu Ser Phe Phe Ala Gly Val Pro Gly Leu Thr
225                 230                 235                 240

Gly Ala Thr Ser Gly Leu Ser Gln Val Thr Gly Leu Phe Gly Ala Ala
                245                 250                 255

Gly Leu Ser Ala Ser Ser Gly Leu Ala His Ala Asp Ser Leu Ala Ser
            260                 265                 270

Ser Ala Ser Leu Pro Ala Leu Ala Gly Ile Gly Gly Ser Gly Phe
            275                 280                 285

Gly Gly Leu Pro Ser Leu Ala Gln Val His Ala Ala Ser Thr Arg Gln
290                 295                 300

Ala Leu Arg Pro Arg Ala Asp Gly Pro Val Gly Ala Ala Ala Glu Gln
305                 310                 315                 320

Val Gly Gly Gln Ser Gln Leu Val Ser Ala Gln Gly Ser Gln Gly Met
                325                 330                 335

Gly Gly Pro Val Gly Met Gly Met His Pro Ser Ser Gly Ala Ser
            340                 345                 350

Lys Gly Thr Thr Thr Lys Lys Tyr Ser Glu Gly Ala Ala Ala Gly Thr
            355                 360                 365

Glu Asp Ala Glu Arg Ala Pro Val Glu Ala Asp Ala Gly Gly Gly Gln
370                 375                 380

Lys Val Leu Val Arg Asn Val Val
385                 390

<210> SEQ ID NO 57
<211> LENGTH: 2232
<212> TYPE: DNA
<213> ORGANISM: Mycobacterium tuberculosis

<400> SEQUENCE: 57
catatgcatc accatcacca tcacgatgtg gcggacatca tcaagggcac cctcggagaa      60
gtgtgggagt tcatcacaaa cgcgctcaac ggcctgaaag agctttggga caagctcacg     120

```
gggtgggtga ccggactgtt ctctcgaggg tggtcgaacc tggagtcctt ctttgcgggc      180
gtccccggct tgaccggcgc gaccagcggc ttgtcgcaag tgactggctt gttcggtgcg      240
gccggtctgt ccgcatcgtc gggcttggct cacgcggata gcctggcgag ctcagccagc      300
ttgcccgccc tggccggcat tggggcgggt ccggttttg ggggcttgcc gagcctggct       360
caggtccatg ccgcctcaac tcggcaggcg ctacggcccc gagctgatgg cccggtcggc      420
gccgctgccg agcaggtcgg cgggcagtcg cagctggtct ccgcgcaggg ttcccaaggt      480
atgggcggac ccgtaggcat gggcggcatg caccctctt cggggcgtc gaaagggacg       540 acgacgaaga agtactcgga aggcgcggcg gcgggcactg aagacgccga gcgcgcgcca      600
gtcgaagctg acgcgggcgg tgggcaaaag gtgctggtac gaaacgtcgt cgaattcatg      660
gtggatttcg gggcgttacc accggagatc aactccgcga ggatgtacgc cggcccgggt      720
tcggcctcgc tggtgccgc ggctcagatg tgggacagcg tggcgagtga cctgttttcg       780
gccgcgtcgg cgtttcagtc ggtggtctgg ggtctgacgg tggggtcgtg gataggttcg      840
tcggcgggtc tgatggtggc ggcggcctcg ccgtatgtgg cgtggatgag cgtcaccgcg      900
gggcaggccg agctgaccgc cgcccaggtc cgggttgctg cggcggccta cgagacggcg      960
tatgggctga cggtgccccc gccggtgatc gccgagaacc gtgctgaact gatgattctg     1020
atagcgacca acctcttggg gcaaaacacc cggcgatcg cggtcaacga ggccgaatac      1080
ggcgagatgt gggcccaaga cgccgccgcg atgtttggct acgccgcggc gacggcgacg     1140
gcgacggcga cgttgctgcc gttcgaggag gcgccggaga tgaccagcgc gggtgggctc     1200
ctcgagcagg ccgccgcggt cgaggaggcc tccgacaccg ccgcggcgaa ccagttgatg     1260
aacaatgtgc cccaggcgct gcaacagctg gcccagccca cgcagggcac cacgccttct     1320
tccaagctgg gtggcctgtg aagacggtc tcgccgcatc ggtcgccgat cagcaacatg      1380
gtgtcgatgc caacaacca catgtcgatg accaactcgg gtgtgtcgat gaccaacacc      1440
ttgagctcga tgttgaaggg cttttgctccg gcggcggccg cccaggccgt gcaaaccgcg     1500
gcgcaaaacg gggtccgggc gatgagctcg ctgggcagct cgctgggttc ttcgggtctg     1560
ggcggtgggg tggccgccaa cttgggtcgg gcggcctcgg tcggttcgtt gtcggtgccg     1620
caggcctggg ccgcggccaa ccaggcagtc accccggcgg cgcggcgct gccgctgacc      1680 agcctgacca gcgccgcgga aagagggccc gggcagatgc tgggcgggct gccggtgggg     1740
cagatgggcg ccagggccgg tgtgggctc agtggtgtgc tgcgtgttcc gccgcgaccc      1800
tatgtgatgc cgcattctcc ggcagccggc gatatcatga gcagagcgtt catcatcgat     1860
ccaacgatca gtgccattga cggcttgtac gaccttctgg ggattggaat acccaaccaa     1920
gggggtatcc tttactcctc actagagtac ttcgaaaaag ccctggagga gctggcagca     1980
gcgtttccgg gtgatggctg gttaggttcg gccgcggaca aatacgccgg caaaaaccgc     2040
aaccacgtga atttttcca ggaactggca gacctcgatc gtcagctcat cagcctgatc      2100
cacgaccagg ccaacgcggt ccagacgacc cgcgacatcc tggagggcgc caagaaaggt     2160
ctcgagttcg tgcgcccggt ggctgtggac ctgacctaca tcccggtcgt cgggcacgcc     2220
ctataagata tc                                                         2232
```

<210> SEQ ID NO 58
<211> LENGTH: 740
<212> TYPE: PRT
<213> ORGANISM: Mycobacterium tuberculosis

<400> SEQUENCE: 58

```
Met His His His His His Asp Val Ala Asp Ile Ile Lys Gly Thr
1               5                   10                  15

Leu Gly Glu Val Trp Glu Phe Ile Thr Asn Ala Leu Asn Gly Leu Lys
            20                  25                  30

Glu Leu Trp Asp Lys Leu Thr Gly Trp Val Thr Gly Leu Phe Ser Arg
        35                  40                  45

Gly Trp Ser Asn Leu Glu Ser Phe Phe Ala Gly Val Pro Gly Leu Thr
    50                  55                  60

Gly Ala Thr Ser Gly Leu Ser Gln Val Thr Gly Leu Phe Gly Ala Ala
65                  70                  75                  80

Gly Leu Ser Ala Ser Ser Gly Leu Ala His Ala Asp Ser Leu Ala Ser
                85                  90                  95

Ser Ala Ser Leu Pro Ala Leu Ala Gly Ile Gly Gly Ser Gly Phe
            100                 105                 110

Gly Gly Leu Pro Ser Leu Ala Gln Val His Ala Ala Ser Thr Arg Gln
        115                 120                 125

Ala Leu Arg Pro Arg Ala Asp Gly Pro Val Gly Ala Ala Ala Glu Gln
    130                 135                 140

Val Gly Gly Gln Ser Gln Leu Val Ser Ala Gln Gly Ser Gln Gly Met
145                 150                 155                 160

Gly Gly Pro Val Gly Met Gly Gly Met His Pro Ser Ser Gly Ala Ser
                165                 170                 175

Lys Gly Thr Thr Thr Lys Lys Tyr Ser Glu Gly Ala Ala Ala Gly Thr
            180                 185                 190

Glu Asp Ala Glu Arg Ala Pro Val Glu Ala Asp Ala Gly Gly Gly Gln
        195                 200                 205

Lys Val Leu Val Arg Asn Val Val Glu Phe Met Val Asp Phe Gly Ala
    210                 215                 220

Leu Pro Pro Glu Ile Asn Ser Ala Arg Met Tyr Ala Gly Pro Gly Ser
225                 230                 235                 240

Ala Ser Leu Val Ala Ala Gln Met Trp Asp Ser Val Ala Ser Asp
                245                 250                 255

Leu Phe Ser Ala Ala Ser Ala Phe Gln Ser Val Val Trp Gly Leu Thr
            260                 265                 270

Val Gly Ser Trp Ile Gly Ser Ser Ala Gly Leu Met Val Ala Ala Ala
        275                 280                 285

Ser Pro Tyr Val Ala Trp Met Ser Val Thr Ala Gly Gln Ala Glu Leu
    290                 295                 300

Thr Ala Ala Gln Val Arg Val Ala Ala Ala Tyr Glu Thr Ala Tyr
305                 310                 315                 320

Gly Leu Thr Val Pro Pro Val Ile Ala Glu Asn Arg Ala Glu Leu
                325                 330                 335

Met Ile Leu Ile Ala Thr Asn Leu Leu Gly Gln Asn Thr Pro Ala Ile
            340                 345                 350

Ala Val Asn Glu Ala Glu Tyr Gly Glu Met Trp Ala Gln Asp Ala Ala
        355                 360                 365

Ala Met Phe Gly Tyr Ala Ala Ala Thr Ala Thr Ala Thr Ala Thr Leu
    370                 375                 380

Leu Pro Phe Glu Glu Ala Pro Glu Met Thr Ser Ala Gly Gly Leu Leu
385                 390                 395                 400

Glu Gln Ala Ala Ala Val Glu Glu Ala Ser Asp Thr Ala Ala Ala Asn
                405                 410                 415

Gln Leu Met Asn Asn Val Pro Gln Ala Leu Gln Gln Leu Ala Gln Pro
```

|     |     |     |     |     | 420 |     |     |     |     | 425 |     |     |     |     | 430 |     |
| --- | --- | --- | --- | --- | --- | --- | --- | --- | --- | --- | --- | --- | --- | --- | --- | --- |

Thr Gln Gly Thr Thr Pro Ser Ser Lys Leu Gly Gly Leu Trp Lys Thr
            435                 440                 445

Val Ser Pro His Arg Ser Pro Ile Ser Asn Met Val Ser Met Ala Asn
        450                 455                 460

Asn His Met Ser Met Thr Asn Ser Gly Val Ser Met Thr Asn Thr Leu
465                 470                 475                 480

Ser Ser Met Leu Lys Gly Phe Ala Pro Ala Ala Ala Gln Ala Val
                485                 490                 495

Gln Thr Ala Ala Gln Asn Gly Val Arg Ala Met Ser Ser Leu Gly Ser
            500                 505                 510

Ser Leu Gly Ser Ser Gly Leu Gly Gly Val Ala Ala Asn Leu Gly
            515                 520                 525

Arg Ala Ala Ser Val Gly Ser Leu Ser Val Pro Gln Ala Trp Ala Ala
        530                 535                 540

Ala Asn Gln Ala Val Thr Pro Ala Ala Arg Ala Leu Pro Leu Thr Ser
545                 550                 555                 560

Leu Thr Ser Ala Ala Glu Arg Gly Pro Gly Gln Met Leu Gly Gly Leu
                565                 570                 575

Pro Val Gly Gln Met Gly Ala Arg Ala Gly Gly Leu Ser Gly Val
            580                 585                 590

Leu Arg Val Pro Pro Arg Pro Tyr Val Met Pro His Ser Pro Ala Ala
        595                 600                 605

Gly Asp Ile Met Ser Arg Ala Phe Ile Ile Asp Pro Thr Ile Ser Ala
610                 615                 620

Ile Asp Gly Leu Tyr Asp Leu Leu Gly Ile Gly Ile Pro Asn Gln Gly
625                 630                 635                 640

Gly Ile Leu Tyr Ser Ser Leu Glu Tyr Phe Glu Lys Ala Leu Glu Glu
                645                 650                 655

Leu Ala Ala Ala Phe Pro Gly Asp Gly Trp Leu Gly Ser Ala Ala Asp
            660                 665                 670

Lys Tyr Ala Gly Lys Asn Arg Asn His Val Asn Phe Phe Gln Glu Leu
        675                 680                 685

Ala Asp Leu Asp Arg Gln Leu Ile Ser Leu Ile His Asp Gln Ala Asn
690                 695                 700

Ala Val Gln Thr Thr Arg Asp Ile Leu Glu Gly Ala Lys Lys Gly Leu
705                 710                 715                 720

Glu Phe Val Arg Pro Val Ala Val Asp Leu Thr Tyr Ile Pro Val Val
                725                 730                 735

Gly His Ala Leu
            740

<210> SEQ ID NO 59
<211> LENGTH: 2365
<212> TYPE: DNA
<213> ORGANISM: Mycobacterium tuberculosis

<400> SEQUENCE: 59
catatgcatc accatcacca tcacatgagc agagcgttca tcatcgatcc aacgatcagt    60
gccattgacg gcttgtacga ccttctgggg attggaatac ccaaccaagg gggtatcctt   120
tactcctcac tagagtactt cgaaaaagcc ctggaggagc tggcagcagc gtttccgggt   180
gatggctggt taggttcggc cgcggacaaa tacgccggca aaaaccgcaa ccacgtgaat   240
tttttccagg aactggcaga cctcgatcgt cagctcatca gcctgatcca cgaccaggcc   300

```
aacgcggtcc agacgacccg cgacatcctg gagggcgcca agaaaggtct cgagttcgtg    360
cgcccggtgg ctgtggacct gacctacatc ccggtcgtcg ggcacgccct atcggccgcc    420
ttccaggcgc cgttttgcgc gggcgcgatg gccgtagtgg gcggcgcgct taagcttatg    480
gtggatttcg gggcgttacc accgagatc aactccgcga ggatgtacgc cggcccgggt    540
tcggcctcgc tggtggccgc ggctcagatg tgggacagcg tggcgagtga cctgttttcg    600
gccgcgtcgc cgtttcagtc ggtggtctgg ggtctgacgg tggggtcgtg ataggttcg     660
tcggcgggtc tgatggtggc ggcggcctcg ccgtatgtgg cgtggatgag cgtcaccgcg    720
gggcaggccg agctgaccgc cgcccaggtc cgggttgctg cggcggccta cgagacggcg    780
tatgggctga cggtgccccc gccggtgatc gccgagaacc gtgctgaact gatgattctg    840
atagcgacca acctcttggg gcaaaacacc ccggcgatcg cggtcaacga ggccgaatac    900
ggcgagatgt gggcccaaga cgccgccgcg atgtttggct acgccgcggc gacggcgacg    960
gcgacggcga cgttgctgcc gttcgaggag gcgccggaga tgaccagcgc gggtgggctc   1020
ctcgagcagg ccgccgcggt cgaggaggcc tccgacaccg ccgcggcgaa ccagttgatg   1080
aacaatgtgc cccaggcgct gcaacagctg gcccagccca cgcagggcac cacgccttct   1140
tccaagctgg gtggcctgtg aagacggtc tcgccgcatc ggtcgccgat cagcaacatg    1200
gtgtcgatgg ccaacaacca catgtcgatg accaactcgg gtgtgtcgat gaccaacacc   1260
ttgagctcga tgttgaaggg cttgctccg gcggcggccg cccaggccgt gcaaaccgcg    1320
gcgcaaaacg gggtccgggc gatgagctcg ctgggcagct cgctgggttc ttcgggtctg   1380
ggcggtgggg tggccgccaa cttgggtcgg gcggcctcgg tcggttcgtt gtcggtgccg   1440
caggcctggg ccgcggccaa ccaggcagtc accccggcgg cgcgggcgct gccgctgacc   1500
agcctgacca gcgccgcgga aagagggccc gggcagatgc tggcgggct gccggtgggg    1560
cagatgggcg ccagggccgg tgtgggctc agtggtgtgc tgcgtgttcc gccgcgaccc    1620
tatgtgatgc cgcattctcc ggcagccggc aagcttactc aactcctcaa attgcttgcc   1680
aaattggcgg agttggtcgc ggccgccatt gcggacatca tttcggatgt ggcggacatc   1740
atcaagggca tcctcggaga agtgtgggag ttcatcacaa acgcgctcaa cggcctgaaa   1800
gagctttggg acaagctcac ggggtgggtg accggactgt tctctcgagg gtggtcgaac   1860
ctggagtcct tctttgcggg cgtccccggc ttgaccggcg cgaccagcgg cttgtcgcaa   1920
gtgactggct tgttcggtgc ggccggtctg tccgcatcgt cgggcttggc tcacgcggat   1980
agcctggcga gctcagccag cttgcccgcc ctggccggca ttgggggcgg gtccggtttt   2040
gggggcttgc cgagcctggc tcaggtccat gccgcctcaa ctcggcaggc gctacggccc   2100
cgagctgatg gccggtcgg cgccgctgcc gagcaggtcg gcgggcagtc gcagctggtc    2160
tccgcgcagg gttcccaagg tatgggcgga cccgtaggca tgggcggcat gcacccctct   2220
tcggggcgt cgaaagggac gacgacgaag aagtactcgg aaggcgcggc ggcgggcact    2280
gaagacgccg agcgcgcgcc agtcgaagct gacgcgggcg gtgggcaaaa ggtgctggta   2340
cgaaacgtcg tctaacggcg aattc                                         2365
```

<210> SEQ ID NO 60
<211> LENGTH: 783
<212> TYPE: PRT
<213> ORGANISM: Mycobacterium tuberculosis

<400> SEQUENCE: 60

Met His His His His His His Met Ser Arg Ala Phe Ile Ile Asp Pro
1               5                   10                  15

```
Thr Ile Ser Ala Ile Asp Gly Leu Tyr Asp Leu Leu Gly Ile Gly Ile
             20                  25                  30

Pro Asn Gln Gly Gly Ile Leu Tyr Ser Ser Leu Glu Tyr Phe Glu Lys
             35                  40                  45

Ala Leu Glu Glu Leu Ala Ala Phe Pro Gly Asp Gly Trp Leu Gly
 50                      55                  60

Ser Ala Ala Asp Lys Tyr Ala Gly Lys Asn Arg Asn His Val Asn Phe
 65                  70                  75                  80

Phe Gln Glu Leu Ala Asp Leu Asp Arg Gln Leu Ile Ser Leu Ile His
                 85                  90                  95

Asp Gln Ala Asn Ala Val Gln Thr Thr Arg Asp Ile Leu Glu Gly Ala
             100                 105                 110

Lys Lys Gly Leu Glu Phe Val Arg Pro Val Ala Val Asp Leu Thr Tyr
             115                 120                 125

Ile Pro Val Val Gly His Ala Leu Ser Ala Ala Phe Gln Ala Pro Phe
 130                     135                 140

Cys Ala Gly Ala Met Ala Val Gly Gly Ala Leu Lys Leu Met Val
 145                 150                 155                 160

Asp Phe Gly Ala Leu Pro Pro Glu Ile Asn Ser Ala Arg Met Tyr Ala
                 165                 170                 175

Gly Pro Gly Ser Ala Ser Leu Val Ala Ala Gln Met Trp Asp Ser
             180                 185                 190

Val Ala Ser Asp Leu Phe Ser Ala Ala Ser Ala Phe Gln Ser Val Val
 195                     200                 205

Trp Gly Leu Thr Val Gly Ser Trp Ile Gly Ser Ser Ala Gly Leu Met
             210                 215                 220

Val Ala Ala Ala Ser Pro Tyr Val Ala Trp Met Ser Val Thr Ala Gly
 225                     230                 235                 240

Gln Ala Glu Leu Thr Ala Ala Gln Val Arg Val Ala Ala Ala Tyr
             245                 250                 255

Glu Thr Ala Tyr Gly Leu Thr Val Pro Pro Val Ile Ala Glu Asn
             260                 265                 270

Arg Ala Glu Leu Met Ile Leu Ile Ala Thr Asn Leu Leu Gly Gln Asn
                 275                 280                 285

Thr Pro Ala Ile Ala Val Asn Glu Ala Glu Tyr Gly Glu Met Trp Ala
             290                 295                 300

Gln Asp Ala Ala Ala Met Phe Gly Tyr Ala Ala Ala Thr Ala Thr Ala
 305                     310                 315                 320

Thr Ala Thr Leu Leu Pro Phe Glu Glu Ala Pro Glu Met Thr Ser Ala
                 325                 330                 335

Gly Gly Leu Leu Glu Gln Ala Ala Val Glu Glu Ala Ser Asp Thr
             340                 345                 350

Ala Ala Ala Asn Gln Leu Met Asn Asn Val Pro Gln Ala Leu Gln Gln
             355                 360                 365

Leu Ala Gln Pro Thr Gln Gly Thr Thr Pro Ser Ser Lys Leu Gly Gly
 370                     375                 380

Leu Trp Lys Thr Val Ser Pro His Arg Ser Pro Ile Ser Asn Met Val
 385                     390                 395                 400

Ser Met Ala Asn Asn His Met Ser Met Thr Ser Gly Val Ser Met
             405                 410                 415

Thr Asn Thr Leu Ser Ser Met Leu Lys Gly Phe Ala Pro Ala Ala Ala
             420                 425                 430

Ala Gln Ala Val Gln Thr Ala Ala Gln Asn Gly Val Arg Ala Met Ser
```

```
        435                 440                 445

Ser Leu Gly Ser Ser Leu Gly Ser Ser Gly Leu Gly Gly Gly Val Ala
    450                 455                 460

Ala Asn Leu Gly Arg Ala Ala Ser Val Gly Ser Leu Ser Val Pro Gln
465                 470                 475                 480

Ala Trp Ala Ala Ala Asn Gln Ala Val Thr Pro Ala Ala Arg Ala Leu
                485                 490                 495

Pro Leu Thr Ser Leu Thr Ser Ala Ala Glu Arg Gly Pro Gly Gln Met
            500                 505                 510

Leu Gly Gly Leu Pro Val Gly Gln Met Gly Ala Arg Ala Gly Gly Gly
        515                 520                 525

Leu Ser Gly Val Leu Arg Val Pro Pro Arg Pro Tyr Val Met Pro His
    530                 535                 540

Ser Pro Ala Ala Gly Lys Leu Thr Gln Leu Leu Lys Leu Leu Ala Lys
545                 550                 555                 560

Leu Ala Glu Leu Val Ala Ala Ala Ile Ala Asp Ile Ile Ser Asp Val
                565                 570                 575

Ala Asp Ile Ile Lys Gly Ile Leu Gly Glu Val Trp Glu Phe Ile Thr
            580                 585                 590

Asn Ala Leu Asn Gly Leu Lys Glu Leu Trp Asp Lys Leu Thr Gly Trp
        595                 600                 605

Val Thr Gly Leu Phe Ser Arg Gly Trp Ser Asn Leu Glu Ser Phe Phe
    610                 615                 620

Ala Gly Val Pro Gly Leu Thr Gly Ala Thr Ser Gly Leu Ser Gln Val
625                 630                 635                 640

Thr Gly Leu Phe Gly Ala Ala Gly Leu Ser Ala Ser Ser Gly Leu Ala
                645                 650                 655

His Ala Asp Ser Leu Ala Ser Ser Ala Ser Leu Pro Ala Leu Ala Gly
            660                 665                 670

Ile Gly Gly Gly Ser Gly Phe Gly Gly Leu Pro Ser Leu Ala Gln Val
        675                 680                 685

His Ala Ala Ser Thr Arg Gln Ala Leu Arg Pro Arg Ala Asp Gly Pro
    690                 695                 700

Val Gly Ala Ala Ala Glu Gln Val Gly Gly Gln Ser Gln Leu Val Ser
705                 710                 715                 720

Ala Gln Gly Ser Gln Gly Met Gly Gly Pro Val Gly Met Gly Gly Met
                725                 730                 735

His Pro Ser Ser Gly Ala Ser Lys Gly Thr Thr Thr Lys Lys Tyr Ser
            740                 745                 750

Glu Gly Ala Ala Ala Gly Thr Glu Asp Ala Glu Arg Ala Pro Val Glu
        755                 760                 765

Ala Asp Ala Gly Gly Gly Gln Lys Val Leu Val Arg Asn Val Val
    770                 775                 780
```

<210> SEQ ID NO 61
<211> LENGTH: 2445
<212> TYPE: DNA
<213> ORGANISM: Mycobacterium tuberculosis

<400> SEQUENCE: 61

```
catatgcatc accatcacca tcacgatgtg gcggacatca tcaagggcat cctcggagaa      60
gtgtgggagt tcatcacaaa cgcgctcaac ggcctgaaag agctttggga caagctcacg     120
gggtgggtga ccggactgtt ctctcgaggg tggtcgaacc tggagtcctt ctttgcgggc     180
gtccccggct tgaccggcgc gaccagcggc ttgtcgcaag tgactggctt gttcggtgcg     240
```

```
gccggtctgt ccgcatcgtc gggcttggct cacgcggata gcctggcgag ctcagccagc    300
ttgcccgccc tggccggcat tgggggcggg tccggttttg ggggcttgcc gagcctggct    360
caggtccatg ccgcctcaac tcggcaggcg ctacggcccc gagctgatgg cccggtcggc    420
gccgctgccg agcaggtcgg cgggcagtcg cagctggtct ccgcgcaggg ttcccaaggt    480
atgggcggac ccgtaggcat gggcggcatg caccccctctt cggggcgtc gaaagggacg    540 acgacgaaga agtactcgga aggcgcggcg gcgggcactg aagacgccga gcgcgcgcca    600
gtcgaagctg acgcgggcgg tgggcaaaag gtgctggtac gaaacgtcgt cgaattcatg    660
gtggatttcg gggcgttacc accggagatc aactccgcga ggatgtacgc cggcccgggt    720
tcggcctcgc tggtgccgc ggctcagatg tgggacagcg tggcgagtga cctgttttcg    780
gccgcgtcgg cgtttcagtc ggtggtctgg ggtctgacgg tggggtcgtg ataggttcg    840 tcggcgggtc tgatggtggc ggcggcctcg ccgtatgtgg cgtggatgag cgtcaccgcg    900
gggcaggccg agctgaccgc cgcccaggtc cgggttgctg cggcggccta cgagacggcg    960
tatgggctga cggtgcccc gccggtgatc gccgagaacc gtgctgaact gatgattctg   1020
atagcgacca acctcttggg gcaaaacacc ccggcgatcg cggtcaacga ggccgaatac   1080
ggcgagatgt gggcccaaga cgccgccgcg atgtttggct acgccgcggc gacggcgacg   1140
gcgacggcga cgttgctgcc gttcgaggag gcgccggaga tgaccagcgc gggtgggctc   1200
ctcgagcagg ccgccgcggt cgaggaggcc tccgacaccg ccgcggcgaa ccagttgatg   1260
aacaatgtgc cccaggcgct gcaacagctg gcccagccca gcagggcac cacgccttct   1320 tccaagctgg gtggcctgtg aagacggtc tcgccgcatc ggtcgccgat cagcaacatg   1380
gtgtcgatgg ccaacaacca catgtcgatg accaactcgg gtgtgtcgat gaccaacacc   1440
ttgagctcga tgttgaaggg cttttgctccg gcggcggccg cccaggccgt gcaaaccgcg   1500
gcgcaaaacg gggtccgggc gatgagctcg ctggcagct cgctgggttc ttcgggtctg   1560
ggcggtgggg tggccgccaa cttgggtcgg gcggcctcgg tcggttcgtt gtcggtgccg   1620
caggcctggg ccgcggccaa ccaggcagtc accccggcgg cgcggggcgct gccgctgacc   1680 agcctgacca gcgccgcgga aagagggccc gggcagatgc tgggcgggct gccggtgggg   1740
cagatgggcg ccagggccgg tggtgggctc agtggtgtgc tgcgtgttcc gccgcgaccc   1800
tatgtgatgc cgcattctcc ggcagccggc gatatcatga gcagagcgtt catcatcgat   1860
ccaacgatca gtgccattga cggcttgtac gaccttctgg ggattggaat acccaaccaa   1920
gggggtatcc tttactcctc actagagtac ttcgaaaaag ccctggagga gctggcagca   1980
gcgtttccgg gtgatggctg gttaggttcg gccgcggaca atacgccgg caaaaaccgc   2040 aaccacgtga attttttcca ggaactggca gacctcgatc gtcagctcat cagcctgatc   2100
cacgaccagg ccaacgcggt ccagacgacc cgcgacatcc tggagggcgc caagaaaggt   2160
ctcgagttcg tgccgccggt ggctgtggac ctgacctaca tcccggtcgt cgggcacgcc   2220
ctatcggccg ccttccaggc gccgttttgc gcgggcgcga tggccgtagt gggcggcgcg   2280
cttgcctact tggtcgtgaa aacgctgatc aacgcgactc aactcctcaa attgcttgcc   2340
aaattggcgg agttggtcgc ggccgccatt gcggacatca tttcggatgt ggcggacatc   2400
atcaagggca tcctcggaga agtgtgggag ttcatctaag atatc              2445
```

<210> SEQ ID NO 62
<211> LENGTH: 811
<212> TYPE: PRT
<213> ORGANISM: Mycobacterium tuberculosis

```
<400> SEQUENCE: 62

Met His His His His His Asp Val Ala Asp Ile Ile Lys Gly Ile
1               5                   10                  15

Leu Gly Glu Val Trp Glu Phe Ile Thr Asn Ala Leu Asn Gly Leu Lys
            20                  25                  30

Glu Leu Trp Asp Lys Leu Thr Gly Trp Val Thr Gly Leu Phe Ser Arg
        35                  40                  45

Gly Trp Ser Asn Leu Glu Ser Phe Phe Ala Gly Val Pro Gly Leu Thr
50                  55                  60

Gly Ala Thr Ser Gly Leu Ser Gln Val Thr Gly Leu Phe Gly Ala Ala
65                  70                  75                  80

Gly Leu Ser Ala Ser Ser Gly Leu Ala His Ala Asp Ser Leu Ala Ser
                85                  90                  95

Ser Ala Ser Leu Pro Ala Leu Ala Gly Ile Gly Gly Ser Gly Phe
            100                 105                 110

Gly Gly Leu Pro Ser Leu Ala Gln Val His Ala Ala Ser Thr Arg Gln
        115                 120                 125

Ala Leu Arg Pro Arg Ala Asp Gly Pro Val Gly Ala Ala Glu Gln
130                 135                 140

Val Gly Gly Gln Ser Gln Leu Val Ser Ala Gln Gly Ser Gln Gly Met
145                 150                 155                 160

Gly Gly Pro Val Gly Met Gly Gly Met His Pro Ser Ser Gly Ala Ser
                165                 170                 175

Lys Gly Thr Thr Thr Lys Lys Tyr Ser Glu Ala Ala Ala Gly Thr
            180                 185                 190

Glu Asp Ala Glu Arg Ala Pro Val Glu Ala Asp Ala Gly Gly Gln
        195                 200                 205

Lys Val Leu Val Arg Asn Val Val Glu Phe Met Val Asp Phe Gly Ala
210                 215                 220

Leu Pro Pro Glu Ile Asn Ser Ala Arg Met Tyr Ala Gly Pro Gly Ser
225                 230                 235                 240

Ala Ser Leu Val Ala Ala Gln Met Trp Asp Ser Val Ala Ser Asp
                245                 250                 255

Leu Phe Ser Ala Ala Ser Ala Phe Gln Ser Val Val Trp Gly Leu Thr
            260                 265                 270

Val Gly Ser Trp Ile Gly Ser Ser Ala Gly Leu Met Val Ala Ala Ala
        275                 280                 285

Ser Pro Tyr Val Ala Trp Met Ser Val Thr Ala Gly Gln Ala Glu Leu
290                 295                 300

Thr Ala Ala Gln Val Arg Val Ala Ala Ala Tyr Glu Thr Ala Tyr
305                 310                 315                 320

Gly Leu Thr Val Pro Pro Val Ile Ala Glu Asn Arg Ala Glu Leu
                325                 330                 335

Met Ile Leu Ile Ala Thr Asn Leu Leu Gly Gln Asn Thr Pro Ala Ile
            340                 345                 350

Ala Val Asn Glu Ala Glu Tyr Gly Glu Met Trp Ala Gln Asp Ala Ala
        355                 360                 365

Ala Met Phe Gly Tyr Ala Ala Ala Thr Ala Thr Ala Thr Ala Thr Leu
370                 375                 380

Leu Pro Phe Glu Glu Ala Pro Glu Met Thr Ser Ala Gly Gly Leu Leu
385                 390                 395                 400

Glu Gln Ala Ala Ala Val Glu Glu Ala Ser Asp Thr Ala Ala Ala Asn
                405                 410                 415
```

```
Gln Leu Met Asn Asn Val Pro Gln Ala Leu Gln Gln Leu Ala Gln Pro
            420                 425                 430
Thr Gln Gly Thr Thr Pro Ser Ser Lys Leu Gly Gly Leu Trp Lys Thr
        435                 440                 445
Val Ser Pro His Arg Ser Pro Ile Ser Asn Met Val Ser Met Ala Asn
450                 455                 460
Asn His Met Ser Met Thr Asn Ser Gly Val Ser Met Thr Asn Thr Leu
465                 470                 475                 480
Ser Ser Met Leu Lys Gly Phe Ala Pro Ala Ala Ala Gln Ala Val
                485                 490                 495
Gln Thr Ala Ala Gln Asn Gly Val Arg Ala Met Ser Ser Leu Gly Ser
            500                 505                 510
Ser Leu Gly Ser Ser Gly Leu Gly Gly Val Ala Ala Asn Leu Gly
        515                 520                 525
Arg Ala Ala Ser Val Gly Ser Leu Ser Val Pro Gln Ala Trp Ala Ala
530                 535                 540
Ala Asn Gln Ala Val Thr Pro Ala Ala Arg Ala Leu Pro Leu Thr Ser
545                 550                 555                 560
Leu Thr Ser Ala Ala Glu Arg Gly Pro Gly Gln Met Leu Gly Gly Leu
                565                 570                 575
Pro Val Gly Gln Met Gly Ala Arg Ala Gly Gly Leu Ser Gly Val
            580                 585                 590
Leu Arg Val Pro Pro Arg Pro Tyr Val Met Pro His Ser Pro Ala Ala
        595                 600                 605
Gly Asp Ile Met Ser Arg Ala Phe Ile Ile Asp Pro Thr Ile Ser Ala
610                 615                 620
Ile Asp Gly Leu Tyr Asp Leu Gly Ile Gly Ile Pro Asn Gln Gly
625                 630                 635                 640
Gly Ile Leu Tyr Ser Ser Leu Glu Tyr Phe Glu Lys Ala Leu Glu Glu
                645                 650                 655
Leu Ala Ala Ala Phe Pro Gly Asp Gly Trp Leu Gly Ser Ala Ala Asp
            660                 665                 670
Lys Tyr Ala Gly Lys Asn Arg Asn His Val Asn Phe Phe Gln Glu Leu
        675                 680                 685
Ala Asp Leu Asp Arg Gln Leu Ile Ser Leu Ile His Asp Gln Ala Asn
690                 695                 700
Ala Val Gln Thr Thr Arg Asp Ile Leu Glu Gly Ala Lys Lys Gly Leu
705                 710                 715                 720
Glu Phe Val Arg Pro Val Ala Val Asp Leu Thr Tyr Ile Pro Val Val
                725                 730                 735
Gly His Ala Leu Ser Ala Ala Phe Gln Ala Pro Phe Cys Ala Gly Ala
            740                 745                 750
Met Ala Val Val Gly Gly Ala Leu Ala Tyr Leu Val Val Lys Thr Leu
        755                 760                 765
Ile Asn Ala Thr Gln Leu Leu Lys Leu Leu Ala Lys Leu Ala Glu Leu
770                 775                 780
Val Ala Ala Ala Ile Ala Asp Ile Ile Ser Asp Val Ala Asp Ile Ile
785                 790                 795                 800
Lys Gly Ile Leu Gly Glu Val Trp Glu Phe Ile
                805                 810

<210> SEQ ID NO 63
<211> LENGTH: 1629
<212> TYPE: DNA
```

-continued

<213> ORGANISM: Mycobacterium tuberculosis

<400> SEQUENCE: 63

```
catatgcatc accatcacca tcacacggcc gcgtccgata acttccagct gtcccagggt      60
gggcagggat cgccattcc gatcgggcag gcgatggcga tcgcgggcca gatccgatcg      120
ggtgggggt cacccaccgt tcatatcggg cctaccgcct tcctcggctt gggtgttgtc      180
gacaacaacg gcaacggcgc acgagtccaa cgcgtggtcg ggagcgctcc ggcggcaagt      240
ctcggcatct ccaccggcga cgtgatcacc gcggtcgacg gcgctccgat caactcggcc      300
accgcgatgg cggacgcgct taacgggcat catcccggtg acgtcatctc ggtgacctgg      360
caaaccaagt cgggcggcac gcgtacaggg aacgtgacat tggccgaggg accccccggcc     420
gaattcctag tacctagagg ttcaatgagc agagcgttca tcatcgatcc aacgatcagt      480
gccattgacg gcttgtacga ccttctgggg attggaatac ccaaccaagg gggtatcctt      540
tactcctcac tagagtactt cgaaaaagcc ctggaggagc tggcagcagc gtttccgggt      600
gatggctggt taggttcggc cgcggacaaa tacgccggca aaaaccgcaa ccacgtgaat      660
tttttccagg aactggcaga cctcgatcgt cagctcatca gcctgatcca cgaccaggcc      720
aacgcggtcc agacgacccg cgacatcctg gagggcgcca agaaaggtct cgagttcgtg      780
cgcccggtgg ctgtggacct gacctacatc ccggtcgtcg gcacgcccct atcggccgcc      840
ttccaggcgc cgttttgcgc gggcgcgatg gccgtagtgg gcggcgcgct tgcctacttg      900
gtcgtgaaaa cgctgatcaa cgcgactcaa ctccctcaaat tgcttgccaa attggcggag      960
ttggtcgcgg ccgccattgc ggacatcatt tcggatgtgg cggacatcat caagggcatc     1020
ctcggagaag tgtgggagtt catcacaaac gcgctcaacg gcctgaaaga gctttgggac     1080
aagctcacgg ggtgggtgac cggactgttc tctcgagggt ggtcgaacct ggagtccttc     1140
tttgcgggcg tccccggctt gaccggcgcg accagcggct tgtcgcaagt gactggcttg     1200
ttcggtgcgg ccggtctgtc cgcatcgtcg ggcttggctc acgcggatag cctggcgagc     1260
tcagccagct tgcccgccct ggccggcatt gggggcgggt ccggttttgg gggcttgccg     1320
agcctggctc aggtccatgc cgcctcaact cggcaggcgc tacggccccg agctgatggc     1380
ccggtcggcg ccgctgccga gcaggtcggc gggcagtcgc agctggtctc cgcgcagggt     1440
tcccaaggta tgggcggacc cgtaggcatg gcggcatgc acccctcttc ggggggcgtcg     1500
aaagggacga cgacgaagaa gtactcggaa ggcgcggcgg cgggcactga agacgccgag     1560
cgcgcgccag tcgaagctga cgcgggcggt gggcaaaagg tgctggtacg aaacgtcgtc     1620
taagaattc                                                            1629
```

<210> SEQ ID NO 64
<211> LENGTH: 539
<212> TYPE: PRT
<213> ORGANISM: Artificial Sequence
<220> FEATURE:
<223> OTHER INFORMATION: Fusion Protein

<400> SEQUENCE: 64

```
Met His His His His His His Thr Ala Ala Ser Asp Asn Phe Gln Leu
1               5                   10                  15

Ser Gln Gly Gly Gln Gly Phe Ala Ile Pro Ile Gly Gln Ala Met Ala
            20                  25                  30

Ile Ala Gly Gln Ile Arg Ser Gly Gly Ser Pro Thr Val His Ile
        35                  40                  45

Gly Pro Thr Ala Phe Leu Gly Leu Gly Val Val Asp Asn Asn Gly Asn
```

-continued

```
            50                  55                  60
Gly Ala Arg Val Gln Arg Val Val Gly Ser Ala Pro Ala Ala Ser Leu
 65                  70                  75                  80
Gly Ile Ser Thr Gly Asp Val Ile Thr Ala Val Asp Gly Ala Pro Ile
                     85                  90                  95
Asn Ser Ala Thr Ala Met Ala Asp Ala Leu Asn Gly His His Pro Gly
                    100                 105                 110
Asp Val Ile Ser Val Thr Trp Gln Thr Lys Ser Gly Thr Arg Thr
                115                 120                 125
Gly Asn Val Thr Leu Ala Glu Gly Pro Pro Ala Glu Phe Leu Val Pro
130                 135                 140
Arg Gly Ser Met Ser Arg Ala Phe Ile Ile Asp Pro Thr Ile Ser Ala
145                 150                 155                 160
Ile Asp Gly Leu Tyr Asp Leu Leu Gly Ile Gly Ile Pro Asn Gln Gly
                    165                 170                 175
Gly Ile Leu Tyr Ser Ser Leu Glu Tyr Phe Glu Lys Ala Leu Glu Glu
                180                 185                 190
Leu Ala Ala Ala Phe Pro Gly Asp Gly Trp Leu Gly Ser Ala Ala Asp
                195                 200                 205
Lys Tyr Ala Gly Lys Asn Arg Asn His Val Asn Phe Phe Gln Glu Leu
                210                 215                 220
Ala Asp Leu Asp Arg Gln Leu Ile Ser Leu Ile His Asp Gln Ala Asn
225                 230                 235                 240
Ala Val Gln Thr Thr Arg Asp Ile Leu Glu Gly Ala Lys Lys Gly Leu
                    245                 250                 255
Glu Phe Val Arg Pro Val Ala Val Asp Leu Thr Tyr Ile Pro Val Val
                260                 265                 270
Gly His Ala Leu Ser Ala Ala Phe Gln Ala Pro Phe Cys Ala Gly Ala
                275                 280                 285
Met Ala Val Val Gly Gly Ala Leu Ala Tyr Leu Val Val Lys Thr Leu
                290                 295                 300
Ile Asn Ala Thr Gln Leu Leu Lys Leu Leu Ala Lys Leu Ala Glu Leu
305                 310                 315                 320
Val Ala Ala Ala Ile Ala Asp Ile Ile Ser Asp Val Ala Asp Ile Ile
                    325                 330                 335
Lys Gly Ile Leu Gly Glu Val Trp Glu Phe Ile Thr Asn Ala Leu Asn
                340                 345                 350
Gly Leu Lys Glu Leu Trp Asp Lys Leu Thr Gly Trp Val Thr Gly Leu
                355                 360                 365
Phe Ser Arg Gly Trp Ser Asn Leu Glu Ser Phe Phe Ala Gly Val Pro
370                 375                 380
Gly Leu Thr Gly Ala Thr Ser Gly Leu Ser Gln Val Thr Gly Leu Phe
385                 390                 395                 400
Gly Ala Ala Gly Leu Ser Ala Ser Ser Gly Leu Ala His Ala Asp Ser
                    405                 410                 415
Leu Ala Ser Ser Ala Ser Leu Pro Ala Leu Ala Gly Ile Gly Gly Gly
                420                 425                 430
Ser Gly Phe Gly Gly Leu Pro Ser Leu Ala Gln Val His Ala Ala Ser
                435                 440                 445
Thr Arg Gln Ala Leu Arg Pro Arg Ala Asp Gly Pro Val Gly Ala Ala
                450                 455                 460
Ala Glu Gln Val Gly Gly Gln Ser Gln Leu Val Ser Ala Gln Gly Ser
465                 470                 475                 480
```

```
Gln Gly Met Gly Gly Pro Val Gly Met Gly Met His Pro Ser Ser
            485                 490                 495

Gly Ala Ser Lys Gly Thr Thr Thr Lys Lys Tyr Ser Glu Gly Ala Ala
        500                 505                 510

Ala Gly Thr Glu Asp Ala Glu Arg Ala Pro Val Glu Ala Asp Ala Gly
        515                 520                 525

Gly Gly Gln Lys Val Leu Val Arg Asn Val Val
        530                 535
```

<210> SEQ ID NO 65
<211> LENGTH: 8794
<212> TYPE: DNA
<213> ORGANISM: Artificial Sequence
<220> FEATURE:
<223> OTHER INFORMATION: Fusion Protein of Mycobacterium Tuberculosis Antigens

<400> SEQUENCE: 65

| | | | | | |
|---|---|---|---|---|---|
| tggcgaatgg | gacgcgccct | gtagcggcgc | attaagcgcg | gcgggtgtgg | tggttacgcg | 60 |
| cagcgtgacc | gctacacttg | ccagcgccct | agcgcccgct | cctttcgctt | tcttcccttc | 120 |
| ctttctcgcc | acgttcgccg | gctttccccg | tcaagctcta | aatcggggc | tcccttagg | 180 |
| gttccgattt | agtgctttac | ggcacctcga | ccccaaaaaa | cttgattagg | gtgatggttc | 240 |
| acgtagtggg | ccatcgccct | gatagacggt | ttttcgccct | ttgacgttgg | agtccacgtt | 300 |
| ctttaatagt | ggactcttgt | tccaaactgg | aacaacactc | aaccctatct | cggtctattc | 360 |
| ttttgattta | taggggattt | tgccgatttc | ggcctattgg | ttaaaaaatg | agctgattta | 420 |
| acaaaaattt | aacgcgaatt | ttaacaaaat | attaacgttt | acaatttcag | gtggcacttt | 480 |
| tcggggaaat | gtgcgcggaa | cccctatttg | tttatttttc | taaatacatt | caaatatgta | 540 |
| tccgctcatg | aattaattct | tagaaaaact | catcgagcat | caaatgaaac | tgcaatttat | 600 |
| tcatatcagg | attatcaata | ccatattttt | gaaaaagccg | tttctgtaat | gaaggagaaa | 660 |
| actcaccgag | gcagttccat | aggatggcaa | gatcctggta | tcggtctgcg | attccgactc | 720 |
| gtccaacatc | aatacaacct | attaatttcc | cctcgtcaaa | aataaggtta | tcaagtgaga | 780 |
| aatcaccatg | agtgacgact | gaatccggtg | agaatggcaa | aagtttatgc | atttctttcc | 840 |
| agacttgttc | aacaggccag | ccattacgct | cgtcatcaaa | atcactcgca | tcaaccaaac | 900 |
| cgttattcat | tcgtgattgc | gcctgagcga | gacgaaatac | gcgatcgctg | ttaaaaggac | 960 |
| aattacaaac | aggaatcgaa | tgcaaccggc | gcaggaacac | tgccagcgca | tcaacaatat | 1020 |
| tttcacctga | atcaggatat | tcttctaata | cctggaatgc | tgttttcccg | gggatcgcag | 1080 |
| tggtgagtaa | ccatgcatca | tcaggagtac | ggataaaatg | cttgatggtc | ggaagaggca | 1140 |
| taaattccgt | cagccagttt | agtctgacca | tctcatctgt | aacatcattg | gcaacgctac | 1200 |
| ctttgccatg | tttcagaaac | aactctggcg | catcgggctt | cccatacaat | cgatagattg | 1260 |
| tcgcacctga | ttgcccgaca | ttatcgcgag | cccatttata | cccatataaa | tcagcatcca | 1320 |
| tgttggaatt | taatcgcggc | ctagagcaag | acgtttcccg | ttgaatatgg | ctcataacac | 1380 |
| cccttgtatt | actgtttatg | taagcagaca | gttttattgt | tcatgaccaa | aatcccttaa | 1440 |
| cgtgagtttt | cgttccactg | agcgtcagac | cccgtagaaa | agatcaaagg | atcttcttga | 1500 |
| gatccttttt | ttctgcgcgt | aatctgctgc | ttgcaaacaa | aaaaaccacc | gctaccagcg | 1560 |
| gtggtttgtt | tgccggatca | agagctacca | actctttttc | cgaaggtaac | tggcttcagc | 1620 |
| agagcgcaga | taccaaatac | tgtccttcta | gtgtagccgt | agttaggcca | ccacttcaag | 1680 |
| aactctgtag | caccgcctac | atacctcgct | ctgctaatcc | tgttaccagt | ggctgctgcc | 1740 |

```
agtggcgata agtcgtgtct taccggggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100 gccttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacgcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
```

```
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatgcagcat caccaccatc accactga    5100 tcgcgtgtcg gtgggcaact gcgcatcgc tcgggtgctc tacgacttcg tgaacaatga   5160
agccctgcct ggcaccgata tcgacccgga cagcttctgg gcgggcgtcg acaargtcgt   5220
cgccgacctg accccgcaga accaagctct gttgaacgcc cgcgacgagc tgcaggcgca   5280
gatcgacaag tggcaccggc gtcggtgat cgagcccatc gacatggatg cctaccgcca   5340
gttcctcacc gagatcggct acctgcttcc cgaacctgat gacttcacca tcaccacgtc   5400
cggtgtcgac gctgagatca ccacgaccgc cggcccccag ctggtggtgc cggtgctcaa   5460
cgcgcggttt gctctgaacg cggccaacgc tcgctggggc tccctctacg acgccttgta   5520
tggcaccgat gtcatccccg agaccgacgg cgccgaaaaa ggcccacgt acaacaaggt   5580 tcgtggcgac aaggtgatcg cgtatgcccg caagttcctc gacgacagtg ttccgctgtc   5640
gtcgggttcc tttggcgacg ccaccggttt cacagtgcag gatggccagc tcgtggttgc   5700
cttgccggat aagtccaccg gcctggccaa ccccggccag ttcgccggct acaccggcgc   5760
agccgagtcg ccgacatcgg tgctgctaat caatcacggt ttgcacatcg agatcctgat   5820
cgatccggag tcgcaggtcg gcaccaccga ccgggccggc gtcaaggacg tgatcctgga   5880
atccgcgatc accacgatca tggacttcga ggactcggtg gccgccgtgg acgccgccga   5940
caaggtgctg ggttatcgga actggctcgg cctgaacaag ggcgacctgg cagcagcggt   6000
agacaaggac ggcaccgctt tcctgcgggt gctcaatagg gaccggaact acaccgcacc   6060
cggcggtggc cagttcacgc tgcctggacg cagcctcatg ttcgtccgca acgtcggtca   6120
cttgatgacg aatgacgcca tcgtcgacac tgacggcagc gaggtgttcg aaggcatcat   6180
ggatgcccta ttcaccggcc tgatcgccat ccacgggcta aaggcagcg acgtcaacgg   6240 gccgctgatc aacagccgca ccggctccat ctacatcgtc aagccgaaga tgcacggtcc   6300
ggccgaggtg gcgtttacct gcgaactgtt cagccgggtt gaagatgtgc tggggttgcc   6360
gcaaaacacc atgaagatcg gcatcatgga cgaggaacgc cggaccacgg tcaacctcaa   6420
ggcgtgcatc aaagctgccg cggaccgcgt ggtgttcatc aacaccgggt tcctggaccg   6480
caccggcgat gaaatccaca cctcgatgga ggccggcccg atggtgcgca agggcaccat   6540
```

```
gaagagccag ccgtggatct tggcctacga ggaccacaac gtcgatgccg gcctggccgc    6600
cgggttcagc ggccgagccc aggtcggcaa gggcatgtgg acaatgaccg agctgatggc    6660
cgacatggtc gagacaaaaa tcgcccagcc gcgcgccggg gccagcaccg cctgggttcc    6720
ctctcccact gcggccaccc tgcatgcgct gcactaccac caggtcgacg tcgccgcggt    6780
gcaacaagga ctggcgggga agcgtcgcgc caccatcgaa caattgctga ccattccgct    6840
ggccaaggaa ttggcctggg ctcccgacga gatccgcgaa gaggtcgaca caactgtca    6900
atccatcctc ggctacgtgg ttcgctgggt tgatcaaggt gtcggctgct cgaaggtgcc    6960
cgacatccac gacgtcgcgc tcatggagga ccgggccacg ctgcgaatct ccagccaatt    7020
gttggccaac tggctgcgcc acggtgtgat caccagcgcg gatgtgcggg ccagcttgga    7080
gcggatggcg ccgttggtcg atcgacaaaa cgcgggcgac gtggcatacc gaccgatggc    7140
acccaacttc gacgcagta tcgccttcct ggccgcgcag gagctgatct tgtccggggc    7200
ccagcagccc aacggctaca ccgagccgat cctgcaccga cgtcgtcggg agtttaaggc    7260
ccgggccgct gagaagccgg ccccatcgga cagggccggt gacgatgcgg ccagggtgca    7320
gaagtacggg ggatcctcgg tggccgacgc cgaacggatt cgccgcgtcg ccgaacgcat    7380
cgtcgccacc aagaagcaag gcaatgacgt cgtcgtcgtc gtctctgcca tgggggatac    7440
caccgacgac ctgctggatc tggctcagca ggtgtgcccg gcgccgccgc ctcgggagct    7500
ggacatgctg cttaccgccg gtgaacgcat ctcgaatgcg ttggtggcca tggccatcga    7560
gtcgctcggc gcgcatgccc ggtcgttcac cggttcgcag gccggggtga tcaccaccgg    7620
cacccacggc aacgccaaga tcatcgacgt cacgccgggg cggctgcaaa ccgcccttga    7680
ggaggggcgg gtcgttttgg tggccggatt ccaaggggtc agccaggaca ccaaggatgt    7740
cacgacgttg ggccgcggcg gctcggacac caccgccgtc gccatggccg ccgcgctggg    7800
tgccgatgtc tgtgagatct acaccgacgt ggacggcatc ttcagcgccg acccgcgcat    7860
cgtgcgcaac gcccgaaagc tcgacaccgt gaccttcgag gaaatgctcg agatggcggc    7920
ctgcggcgcg aaggtgctga tgctgcgctg cgtggaatac gctcgccgcc ataatattcc    7980
ggtgcacgtc cggtcgtcgt actcggacag accgggcacc gtcgttgtcg gatcgatcaa    8040
ggacgtaccc atggaagacc ccatcctgac cggagtcgcg cacgaccgca gcgaggccaa    8100
ggtgaccatc gtcgggctgc ccgacatccc cgggtatgcg gccaaggtgt ttagggcggt    8160
ggccagacgc cgacgtcaac atcgacatgg tgctgcagaa cgtctccaag gtcgaggacg    8220
gcaagaccga catcaccttc acctgctccc gcagacgtcg ggcccgccgc cgtggaaaaa    8280
ctggactcgc tcagaaacga gatcggcttc tacacagctg ctgtacgacg accacatcgg    8340
caaggtatcg ctgatcggtg ccggcatgcg cagccacccc ggggtcaccg cgacgttctg    8400
tgaggcgctg gcggcggtgg gggtcaacat cgagctgatc tccacctcgg aagatcagag    8460
atctcggtgt tgtgccgcga caccgaactg gacaaggccg tggtcgcgct gcatgaagcg    8520
ttcgggctcg gcggcgacga ggaggccacg gtgtacgcgg ggacgggacg gtagatgggc    8580
ctgtcaatag tgaattcatc gatgtgcaga tatccatcac actggcggcc gctcgagcac    8640
caccaccacc accactgaga tccggctgct aacaaagccc gaaaggaagc tgagttggct    8700
gctgccaccg ctgagcaata actagcataa cccccttgggg cctctaaacg ggtcttgagg    8760
ggttttttgc tgaaaggagg aactatatcc ggat                                8794
```

<210> SEQ ID NO 66
<211> LENGTH: 24

-continued

```
<212> TYPE: DNA
<213> ORGANISM: Artificial Sequence
<220> FEATURE:
<223> OTHER INFORMATION: Nucleic acid region encoding HIS tag

<400> SEQUENCE: 66
atgcagcatc accaccatca ccac                                            24

<210> SEQ ID NO 67
<211> LENGTH: 8217
<212> TYPE: DNA
<213> ORGANISM: Artificial Sequence
<220> FEATURE:
<223> OTHER INFORMATION: Peptide sequence from Mycobacterium
      tuberculosis

<400> SEQUENCE: 67
tggcgaatgg gacgcgccct gtagcggcgc attaagcgcg gcgggtgtgg tggttacgcg       60
cagcgtgacc gctacacttg ccagcgccct agcgcccgct cctttcgctt tcttcccttc      120
ctttctcgcc acgttcgccg gctttccccg tcaagctcta atcgggggc tccctttagg       180 gttccgattt agtgctttac ggcacctcga ccccaaaaaa cttgattagg gtgatggttc      240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta tagggatttt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg aattaattct tagaaaaact catcgagcat caaatgaaac tgcaatttat    600
tcatatcagg attatcaata ccatattttt gaaaagccg tttctgtaat gaaggagaaa     660
actcaccgag gcagttccat aggatggcaa gatcctggta tcggtctgcg attccgactc    720
gtccaacatc aatacaacct attaatttcc cctcgtcaaa aataaggtta tcaagtgaga   780
aatcaccatg agtgacgact gaatccggtg agaatggcaa aagtttatgc atttctttcc   840
agacttgttc aacaggccag ccattacgct cgtcatcaaa atcactcgca tcaaccaaac   900
cgttattcat tcgtgattgc gcctgagcga cgaaatac gcgatcgctg ttaaaaggac     960
aattacaaac aggaatcgaa tgcaaccggc gcaggaacac tgccagcgca tcaacaatat  1020
tttcacctga atcaggatat tcttctaata cctggaatgc tgttttcccg gggatcgcag  1080
tggtgagtaa ccatgcatca tcaggagtac ggataaaatg cttgatggtc ggaagaggca  1140
taaattccgt cagccagttt agtctgacca tctcatctgt aacatcattg gcaacgctac  1200
ctttgccatg tttcagaaac aactctggcg catcgggctt cccatacaat cgatagattg  1260
tcgcacctga ttgcccgaca ttatcgcgag cccatttata cccatataaa tcagcatcca  1320
tgttggaatt taatcgcggc ctagagcaag acgtttcccg ttgaatatgg ctcataacac  1380
cccttgtatt actgtttatg taagcagaca gttttattgt tcatgaccaa atcccttaa   1440 cgtgagtttt cgttccactg agcgtcagac cccgtagaaa agatcaaagg atcttcttga  1500 gatcctttt ttctgcgcgt aatctgctgc ttgcaaacaa aaaaccacc gctaccagcg    1560 gtggtttgtt tgccggatca agagctacca actcttttc cgaaggtaac tggcttcagc   1620
agagcgcaga taccaaatac tgtccttcta gtgtagccgt agttaggcca ccacttcaag  1680
aactctgtag caccgcctac atacctcgct ctgctaatcc tgttaccagt ggctgctgcc   1740
agtggcgata gtcgtgtct taccggggttg gactcaagac gatagttacc ggataaggcg  1800
```

```
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag agagcgcac gagggagctt    1980 ccaggggaa acgcctggta tctttatagt cctgtcgggt ttcgccacct ctgacttgag    2040
cgtcgatttt tgtgatgctc gtcaggggg cggagcctat ggaaaaacgc cagcaacgcg    2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg gggtaatga taccgatgaa    2760 acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
```

```
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatgggccat catcatcatc atcacgtgat    5100
cgacatcatc gggaccagcc ccacatcctg gaacaggcg gcggcggagg cggtccagcg    5160
ggcgcgggat agcgtcgatg acatccgcgt cgctcgggtc attgagcagg acatggccgt    5220
ggacagcgcc ggcaagatca cctaccgcat caagctcgaa gtgtcgttca agatgaggcc    5280
ggcgcaaccg aggtgtggct cgaaaccacc gagcggttcg cctgaaacgg cgccggcgc    5340 cggtactgtc gcgactaccc ccgcgtcgtc gccggtgacg ttggcggaga ccggtagcac    5400
gctgctctac ccgctgttca acctgtgggg tccggccttt cacgagaggt atccgaacgt    5460
cacgatcacc gctcagggca ccggttctgg tgccgggatc gcgcaggccg ccgccgggac    5520
ggtcaacatt ggggcctccg acgcctatct gtcggaaggt gatatggccg cgcacaaggg    5580
gctgatgaac atcgcgctag ccatctccgc tcagcaggtc aactacaaac tgcccggagt    5640
gagcgagcac ctcaagctga acggaaaagt cctggcggcc atgtaccagg gcaccatcaa    5700
aacctgggac gacccgcaga tcgctgcgct caaccccggc gtgaacctgc ccggcaccgc    5760
ggtagttccg ctgcaccgct ccgacgggtc cggtgacacc ttcttgttca cccagtacct    5820
gtccaagcaa gatcccgagg gctggggcaa gtcgcccggc ttcggcacca ccgtcgactt    5880
cccggcggtg ccgggtgcgc tgggtgagaa cggcaacggc ggcatggtga ccggttgcgc    5940
cgagacaccg ggctgcgtgg cctatatcgg catcagcttc ctcgaccagg ccagtcaacg    6000
gggactcggc gaggcccaac taggcaatag ctctggcaat ttcttgttgc ccgacgcgca    6060
aagcattcag gccgcggcgg ctggcttcgc atcgaaaacc ccggcgaacc aggcgatttc    6120
gatgatcgac gggcccgccc cggacggcta cccgatcatc aactacgagt acgccatcgt    6180
caacaaccgg caaaaggacg ccgccaccgc gcagaccttg caggcatttc tgcactgggc    6240
gatcaccgac ggcaacaagg cctcgttcct cgaccaggtt catttccagc cgctgccgcc    6300
cgcggtggtg aagttgtctg acgcgttgat cgcgacgatt tccagcgctg agatgaagac    6360
cgatgccgct accctcgcgc aggaggcagg taatttcgag cggatctccg cgacctgaa    6420 aacccagatc gaccaggtgg agtcgacggc aggttcgttg cagggccagt ggcgcggcgc    6480
ggcggggacg gccgcccagg ccgcggtggt gcgcttccaa gaagcagcca ataagcagaa    6540
gcaggaactc gacgagatct cgacgaatat tcgtcaggcc ggcgtccaat actcgagggc    6600
```

```
cgacgaggag cagcagcagg cgctgtcctc gcaaatgggc tttactcagt cgcagaccgt    6660
gacggtggat cagcaagaga ttttgaacag ggccaacgag gtggaggccc cgatggcgga    6720
cccaccgact gatgtcccca tcacaccgtg cgaactcacg gcggctaaaa acgccgccca    6780
acagctggta ttgtccgccg acaacatgcg ggaatacctg gcggccggtg ccaaagagcg    6840
gcagcgtctg gcgacctcgc tgcgcaacgc ggccaaggcg tatggcgagg ttgatgagga    6900
ggctgcgacc gcgctggaca acgacggcga aggaactgtg caggcagaat cggccggggc    6960
cgtcggaggg gacagttcgg ccgaactaac cgatacgccg agggtggcca cggccggtga    7020
acccaacttc atggatctca agaagcggca aggaagctc gaaacgggcg accaaggcgc    7080
atcgctcgcg cactttgcgg atgggtggaa cactttcaac ctgacgctgc aaggcgacgt    7140
caagcggttc cggggtttg acaactggga aggcgatgcg gctaccgctt gcgaggcttc    7200
gctcgatcaa caacggcaat ggatactcca catggccaaa ttgagcgctg cgatggccaa    7260
gcaggctcaa tatgtcgcgc agctgcacgt gtgggctagg cgggaacatc cgacttatga    7320
agacatagtc gggctcgaac ggctttacgc ggaaaaccct tcggcccgcg accaaattct    7380
cccggtgtac gcggagtatc agcagaggtc ggagaaggtg ctgaccgaat acaacaacaa    7440
ggcagccctg gaaccggtaa acccgccgaa gcctcccccc gccatcaaga tcgacccgcc    7500
cccgcctccg caagagcagg gattgatccc tggcttcctg atgccgccgt ctgacggctc    7560
cggtgtgact cccggtaccg ggatgccagc cgcaccgatg gttccgccta ccggatcgcc    7620
gggtggtggc ctcccggctg acacggcggc gcagctgacg tcggctgggc gggaagccgc    7680
agcgctgtcg ggcgacgtgg cggtcaaagc ggcatcgctc ggtggcggtg gaggcggcgg    7740
ggtgccgtcg gcgccgttgg gatccgcgat cgggggcgcc gaatcggtgc ggcccgctgg    7800
cgctggtgac attgccggct taggccaggg aagggccggc ggcggcgccg cgctgggcgg    7860
cggtggcatg ggaatgccga tgggtgccgc gcatcaggga caaggggcg ccaagtccaa    7920 gggttctcag caggaagacg aggcgctcta caccgaggat cgggcatgga ccgaggccgt    7980
cattggtaac cgtcggcgcc aggacagtaa ggagtcgaag tgaattctgc agatatccat    8040
cacactggcg gccgctcgag caccaccacc accaccactg agatccggct gctaacaaag    8100
cccgaaagga agctgagttg gctgctgcca ccgctgagca ataactagca taaccccttg    8160
gggcctctaa acgggtcttg aggggttttt tgctgaaagg aggaactata tccggat    8217
```

<210> SEQ ID NO 68
<211> LENGTH: 60
<212> TYPE: DNA
<213> ORGANISM: Artificial Sequence
<220> FEATURE:
<223> OTHER INFORMATION: Nucleic acid encoding Mycobacterium
      tuberculosis peptide

<400> SEQUENCE: 68
atgagcagag cgttcatcat cgatccaacg atcagtgcca ttgacggctt gtacgacctt              60

<210> SEQ ID NO 69
<211> LENGTH: 60
<212> TYPE: DNA
<213> ORGANISM: Artificial Sequence
<220> FEATURE:
<223> OTHER INFORMATION: Nucleic acid encoding Mycobacterium
      tuberculosis peptide

<400> SEQUENCE: 69
attgacggct tgtacgacct tctggggatt ggaataccca accaggggg tatcctttac              60

<210> SEQ ID NO 70
<211> LENGTH: 60
<212> TYPE: DNA
<213> ORGANISM: Artificial Sequence
<220> FEATURE:
<223> OTHER INFORMATION: Nucleic acid encoding Mycobacterium tuberculosis peptide

<400> SEQUENCE: 70
aaccaagggg gtatccttta ctcctcacta gagtacttcg aaaaagccct ggaggagctg 60

<210> SEQ ID NO 71
<211> LENGTH: 60
<212> TYPE: DNA
<213> ORGANISM: Artificial Sequence
<220> FEATURE:
<223> OTHER INFORMATION: Nucleic acid encoding Mycobacterium tuberculosis peptide

<400> SEQUENCE: 71
gaaaaagccc tggaggagct ggcagcagcg tttccgggtg atggctggtt aggttcggcc 60

<210> SEQ ID NO 72
<211> LENGTH: 60
<212> TYPE: DNA
<213> ORGANISM: Artificial Sequence
<220> FEATURE:
<223> OTHER INFORMATION: Nucleic acid encoding Mycobacterium tuberculosis peptide

<400> SEQUENCE: 72
gatggctggt taggttcggc cgcggacaaa tacgccggca aaaaccgcaa ccacgtgaat 60

<210> SEQ ID NO 73
<211> LENGTH: 60
<212> TYPE: DNA
<213> ORGANISM: Artificial Sequence
<220> FEATURE:
<223> OTHER INFORMATION: Nucleic acid encoding Mycobacterium tuberculosis peptide

<400> SEQUENCE: 73
aaaaaccgca accacgtgaa tttttttccag gaactggcag acctcgatcg tcagctcatc 60

<210> SEQ ID NO 74
<211> LENGTH: 60
<212> TYPE: DNA
<213> ORGANISM: Artificial Sequence
<220> FEATURE:
<223> OTHER INFORMATION: Nucleic acid encoding Mycobacterium tuberculosis peptide

<400> SEQUENCE: 74
gacctcgatc gtcagctcat cagcctgatc cacgaccagg ccaacgcggt ccagacgacc 60

<210> SEQ ID NO 75
<211> LENGTH: 60
<212> TYPE: DNA
<213> ORGANISM: Artificial Sequence
<220> FEATURE:
<223> OTHER INFORMATION: Nucleic acid encoding Mycobacterium tuberculosis peptide

<400> SEQUENCE: 75
gccaacgcgg tccagacgac ccgcgacatc ctggagggcg ccaagaaagg tctcgagttc 60

<210> SEQ ID NO 76

<211> LENGTH: 60
<212> TYPE: DNA
<213> ORGANISM: Artificial Sequence
<220> FEATURE:
<223> OTHER INFORMATION: Nucleic acid encoding Mycobacterium tuberculosis peptide

<400> SEQUENCE: 76
gccaagaaag gtctcgagtt cgtgcgcccg gtggctgtgg acctgaccta catcccggtc 60

<210> SEQ ID NO 77
<211> LENGTH: 60
<212> TYPE: DNA
<213> ORGANISM: Artificial Sequence
<220> FEATURE:
<223> OTHER INFORMATION: Nucleic acid encoding Mycobacterium tuberculosis peptide

<400> SEQUENCE: 77
gacctgacct acatcccggt cgtcgggcac gccctatcgg ccgccttcca ggcgccgttt 60

<210> SEQ ID NO 78
<211> LENGTH: 60
<212> TYPE: DNA
<213> ORGANISM: Artificial Sequence
<220> FEATURE:
<223> OTHER INFORMATION: Nucleic acid encoding Mycobacterium tuberculosis peptide

<400> SEQUENCE: 78
gccgccttcc aggcgccgtt ttgcgcgggc gcgatggccg tagtgggcgg cgcgcttgcc 60

<210> SEQ ID NO 79
<211> LENGTH: 60
<212> TYPE: DNA
<213> ORGANISM: Artificial Sequence
<220> FEATURE:
<223> OTHER INFORMATION: Nucleic acid encoding Mycobacterium tuberculosis peptide

<400> SEQUENCE: 79
gtagtgggcg gcgcgcttgc ctacttggtc gtgaaaacgc tgatcaacgc gactcaactc 60

<210> SEQ ID NO 80
<211> LENGTH: 60
<212> TYPE: DNA
<213> ORGANISM: Artificial Sequence
<220> FEATURE:
<223> OTHER INFORMATION: Nucleic acid encoding Mycobacterium tuberculosis peptide

<400> SEQUENCE: 80
ctgatcaacg cgactcaact cctcaaattg cttgccaaat tggcggagtt ggtcgcggcc 60

<210> SEQ ID NO 81
<211> LENGTH: 60
<212> TYPE: DNA
<213> ORGANISM: Artificial Sequence
<220> FEATURE:
<223> OTHER INFORMATION: Nucleic acid encoding Mycobacterium tuberculosis peptide

<400> SEQUENCE: 81
ttggcggagt tggtcgcggc cgccattgcg gacatcattt cggatgtggc ggacatcatc 60

<210> SEQ ID NO 82
<211> LENGTH: 60
<212> TYPE: DNA

-continued

<213> ORGANISM: Artificial Sequence
<220> FEATURE:
<223> OTHER INFORMATION: Nucleic acid encoding Mycobacterium tuberculosis peptide

<400> SEQUENCE: 82
tcggatgtgg cggacatcat caagggcatc ctcggagaag tgtgggagtt catcacaaac 60

<210> SEQ ID NO 83
<211> LENGTH: 60
<212> TYPE: DNA
<213> ORGANISM: Artificial Sequence
<220> FEATURE:
<223> OTHER INFORMATION: Nucleic acid encoding Mycobacterium tuberculosis peptide

<400> SEQUENCE: 83
gtgtgggagt tcatcacaaa cgcgctcaac ggcctgaaag agctttggga caagctcacg 60

<210> SEQ ID NO 84
<211> LENGTH: 60
<212> TYPE: DNA
<213> ORGANISM: Artificial Sequence
<220> FEATURE:
<223> OTHER INFORMATION: Nucleic acid encoding Mycobacterium tuberculosis peptide

<400> SEQUENCE: 84
gagctttggg acaagctcac ggggtgggtg accggactgt tctctcgagg gtggtcgaac 60

<210> SEQ ID NO 85
<211> LENGTH: 60
<212> TYPE: DNA
<213> ORGANISM: Artificial Sequence
<220> FEATURE:
<223> OTHER INFORMATION: Nucleic acid encoding Mycobacterium tuberculosis peptide

<400> SEQUENCE: 85
ttctctcgag ggtggtcgaa cctggagtcc ttctttgcgg gcgtccccgg cttgaccggc 60

<210> SEQ ID NO 86
<211> LENGTH: 60
<212> TYPE: DNA
<213> ORGANISM: Artificial Sequence
<220> FEATURE:
<223> OTHER INFORMATION: Nucleic acid encoding Mycobacterium tuberculosis peptide

<400> SEQUENCE: 86
ggcgtccccg gcttgaccgg cgcgaccagc ggcttgtcgc aagtgactgg cttgttcggt 60

<210> SEQ ID NO 87
<211> LENGTH: 60
<212> TYPE: DNA
<213> ORGANISM: Artificial Sequence
<220> FEATURE:
<223> OTHER INFORMATION: Nucleic acid encoding Mycobacterium tuberculosis peptides

<400> SEQUENCE: 87
caagtgactg gcttgttcgg tgcggccggt ctgtccgcat cgtcgggctt ggctcacgcg 60

<210> SEQ ID NO 88
<211> LENGTH: 60
<212> TYPE: DNA
<213> ORGANISM: Artificial Sequence
<220> FEATURE:

```
<223> OTHER INFORMATION: Nucleic acid encoding Mycobacterium
      tuberculosis peptides

<400> SEQUENCE: 88
tcgtcgggct tggctcac

```
<400> SEQUENCE: 94
cccgtaggca tgggcggcat gcaccctct cggggggcgt cgaaagggac gacgacgaag    60

<210> SEQ ID NO 95
<211> LENGTH: 60
<212> TYPE: DNA
<213> ORGANISM: Artificial Sequence
<220> FEATURE:
<223> OTHER INFORMATION: Nucleic acid encoding Mycobacterium
      tuberculosis peptides

<400> SEQUENCE: 95
tcgaaaggga cgacgacgaa gaagtactcg gaaggcgcgg cggcgggcac tgaagacgcc    60

<210> SEQ ID NO 96
<211> LENGTH: 60
<212> TYPE: DNA
<213> ORGANISM: Artificial Sequence
<220> FEATURE:
<223> OTHER INFORMATION: Nucleic acid encoding Mycobacterium
      tuberculosis peptides

<400> SEQUENCE: 96
gcggcgggca ctgaagacgc cgagcgcgcg ccagtcgaag ctgacgcggg cggtgggcaa    60

<210> SEQ ID NO 97
<211> LENGTH: 60
<212> TYPE: DNA
<213> ORGANISM: Artificial Sequence
<220> FEATURE:
<223> OTHER INFORMATION: Nucleic acid encoding Mycobactrium
      tuberculosis peptide

<400> SEQUENCE: 97
cgcgcgccag tcgaagctga cgcgggcggt gggcaaaagg tgctggtacg aaacgtcgtc    60

<210> SEQ ID NO 98
<211> LENGTH: 20
<212> TYPE: PRT
<213> ORGANISM: Artificial Sequence
<220> FEATURE:
<223> OTHER INFORMATION: Peptide sequence from Mycobacterium
      tuberculosis

<400> SEQUENCE: 98

Met Ser Arg Ala Phe Ile Ile Asp Pro Thr Ile Ser Ala Ile Asp Gly
1               5                   10                  15

Leu Tyr Asp Leu
            20

<210> SEQ ID NO 99
<211> LENGTH: 20
<212> TYPE: PRT
<213> ORGANISM: Artificial Sequence
<220> FEATURE:
<223> OTHER INFORMATION: Peptide from Mycobacterium tuberculosis

<400> SEQUENCE: 99

Ile Asp Gly Leu Tyr Asp Leu Leu Gly Ile Gly Ile Pro Asn Gln Gly
1               5                   10                  15

Gly Ile Leu Tyr
            20

<210> SEQ ID NO 100
<211> LENGTH: 20
```

```
<212> TYPE: PRT
<213> ORGANISM: Artificial Sequence
<220> FEATURE:
<223> OTHER INFORMATION: Peptide sequence from Mycobacterium
      tuberculosis

<400> SEQUENCE: 100

Asn Gln Gly Gly Ile Leu Tyr Ser Ser Leu Glu Tyr Phe Glu Lys Ala
1               5                   10                  15

Leu Glu Glu Leu
            20

<210> SEQ ID NO 101
<211> LENGTH: 20
<212> TYPE: PRT
<213> ORGANISM: Artificial Sequence
<220> FEATURE:
<223> OTHER INFORMATION: Peptide sequence from Mycobacterium
      tuberculosis

<400> SEQUENCE: 101

Glu Lys Ala Leu Glu Glu Leu Ala Ala Ala Phe Pro Gly Asp Gly Trp
1               5                   10                  15

Leu Gly Ser Ala
            20

<210> SEQ ID NO 102
<211> LENGTH: 20
<212> TYPE: PRT
<213> ORGANISM: Artificial Sequence
<220> FEATURE:
<223> OTHER INFORMATION: Peptide sequence from Mycobacterium
      tuberculosis

<400> SEQUENCE: 102

Asp Gly Trp Leu Gly Ser Ala Ala Asp Lys Tyr Ala Gly Lys Asn Arg
1               5                   10                  15

Asn His Val Asn
            20

<210> SEQ ID NO 103
<211> LENGTH: 20
<212> TYPE: PRT
<213> ORGANISM: Artificial Sequence
<220> FEATURE:
<223> OTHER INFORMATION: Peptide sequence from Mycobacterium
      tuberculosis

<400> SEQUENCE: 103

Lys Asn Arg Asn His Val Asn Phe Phe Gln Glu Leu Ala Asp Leu Asp
1               5                   10                  15

Arg Gln Leu Ile
            20

<210> SEQ ID NO 104
<211> LENGTH: 20
<212> TYPE: PRT
<213> ORGANISM: Artificial Sequence
<220> FEATURE:
<223> OTHER INFORMATION: Peptide sequence from Mycobacterium
      tuberculosis

<400> SEQUENCE: 104

Asp Leu Asp Arg Gln Leu Ile Ser Leu Ile His Asp Gln Ala Asn Ala
1               5                   10                  15

Val Gln Thr Thr
```

```
<210> SEQ ID NO 105
<211> LENGTH: 20
<212> TYPE: PRT
<213> ORGANISM: Artificial Sequence
<220> FEATURE:
<223> OTHER INFORMATION: Peptide sequence from Mycobacterium
      tuberculosis

<400> SEQUENCE: 105

Ala Asn Ala Val Gln Thr Thr Arg Asp Ile Leu Glu Gly Ala Lys Lys
1               5                  10                  15

Gly Leu Glu Phe
            20

<210> SEQ ID NO 106
<211> LENGTH: 20
<212> TYPE: PRT
<213> ORGANISM: Artificial Sequence
<220> FEATURE:
<223> OTHER INFORMATION: Peptide sequence from Mycobacterium
      tuberculosis

<400> SEQUENCE: 106

Ala Lys Lys Gly Leu Glu Phe Val Arg Pro Val Ala Val Asp Leu Thr
1               5                  10                  15

Tyr Ile Pro Val
            20

<210> SEQ ID NO 107
<211> LENGTH: 20
<212> TYPE: PRT
<213> ORGANISM: Artificial Sequence
<220> FEATURE:
<223> OTHER INFORMATION: Peptide sequence from Mycobacterium
      tuberculosis

<400> SEQUENCE: 107

Asp Leu Thr Tyr Ile Pro Val Val Gly His Ala Leu Ser Ala Ala Phe
1               5                  10                  15

Gln Ala Pro Phe
            20

<210> SEQ ID NO 108
<211> LENGTH: 20
<212> TYPE: PRT
<213> ORGANISM: Artificial Sequence
<220> FEATURE:
<223> OTHER INFORMATION: Peptide sequence from Mycobacterium
      tuberculosis

<400> SEQUENCE: 108

Ala Ala Phe Gln Ala Pro Phe Cys Ala Gly Ala Met Ala Val Val Gly
1               5                  10                  15

Gly Ala Leu Ala
            20

<210> SEQ ID NO 109
<211> LENGTH: 20
<212> TYPE: PRT
<213> ORGANISM: Artificial Sequence
<220> FEATURE:
<223> OTHER INFORMATION: Peptide sequence from Mycobacterium
      tuberculosis

<400> SEQUENCE: 109
```

```
Val Val Gly Gly Ala Leu Ala Tyr Leu Val Val Lys Thr Leu Ile Asn
1               5                   10                  15

Ala Thr Gln Leu
            20

<210> SEQ ID NO 110
<211> LENGTH: 20
<212> TYPE: PRT
<213> ORGANISM: Artificial Sequence
<220> FEATURE:
<223> OTHER INFORMATION: Peptide sequence from Mycobacterium
      tuberculosis

<400> SEQUENCE: 110

Leu Ile Asn Ala Thr Gln Leu Leu Lys Leu Leu Ala Lys Leu Ala Glu
1               5                   10                  15

Leu Val Ala Ala
            20

<210> SEQ ID NO 111
<211> LENGTH: 20
<212> TYPE: PRT
<213> ORGANISM: Artificial Sequence
<220> FEATURE:
<223> OTHER INFORMATION: Peptide sequence from Mycobacterium
      tuberculosis

<400> SEQUENCE: 111

Leu Ala Glu Leu Val Ala Ala Ile Ala Asp Ile Ile Ser Asp Val
1               5                   10                  15

Ala Asp Ile Ile
            20

<210> SEQ ID NO 112
<211> LENGTH: 20
<212> TYPE: PRT
<213> ORGANISM: Artificial Sequence
<220> FEATURE:
<223> OTHER INFORMATION: Artificial Sequence Peptide sequence from
      Mycobacterium tuberculosis

<400> SEQUENCE: 112

Ser Asp Val Ala Asp Ile Ile Lys Gly Ile Leu Gly Glu Val Trp Glu
1               5                   10                  15

Phe Ile Thr Asn
            20

<210> SEQ ID NO 113
<211> LENGTH: 20
<212> TYPE: PRT
<213> ORGANISM: Artificial Sequence
<220> FEATURE:
<223> OTHER INFORMATION: Peptide sequence from Mycobacterium
      tuberculosis

<400> SEQUENCE: 113

Val Trp Glu Phe Ile Thr Asn Ala Leu Asn Gly Leu Lys Glu Leu Trp
1               5                   10                  15

Asp Lys Leu Thr
            20

<210> SEQ ID NO 114
<211> LENGTH: 20
<212> TYPE: PRT
<213> ORGANISM: Artificial Sequence
```

```
<220> FEATURE:
<223> OTHER INFORMATION: Peptide sequence from Mycobacterium
      tuberculosis

<400> SEQUENCE: 114

Glu Leu Trp Asp Lys Leu Thr Gly Trp Val Thr Gly Leu Phe Ser Arg
1               5                   10                  15

Gly Trp Ser Asn
            20

<210> SEQ ID NO 115
<211> LENGTH: 20
<212> TYPE: PRT
<213> ORGANISM: Artificial Sequence
<220> FEATURE:
<223> OTHER INFORMATION: Peptide sequence from Mycobacterium
      tuberculosis

<400> SEQUENCE: 115

Phe Ser Arg Gly Trp Ser Asn Leu Glu Ser Phe Phe Ala Gly Val Pro
1               5                   10                  15

Gly Leu Thr Gly
            20

<210> SEQ ID NO 116
<211> LENGTH: 20
<212> TYPE: PRT
<213> ORGANISM: Artificial Sequence
<220> FEATURE:
<223> OTHER INFORMATION: Peptide sequence from Mycobacterium
      tuberculosis

<400> SEQUENCE: 116

Gly Val Pro Gly Leu Thr Gly Ala Thr Ser Gly Leu Ser Gln Val Thr
1               5                   10                  15

Gly Leu Phe Gly
            20

<210> SEQ ID NO 117
<211> LENGTH: 20
<212> TYPE: PRT
<213> ORGANISM: Artificial Sequence
<220> FEATURE:
<223> OTHER INFORMATION: Peptide sequence from Mycobacterium
      tuberculosis

<400> SEQUENCE: 117

Gln Val Thr Gly Leu Phe Gly Ala Ala Gly Leu Ser Ala Ser Ser Gly
1               5                   10                  15

Leu Ala His Ala
            20

<210> SEQ ID NO 118
<211> LENGTH: 20
<212> TYPE: PRT
<213> ORGANISM: Artificial Sequence
<220> FEATURE:
<223> OTHER INFORMATION: Peptide sequence from Mycobacterium
      tuberculosis

<400> SEQUENCE: 118

Gln Val Thr Gly Leu Phe Gly Ala Ala Gly Leu Ser Ala Ser Ser Gly
1               5                   10                  15

Leu Ala His Ala
            20
```

```
<210> SEQ ID NO 119
<211> LENGTH: 20
<212> TYPE: PRT
<213> ORGANISM: Artificial Sequence
<220> FEATURE:
<223> OTHER INFORMATION: Artificial Sequence Peptide sequence from
      Mycobacterium tuberculosis

<400> SEQUENCE: 119

Ser Ser Gly Leu Ala His Ala Asp Ser Leu Ala Ser Ser Ala Ser Leu
1               5                   10                  15

Pro Ala Leu Ala
            20

<210> SEQ ID NO 120
<211> LENGTH: 20
<212> TYPE: PRT
<213> ORGANISM: Artificial Sequence
<220> FEATURE:
<223> OTHER INFORMATION: Peptide sequence from Mycobacterium
      tuberculosis

<400> SEQUENCE: 120

Gly Phe Gly Gly Leu Pro Ser Leu Ala Gln Val His Ala Ala Ser Thr
1               5                   10                  15

Arg Gln Ala Leu
            20

<210> SEQ ID NO 121
<211> LENGTH: 20
<212> TYPE: PRT
<213> ORGANISM: Artificial Sequence
<220> FEATURE:
<223> OTHER INFORMATION: Peptide sequence from Mycobacterium
      tuberculosis

<400> SEQUENCE: 121

Ala Ser Thr Arg Gln Ala Leu Arg Pro Arg Ala Asp Gly Pro Val Gly
1               5                   10                  15

Ala Ala Ala Glu
            20

<210> SEQ ID NO 122
<211> LENGTH: 20
<212> TYPE: PRT
<213> ORGANISM: Artificial Sequence
<220> FEATURE:
<223> OTHER INFORMATION: Peptide sequence from Mycobacterium
      tuberculosis

<400> SEQUENCE: 122

Pro Val Gly Ala Ala Ala Glu Gln Val Gly Gly Gln Ser Gln Leu Val
1               5                   10                  15

Ser Ala Gln Gly
            20

<210> SEQ ID NO 123
<211> LENGTH: 19
<212> TYPE: PRT
<213> ORGANISM: Artificial Sequence
<220> FEATURE:
<223> OTHER INFORMATION: Peptide sequence from Mycobacterium
      tuberculosis

<400> SEQUENCE: 123

Gln Leu Val Ser Ala Gln Gly Ser Gln Gly Met Gly Gly Pro Val Gly
```

```
                1               5                   10                  15

Met Gly Gly

<210> SEQ ID NO 124
<211> LENGTH: 20
<212> TYPE: PRT
<213> ORGANISM: Artificial Sequence
<220> FEATURE:
<223> OTHER INFORMATION: Peptide sequence from Mycobacterium
      tuberculosis

<400> SEQUENCE: 124

Pro Val Gly Met Gly Gly Met His Pro Ser Ser Gly Ala Ser Lys Gly
1               5                   10                  15

Thr Thr Thr Lys
            20

<210> SEQ ID NO 125
<211> LENGTH: 20
<212> TYPE: PRT
<213> ORGANISM: Artificial Sequence
<220> FEATURE:
<223> OTHER INFORMATION: Peptide sequence from Mycobacterium
      tuberculosis

<400> SEQUENCE: 125

Ser Lys Gly Thr Thr Thr Lys Lys Tyr Ser Glu Gly Ala Ala Ala Gly
1               5                   10                  15

Thr Glu Asp Ala
            20

<210> SEQ ID NO 126
<211> LENGTH: 20
<212> TYPE: PRT
<213> ORGANISM: Artificial Sequence
<220> FEATURE:
<223> OTHER INFORMATION: Peptide sequence from Mycobacterium
      tuberculosis

<400> SEQUENCE: 126

Ala Ala Gly Thr Glu Asp Ala Glu Arg Ala Pro Val Glu Ala Asp Ala
1               5                   10                  15

Gly Gly Gly Gln
            20

<210> SEQ ID NO 127
<211> LENGTH: 20
<212> TYPE: PRT
<213> ORGANISM: Artificial Sequence
<220> FEATURE:
<223> OTHER INFORMATION: Peptide sequence from Mycobacterium
      tuberculosis

<400> SEQUENCE: 127

Arg Ala Pro Val Glu Ala Asp Ala Gly Gly Gly Gln Lys Val Leu Val
1               5                   10                  15

Arg Asn Val Val
            20

<210> SEQ ID NO 128
<211> LENGTH: 84
<212> TYPE: PRT
<213> ORGANISM: Mycobacterium tuberculosis

<400> SEQUENCE: 128
```

-continued

| Asp | Pro | Pro | Asp | Pro | His | Gln | Pro | Asp | Met | Thr | Lys | Gly | Tyr | Cys | Pro |
|---|---|---|---|---|---|---|---|---|---|---|---|---|---|---|---|
| 1 | | | | 5 | | | | | 10 | | | | | 15 | |

| Gly | Gly | Arg | Trp | Gly | Phe | Gly | Asp | Leu | Ala | Val | Cys | Asp | Gly | Glu | Lys |
|---|---|---|---|---|---|---|---|---|---|---|---|---|---|---|---|
| | | | 20 | | | | | 25 | | | | | 30 | | |

| Tyr | Pro | Asp | Gly | Ser | Phe | Trp | His | Gln | Trp | Met | Gln | Thr | Trp | Phe | Thr |
|---|---|---|---|---|---|---|---|---|---|---|---|---|---|---|---|
| | | 35 | | | | | 40 | | | | | 45 | | | |

| Gly | Pro | Gln | Phe | Tyr | Phe | Asp | Cys | Val | Ser | Gly | Gly | Glu | Pro | Leu | Pro |
|---|---|---|---|---|---|---|---|---|---|---|---|---|---|---|---|
| | 50 | | | | | 55 | | | | | 60 | | | | |

| Gly | Pro | Pro | Pro | Pro | Gly | Gly | Cys | Gly | Gly | Ala | Ile | Pro | Ser | Glu | Gln |
|---|---|---|---|---|---|---|---|---|---|---|---|---|---|---|---|
| 65 | | | | | 70 | | | | | 75 | | | | | 80 |

Pro Asn Ala Pro

<210> SEQ ID NO 129
<211> LENGTH: 2836
<212> TYPE: DNA
<213> ORGANISM: Mycobacterium tuberculosis
<220> FEATURE:
<221> NAME/KEY: misc_feature
<222> LOCATION: (104)..(104)
<223> OTHER INFORMATION: n is a, c, g, or t

<400> SEQUENCE: 129

```
gttgattccg ttcgcggcgc cgccgaagac caccaactcc gctggggtgg tcgcacaggc      60
ggttgcgtcg gtcagctggc cgaatcccaa tgattggtgg ctcngtgcgg ttgctgggct     120
cgattacccc cacggaaagg acgacgatcg ttcgtttgct cggtcagtcg tacttggcga    180
cgggcatggc gcggtttctt acctcgatcg cacagcagct gaccttcggc caggggggca    240
caacggctgg ctccggcgga gcctggtacc caacgccaca attcgccggc ctgggtgcag    300
gcccggcggt gtcggcgagt ttggcgcggg cggagccggt cggagggttg tcggtgccgc    360
caagttgggc cgtcgcggct ccggccttcg cggagaagcc tgaggcgggc acgccgatgt    420
ccgtcatcgg cgaagcgtcc agctgcggtc agggaggcct gcttcgaggc ataccgctgg    480
cgagagcggg gcggcgtaca ggcgccttcg ctcaccgata cgggttccgc cacagcgtga    540
ttaccggtc tccgtcggcg ggatagcttt cgatccggtc tgcgcggccg ccggaaatgc      600
tgcagatagc gatcgaccgc gccggtcggt aaacgccgca cacggcacta tcaatgcgca    660
cggcgggcgt tgatgccaaa ttgaccgtcc cgacgggggct ttatctgcgg caagatttca    720
tccccagccc ggtcggtggg ccgataaata cgctggtcag cgcgactctt ccggctgaat    780
tcgatgctct gggcgcccgc tcgacgccga gtatctcgag tgggccgcaa acccggtcaa    840
acgctgttac tgtggcgtta ccacaggtga atttgcggtg ccaactggtg aacacttgcg    900
aacgggtggc atcgaaatca acttgttgcg ttgcagtgat ctactctctt gcagagagcc    960
gttgctggga ttaattggga gaggaagaca gcatgtcgtt cgtgaccaca cagccggaag   1020
ccctggcagc tgcggcggcg aacctacagg gtattggcac gacaatgaac gcccagaacg   1080
cggccgcggc tgctccaacc accggagtag tgcccgcagc cgccgatgaa gtatcagcgc   1140
tgaccgcggc tcagttttgct gcgcacgcgc agatgtacca aacggtcagc gcccaggccg   1200
cggccattca cgaaatgttc gtgaacacgc tggtggccag ttctggctca tacgcggcca   1260
ccgaggcggc caacgcagcc gctgccggct gaacgggctc gcacgaacct gctgaaggag   1320
agggggaaca tccggagttc tcgggtcagg ggttgcgcca gcgcccagcc gattcagcta   1380
tcggcgtcca taacagcaga cgatctaggc attcagtact aaggagacag gcaacatggc   1440
ctcacgtttt atgacggatc cgcatgcgat gcggacatg gcgggccgtt ttgaggtgca    1500
cgcccagacg gtggaggacg aggctcgccg gatgtgggcg tccgcgcaaa acatttccgg   1560
```

```
tgcgggctgg agtggcatgg ccgaggcgac ctcgctagac accatgacct agatgaatca    1620
ggcgtttcgc aacatcgtga acatgctgca cggggtgcgt gacgggctgg ttcgcgacgc    1680
caacaactac gaacagcaag agcaggcctc ccagcagatc ctgagcagct agcgccgaaa    1740
gccacagctg cgtacgcttt ctcacattag gagaacacca atatgacgat taattaccag    1800
ttcggggacg tcgacgctca tggcgccatg atccgcgctc aggcggcgtc gcttgaggcg    1860
gagcatcagg ccatcgttcg tgatgtgttg gccgcgggtg acttttgggg cggcgccggt    1920
tcggtggctt gccaggagtt cattacccag ttgggccgta acttccaggt gatctacgag    1980
caggccaacg cccacgggca gaaggtgcag gctgccggca caacatggc gcaaaccgac      2040 agcgccgtcg gctccagctg ggcctaaaac tgaacttcag tcgcggcagc acaccaacca    2100
gccggtgtgc tgctgtgtcc tgcagttaac tagcactcga ccgctgaggt agcgatggat    2160
caacagagta cccgcaccga catcaccgtc aacgtcgacg gcttctggat gcttcaggcg    2220
ctactggata tccgccacgt tgcgcctgag ttacgttgcc ggccgtacgt ctccaccgat    2280
tccaatgact ggctaaacga gcaccggggg atggcggtca tgcgcgagca gggcattgtc    2340
gtcaacgacg cggtcaacga acaggtcgct gcccggatga aggtgcttgc cgcacctgat    2400
cttgaagtcg tcgccctgct gtcacgcggc aagttgctgt acggggtcat agacgacgag    2460
aaccagccgc cgggttcgcg tgacatccct gacaatgagt tccgggtggt gttggcccgg    2520
cgaggccagc actgggtgtc ggcggtacgg gttggcaatg acatcaccgt cgatgacgtg    2580
acggtctcgg atagcgcctc gatcgccgca ctggtaatgg acggtctgga gtcgattcac    2640
cacgccgacc cagccgcgat caacgcggtc aacgtgccaa tggaggagat ctcgtgccga    2700
attcggcacg aggcacgagg cggtgtcggt gacgacggga tcgatcacga tcatcgaccg    2760
gccgggatcc ttggcgatct cgttgagcac gacccgggcc cgcgggaagc tctgcgacat    2820
ccatgggttc ttcccg                                                    2836

<210> SEQ ID NO 130
<211> LENGTH: 15
<212> TYPE: PRT
<213> ORGANISM: Artificial Sequence
<220> FEATURE:
<223> OTHER INFORMATION: Mtb9.9A (MTI-A) ORF peptide

<400> SEQUENCE: 130

Met Thr Ile Asn Tyr Gln Phe Gly Asp Val Asp Ala His Gly Ala
1               5                   10                  15

<210> SEQ ID NO 131
<211> LENGTH: 15
<212> TYPE: PRT
<213> ORGANISM: Artificial Sequence
<220> FEATURE:
<223> OTHER INFORMATION: Mtb9.9A (MTI-A) ORF peptide

<400> SEQUENCE: 131

Gln Phe Gly Asp Val Asp Ala His Gly Ala Met Ile Arg Ala Gln
1               5                   10                  15

<210> SEQ ID NO 132
<211> LENGTH: 15
<212> TYPE: PRT
<213> ORGANISM: Artificial Sequence
<220> FEATURE:
<223> OTHER INFORMATION: Mtb9.9A (MTI-A) ORF peptide

<400> SEQUENCE: 132
```

Asp Ala His Gly Ala Met Ile Arg Ala Gln Ala Ala Ser Leu Glu
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: Mtb9.9A (MTI-A) ORF peptide

<400> SEQUENCE: 133

Met Ile Arg Ala Gln Ala Ala Ser Leu Glu Ala Glu His Gln Ala
1               5                   10                  15

<210> SEQ ID NO 134
<211> LENGTH: 15
<212> TYPE: PRT
<213> ORGANISM: Artificial Sequence
<220> FEATURE:
<223> OTHER INFORMATION: Mtb9.9A (MTI-A) ORF peptide

<400> SEQUENCE: 134

Ala Ala Ser Leu Glu Ala Glu His Gln Ala Ile Val Arg Asp Val
1               5                   10                  15

<210> SEQ ID NO 135
<211> LENGTH: 15
<212> TYPE: PRT
<213> ORGANISM: Artificial Sequence
<220> FEATURE:
<223> OTHER INFORMATION: Mtb9.9A (MTI-A) ORF peptide

<400> SEQUENCE: 135

Ala Glu His Gln Ala Ile Val Arg Asp Val Leu Ala Ala Gly Asp
1               5                   10                  15

<210> SEQ ID NO 136
<211> LENGTH: 15
<212> TYPE: PRT
<213> ORGANISM: Artificial Sequence
<220> FEATURE:
<223> OTHER INFORMATION: Mtb9.9A (MTI-A) ORF peptide

<400> SEQUENCE: 136

Ile Val Arg Asp Val Leu Ala Ala Gly Asp Phe Trp Gly Gly Ala
1               5                   10                  15

<210> SEQ ID NO 137
<211> LENGTH: 16
<212> TYPE: PRT
<213> ORGANISM: Artificial Sequence
<220> FEATURE:
<223> OTHER INFORMATION: Mtb9.9A (MTI-A) ORF peptide

<400> SEQUENCE: 137

Leu Ala Ala Gly Asp Phe Trp Gly Gly Ala Gly Ser Val Ala Cys Gln
1               5                   10                  15

<210> SEQ ID NO 138
<211> LENGTH: 15
<212> TYPE: PRT
<213> ORGANISM: Artificial Sequence
<220> FEATURE:
<223> OTHER INFORMATION: Mtb9.9A (MTI-A) ORF peptide

<400> SEQUENCE: 138

Phe Trp Gly Gly Ala Gly Ser Val Ala Cys Gln Glu Phe Ile Thr

```
<210> SEQ ID NO 139
<211> LENGTH: 15
<212> TYPE: PRT
<213> ORGANISM: Artificial Sequence
<220> FEATURE:
<223> OTHER INFORMATION: Mtb9.9A (MTI-A) ORF peptide

<400> SEQUENCE: 139

Gly Ser Val Ala Cys Gln Glu Phe Ile Thr Gln Leu Gly Arg Asn
1               5                   10                  15

<210> SEQ ID NO 140
<211> LENGTH: 18
<212> TYPE: PRT
<213> ORGANISM: Artificial Sequence
<220> FEATURE:
<223> OTHER INFORMATION: Mtb9.9A (MTI-A) ORF peptide

<400> SEQUENCE: 140

Gln Glu Phe Ile Thr Gln Leu Gly Arg Asn Phe Gln Val Ile Tyr Glu
1               5                   10                  15

Gln Ala

<210> SEQ ID NO 141
<211> LENGTH: 15
<212> TYPE: PRT
<213> ORGANISM: Artificial Sequence
<220> FEATURE:
<223> OTHER INFORMATION: Mtb9.9A (MTI-A) ORF peptide

<400> SEQUENCE: 141

Arg Asn Phe Gln Val Ile Tyr Glu Gln Ala Asn Ala His Gly Gln
1               5                   10                  15

<210> SEQ ID NO 142
<211> LENGTH: 15
<212> TYPE: PRT
<213> ORGANISM: Artificial Sequence
<220> FEATURE:
<223> OTHER INFORMATION: Mtb9.9A (MTI-A) ORF peptide

<400> SEQUENCE: 142

Ile Tyr Glu Gln Ala Asn Ala His Gly Gln Lys Val Gln Ala Ala
1               5                   10                  15

<210> SEQ ID NO 143
<211> LENGTH: 15
<212> TYPE: PRT
<213> ORGANISM: Artificial Sequence
<220> FEATURE:
<223> OTHER INFORMATION: Mtb9.9A (MTI-A) ORF peptide

<400> SEQUENCE: 143

Asn Ala His Gly Gln Lys Val Gln Ala Ala Gly Asn Asn Met Ala
1               5                   10                  15

<210> SEQ ID NO 144
<211> LENGTH: 15
<212> TYPE: PRT
<213> ORGANISM: Artificial Sequence
<220> FEATURE:
<223> OTHER INFORMATION: Mtb9.9A (MTI-A) ORF peptide

<400> SEQUENCE: 144

Lys Val Gln Ala Ala Gly Asn Asn Met Ala Gln Thr Asp Ser Ala
1               5                   10                  15
```

```
                1               5                  10                 15
```

```
<210> SEQ ID NO 145
<211> LENGTH: 16
<212> TYPE: PRT
<213> ORGANISM: Artificial Sequence
<220> FEATURE:
<223> OTHER INFORMATION: Mtb9.9A (MTI-A) ORF peptide

<400> SEQUENCE: 145

Gly Asn Asn Met Ala Gln Thr Asp Ser Ala Val Gly Ser Ser Trp Ala
1               5                  10                 15

<210> SEQ ID NO 146
<211> LENGTH: 15
<212> TYPE: PRT
<213> ORGANISM: Artificial Sequence
<220> FEATURE:
<223> OTHER INFORMATION: Mtb9.8 ORF peptide

<400> SEQUENCE: 146

Met Ser Leu Leu Asp Ala His Ile Pro Gln Leu Val Ala Ser Gln
1               5                  10                 15

<210> SEQ ID NO 147
<211> LENGTH: 15
<212> TYPE: PRT
<213> ORGANISM: Artificial Sequence
<220> FEATURE:
<223> OTHER INFORMATION: Mtb9.8 ORF peptide

<400> SEQUENCE: 147

Ala His Ile Pro Gln Leu Val Ala Ser Gln Ser Ala Phe Ala Ala
1               5                  10                 15

<210> SEQ ID NO 148
<211> LENGTH: 15
<212> TYPE: PRT
<213> ORGANISM: Artificial Sequence
<220> FEATURE:
<223> OTHER INFORMATION: Mtb9.8 ORF peptide

<400> SEQUENCE: 148

Leu Val Ala Ser Gln Ser Ala Phe Ala Ala Lys Ala Gly Leu Met
1               5                  10                 15

<210> SEQ ID NO 149
<211> LENGTH: 15
<212> TYPE: PRT
<213> ORGANISM: Artificial Sequence
<220> FEATURE:
<223> OTHER INFORMATION: Mtb9.8 ORF peptide

<400> SEQUENCE: 149

Ser Ala Phe Ala Ala Lys Ala Gly Leu Met Arg His Thr Ile Gly
1               5                  10                 15

<210> SEQ ID NO 150
<211> LENGTH: 14
<212> TYPE: PRT
<213> ORGANISM: Artificial Sequence
<220> FEATURE:
<223> OTHER INFORMATION: Mtb9.8 ORF peptide

<400> SEQUENCE: 150

Lys Ala Gly Leu Met His Thr Ile Gly Gln Ala Glu Gln Ala
1               5                  10
```

<210> SEQ ID NO 151
<211> LENGTH: 15
<212> TYPE: PRT
<213> ORGANISM: Artificial Sequence
<220> FEATURE:
<223> OTHER INFORMATION: Mtb9.8 ORF peptide

<400> SEQUENCE: 151

Arg His Thr Ile Gly Gln Ala Glu Gln Ala Ala Met Ser Ala Gln
1               5                   10                  15

<210> SEQ ID NO 152
<211> LENGTH: 15
<212> TYPE: PRT
<213> ORGANISM: Artificial Sequence
<220> FEATURE:
<223> OTHER INFORMATION: Mtb9.8 ORF peptide

<400> SEQUENCE: 152

Gln Ala Glu Gln Ala Ala Met Ser Ala Gln Ala Phe His Gln Gly
1               5                   10                  15

<210> SEQ ID NO 153
<211> LENGTH: 15
<212> TYPE: PRT
<213> ORGANISM: Artificial Sequence
<220> FEATURE:
<223> OTHER INFORMATION: Mtb9.8 ORF peptide

<400> SEQUENCE: 153

Ala Met Ser Ala Gln Ala Phe His Gln Gly Glu Ser Ser Ala Ala
1               5                   10                  15

<210> SEQ ID NO 154
<211> LENGTH: 15
<212> TYPE: PRT
<213> ORGANISM: Artificial Sequence
<220> FEATURE:
<223> OTHER INFORMATION: Mtb9.8 ORF peptide

<400> SEQUENCE: 154

Ala Phe His Gln Gly Glu Ser Ser Ala Ala Phe Gln Ala Ala His
1               5                   10                  15

<210> SEQ ID NO 155
<211> LENGTH: 15
<212> TYPE: PRT
<213> ORGANISM: Artificial Sequence
<220> FEATURE:
<223> OTHER INFORMATION: Mtb9.8 ORF peptide

<400> SEQUENCE: 155

Glu Ser Ser Ala Ala Phe Gln Ala Ala His Ala Arg Phe Val Ala
1               5                   10                  15

<210> SEQ ID NO 156
<211> LENGTH: 15
<212> TYPE: PRT
<213> ORGANISM: Artificial Sequence
<220> FEATURE:
<223> OTHER INFORMATION: Mtb9.8 ORF peptide

<400> SEQUENCE: 156

Phe Gln Ala Ala His Ala Arg Phe Val Ala Ala Ala Lys Val
1               5                   10                  15

<210> SEQ ID NO 157

```
<211> LENGTH: 15
<212> TYPE: PRT
<213> ORGANISM: Artificial Sequence
<220> FEATURE:
<223> OTHER INFORMATION: Mtb9.8 ORF peptide

<400> SEQUENCE: 157

Ala Arg Phe Val Ala Ala Ala Lys Val Asn Thr Leu Leu Asp
1               5                   10                  15

<210> SEQ ID NO 158
<211> LENGTH: 15
<212> TYPE: PRT
<213> ORGANISM: Artificial Sequence
<220> FEATURE:
<223> OTHER INFORMATION: Mtb9.8 ORF peptide

<400> SEQUENCE: 158

Ala Ala Ala Lys Val Asn Thr Leu Leu Asp Val Ala Gln Ala Asn
1               5                   10                  15

<210> SEQ ID NO 159
<211> LENGTH: 15
<212> TYPE: PRT
<213> ORGANISM: Artificial Sequence
<220> FEATURE:
<223> OTHER INFORMATION: Mtb9.8 ORF peptide

<400> SEQUENCE: 159

Asn Thr Leu Leu Asp Val Ala Gln Ala Asn Leu Gly Glu Ala Ala
1               5                   10                  15

<210> SEQ ID NO 160
<211> LENGTH: 16
<212> TYPE: PRT
<213> ORGANISM: Artificial Sequence
<220> FEATURE:
<223> OTHER INFORMATION: Mtb9.8 ORF peptide

<400> SEQUENCE: 160

Val Ala Gln Ala Asn Leu Gly Glu Ala Ala Gly Thr Tyr Val Ala Ala
1               5                   10                  15

<210> SEQ ID NO 161
<211> LENGTH: 29
<212> TYPE: DNA
<213> ORGANISM: Artificial Sequence
<220> FEATURE:
<223> OTHER INFORMATION: PCR primer

<400> SEQUENCE: 161
cgtaatcacg tgcagaagta cggcggatc                                    29

<210> SEQ ID NO 162
<211> LENGTH: 31
<212> TYPE: DNA
<213> ORGANISM: Artificial Sequence
<220> FEATURE:
<223> OTHER INFORMATION: PCR primer

<400> SEQUENCE: 162
ccgactagaa ttcactattg acaggcccat c                                 31

<210> SEQ ID NO 163
<211> LENGTH: 30
<212> TYPE: DNA
<213> ORGANISM: Artificial Sequence
<220> FEATURE:
```

<223> OTHER INFORMATION: PCR primer

<400> SEQUENCE: 163
ctaagtagta ctgatcgcgt gtcggtgggc            30

<210> SEQ ID NO 164
<211> LENGTH: 28
<212> TYPE: DNA
<213> ORGANISM: Artificial Sequence
<220> FEATURE:
<223> OTHER INFORMATION: PCR primer

<400> SEQUENCE: 164
catcgatagg cctggccgca tcgtcacc              28

<210> SEQ ID NO 165
<211> LENGTH: 27
<212> TYPE: DNA
<213> ORGANISM: Artificial Sequence
<220> FEATURE:
<223> OTHER INFORMATION: PCR primer

<400> SEQUENCE: 165
ctagttagta ctcagtcgca gaccgtg               27

<210> SEQ ID NO 166
<211> LENGTH: 25
<212> TYPE: DNA
<213> ORGANISM: Artificial Sequence
<220> FEATURE:
<223> OTHER INFORMATION: PCR primer

<400> SEQUENCE: 166
gcagtgacga attcacttcg actcc                 25

<210> SEQ ID NO 167
<211> LENGTH: 33
<212> TYPE: DNA
<213> ORGANISM: Artificial Sequence
<220> FEATURE:
<223> OTHER INFORMATION: PCR primer

<400> SEQUENCE: 167
ggatccagcg ctgagatgaa gaccgatgcc gct        33

<210> SEQ ID NO 168
<211> LENGTH: 38
<212> TYPE: DNA
<213> ORGANISM: Artificial Sequence
<220> FEATURE:
<223> OTHER INFORMATION: PCR primer

<400> SEQUENCE: 168
ggatatctgc agaattcagg tttaaagccc atttgcga   38

<210> SEQ ID NO 169
<211> LENGTH: 26
<212> TYPE: DNA
<213> ORGANISM: Artificial Sequence
<220> FEATURE:
<223> OTHER INFORMATION: PCR primer

<400> SEQUENCE: 169
tgtggctcga aaccaccgag cggttc                26

<210> SEQ ID NO 170

```
<211> LENGTH: 33
<212> TYPE: DNA
<213> ORGANISM: Artificial Sequence
<220> FEATURE:
<223> OTHER INFORMATION: PCR primer

<400> SEQUENCE: 170
gagagaattc tcagaagccc atttgcgagg aca                                    33

<210> SEQ ID NO 171
<211> LENGTH: 50
<212> TYPE: DNA
<213> ORGANISM: Artificial Sequence
<220> FEATURE:
<223> OTHER INFORMATION: PCR primer

<400> SEQUENCE: 171
caattacata tgcatcacca tcaccatcac atgagcagag cgttcatcat                  50

<210> SEQ ID NO 172
<211> LENGTH: 31
<212> TYPE: DNA
<213> ORGANISM: Artificial Sequence
<220> FEATURE:
<223> OTHER INFORMATION: PCR primer

<400> SEQUENCE: 172
catggaattc gccgttagac gacgtttcgt a                                      31

<210> SEQ ID NO 173
<211> LENGTH: 51
<212> TYPE: DNA
<213> ORGANISM: Artificial Sequence
<220> FEATURE:
<223> OTHER INFORMATION: PCR primer

<400> SEQUENCE: 173
caattacata tgcatcacca tcaccatcac acggccgcgt ccgataactt c                51

<210> SEQ ID NO 174
<211> LENGTH: 33
<212> TYPE: DNA
<213> ORGANISM: Artificial Sequence
<220> FEATURE:
<223> OTHER INFORMATION: PCR primer

<400> SEQUENCE: 174
ctaatcgaat tcggccgggg gtccctcggc caa                                    33

<210> SEQ ID NO 175
<211> LENGTH: 51
<212> TYPE: DNA
<213> ORGANISM: Mycobacterium tuberculosis

<400> SEQUENCE: 175
caattacata tgcatcacca tcaccatcac atgagcagag cgttcatcat c                51

<210> SEQ ID NO 176
<211> LENGTH: 31
<212> TYPE: DNA
<213> ORGANISM: Artificial Sequence
<220> FEATURE:
<223> OTHER INFORMATION: PCR primer

<400> SEQUENCE: 176
catggaattc gccgttagac gacgtttcgt a                                      31
```

```
<210> SEQ ID NO 177
<211> LENGTH: 39
<212> TYPE: DNA
<213> ORGANISM: Artificial Sequence
<220> FEATURE:
<223> OTHER INFORMATION: PCR primer

<400> SEQUENCE: 177
catcaccatc accatcacac ggccgcgtcc gataacttc                               39

<210> SEQ ID NO 178
<211> LENGTH: 33
<212> TYPE: DNA
<213> ORGANISM: Artificial Sequence
<220> FEATURE:
<223> OTHER INFORMATION: PCR primer

<400> SEQUENCE: 178
ctaatcgaat tcggccgggg gtccctcggc caa                                     33
```

What is claimed is:

1. A method for the treatment and/or prevention of tuberculosis, comprising administering an effective amount of a composition comprising an isolated nucleic acid molecule encoding at least two heterologous antigens from Mycobacterium tuberculosis, wherein the antigens are selected from the group consisting of Mtb81 (SEQ ID NO:2), Mo2 (SEQ ID NO:4), TbRa3 (SEQ ID NO:6), 38 kD (SEQ ID NO:8), FL TbH4 (SEQ ID NO:12), HTCC#1 (Mtb40) (SEQ ID NO:14), TbH9 (SEQ ID NO:26), MTCC#2 (Mtb41) (SEQ ID NO:32), DPEP (SEQ ID NO:40), DPPD (SEQ ID NO:44), TbRa12 (SEQ ID NO:28), Mtb59 (SEQ ID NO:50), Mtb82 (SEQ ID NO:48), Erd14 (Mtb16) (SEQ ID NO:42), DPV (Mtb8.4) (SEQ ID NO:38), MSL (Mtb9.8) (SEQ ID NO:36), MTI (Mtb9.9A, also known as MTI-A) (SEQ ID NO:34), ESAT-6 (SEQ ID NO:46), α-crystalline, and 85 complex.

2. A method for the treatment and/or prevention of tuberculosis comprising administering an effective amount of a composition comprising an isolated nucleic acid molecule encoding a fusion polypeptide comprising at least two heterologous antigens from Mycobacterium tuberculosis, wherein the antigens are selected from the group consisting of Mtb81 (SEQ ID NO:2), Mo2 (SEQ ID NO:4), TbRa3 (SEQ ID NO:6), 38 kD (SEQ ID NO:8), FL TbH4 (SEQ ID NO:12), HTCC#1 (Mtb40) (SEQ ID NO:14), TbH9 (SEQ ID NO:26), MTCC#2 (Mtb41) (SEQ ID NO:32), DPEP (SEQ ID NO:40), DPPD (SEQ ID NO:44), TbRa12 (SEQ ID NO:28), Mtb59 (SEQ ID NO:50), Mtb82 (SEQ ID NO:48), Erd14 (Mtb16) (SEQ ID NO:42), DPV (Mtb8.4) (SEQ ID NO:38), MSL (Mtb9.8) (SEQ ID NO:36), MTI (Mtb9.9A, also known as MTI-A) (SEQ ID NO:34), ESAT-6 (SEQ ID NO:46), α-crystalline, and 85 complex, wherein the antigens are linked to form a fusion polypeptide.

3. A method for the treatment and/or prevention of tuberculosis comprising administering an effective amount of a composition comprising: (a) an isolated nucleic acid molecule encoding a first M. tuberculosis antigen; and (b) an isolated nucleic acid molecule encoding a second M. tuberculosis antigen; wherein said first and second M. tuberculosis antigens are selected from the group consisting of Mtb81 (SEQ ID NO:2), Mo2 (SEQ ID NO:4), TbRa3 (SEQ ID NO:6), 38 kD (SEQ ID NO:8), FL TbH4 (SEQ ID NO:12), HTCC#1 (Mtb40) (SEQ ID NO:14), TbH9 (SEQ ID NO:26), MTCC#2 (Mtb41) (SEQ ID NO:32), DPEP (SEQ ID NO:40), DPPD (SEQ ID NO:44), TbRa12 (SEQ ID NO:28), Mtb59 (SEQ ID NO:50), Mtb82 (SEQ ID NO:48), Erd14 (Mtb16) (SEQ ID NO:42), DPV (Mtb8.4) (SEQ ID NO:38), MSL (Mtb9.8) (SEQ ID NO:36), MTI (Mtb9.9A, also known as MTI-A) (SEQ ID NO:34), ESAT-6 (SEQ ID NO:46), α-crystalline, and 85 complex, and wherein said first and second M. tuberculosis antigens are not the same.

4. The method of claim 1, wherein the composition further comprises a pharmaceutically-acceptable excipient.

5. The method of claim 1, wherein the composition further comprises an adjuvant.

6. The method of claim 2, wherein the composition further comprises a pharmaceutically-acceptable excipient.

7. The method of claim 2, wherein the composition further comprises an adjuvant.

8. The method of claim 3, wherein the composition further comprises a pharmaceutically-acceptable excipient.

9. The method of claim 3, wherein the composition further comprises an adjuvant.

* * * * *